US010233228B2

(12) United States Patent
Plumridge et al.

(10) Patent No.: US 10,233,228 B2
(45) Date of Patent: Mar. 19, 2019

(54) ALBUMIN DERIVATIVES AND VARIANTS

(75) Inventors: Andrew Plumridge, Derbyshire (GB); Darrell Sleep, Nottingham (GB); Inger Sandlie, Oslo (NO); Jan Terje Andersen, Oslo (NO); Jason Cameron, Nottingham (GB); Leslie Evans, Nottingham (GB); Steven Athwal, Nottingham (GB); Elizabeth Allan, Nottingham (GB); Esben Peter Friis, Herlev (DK)

(73) Assignee: ALBUMEDIX LTD, Nottingham (GB)

( * ) Notice: Subject to any disclaimer, the term of this patent is extended or adjusted under 35 U.S.C. 154(b) by 689 days.

(21) Appl. No.: 13/640,235

(22) PCT Filed: Apr. 8, 2011

(86) PCT No.: PCT/EP2011/055577
§ 371 (c)(1),
(2), (4) Date: Oct. 9, 2012

(87) PCT Pub. No.: WO2011/124718
PCT Pub. Date: Oct. 13, 2011

(65) Prior Publication Data
US 2013/0028930 A1 Jan. 31, 2013

Related U.S. Application Data

(60) Provisional application No. 61/326,952, filed on Apr. 22, 2010, provisional application No. 61/381,255, filed on Sep. 9, 2010, provisional application No. 61/468,149, filed on Mar. 28, 2011.

(30) Foreign Application Priority Data

Apr. 9, 2010 (EP) .................................... 10159450
Aug. 26, 2010 (EP) .................................... 10174164
Mar. 18, 2011 (EP) .................................... 11158921

(51) Int. Cl.
*C07K 14/765* (2006.01)

(52) U.S. Cl.
CPC ........ *C07K 14/765* (2013.01); *C07K 2319/00* (2013.01)

(58) Field of Classification Search
None
See application file for complete search history.

(56) References Cited

U.S. PATENT DOCUMENTS

| 2,714,586 | A | 8/1955 | Lynch et al. |
| 4,302,386 | A | 11/1981 | Stevens |
| 4,741,900 | A | 5/1988 | Alvarez et al. |
| 4,757,006 | A | 7/1988 | Toole, Jr. et al. |
| 4,784,950 | A | 11/1988 | Hagen et al. |
| 4,795,805 | A | 1/1989 | Itoh et al. |
| 4,868,112 | A | 9/1989 | Toole, Jr. |
| 5,073,627 | A | 12/1991 | Curtis et al. |
| 5,208,020 | A | 5/1993 | Chari et al. |
| 5,223,409 | A | 6/1993 | Ladner et al. |
| 5,264,586 | A | 11/1993 | Nicolaou et al. |
| 5,294,699 | A | 3/1994 | Ohmura et al. |
| 5,380,712 | A | 1/1995 | Ballance et al. |
| 5,625,041 | A | 4/1997 | Johnson et al. |
| 5,698,426 | A | 12/1997 | Huse |
| 5,712,374 | A | 1/1998 | Kuntsmann et al. |
| 5,714,377 | A | 2/1998 | Tanner et al. |
| 5,714,586 | A | 2/1998 | Kunstmann et al. |
| 5,716,808 | A | 2/1998 | Raymond |
| 5,728,553 | A | 3/1998 | Goodey et al. |
| 5,736,383 | A | 4/1998 | Raymond |
| 5,766,883 | A | 6/1998 | Ballance et al. |
| 5,773,001 | A | 6/1998 | Hamann et al. |
| 5,824,837 | A | 10/1998 | Chen et al. |
| 5,854,039 | A | 12/1998 | Raymond et al. |
| 5,876,969 | A | 3/1999 | Fleer et al. |
| 5,888,768 | A | 3/1999 | Raymond |
| 5,948,609 | A | 9/1999 | Carter |
| 6,509,313 | B1 | 1/2003 | Smith |
| 6,599,873 | B1 | 7/2003 | Sommer et al. |
| 6,686,179 | B2 | 2/2004 | Fleer et al. |
| 6,905,688 | B2 | 6/2005 | Rosen et al. |
| 6,926,898 | B2 | 8/2005 | Rosen et al. |
| 6,949,691 | B2 | 9/2005 | Carter |
| 6,972,322 | B2 | 12/2005 | Fleer et al. |
| 6,987,006 | B2 | 1/2006 | Fleer et al. |
| 6,989,365 | B2 | 1/2006 | Fleer et al. |
| 6,994,857 | B2 | 2/2006 | Rosen et al. |

(Continued)

FOREIGN PATENT DOCUMENTS

| CA | 2611540 | 5/2009 |
| CA | 2562249 | 4/2016 |

(Continued)

OTHER PUBLICATIONS

Werle et al 2006, Amino Acids 30(4), 351-367.
Bar-Or et al, 2006, Clin Chim Ada 365(1-2), 346-349.
Brennan et al, 2000, Biochim Biophys Acta 1481(2), 337-343.
Cronican et al, 2010—Geneseq, Access No. AXS56687.
Dagnino et al, 2010, Clinic Chimica Acta 411, 1711-1715.
Iwao et al, 2009, Biochem Biophys Acta 1794(4), 634-641.
Andersen et al, 2006, Eur J Immunol 36, 3044-3051.
Andersen et al, 2007, Clinic Chem 53(12), 2216.
Andersen et al, 2008, FEBS J 275(16), 4097-4110.
Andersen et al, 2009, Drug Metab Pharmacokinet 24 (4), 318-332.
Andersen et al, 2010, Clinical Biochem 43, 367-372.
Andersen et al, 2010, J Biol Chem 285(7), 4826-4836.
Andersen et al, 2012, Nature, 1-9.

(Continued)

*Primary Examiner* — Anand U Desai
(74) *Attorney, Agent, or Firm* — Knobbe Martens Olson & Bear LLP

(57) ABSTRACT

The application discloses albumin derivatives comprising or consisting of domain III and at least one further domain wherein the derivative or variant is not a naturally occurring albumin derivative or variant. The derivatives may be used in conjugates and fusion polypeptides.

18 Claims, 15 Drawing Sheets

Specification includes a Sequence Listing.

(56) References Cited

U.S. PATENT DOCUMENTS

| | | |
|---|---|---|
| 7,041,478 B2 | 5/2006 | Fleer et al. |
| 7,041,802 B2 | 5/2006 | Young et al. |
| 7,041,803 B2 | 5/2006 | Ni et al. |
| 7,045,318 B2 | 5/2006 | Ballance |
| 7,053,190 B2 | 5/2006 | Ruben et al. |
| 7,056,701 B2 | 6/2006 | Fleer et al. |
| 7,081,354 B2 | 7/2006 | Fleer et al. |
| 7,094,577 B2 | 8/2006 | Fleer et al. |
| 7,141,547 B2 | 11/2006 | Rosen et al. |
| 7,196,164 B2 | 3/2007 | Rosen et al. |
| 7,253,259 B2* | 8/2007 | Otagiri ............... C07K 14/765 530/350 |
| 7,271,149 B2 | 9/2007 | Glaesner et al. |
| 7,358,416 B2 | 4/2008 | Roopenian |
| 7,410,779 B2 | 8/2008 | Fleer et al. |
| 7,425,622 B2 | 9/2008 | Rosen |
| 7,435,410 B2 | 10/2008 | Fleer et al. |
| 7,465,707 B2 | 12/2008 | Ni et al. |
| 7,482,013 B2 | 1/2009 | Ballance et al. |
| 7,507,413 B2 | 3/2009 | Rosen et al. |
| 7,507,414 B2 | 3/2009 | Rosen et al. |
| 7,514,079 B2 | 4/2009 | Rosen et al. |
| 7,550,432 B2 | 6/2009 | Ballance |
| 7,569,215 B2 | 8/2009 | Wittrup et al. |
| 7,572,619 B2 | 8/2009 | Hauser et al. |
| 7,592,010 B2 | 9/2009 | Rosen et al. |
| 7,597,886 B2 | 10/2009 | Yu et al. |
| 7,615,537 B2 | 11/2009 | Sea ria et al. |
| 7,785,599 B2 | 8/2010 | Ballance et al. |
| 7,833,521 B2 | 11/2010 | Fleer et al. |
| 7,850,963 B2 | 12/2010 | Rosen et al. |
| 7,851,596 B2 | 12/2010 | Gentz et al. |
| 7,862,818 B2 | 1/2011 | Raschke et al. |
| 7,951,360 B2 | 5/2011 | Wittrup et al. |
| 7,998,691 B2 | 8/2011 | Kulaksiz et al. |
| 8,012,464 B2 | 9/2011 | Rosen et al. |
| 8,080,651 B2 | 12/2011 | Goldberg |
| 8,697,650 B2 | 4/2014 | Gao et al. |
| 8,748,380 B2 | 6/2014 | Plumridge et al. |
| 8,822,417 B2 | 9/2014 | Andersen et al. |
| 9,944,691 B2 | 4/2018 | Delahay |
| 2002/0123080 A1 | 9/2002 | Sonnenschein et al. |
| 2002/0151011 A1 | 10/2002 | Fleer et al. |
| 2003/0091565 A1 | 5/2003 | Beltzer et al. |
| 2003/0104578 A1 | 6/2003 | Ballance |
| 2004/0063635 A1 | 4/2004 | Yu |
| 2004/0171154 A1 | 9/2004 | Storici et al. |
| 2005/0142106 A1 | 6/2005 | Wittrup et al. |
| 2005/0222026 A1 | 10/2005 | Otagiri |
| 2005/0256303 A1 | 11/2005 | Otagiri et al. |
| 2006/0018859 A1 | 1/2006 | Carter |
| 2006/0051859 A1 | 3/2006 | Fu |
| 2006/0171892 A1 | 8/2006 | Woodrow |
| 2006/0178301 A1 | 8/2006 | Jurs |
| 2007/0041987 A1* | 2/2007 | Carter ............... A61K 39/385 424/185.1 |
| 2007/0092940 A1 | 4/2007 | Eigenbrot |
| 2008/0108560 A1 | 5/2008 | Beals et al. |
| 2008/0167238 A1* | 7/2008 | Rosen ............... C07K 14/765 514/3.8 |
| 2009/0029914 A1 | 1/2009 | Rosen et al. |
| 2010/0129846 A1 | 5/2010 | Goldknopf |
| 2011/0091412 A1 | 4/2011 | Wittrup et al. |
| 2011/0151490 A1 | 6/2011 | Hillman |
| 2011/0313133 A1 | 12/2011 | Finnis |
| 2012/0220530 A1 | 8/2012 | Plumridge |
| 2012/0322739 A1 | 12/2012 | Andersen et al. |
| 2013/0028930 A1 | 1/2013 | Plumridge |
| 2013/0053322 A1 | 2/2013 | Gao |
| 2013/0225496 A1 | 8/2013 | Plumridge |
| 2014/0128326 A1 | 5/2014 | Cameron |
| 2014/0148392 A1 | 5/2014 | Gao et al. |
| 2014/0234311 A1 | 8/2014 | Sleep et al. |
| 2014/0248682 A1 | 9/2014 | Gao et al. |
| 2014/0315816 A1 | 10/2014 | Andersen et al. |
| 2014/0315817 A1 | 10/2014 | Schmidt et al. |
| 2015/0210752 A1 | 7/2015 | Cameron |
| 2016/0075763 A1 | 3/2016 | Sleep et al. |
| 2017/0081389 A1 | 3/2017 | Finnis et al. |
| 2018/0072792 A1 | 3/2018 | Sleep et al. |
| 2018/0105576 A1 | 4/2018 | Sleep et al. |
| 2018/0105577 A1 | 4/2018 | Sleep et al. |
| 2018/0105578 A1 | 4/2018 | Sleep et al. |
| 2018/0162925 A1 | 6/2018 | Sleep et al. |

FOREIGN PATENT DOCUMENTS

| | | |
|---|---|---|
| CN | 1405182 | 3/2003 |
| CN | 101875693 B | 7/2012 |
| EP | 0 286 424 | 10/1988 |
| EP | 0319067 | 6/1989 |
| EP | 0 413 622 | 2/1991 |
| EP | 0438102 | 7/1991 |
| EP | 0510693 A2 | 4/1992 |
| EP | 0 305 216 | 8/1995 |
| EP | 1 681 304 | 7/2006 |
| JP | 2005-206577 | 8/2005 |
| JP | 4983148 | 7/2012 |
| KR | 2005-0075134 | 7/2005 |
| RU | 2369404 | 10/2009 |
| WO | WO 90/13653 | 11/1990 |
| WO | WO 93/21232 | 10/1993 |
| WO | WO 94/11026 | 5/1994 |
| WO | WO 1995/17413 | 6/1995 |
| WO | WO 1995/22625 | 8/1995 |
| WO | WO 95/23857 | 9/1995 |
| WO | WO 1995/24427 | 9/1995 |
| WO | WO 97/24445 | 7/1997 |
| WO | 99/28348 A1 | 6/1999 |
| WO | WO 00/008207 | 2/2000 |
| WO | 00/044772 A2 | 8/2000 |
| WO | 00/069902 A1 | 11/2000 |
| WO | 01/79271 A1 | 10/2001 |
| WO | WO 01/79258 | 10/2001 |
| WO | WO 01/79442 | 10/2001 |
| WO | WO 01/79443 | 10/2001 |
| WO | WO 01/79444 | 10/2001 |
| WO | WO 01/79480 | 10/2001 |
| WO | WO 2002/022809 | 3/2002 |
| WO | WO 02/43658 | 6/2002 |
| WO | WO 02/083897 | 10/2002 |
| WO | WO 02/102830 | 12/2002 |
| WO | 03/059934 A2 | 7/2003 |
| WO | 03/060071 A2 | 7/2003 |
| WO | 03/066085 A1 | 8/2003 |
| WO | 03/066824 A2 | 8/2003 |
| WO | WO 2004/101620 | 1/2004 |
| WO | 2004/011499 A1 | 2/2004 |
| WO | 2004/082640 A2 | 9/2004 |
| WO | WO 2004/083245 A2 | 9/2004 |
| WO | 2005/003296 A2 | 1/2005 |
| WO | WO 05/061718 | 7/2005 |
| WO | WO 05/061719 | 7/2005 |
| WO | WO 05/077042 | 8/2005 |
| WO | WO 2005/082423 | 9/2005 |
| WO | 2006/066595 A2 | 6/2006 |
| WO | WO 06/067511 | 6/2006 |
| WO | WO 06/073195 | 7/2006 |
| WO | WO 2006/118772 | 11/2006 |
| WO | WO 2006/136831 | 12/2006 |
| WO | WO 07/021494 | 2/2007 |
| WO | WO 07/071068 | 6/2007 |
| WO | 2007/112940 A2 | 10/2007 |
| WO | WO 07/146038 | 12/2007 |
| WO | WO 2008/007146 | 1/2008 |
| WO | WO 08/030558 | 3/2008 |
| WO | 2009/019314 A1 | 2/2009 |
| WO | WO 2009/081201 | 7/2009 |
| WO | WO 09/126920 | 10/2009 |
| WO | WO 09/134808 | 11/2009 |
| WO | WO 10/059315 | 5/2010 |
| WO | 2010/.68278 A2 | 6/2010 |
| WO | WO 10/065950 | 6/2010 |
| WO | 2010/092135 A2 | 8/2010 |

(56) References Cited

FOREIGN PATENT DOCUMENTS

| WO | 2010/118169 A2 | 10/2010 |
|---|---|---|
| WO | WO 10/118169 | 10/2010 |
| WO | WO 10/129023 | 11/2010 |
| WO | 2010/138814 A2 | 12/2010 |
| WO | WO 10/141329 | 12/2010 |
| WO | 2011/011315 A1 | 1/2011 |
| WO | WO 11/011797 | 1/2011 |
| WO | WO 2011/018611 | 2/2011 |
| WO | WO 11/044563 | 4/2011 |
| WO | 2011/0511489 A2 | 5/2011 |
| WO | WO 11/079175 | 6/2011 |
| WO | 2011/103076 A1 | 8/2011 |
| WO | WO 11/124718 | 10/2011 |
| WO | 2011/146902 A1 | 11/2011 |
| WO | 2011/161127 A1 | 12/2011 |
| WO | WO 2012/020143 | 2/2012 |
| WO | WO 12/059486 | 5/2012 |
| WO | 2012/112188 A1 | 8/2012 |
| WO | WO 12/150319 | 11/2012 |
| WO | WO 13/010840 | 1/2013 |
| WO | WO 13/075066 | 5/2013 |
| WO | WO 13/135896 | 9/2013 |
| WO | WO 14/005596 | 1/2014 |
| WO | WO 14/072481 | 5/2014 |
| WO | WO 14/179657 | 11/2014 |
| WO | WO 2015/036579 | 3/2015 |

OTHER PUBLICATIONS

Anderson et al, 2006, Trends Immunol 27(7), 343-348.
Barash et al, 1993, Trans Res 2, 266-276.
Benotti et al, 1979, Crit Care Med 7(12), 520-525.
Berntzen et al, 2005, J Immun Method 298, 93-104.
Carlson et al, 1992, Proc Natl Acad Sci USA 89, 8225-8229.
Chaudhury et al, 2003. J Exp Med 197(3), 315-322.
Chaudhury et al, 2006, Biochemistry 45, 4983-4990.
Curry et al, 1998, Nat Stuct Biol 5(9), 827-835.
Farran et al, 2002, Trans Res 11, 337-346.
Fleer et al,1991, Biotech 9, 968-975.
Galliano et al, 1993, Biochim Biophys Acta 1225, 27-32.
Hansen et al, 2005, Biochim et Biophys Acta (Prot & Proteom) 1747(1), 81-88.
Ishima et al, 2007, J Pharma Exp Therapeutics 320(3), 969-977.
Iwao et al, 2006, Biochim et Biophys Acta 1764(4), 743-749.
Iwao et al, 2007, B B A Prot Proteomics 1774, 1582-1590.
Kenanova et al, 2009, J Nucl Med 50(Supp 2) 1582-Ab.
Kenanova et al, 2010, Prot Eng Des 23, 789-798.
Kobayashi et al, 1998, Thera Apheresis 2, 257-262.
Kratz, 2008, J Controlled Release 132, 171-183.
Kurtzhals et al, 1995, Biochem J 312, 725-731.
Mezo et al 2010. J Biol Chem 285(36), 27694-27701.
Minchiotti et al, 1987, Biochim Biophys Acta 916, 411-418.
Minchiotti et al, 2008, Human Mutation 29(8), 1007-1016.
NCBI Database Access No. 103600 (2011).
NCP web catalog 2005 downloaded Feb. 24, 2011.
Needleman et al, 1970, J Mol Biol 48, 443-453.
Olafsen et al, 2006, Nature Protocol 1(4), 2048-2060.
Otagiri et al, 2009, Biol Pharm Bull 32 (4), 527-534.
Peach et al, 1991, Biochim Biophys Acta 1097, 49-54.
Peters et al, 1996, All about Albumin—Review, 1.
Peters et al, 1996, All about Albumin, 245-246.
Peters, 1985, Adv Prot Chem 37, 161-245.
Peters, 1996, All About Albumin, Academic Press, iv-ix.
Rice et al, 2000, Trends Genet 16, 276-277.
Roopenian et al, 2007, Nat Rev Immunol 7, 715-525.
Roopenian et al, 2010, Methods Mol Biol 602, 93-104.
Sheffield et al, 2000, Thrombosis Research 99(6), 613-621.
Sijmons et al, 1990, Biotech 8, 217-221.
Simard et al 2005, Proc Natl Acad Sci USA 102(50), 17958-17963.
Sleep, 1990, Biotechnology 8, 42-46.
Sugio et al, 1999, Prot Eng 12(6), 439-446.
Takahashi et al, 1987, Proc Natl Acad Sci USA 84, 4413-4417.
Ward et al, 2009, Adv Immunol 103, 77-115.
Dockal et al. 1999. The three recombinant domains of human serum albumin: Structural characterization and ligand binding properties. *J. Biol. Chem.*, 274:29303-29310.
Schulte, S. "Use of albumin fusion technology to prolong the half-life of recombinant factor vlla." Thromb Res., 2008, 122 Suppl 4:S14-9.
Watkins et al. 1993 cDNA and protein sequence of polymorphic macaque albumins that differ in bilirubin binding. *Proc. Natl. Acad. Sci, USA*, 90:2409-2413.
Andersen et al., Aug. 16, 2013, Single-chain variable fragment albumin fusions bind the neonatal Fc receptor (FcRn) in a species-dependent manner: implications for in vivo half-life evaluation of albumin fusion therapeutics, J Biol Chem., 288(33):24277-85.
Andersen et al., May 2014, Extending serum half-life of albumin by engineering neonatal Fc receptor (FcRn) binding, J Biol Chem., 289(19):13492-502.
Balan et al., 2006, A phase I/II study evaluating escalating doses of recombinant human albumin-interferon-α fusion protein in chronic hepatitis C patients who have failed previous interferon-α-based therapy, Antiviral Therapy, 11(1):35-45.
Ballesta-Claver et al., 2011, Disposable luminol copolymer-based biosensor for uric acid in urine, Analytica Chimica Acta, 702:254-261.
Barr et al., 1996, C-Type Natriuretic Peptide, Peptides 17:1243-1251.
Bergman et al., Jun. 2012, Development of a mathematical model for neonatal Rc receptor recycling to design human serum albumin mutants with extended half-lives, Medimmune FcRn recycling model for mutant albumins, poster, $21^{st}$ Page meeting, Venice Italy, 1 p.
Bhattacharya et al., 2000, Binding of the general anesthetics propofol and halothane to human serum albumin. High resolution crystal structures, J. Biol. Chem., 275(49):38731-38738.
Bhattacharya et al., 2000, Crystallographic analysis reveals common modes of binding of medium and long-chain fatty acids to human serum albumin, J. Mol. Biol., 303:721-732.
Blackburn, 2007, Maternal, Fetal and Neonatal Physiology: a Clinical Perspective, 3rd ed., pp. 197-198.
Bosse et al., 2005, Phase I comparability of recombinant human albumin and human serum albumin, J Clin Pharmacol, 35:57-67.
Bowe et al., 2001, FGF-23 inhibits renal tubular phosphate transport and is a PHEX substrate, Biochem. Biophys. Res. Commun., 284:977-981.
Broze et al., Feb. 25, 1980, Purification and properties of human coagulation factor VII, The Journal of Biological Chemistry, 255(4):1242-1247.
Bunting et al., 2012, Enhanced albumins and albumin fusion technology: tuning circulatory half-life with Novozymes Albufuse® Flex to meet medical needs, Poster, Biopharma NZ, 1 p.
Burmeister et al., 1994, Crystal structure at 2.2 Å result ion of the MHC-related neonatal Fc receptor, Nature, 372(6504):336-343.
Burmeister et al., 1994, Crystal structure of the complex of rat neonatal Fc receptor with Fc, Nature, 372(6504):379-383.
Cai et al., Jun. 2010, QPSOBT: One codon usage optimization software for protein heterologous expression, J Bioinformatics Sequence Analysis, 2(2):25-29.
Cantor et al., 1980, Box 21-2. Reoxidation and refolding of reduced proteins. Biophysical chemistry. Part III: The behavior of biological macromolecules, p. 1104.
Carter et al., 1989, Three dimensional structure of human serum albumin, Science, 244(4909):1195-1198.
Chari et al., 1992, Immunoconjugates Containing Novel Maytansinoids: Promising Anticancer Drugs Cancer Research 52:127-131.
Chen et al., 2003, ZDOCK: an initial-stage protein-docking algorithm, Protein, 52:80-87.
Condreay et al., 2007, Baculovirus Expression Vectors for Insect and Mammalian Cells, Current Drug Targets, 8:1126-1131.
Cornell et al., 1981, The environment of the sulfhydryl group in human plasma albumin as determined by spin labelling, Arch Biochem Biophys, 209(1):1-6.

(56) References Cited

OTHER PUBLICATIONS

Crystal Structure of Human Serum Albumin AT 2.5 A Resolution, PDB Accession: 1A06. publically available in 1999, 125 pp.
Database NCBI—Access No. 1A06_A (Jun. 1998).
Database NCBI—Access No. AAC63407 (Oct. 1998).
Database NCBI—Access No. AAD09358 (Jan. 1999).
Database NCBI—Access No. AAL08579 (Sep. 2001).
Database NCBI—Access No. AAL56646 (Jan. 2002).
Database NCBI—Access No. AAM46104 (Jun. 2002).
Database NCBI—Access No. AAQ20088 (May 2004).
Database NCBI—Access No. ACF10391 (Jul. 2008).
Database NCBI—Access No. NP_001004887 (Feb. 2011).
Database NCBI—Access No. NP_001127106 (May 2011).
Database NCBI—Access No. P02768 (Apr. 2011).
Database NCBI—Access No. P02770 (May 2011).
Database NCBI—Access No. P07724 (May 2011).
Database NCBI—Access No. P21847 (Nov. 2010).
Database NCBI—Access No. P21848 (May 2011).
Database NCBI—Access No. P35747 (May 2011).
Database NCBI—Access No. P83517 (May 2011).
Database NCBI—Access No. Q03156 (May 2011).
Database NCBI—Access No. Q6WDN9-1 (Nov. 2006).
Database NCBI—Access No. Q91274 (Aug. 2010).
Database NCBI—Access No. QXLE4 (May 2011).
Database NCBI—Access No. S59517 (Mar. 2000).
Database Swiss prot—Access No. P49822 (Jun. 2009).
Database Swissprot—Access No. 073860 (Jun. 2009).
Database Swissprot—Access No. P01012 (Jun. 2009).
Database Swissprot—Access No. P02768 (May 2009).
Database Swissprot—Access No. P02769 (Jun. 2009).
Database Swissprot—Access No. P08835 (May 2009).
Database Swissprot—Access No. P14639 (May 2009).
Database Swissprot—Access No. P19121 (Jun. 2009).
Database Swissprot—Access No. P49064 (May 2009).
Database Swissprot—Access No. P49065 (May 2009).
Database Swissprot—Access No. Q28522 (May 2009).
DeMarco et al., 2007, Schistosome albumin is of host, not parasite, origin, Int J Parasit., 37(11):2101-1208.
Di Stefano et al., 2004, A novel method for coupling doxorubicin to lactosaminated human albumin by an acid sensitive hydrazone bond; synthesis, characterization and preliminary biological properties of the conjugate, Eur J Pharm Sci, 23:393-397.
Dickinson et al., Oct. 1999, Bidirectional FcRn-dependent IgG transport in a polarized human intestinal epithelial cell line, J Clin Invest., 104(7):903-911.
Doronina et al., 2003, Development of potent monoclonal antibody auristatin conjugates for cancer therapy, Nat Biotechnol, 21:778-784.
Elble, 1992, A simple and efficient procedure for transformation of yeasts, Biotechniques 13(1):18-20.
Feng et al., 2011, Design, expression and characterization of a soluble single-chain functional human neonatal Fc receptor, Protein Expression and Purification, 79:66-71.
Ferrara et al., 1999, Pathophysiologic mechanisms of acute graft-vs.-host disease, Biology of Blood and Marrow Transplantation, 5:347-56.
Flanagan, Jun. 15, 2009, Protein engineering reaches new frontiers: more detailed knowledge of structure and function drives field forward quickly, Gen Eng Biotech News, 11(12):1-4.
Francisco et al., Aug. 2003, cAC10-vcMMAE, an anti-CD30-monomethyl auristatin E conjugate with potent and selective anti-tumor activity, Blood, 102(4):1458-1465.
Fu et al., 2004, Fibroblast growth factor 19 increases metabolic rate and reverses dietary and leptin-deficient diabetes. Endocrinology. 145:2594-2603.
Galliano et al., 1986, Structural characterization of a chain termination mutant of human serum albumin, J. Biol. Chem., 261:4283-4287.
Gao et al., 2004, UpGene: Application of a Web-Based DNA Codon Optimization Algorithm, Biotechnol Prog, 20:443-448.
Garnier et al., 1994, Scale-Up of the Adenovirus Expression System for the Production of Recombinant Protein in Human 293S Cells, Cytotechnology, 15:145-155.
Gibbs et al., Apr. 13, 2007, Evolutionary and biomedical insights from the Rhesus Macaque genome, Science, 316(5822):222-234.
Graf et al., 2000, Concerted Action of Multiple cis-Acting Sequences Is Required for Rev Dependence of Late Human Immunodeficiency Virus Type 1 Gene Expression, J Virol 74:10822-10826.
Grantham et al., 1980, Codon Frequencies in 119 Individual Genes Confirm Consistent Choices of Degenerate Bases According to Genome Type, Nuc. Acids Res. 8(9):1893-1912.
Grosjean et al., 1982, Preferential Codon Usage in Prokaryotic Genes; The Optimal Codon-Anticodon Interaction Energy and the Selective Codon Usage in Efficiently Expressed Genes, Gene, 18:199-209.
Gustafsson et al., 2004, Codon bias and heterologous protein expression, Trends in Biotechnol. 22:346-353.
Gutniak et al., 1992, Antidiabetogenic Effect of Glucagon-like Peptide-1 (7-36) amide in Normal Subjects and Patients with Diabetes Mellitus N Engl J Med 326:1316-1322.
Haas et al., 1996, Codon usage limitation in the expression of HIV-1 envelope glycoprotein, Curr. Biol. 6:315-324.
Hagen et al., 1986, Characterization of a cDNA coding for human factor VII, Proc. Natl. Acad. Sci. USA, 83:2412-2416.
Hall et al., 2012, Interspecies scaling in pharmacokinetics: a novel whole-body physiologically based modeling framework to discovery drug biodistribution mechanisms in Vivo, J Pharma Sci, 101:1221-1241.
Hallstrom et al., 2008, S-nitroso human serum albumin reduces ischaemia/reperfusion injury in the pig heart after unprotected warm ischaemia, Cardiovascular Res, 77:506-514.
Haspel et al., 1999, Effects of barbiturates on facilitative glucose transporters are pharmacologically specific and isoform selective, J Membr Biol, 169:45-53.
Hay et al., Apr. 9, 2009, ThioTransferrin: a recombinant human transferrin engineered fir site specific drug conjugation and delivery, Oral Presentation, 5th Annual PEGS, Boston, MA, 22 pp.
Henrotte et al., 2004, Investigation of non-covalent interactions between paramagnetic complexes and human serum albumin by electrospray mass spectrometry, Rapid Comm Mass Spectro, 18:1919-1924.
Herzog et al., 1999, long-term correction of canine hemophilia B by gene transfer of blood coagulation factor IX mediated by adeno-associated viral vector, Nature Medicine, 5(1):56-63.
Hillier et al, Apr. 2007, Generation and annotation of the DNA sequences of human chromosomes 2 and 4, Nature, 434:724-731.
Hinman et al., 1993, Preparation and Characterization of Monoclonal Antibody Conjugates of the Calicheamicins: A Novel and Potent Family of Antitumor Antibiotics, Cancer Research 53:3336-3342.
Holm, 1986, Codon usage and gene expression, Nuc. Acids Res. 14:3075-3087.
Holt et al., 2003, Definition of a novel growth factor-dependent signal cascade for the suppression of bile acid biosynthesis, Genes Dev, 17:1581-1591.
Houghton et al., 1980, The complete amino acid sequence of human fibroblast interferon as deduced using synthetic oligodeoxyribonucleotide primers of reverse transcriptase, Nucleic Acids Res., 8(13):2885-2894.
Howard et al., 1989, Intracerebral Drug Delivery in Rats with Lesion-Induced Memory Deficits, J. Neurosurg. 71:105-112.
Huang et al., Sep. 2002, serum albumin [homo sapiens] GenBank: AAN17825.1, http://www/ncbi/nlm.nih.gov/protien/aan17825.
Ikemura, 1982, Correlation between the abundance of yeast transfer RNAs and the occurrence of the respective codons in protein genes. Differences in synonymous codon choice patterns of yeast and *Escherichia coli* with reference to the abundance of isoaccepting transfer RNAs J. Mol. Biol. 158:573-597.
Ito et al., 1983, Transformation of intact yeast cells treated with alkali cations, J Bacteriol, 153(1):163-168.
Jaye et al., 1983, Isolation of a human anti-haemophilic factor IX cDNA clone using a unique 52-base synthetic oligonucleotide probe deduced from the amino acid sequence of bovine factor IX, Nucleic Acids Res. 11(8):2325-2335.

(56) References Cited

OTHER PUBLICATIONS

Jerdeva et al., Comparison of FcRn- and pIgR-mediated transport in MOCK cells by fluorescence confocal microscopy. Traffic. Sep. 2010;11 (9):1205-20.
Kabsch et al., 1983, Dictionary of protein secondary structure: pattern recognition of hydrogen-bonded and geometrical features, Biopolymers, 22(12):2577-2637.
Kaneko et al., Jan. 2008, Subdomain IIIA of dog albumin contains a binding site similar to site II of human albumin, Drug Megab. Disposition 36:81-86.
Kenanova et al., 2005, Tailoring the pharmacokinetics and positron emission tomography imaging properties of anti-carcinoembryonic antigen single-chain Fv-Fc antibody fragments, Cancer Res, 65(2):622-631.
Kenanova et al., 2007, Radioiodinated versus radiometal-labeled anti-carcinoembryonic antigen single-chain Fv-Fc antibody fragments; optimal pharmacokinetics for therapy, Cancer Res, 67(2):718-726.
Khan et al., 2002, Bilirubin binding properties of pigeon serum albumin and its comparison with human serum albumin, J Biol Macromol., 30(3-4):171-178.
Kharitonenkov et al., 2005, FGF-21 as a novel metabolic regulator, J. Clin. Invest., 115(6):1627-1635.
Kim et al., Mar. 2003, Development and characterization of a glucagon-like peptide 1-albumin conjugate: the ability to activate the glucagon-like peptide 1 receptor in vivo, Diabetes, 52:751-759.
Kragh-Hansen et al., 2002, Practical aspects of the ligand-binding and enzymatic properties of human serum albumin, Biol Pharm Bull, 25(6):695-704.
Kragh-Hansen et al., 2004, Structural analysis and fatty acid-binding properties of two Croatian variants of human serum albumin, Clinical Chimica Acta, 349:105-112.
Kuo et al., 2010, Neonatal Fc receptor: from immunity to therapeutics, J Clin Immunol, 30(6):777-789.
Kurtzhals et al., 1997, Effect of fatty acids and selected drugs on the albumin binding of a long-acting, acylated insulin analogue, J Pharma Sci, 86:1365-1368.
Laftah et al., May 15, 2004, Effect of hepcidin on intestinal iron absorption in mice, Blood, 103(10):3940-3944.
Larsen et al., 2004, Use of the Gottingen minipig as a model of diabetes, with special focus on type 1 diabetes research,, ILAR Journal, 45(3):303-313.
Leger et al., 2004, Identification of CJC-1131-albumin bioconjugate as a stable and bioactive GLP-1(7-36) analog, Bioorg Med Chem Lttrs, 14:4395-4398.
Leger et al., 2003, Synthesis and in vitro analysis of atrial natriuretic peptide-albumin conjugates, Bioorganic Medical Chem Lttrs, 13:3571-3575.
Li et al., 2001, Bipartite regulation of different components of the MHC class 1 antigen-processing machinery during dendritic cell maturation, Intl Immunol, 13(12):1515-1523.
Liu et al., 2009, A high-yield and scaleable adenovirus vector production process based on high density perfusion culture of HEK 293 cells as suspended aggregates, J. Bioscience and Bioengineering, 107:524-529.
Lode et al., Jul. 15, 1998, Targeted Therapy with a Novel Enediyene Antibiotic Calicheamicin theta11 Effectively Suppresses Growth and Dissemination of Liver Metastases in a Syngeneic Model of Murine Neuroblastoma, Cancer Research, 58:2925-2928.
Luckow et al., 1993, Efficient Generation of Infectious Recombinant Baculoviruses by Site-Specific Transposon-Mediated Insertion of Foreign Genes into a Baculovirus Genome Propagated in *Escherichia coli*, J. Virol. 67:4566-4579.
Mahmood, 2004, Chapter 7: Principles, issues and applications of interspecies scaling, in New Drug Development, Sahajwalla ed., Marcel Dekker, Inc., New York, pp. 137-163.
McClenaghan et al., Aug. 1996, Characterization of a novel glucose-responsive insulin-secreting cell line, BRIN-BD11 ,produced by electrofusion, Diabetes, 45:1132-1140.

McGregor, 2008, Discovering and improving novel peptide therapeutics, Curr Opin Pharmacol, 8(5):616-619.
Miguel et al., 2003, Cooperative enhancement of insulinotropic action of GLP-1 by acetylcholine uncovers paradoxical inhibitory effect of beta cell muscarinic receptor activation on adenylate cyclase activity Biochem Pharm., 65:283-292.
Minchiotti et al., 1990, The molecular defect of albumin Castel di Sangro: 536 Lys → Gllu, Biochem Bioph Acta, 1039:204-208.
Minchiotti et al., 2001, A nucleotide insertion and frameshift cause albumin Kenitra, an extended and O-glycosylated mutant of human serum albumin with two additional disulfide bridges, Eur J Biochem, 268:344-352.
Montoyo et al., 2009, Conditional deletion of the MHC class 1-related receptor FcRn reveals the sites of IgG homeostasis in mice, Proc Natl Acad Sci USA, 106(8):2788-2793.
Morrissey et al., Feb. 1, 1993, Quantitation of activated factor VII levels in plasma using a tissue factor mutant selectively deficient in promoting factor VII activation, Blood, 81(3):734-744.
Muller et a., 2007, Improved pharmacokinetics of recombinant bispecific antibody molecules by fusion to human serum albumin, J Bio Chem, 282(17):12650-12660.
Nauck et al., 1993, Normalization of fasting hyperglycaemia by exogenous glucagon-like peptide 1 (7-36 amide) in type 2 (non-insulin-dependent) diabetic patients, Diabetologia 36:741-744.
Nauck et al., 1993, Preserved incretin activity of glucagon-like peptide 1 [7-36 amide] but not of synthetic human gastric inhibitory polypeptide in patients with type-2 diabetes mellitus. Clin Invest, 91:301-307.
Nierman et al., 2007, EMBL Access No. AAHF0100013.
Ober et al. 2001, Differences in promiscuity for antibody—FcRn interactions across species: implications for therapeutic antibodies, Int Immunol 13(12):1551-1559.
Ober et al., 2004, Exocytosis of IgG as medicated by the receptor, FcRn: an analysis at the single-molecule level, Proc Natl Acad Sci USA, 101(30):11076-11081.
Ober et al., 2004, Visualizing the site and dynamics of IgG salvage by the MHC class I-related receptor, FcRn, J Immunol, 172(4):2021-2029.
Oganesyan et al., 2014, Structural insights into neonatal Fc receptor-based recycling mechanisms, J Biol Chem 289(11):7812-24.
O'Hara et al., Aug. 1987, Nucleotide sequence of the gene coding for human factor VII, a vitamin K-dependent protein participating in blood coagulation, PNAS USA, 84:5158-5162.
O'Neill et al., 2008, Scale-up of Agrobacterium-mediated transient protein expression in bioreactor-grown Nicotiana glutinosa plant cell suspension culture, Biotechnol. Prog. 24:372-376.
Osborn et al., 2002, Pharmacokinetic and pharmacodynamic studies of a human serum albumin-interferon-α fusion protein in cynomolgus monkeys, J Pharmacol Exp Ther, 303(2):540-548.
Peters, 1996, All about Albumin: Biochemistry, Genetics and Medical Applications, Academic Press, Cooperstown, NY, pp. 9-23, 170-181, 245-250.
Pierce, Crosslinking Reagents Technical Handbook, downloaded Feb. 9, 2009, 48 pp.
Pittman et al., 1993, Biochemical, immunological, and in vivo functional characterization of B-domain-deleted factor VIII, Blood, 81:2925-2935.
Prabhat et al., 2007, Elucidation of intracellular recycling pathways leading to exocytosis of the Fc receptor, FcRn, by using multifocal plane microscopy, Proc Natl Acad Sci USA, 104(14):5889-5894.
Rakestraw et al., 2009, Directed evolution of a secretory leader for the improved expression of heterologous proteins and full-length antibodies in *Saccharomyces cerevisiae*, Biotechnology and Bioengineering, 103(6):1192-1201.
Rao et al , 2003, Interleukin-2 mutants with enhanced alpha-receptor subunit binding affinity, Protein. Eng., 16:1081-1087.
Rao et al., 2005, High-affinity CD25-binding IL-2 mutants potently stimulate persistent T cell growth, Biochemistry 44:10696-10701.
Riminucci et al., Sep. 2003, FGF-23 in fibrous dysplasia of bone and its relationship to renal phosphate wasting, J Clin Invest, 112(5):683-92.

(56) References Cited

OTHER PUBLICATIONS

Rinderknecht et al., Jun. 10, 1984, Natural Human Interferon-gamma. Complete amino acid sequence and determination of sites of glycosylation, J. Biol. Chem., 259(11):6790-6797.
Roopenian et al., 2003, The MHC class I-like IgG receptor controls perinatal IgG transport, IgG homeostasis, and fate of IgG-Fc-coupled drugs, J Immunol, 170(7):3528-3533.
Sabater-Lleal et al., 2006, Human F7 sequence is split into three deep clades that are related to FVII plasma levels, Hum Genet 118:741-751.
Sayle et al. Sep. 1995, RASMOL: biomolecular graphics for all, TIBS 20, 374-377.
Schmidt et al., Nov. 5, 2013, Crystal Structure of an HAS/FcRn Complex Reveals Recycling by Competitive Mimicry of HSA Ligands at a pH-Dependent Hydrophobic Interface, Structure 21:1966-1978 and supplemental material.
Several (definition), dictionary.com, accessed on Oct. 30, 2015, 4 pp.
Shimada et al., 2004, FGF-23 Is a Potent Regulator of Vitamin D Metabolism and Phosphate Homeostasis, J. Clin. Invest, 19(3):429-435.
Silveira et al., 1994, Activation of Coagulation Factor Vii During Alimentary Lipemia, Arteriosclerosis and Thrombosis, 14:60-69.
Simard et al., 2006, Location of High and Low Affinity Fatty Acid Binding Sites on Human Serum Albumin Revealed by NMR Drug-competition Analysis, Journal of Molecular Biology, 361:336-351.
Singh et. al., 2008, GASCO: Genetic Algorithm Simulation for Codon Optimization, In Silico Biology 8:187-192.
Sleep et al., 1991, *Saccharomyces cerevisiae* strains that overexpress heterologous proteins, Nature Biotechnol, 9(2):183-187.
Sleep et al., 2001, Yeast 2 µ m plasmid copy number is elevated by a mutation in the nuclear gene UBC4, Yeast, 18(5):403-421.
Sleep, 2012, Produce Proteins with Tailored Circulatory Half Life to Meet Patient's Specific Medical Needs, Keynote Address, Drug Delivery Partnerships. Las Vegas, NV. Jan. 25-27, 2012.
Sorensen et al., 2004, Whole blood clot formation phenotypes in hemophilia A and rare coagulation disorders. Patterns of response to recombinant factor Vila J. Thrombosis and Haemostasis 2:102-110.
Spiekermann et al., Receptor-mediated Immunoglobulin G Transport Across Mucosal Barriers in Adult Life J Exp Med. Aug. 5, 2002;196(3):303-10, and correction.
Stehle et al., 1997, Plasma protein (albumin) catabolism by the tumor itself—implications for tumor metabolism and the genesis of cachexia, Crit Rev Oncol Hematol, 26(2):77-100.
Stewart et al., Apr. 1, 2003, Interdomain zinc site on human albumin, Proc Nat Acad Sci USA, 100(7):3701-3706.
Suzuki et al., 2010, Importance of Neonatal FcR in Regulating the Serum Half-Life of Therapeutic Proteins Containing the Fc Domain of Human IgG1: A Comparative Study of the Affinity of Monoclonal Antibodies and Fc-Fusion Proteins to Human Neonatal FcR, The Journal of Immunology, 184:1968-1976.
Sykes et al., May 1, 1994, Interleukin-2 inhibits graft-versus-host disease-promoting activity of CD4+ cells while preserving CD4- and CD8-mediated graft-versus-Leukemia effects, Blood, 83(9):2560-2569.
Tesar et al., Ligand valency affects transcytosis, recycling and intracellular trafficking mediated by the neonatal Fc receptor Traffic. Sep. 2006;7(9):1127-42.
Thibaudeau et al., 2005, Synthesis and evaluation of insulin—human serum albumin conjugates, Biocon Chem, 16(4):1000-1008.
Thim et al., 1988, Amino acid sequence and posttranslational modifications of human factor Vila from plasma and transfected baby hamster kidney cells, Biochemistry, 27:7785-7793.
Toole et al., 1984, Molecular cloning of a cDNA encoding human antihaemophilic factor Nature, 312:342-347.
Tsakiridis et al., 1995, Multiple roles of phosphatidylinositol 3-kinase in regulation of glucose transport, amino acid transport, and glucose transporters in L6 skeletal muscle cells, Endocrinology, 136(10):4315-4322.

Ueda et al., 2009, Chemoenzymatic Synthesis of Glycosylated Glucagon-like Peptide 1: Effect of Glycosylation on Proteolytic Resistance and in Vivo Blood Glucose-Lowering Activity, J. ACS Articles, 131:6237-6245.
Uniprot Database Accession No. F7HCHO, Jul. 27, 2011, 2 pp.
UniProt Database Accession No. A6NBZ8 (A6NBZ8_Human), Version 24, modified Mar. 8, 2011, accessed at http://www.uniprot.org/uniprot/A6NBZ8 on Mar. 23, 2011.
Urso et al., 1999, Differences in signaling properties of the cytoplasmic domains of the insulin receptor and insulin-like growth factor receptor in 3T3-L 1 adipocytes, J Biol Chem, 274:30864-30873.
Van Deijk et al., 1983, Evaluation of a Coagulation Assay Determining the Activity State of Factor VII in Plasma Haemostasis, 13:192-197.
Van der Spoel et al., 2005, GROMACS: fast, flexible, and free, J Comp Chem, 22:1701-1718.
Vestberg et al., 1992, High-affinity binding of warfarin, salicylate and diazepam to natural mutants of human serum albumin modified in the c-terminal end, Biochem Pharmacol, 44(8):1515-1521.
Wain-Hobson et al. 1981, Preferential codon usage in genes, Gene 13:355-364.
Wang et al., 1997, Regulation of glucose transporters and hexose uptake in 3T3-L 1 adipocytes: glucagon-like peptide-1 and insulin interactions, J Mol Endocrinol, 19:241-248.
Wang et al., 2008, Overexpression of fibroblast growth factor 23 suppresses osteoblast differentiation and matrix mineralization in vitro. J Bone Miner Res. 23(6):939-948.
Wani et al., 2006, Familial hypercatabolic hypoproteinemia caused by deficiency of he neonatal Fc receptor, FcRn, due to a mutant β2-microglobulin gene, Proc Natl Acad Sci USA 103(13):5084-5089.
Watkins et al., A donor splice mutation and a single-base deletion produce two carboxy-terminal variants of human serum albumin, Proc. Natl. Acad. Sci. 88:5959-5963.
West et al., 2000, Crystal structure and immunoglobulin G binding properties of the human major histocompatibility complex-related Fc receptor, Biochemistry 39(32):9698-9708.
Wildgoose et al., 1992, Measurement of basal levels of factor Vila in hemophilia A and B patients, Blood, 80:25-28.
Wood et al., 1984, Expression of active human factor VIII from recombinant DNA clones, Nature 312:330-337.
Wu et al., Apr. 5, 1987, Receptor-mediated in vitro gene transformation by a soluble DNA carrier system, J. Biol. Chem., 262(10):4429-4432.
Wu et al., Dec. 1989, Urate Oxidase: Primary Structure and Evolutionary Implications, PNAS USA, 86:9412-9416.
Wunder et al., 2003, Albumin-based drug delivery as novel therapeutic approach for rheumatoid arthritis, The Journal Immunology, 170:4793-4801.
Yoshida et al., Human neonatal Fc receptor mediates transport of IgG into luminal secretions for delivery of antigens to mucosal dendritic cells Immunity. Jun. 2004;20(6):769-83.
Zalevsky et al., Feb. 2010, Enhanced antibody half-life improves in vivo activity, Nature Biotechnology, 28(2):157-159.
Zheng et al., 2012, Minipig as a potential translatable model for monoclonal antibody pharmacokinetics after intravenous and subcutaneous administration, mAbs, 4(2):243-255.
Zhu et al., Calnexin and ERp57 facilitate the assembly of the neonatal Fc receptor for IgG with beta 2-microglobulin in the endoplasmic reticulum J Immunol, Jul. 15, 2005;175(2):967-76.
Zhu et al., MHC class I-related neonatal Fc receptor for IgG is functionally expressed in monocytes, intestinal macrophages, and dendritic cells J Immuno, Mar. 1, 2001;166(5):3266-76.
International Search Report and Written Opinion of International Application No. PCT/US2012/065733, dated May 21, 2013.
International Search Report of PCT/US2014/036508 dated Oct. 9, 2014.
Written Opinion of the International Searching Authority for PCT/US2014/036508 dated Oct. 9, 2014.
International Search Report, International Patent Application No. PCT/IB2014/003002, dated Aug. 12, 2015.

(56) References Cited

OTHER PUBLICATIONS

Adams et al., 2013. The Adaptable Major Histocompatibility Complex (MHC) Fold: Structure and Function of Nonclassical and MHC Class I-Like Molecules. Annu Rev Immunol. 31:529-561.
Akilesh et al., 2007. Neonatal FcR expression in bone marrow-derived cells functions to protect serum IgG from catabolism. J Immunol. (Baltimore, Md.: 1950) 179:4580-4588.
Allan et al "Enhanced albumins and albumin fusion technology" May 4, 2012 XP055109701 Retrieved from the Internet: URL:http:\\www.biopharma.novozymes.com/en/information-centre/posters-and-presentations/Documents/PEGS%20poster%202012_EZAL.pdf.
Altschul et al., 1997, Gapped BLAST and PSI-BLAST: A new genertion of protein database search programs. Nucleic Acids Res. 25(17):3389-3402.
Amthor et al., 2004, Albumin targeting of damaged muscle fibres in the mdx mouse can be monitored by MRI. Neuromuscular Disorders 14(12): 791-796.
Averyhart-Fullard et al., 1990. Cloning and Thyroid Hormone Regulation of Albumin mRNA in *Rana catesbeiana* Tadpole Liver, Mol Endocrinol. 4(10):1556-1563.
Barton et al., 1990, Site-directed, recombination-mediated mutagenesis of a complex gene locus. Nucleic Acids Res. 18(24):7349-4955.
Basle, Mar. 26, 2010, Protein chemical modification on endogenous amino acids, Chemistry & Biology, 17:213-227.
Beeken et al., 1962. Studies of $I^{131}$-albumin catabolism and distribution in normal young male adults. The Journal of clinical investigation 41,1312-1333.
Bennhold et al., 1959. Comparative studies on the half-life of I131-labeled albumins and nonradioactive human serum albumin in a case of analbuminemia. J Clin Invest. 38:863-872.
Boder et al., 1997. Yeast surface display for screening combinatorial polypeptide libraries. Nat Biotechnol. 15(6):553-557.
Boder et al., 2000. Directed evolution of antibody fragments with monovalent femtomolar antigen-binding affinity. PNAS U.S.A. 97:10701-10705.
Bos et al., 1989. The molecular mechanism of the neutral-to-base transition of human serum albumin. J Biol Chem. 264:953-959.
Bowie et al., 1989, Identifying determinants of folding and activity for a protein of unknown structure. PNAS U.S.A. 86(7):2152-2156.
Calissano et al., 1996, In vivo site-directed mutagenesis of Neurospora crassa beta-tubulin gene by spheroplasts transformation with oligonucleotides. Fungal Genetics Reports 43(Article 5) pp. 5.
CAPlus accession No. 2005:1283404, "Standard Albumin Gene . . . ", STN entry date Dec. 8, 2005; 1 page.
Chapman A.P., 2002, PEGylated antibodies and antibody fragments for improved therapy: A review. Adv. Drug Deliv. Rev. 54:531-545.
Chen et al., 2013, Human serum albumin from recombinant DNA technology: challenges and strategies, Biochimica et Biophysica Acta, 1830:5515-5525.
Chao et al. 2006. Isolating and engineering human antibodies using yeast surface display. Nature protocols 1(2):755-768.
Curry, S., 2009. Lessons from the crystallographic analysis of small molecule binding to human serum albumin. Drug Metab Pharmacokinet. 24(4):342-357.
Dall'Acqua et al., 2002. Increasing the affinity of a human IgG1 for the neonatal Fc receptor: Biological consequences. J Immunol. 169:5171-5180.
Daniels et al., 2006, The transferrin receptor part II: Targeted delivery of therapeutic agents into cancer cells. Clin Immunol. 121(2):159-176.
Database EMBL accession No. BAG37325; Jan. 12, 2008, "*Homo sapiens* hypothetical protein", 2 pages.
Datta-Mannan et al., 2007. Monoclonal antibody clearance: Impact of modulating the interaction of IgG with the neonatal Fc receptor. J Biol Chem. 282(3):1709-1717.
Datta-Mannan et al. 2012. FcRn affinity-pharmacokinetic relationship of five human IgG4 antibodies engineered for improved in vitro FcRn binding properties in cynomolgus monkeys. Drug Metabol Dispos. 40(8):1545-1555.
Debinski W., 2002, Local treatment of brain tumors with targeted chimera cytotoxic proteins. Cancer Invest. 20(5):801-809.
Derbyshire et al., 1986, A simple and efficient procedure for saturation mutagenesis using mixed oligodeoxynucleotides. Gene 46(2-3):145-152.
Dugaiczyk et al, Jan. 1982, Nucleotide sequence and the encoded amino acids of human serum albumin mRNA, PNAS, USA, 79:71-75.
Edgar R.C., 2004, MUSCLE: multiple sequence alignment with high accuracy and high throughput. Nucleic Acids Res. 32(5):1792-1797.
Edgar R.C., 2004, MUSCLE: a multiple sequence alignment method with reduced time and space complexity. BMC Bioinformatics. 5(1):113 in 19 pages.
Emsley et al., 2010. Features and development of Coot. Acta crystallographica Section D, Biol. Crystallo. 66:486-501.
Fontaine et al., Long-term stabilization of maleeimide-thiol conjugates. Bioconjug Chem. 26(1):145-152.
Franklin et al., May 1980, Localization of the amino acid substitution site in a new variant of human serum albumin, albumin Mexico-2, PNAS. USA, 77(5):2505-2509.
Fritzer et al., 1996, Cytotoxic effects of a doxorubicin-transferrin conjugate in multidrug-resistant KB cells. Biochem Pharmacol. 51(4):489-493.
Gabrielsson et al. 2007. Pharmacokinetic and Pharmacodynamic Data Analysis: Concepts and Applications, 4th ed. (Swedish Pharmaceutical Press: Stockholm); Table of Contents in 9 pages.
Gama Sosa et al., 2010, Animal transgenesis: an overview, Brain Struct Funct, 214:91-109.
Ghetie et al., 1997. Increasing the serum persistence of an IgG fragment by random mutagenesis. Nature Biotech. 15:637-640.
Ghuman et al., 2005, Structural basis of the drug-binding specificity of human serum albumin. J Mol Bol. 353:38-52.
Gough et al., 2001, Assignment of Homology to Genome Sequences using a Library of Hidden Markov Models that Represent all Proteins of Known Structure. J Mol Biol. 313:903-919.
Guo et al., 1995, 3'-end-forming signals of yeast mRNA. Mol Cell Biol. 15(11):5983-5990.
Gurbaxani et al., 2006. Analysis of a family of antibodies with different half-lives in mice fails to find a correlation between affinity for FcRn and serum half-life. Mol Immunol. 43(9):1462-1473.
Ha et al.,2006,Fatty acids bound to human serum albumin and its structural variants modulate apolipoprotein B secretion in HepG2 cells, Biochem Biophys Acta 1761:717-724.
Hawkins et al., 2008, Protein nanoparticles as drug carriers in clinical medicine. Adv Drug Deliv Rev. 60(8):876-885.
He et al., 1992. Atomic structure and chemistry of human serum albumin. Nature 358(6383):209-215.
Hinton et al., 2004. Engineered human IgG antibodies with longer serum half-lives in primates. J Biol Chem. 279(8):6213-6216.
Hinton et al., 2006. An engineered human IgG1 antibody with longer serum half-life. J Immunol. 176:346-356.
Ho et al. (1993). X-ray and primary structure of horse serum albumin (Equus caballus) at 0.27-nm resolution. Eur J Biochem. 215(1):205-212.
Holm et al., 1998, Dictionary of recurrent domains in protein structures. Proteins 33(1):88-96.
Holm et al., 2000, DaliLite workbench for protein structure comparison. Bioinformatics 16(6):566-567.
Huang et al., 2007, Efficient gene delivery targeted to the brain using a transferrin-conjugated polyethyleneglycol-modified polyamidoamine dendrimer. FASEB J. 21(4):1117-1125.
Humphries et al., 1994, Conjugation of synthetic peptides to carrier proteins for cell adhesion studies. J Tissue Cult Meth. 16(3-4):239-242.
Humphreys et al., 2007, Alternative antibody Fab' fragment PEGylation strategies: combination of strong reducing agents, disruption of the interchain disulphide bond and disulphide engineering. Protein Eng Des Sel. 20(5):227-234.
Hussain et al., 2006, Fat-free Albumin as a Novel Drug Delivery System. Int'l J Peptide Res Therapeutics 12(3):311-315.

(56) References Cited

OTHER PUBLICATIONS

Israel et al., 1993. Immunoglobulin G binding sites on the human foetal intestine: a possible mechanism for the passive transfer of immunity from mother to infant. Immunol. 79(1):77-81.
Iwao et al., 2007, Effect of one point mutation on the structural and pharmacokinetic properties of human serum albumin, The Pharmaceutical Society of Japan, Summary of Annual Meeting, 127(3):154 (w/Translation).
Jones D.T., 1999, GenTHREADER: An efficient and reliable protein fold recognition method for genomic sequences. J Mol Biol. 287(4):797-815.
Kabsch W., 2010. XDS. Acta crystallographica Section D, Biol Crystallogr. 66:125-132.
Kacskovics et al., 2011, Recent advances using FcRn overexpression, Landes Bioscience 3(5) 431-439.
Katoh et al., 2002, MAFFT: A novel method for rapid multiple sequence alignment based on fast Fourier transform. Nucleic Acids Res. 30(14):3059-3066.
Katoh et al., 2005, MAFFT Version 5: Improvement in accuracy of multiple sequence alignment. Nucleic Acids Res. 33(2):511-518.
Katoh et al., 2009, Multiple alignment of DNA sequences with MAFFT. Methods Mol Biol. 537:39-64.
Katoh et al., 2010, Parallelization of the MAFFT multiple sequence alignment program. Bioinformatics 26(15): 1899-1900.
Kavimandan et al., 2006, Synthesis and characterization of insulin-transferrin conjugates. Bioconjug Chem. 17(6):1376-1384.
Kawamata et al., Aug. 10, 2010 Generation of genetically modified rats from embryonic stem cells, PNAS, 107(32):14223-14228.
Kiessling et al., 2002, Magnetic resonance imaging of nude mide with heterotransplanted high-grade squamous cell carcinomas: use of a low-loaded,covalently bound Gd-Has conjugate as contrast agent with high tumor affinity. Invest Radiol.37(4):193-198.
Kim et al., 2006. Albumin turnover: FcRn-mediated recycling saves as much albumin from degradation as the liver produces. Am J Physiol Gastrointest Liver Physiol. 290:G352-G360.
Kim et al., 2007. Kinetics of FcRn-mediated recycling of IgG and albumin in human: Pathophysiology and therapeutic implications using a simplified mechanism-based model. Clin Immunol. 122(2):146-155.
Kjeldsen et al., 1998, Secretory expression of human albumin domains in *Saccharomyces cerevisiae* and their binding of myristic acid and an acylated insulin analogue. Protein Expr Purif. 13(2):163-169.
Kontermann, 2011, Strategies for extended serum half-life or protein therapeutics, Curr Opin Biotech. 22:1-9.
Kren et al., 1998, In vivo site-directed mutagenesis of the factor IX gene by chimeric RNA/DNA oligonucleotides. Nat Med. 4(3):285-290.
Krieger et al., Jul. 4, 2014, YASARA View—molecular graphics for all devices—from smartphones to workstations. Bioinformatics 30(20) 2981-2982.
Krissinel et al., 2007. Inference of macromolecular assemblies from crystalline state. Journal of molecular biology 372, 774-797 (2007).
Kuo et al., 2011. Neonatal Fc receptor and IgG-based therapeutics. mAbs 3(5):422-430.
Labro et al., 1986. A proton nuclear magnetic resonance study of human serum albumin in the neutral pH region. Biochim Biophys Acta 873(2):267-278.
Lawn et al, 1981, The sequence of human serum albumin cDNA and its expression in *E. coli*, Nucl Acids Res. 9(22):6103-6114.
Lee et al., 2005, Evaluation of transferrin-polyethylenimine conjugate for targeted gene delivery. Arch Pharm Res. 28(6):722-729.
Li et al., 2008, Germline competent embryonic stem cells derived from rat blastocysts, Cell, 135:1299-1310.
Lim et al., 2004, Transferrin-oligomers as potential carriers in anticancer drug delivery. Pharm Res. 21(11):1985-1992.
Lindahl et al., 2000, Identification of related proteins on family, superfamily and fold level. J Mol Biol. 295(3):613-615.
Lowman et al., 1991, Selecting high-affinity binding proteins by monovalent phage display. Biochemistry 30(45):10832-10838.

Martin et al., 1982, Irreversible coupling of immunoglobulin fragments to preformed vesicles. An improved method for liposome targeting. J Biol Chem. 257(1):286-288.
Martin et al., 2001. Crystal structure at 2.8 Å of an FcRn/heterodimeric Fc complex: Mechanism of pH-dependent binding. Mol Cell 7(4):867-877.
McCoy et al., 2007. Phaser crystallographic software. J Applied Crystallogr. 40:658-674.
McGraw et al., 1987, Functional expression of the human transferring receptor cDNA in Chinese hamster ovary cells deficient in endogenous transferring receptor. J Cell Biol. 105(1):207-214.
McGuffin et al., 2003, Improvement of the GenTHREADER method for genomic fold recognition. Bioinformatics 19(7):874-881.
Minghetti et al., 1986, Molecular structure of the human albumin gene is revealed by nucleotide sequence within q11-22 of chromosome 4*, J. Bio Chem. 261(15): 6747-6757.
Mishra et al., 2006, Targeted brain delivery of AZT via transferrin anchored pegylated albumin nanoparticles. J Drug Targeting 14(1):45-53.
Munoz et al., 2009, Constraints to progress in embryonic stem cells from domestic species, Stem Cell Rev and Rep, 5:6-9.
Murshudov et al., 1997. Refinement of macromolecular structures by the maximum-likelihood method. Acta Crystallogr D Biol Crystallogr. 53(Pt 3):240-255.
Ner et al., 1988, A simple and efficient procedure for generating random point mutations and for codon replacements using mixed oligodeoxynucleotides. DNA 7(2):127-134.
Ness et al., 1999, DNA shuffling of subgenomic sequences of subtilisin. Nature Biotechnol. 17(9):893-896.
Neumann et al., 2010, Native albumin for targeted drug delivery, Expert Opin. Drug Deliv., 7(8):1-11.
Nobs et al., 2004, Current methods for attaching targeting ligands to liposomes and nanoparticles. J Pharma Sci. 93(8):1980-1992.
O'Keefe et al., 1985, Characterization of a transferrin-diphtheria toxin conjugate. J Biol Chem. 260(2):932-937.
Öner et al., 1993, Preparation of small gelatin and albumin microparticles by a carbon dioxide atomization. Pharm Res., 10(9):1385-1388.
Pandjaitan et al., 2000, *Escherichia coli* expression and purification of recombinant dog albumin, a cross-reactive animal allergen. J Allergy Clin Immunol. 105(2 Pt):279-285.
Payne et al., 2008, Modulation of chaperone gene expression in mutagenized *Saccharomyces cerevisiae* strains developed for recombinant human albumin production results in increased production of multiple heterologous proteins. Appl Environ Microbiol. 74(24):7759-7766.
Petitpas et al., 2001, Crystal structures of human serum albumin complexed with monounsaturated and polyunsaturated fatty acids. J Mol Biol. 314(5):955-960.
Petitpas et al., 2001, Crystal Structure Analysis of Warfarin Binding to Human Serum Albumin—Anatomy of Drug Site I. J Biol Chem 276(25):22804-22809.
Petitpas et al., 2003. Structural basis of albumin-thyroxine interactions and familial dysalbuminemic hyperthyroxinemia. PNAS U.S. A. 100(11):6440-6445 (2003).
Petkova et al., 2006. Enhanced half-life of genetically engineered human IgG1 antibodies in a humanized FcRn mouse model: potential application in humorally mediated autoimmune disease. Int immunol. 18(12):1759-1769.
Piedrahita et al., 2011, Perspectives on transgenic livestock in agriculture and biomedicine: an update, Repro Fertility Develop., 23:56-63.
Presley et al., 1993, The End2 mutation in CHO cells slows the exit of Transferring receptors from the recycling compartment byt bulk membrane recycling is unaffected. J Cell Biol. 122(6):1231-1241.
Rakestraw et al., 2006. A flow cytometric assay for screening improved heterologous protein secretion in yeast. Biotechnol Prog. 22(4):1200-1208.
Reidhaar-Olson et al., 1988, Combinatorial cassette mutagenesis as a probe of the informational content of protein sequences. Science 241(4861):53-57.
Rodewald et al., 1984, Receptor-mediated transport of IgG. J Cell Biol. 99:159s-164s.

(56) References Cited

OTHER PUBLICATIONS

Romanos et al., 1992, Foreign gene expression in yeast: a review. Yeast 8: 423-488.
Sand et al, Dec. 12, 2014, Interaction with both domain I and III of albumin is required for optimal pH-dependent binding to the neonatal Fc receptor (FcRn)*, J Biol Chem 289(50):34583-35894.
Scherer et al., 1979, Replacement of chromosome segments with altered DNA sequences constructed in vitro. PNAS U.S.A. 76(10):4951-4955.
Shindyalov et al., 1998, Protein structure alignment by incremental combinatorial extension (CE) of the optimal path. Protein Eng. 11(9):739-747.
Sleep et al., 2013, Albumin as a versatile platform for drug half-life extension, Biochimca et Biophysica Acta, p://dx/doi/org/10.1016/j.bbagen.2013.04.023; in 9 pages.
Smith et al., Jun. 2015 (online), A platform for efficient, thiol-stable conugation to albumin's native single accessible cysteine. Org Biomol Chem. 13(29):7946-7949.
Sogami et al., 1968. Isomerization reactions of charcoal-defatted bovine plasma albumin. The N-F transition and acid expansion. Biochemistry 7(6): 2172-2182.
Sogami et al., 1969. The microheterogeneity of plasma albumins. V. Permutations in disulfide pairings as a probable source of microheterogeneity in bovine albumin. Biochemistry 8(1):49-58.
Spiegelberg et al., 1968, Catabolism of human γG-immunoglobulins of different heavy chain subclasses. I. Catabolism of γG-myeloma proteins in man. J Clin Invest. 47(10):2323-2330.
Stapleton et al., 2011. Competition for FcRn-mediated transport gives rise to short half-life of human IgG3 and offers therapeutic potential. Nature Comm. 2:599; 9 pages.
Storici et al., 2001, In vivo site-directed mutagenesis using oligonucleotides. Nat Biotechnol. 19(8):773-776.
Sundaram et al, Aug. 21, 1998, Chimeric constructs between human and rat equilibrative nucleoside transporters (hENT1 and rENT1) reveal hENT1 structural domains interacting with coronary vasoactive drugs, J. Bio Chemistry, 273(34):21519-21525.
Syed et al., 1997, Potent antithrombin activity and delayed clearance from the circulation characterize recombinant hirudin genetically fused to albumin, Blood 89(9):3243-3252.
Thompson et al., 1994, CLUSTAL W: Improving the sensitivity of progressive multiple sequence alignment through sequence weighting, position-specific gap penalties and weight matrix choice. Nucleic Acids Res. 22(22):4673-4680.
Tian et al., 2004, Accurate multiplex gene synthesis from programmable DNA microchips. Nature 432(7020):1050-1054.
Valkonen et al., 2003, Effects of inactivation and constitutive expression of the unfolded-protein response pathway on protein production in the yeast *Saccharomyces cerevisiae*. Applied Environ Microbiol., 69(4):2065-2072.
Viuff et al., 2016, Generation of a double transgenic humanized neonatal Fc receptor (FcRn)/albumin mouse to study the pharmacokinetics of albumin-linked drugs, J Controlled Release, 223:22-30.
Wang et al. 2011. Monoclonal antibodies with identical Fc sequences can bind to FcRn differentially with pharmacokinetic consequences. Drug Metabol Disposition. 39:1469-1477.
Weaver et al., 2003, Transferrin receptor ligand-targeted toxin conjugate (Tf-CRM107) for therapy of malignant gliomas. J Neurooncol. 65(1):3-13.
Wenning et al., 1998, Quantitative analysis of protein synthesis inhibition and recovery in CRM107 immunotoxin-treated HeLac cells. Biotechol Bioeng. 57(4):484-496.
Widera et al., 2003, Transcytosis of GCSF-transferring across rat alveolar epithelial cell monolayers. Pharm Res. 20(8):1231-1238.
Xia et al., 2000, Hypoglycemic effect of insulin-transferrin conjugate in streptozotocin-induced diabetic rats. J Pharmacol Exp Ther. 295(2):594-600.
Yang et al., 2012, Genetic modification of domestic animals for agricultre and biomedical applications, in Ghista [Ed], *Biomedical Science, Engineering and Technology*, Chapter 29, pp. 697-726.
Yazdi et al., 1994, Quantitative Analysis of Protein Synthesis Inhibition by Transferrin-Toxin Conjugates. Cancer Res. 54(24):6387-6394.
Yeung et al., 2009. Engineering human IgG1 affinity to human neonatal Fc receptor: Impact of affinity improvement on pharmacokinetics in primates. J immunol. 182:7663-7671.
Yin et al., 2007, Select what you need: a comparative evaluation of the advantages and limitations of frequently used expression systems for foreign genes, J Biotech., 127:335-347.

* cited by examiner

Figure 1
A.
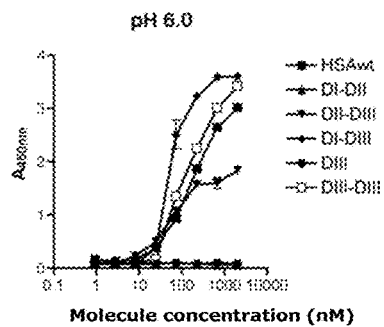
B.
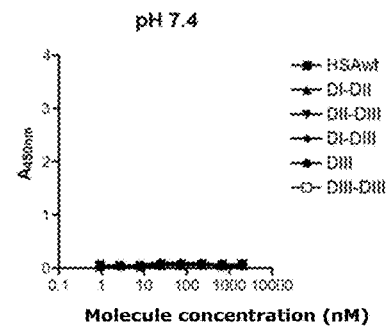
Figure 2
A.
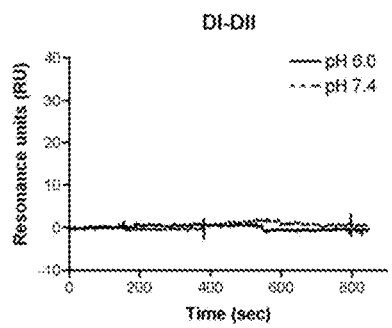
B.
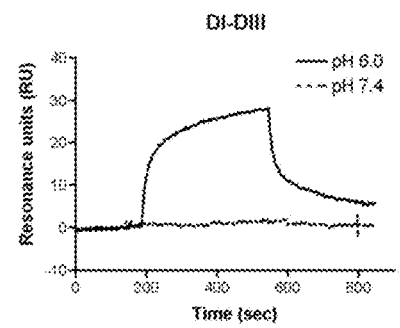
C.
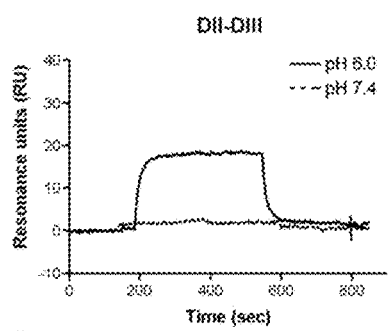
D.
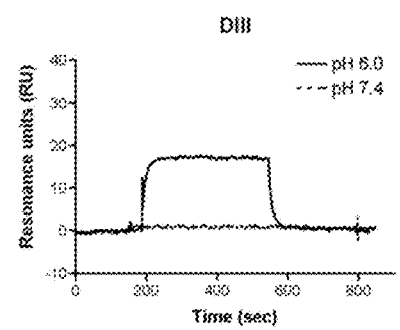
E.
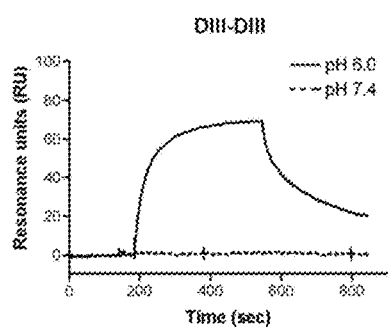
F.
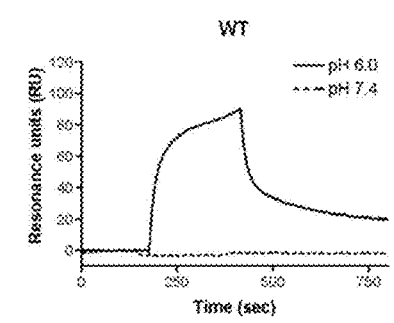

Figure 4

```
Hu_1_2_3    1  DAHKSEVAHRFKDLGEENFKALVLIAFAQYLQQCPFEDHVKLVNEVTEFAKTCVADESAE
Hu_1_3      1  DAHKSEVAHRFKDLGEENFKALVLIAFAQYLQQCPFEDHVKLVNEVTEFAKTCVADESAE
Hu_2_3      1  ------------------------------------------------------------
Mac_mul     1  ETHKSEVAHRFKDLGEEHFKGLVLIAFSQYLQQCPFEEHVKLVNEVTEFAKTCVADESAE
Rat         1  EAHKSETAHRFKDLGEQHFKGLVLIAFSQYLQKCPFEEHVKLVEVTEFAKTCVADENAE
Mouse       1  EAHKSEIAHRENDLGEQHFKGLVLIAFSQYLQKCSYEEHAKLVEVTEFAKTCVADESAA Hu_1_2_3   61  NCDKSLHTLFGDKLCTVATLRETYGEMADCCAKQEPERNECFLQHKDDNPNLPRLVRPEV
Hu_1_3     61  NCDKSLHTLFGDKLCTVATLRETYGEMADCCAKQEPERNECFLQHKDDNPNLPRLVRPEV
Hu_2_3      1  ------------------------------------------------------------
Mac_mul    61  NCDKSLHTLFGDKLCTVATLRETYGEMADCCAKQEPERNECFLQHKDDNPNLPPLVRPEV
Rat        61  NCDKSLHTLFGDKLCAIPKLRENYGELADCCAKQEPERNECFLQHKDDNPNLPPFQRPEA
Mouse      61  NCDKSLHTLFGDKLCAIPNLRENYGELADCCTKQEPERNECFLQHKDDNPSLPPFERPEA Hu_1_2_3  121  DVMCTAFHDNEETFLKKYLYEIARRHPYFYAPELLFFAKRYKAAFTECCQAADKAACLLP
Hu_1_3    121  DVMCTAFHDNEETFLKKYLYEIARRHPYFYAPELLFFAKRYKAAFTECCQAADKAACLLP
Hu_2_3      1  ------------------------------------------------------------
Mac_mul   121  DVMCTAFHDNEATFLKKYLYEVARRHPYFYAPELLFFAARYKAAFAECCQAADKAACLLP
Rat       121  AMCTSFQNNPTIFLGHYLHEVARRHPYFYAPELIIAEIYNEVLTQCCTESDKAACLTP
Mouse     121  AMCTSFKNNPTTEGHYLHEVARRHPYFYAPELIIAEQYNEILTQCCAEADKESCLTP Hu_1_2_3  181  KLDELRDEGKASSAKQRLKCASLQKFGERAFKAWAVARLSQRFPKAEFAEVSKLVTDLTK
Hu_1_3    181  KLDELRDEGKASSA----------------------------------------------
Hu_2_3      1  --DELRDEGKASSAKQRLKCASLQKFGERAFKAWAVARLSQRFPKAEFAEVSKLVTDLTK
Mac_mul   181  KLDELRDEGKASSAKQRLKCASLQKFGERAFKAWAVARLSQRFPKAEFAEVSKLVTDLTK
Rat       181  KLDALKKLVAAVTQRLKCSSLQLFGERAFKAWAVARLSQRFPNAEFAEVSKLATDLTK
Mouse     181  KLDGLKKLVSSVTQRLKCSSIQKFGERAFKAWAVARLSQTFPNAIFAEVSKLATDLTK Hu_1_2_3  241  VHTECCHGDLLECADDRADLAKYICENQDSISSKLKECCEKPLLEKSHCIAEVENDEMPA
Hu_1_3    195  ------------------------------------------------------------
Hu_2_3     59  VHTECCHGDLLECADDRADLAKYICENQDSISSKLKECCEKPLLEKSHCIAEVENDEMPA
Mac_mul   241  VHTECCHGDLLECADDRADLAKYMCENQDSISSKLKECCDKPLLEKSHCLAEVENDEMPA
Rat       241  NKECCHGDLLECADDRALAKYMCENQAIISSKLQACCDKPALQKSQCLAEEHDNLPA
Mouse     241  VNKECCHGDLLECADDRALAKYMCENQAIISSKLQTCCDKPLLKAEHCLSEVEHDTMPA Hu_1_2_3  301  DLPSLAADFVESKDVCKNYAEAKDVFLGMFLYEYARRHPDYSVVLLLRLAKTYETTLEKC
Hu_1_3    195  ------------------------------------------------------------
Hu_2_3    119  DLPSLAADFVESKDVCKNYAEAKDVFLGMFLYEYARRHPDYSVVLLLRLAKTYETTLEKC
Mac_mul   301  DLPSLAADEVESKDVCKNYAEAKDVFLGMFLYEYARRHPDYSVVLLLRLAKAYEATLEKC
Rat       301  DLPSLAADFVEDKDVCKNYAEAKDVFLGTFLYEYSRRHPDYSVSLLLRLAKKYEATLEKC
Mouse     301  DLEAAADEVEDQVCKNYAEAKDVFLGTFLYEYSRRHPDYSVSLLLRLAKKYEATLEKC Hu_1_2_3  361  CAAADPHECYAKVFDEFKPLVEEPQNLIKQNCELFEQLGEYKFQNALLVRYTKKVPQVST
Hu_1_3    195  -----------------VEEPQNLIKQNCELFEQLGEYKFQNALLVRYTKKVPQVST
Hu_2_3    179  CAAADPHECYAKVFDEFKPLVEEPQNLIKQNCELFEQLGEYKFQNALLVRYTKKVPQVST
Mac_mul   361  CAAADPHECYAKVFDEFQPLVEEPQNLIKQNCELFEQLGEYKFQNALLVRYTKKVPQVST
Rat       361  CAEDDRPACYTVLAEFQPLVEEPKNLIKTNCELIEKLGEYGFQNALLVRYTQKAPQVST
Mouse     361  CAEANPPACYTVLAEFQPLVEEPKNLIKTNCEIERLGEYGFQNALLVRYTQKAPQVST
```

Figure 4 (continued)

```
Hu_1_2_3  421  PTLVEVSRNLGKVGSKCCKHPEAKRMPCAEDYLSVVLNQLCVLHEKTPVSRVTKCCTES
Hu_1_3    235  PTLVEVSRNLGKVGSKCCKHPEAKRMPCAEDYLSVVLNQLCVLHEKTPVSRVTKCCTES
Hu_2_3    239  PTLVEVSRNLGKVGSKCCKHPEAKRMPCAEDYLSVVLNQLCVLHEKTPVSRVTKCCTES
Mac_mul   421  PTLVEVSRNLGKVGAKCCKLPEAKRMPCAEDYLSVVLNRLCVLHEKTPVSVTKCCTES
Rat       421  PTLVEAARNLGKVGSKCCTLPEAQRPCVEDYLSALNRLCVLHEKTPVSVTKCCGS
Mouse     421  PTLVEAARNLGKVGSKCCTLPEDQRPCVEDYLSALNRCLHEKTPVSHVTKCCGS Hu_1_2_3  481  LVNRRPCFSALEVDETYVPKEFNAETFTFHADICTLSEKEQIKKQTALVELVKHKPKAT
Hu_1_3    295  LVNRRPCFSALEVDETYVPKEFNAETFTFHADICTLSEKEQIKKQTALVELVKHKPKAT
Hu_2_3    299  LVNRRPCFSALEVDETYVPKEFNAETFTFHADICTLSEKEQIKKQTALVELVKHKPKAT
Mac_mul   481  LVNRRPCFSALEVDEAYVPKAFNAETFTFHADICTLSEKEQKKQTALVELVKHKPKAT
Rat       481  LVERRPCFSALTVDETYVPKEFKAETFTFHSDICTLPKEQIKKQTALAELVKHKPKAT
Mouse     481  LVERRPCFSALTVDETYVPKEFKAETFTFHSDICTLPKEQIKKQTALAELVKHKPKAT
                                       ↑
                                      500

Hu_1_2_3  541  KEQLKAVMDDFAAFVEKCCKADDKETCFAEEGKKLVAASQAAL   (SEQ ID NO. 1)
Hu_1_3    355  KEQLKAVMDDFAAFVEKCCKADDKETCFAEEGKKLVAASQAAL   (SEQ ID NO. 23)
Hu_2_3    359  KEQLKAVMDDFAAFVEKCCKADDKETCFAEEGKKLVAASQAAL   (SEQ ID NO. 21)
Mac_mul   541  KEQLKAVMDNFAAFVEKCCKADDKEACFAEEGPKFVAASQAAL-  (SEQ ID NO. 6)
Rat       541  EQLKTVMGDFAQFVKCCKAADINCFATEGPNLVARSKEAL-     (SEQ ID NO. 9)
Mouse     541  AEQLKTVMDDFAQFTCCKAADKTCFSTEGPNEVTRCKDAL-     (SEQ ID NO. 10)
               ↑                          ↑
              550                        573
```

Figure 5

```
Human        1 ----------------------------------DA-HKSEIAHRFKDLGEENFK
Mouse        1 ----------------------------------A--HKSEIAHRFNDLGEQHFKG
Sheep        1 ----------------------------------DT-HKSEIAHRFNDLGEENFQG
Rabbit       1 ----------------------------------A--HKSEIAHRFND-GEEHFIG
Goat         1 ----------------------------------DT-HKSEIAHRFNDLGEENFQG
Chimp        1 MNESSCCSTSLPAFGVEVXDSGHSSSSAYSRGV--FRRDA-HKSEIAHRFKDLGEENFK
Macaque      1 ------------MKWVTFSLLFLFSSAYSRGV--FRRDT-HKSEIAHRFKDLGEEHFKG
Hamster      1 ------------MKWVTFILLFXSDSAXSRGX--FRRDA-HKSEIAHRFKDLGEQHFKG
Guinea_Pig   1 ------------MKWVTFSLLFLFSSVYSRGV--FRRA--HKSEIAHRFNDLGEGHFKG
Rat          1 ------------MKWVTFILLFXSGSAXSRGV--FRRXA-HKSEIAHRFKDLGEEHFKG
Cow          1 ------------MKWVTFSLLILFSSAYSRGV--FRRDT-HKSEIAHRFKDLGEEHFKG
Horse        1 ------------MKWVTFSLLFLFSSAYSRGV--LRRDT-HKSEIAHRFNDLGEKHFKG
Donkey       1 ------------MKWVTFSLLFLFSSAYFRGV--LRRDT-HKSEIAHRFNDLGEKHFKG
Dog          1 ------------MKWVTFSLXFLFSSAYSRGX--VRRXA-YKSEIAHRXNDLGEEHFXX
Chicken      1 ------------MRWVTLSEXLFSSAXSRNXQRFARDAEHKSEIAHRXNDLKEEFFK
Pig          1 ------------MKWVTFSLLFLFSSAYSRGV--FRRDT-YKSEIAHRFKDLGEQYFKG
                                                        ↑
                                                   (D1-Start)

Human       22 LVLIAFAQYLQQCPFEEHVKLVNEVTEFAKTCVADESAENCDKSLHTLFGDKLCTVATLR
Mouse       22 LVLIAFSQYLQKCSXXEHAKLVXEVTXFAKTCVADESAANCDKSLHTLFGDKLCAXPNLR
Sheep       22 LVLIAFSQYLQQCPFXEHVKLVXXTEFAKTCVADESHAGCDKSLHTLFGDXLCKVATLR
Rabbit      22 LVLIXFSQYLQKCPXEEHVKLVKEVXLAKACVADESAANCDKSLHDXFGDXXCAXPLR
Goat        22 LVLIAFSQYLQQCPFXEHVKLVXXTEFAKTCVADESHAGCDKSLHTLFGDXLCKVATLR
Chimp       58 LVLIAFAQYLQQCPFEEHVKLVNEVTEFAKTCVADESAENCDKSLHTLFGDKLCTVATLR
Macaque     46 LVLIAFSQYLQQCPFEEHVKLVNEVTEFAKTCVADESAENCDKSLHTLFGDKLCTVATLR
Hamster     46 LVLIAFSQYLQKCPXEEHVKLVXEVTXFAKTCVADESAENCDKSLHTLFGDKLCAXPTLR
Guinea_Pig  46 LVLITISQHLQKSPFEEHVKLVNEVTXFAKACVADESAQNCXXXATLFGDKXCAXPLR
Rat         46 LVLIAFSQYLQKCPXEEHVKLVXEVTXFAKTCVADENAENCDKSXHTLFGDKLCAXPKLR
Cow         46 LVLIAFSQYLQQCPFXEHVKLVNEXTEFAKTCVADESHAGCKSLHTLFGDXLCKVATLR
Horse       46 LVLIAFSQYLQQCPFEEHVKLVNEVTEFAKKCAADESAENCDKSLHTLFGDKLCTVATLR
Donkey      46 LVLIAFSQYLQQCPFEEHVKLVNEVTEFAKKCAADESAENCDKSLHTLFGDKLCTVATLR
Dog         46 LVLIAFSQYLQQCPFEEHVKLAKEVTEFAKACAXESXANCDKSLHTLFGDKLCTVAXLR
Chicken     49 AXIXEAQYLQRCSXGLSKLVXVXXLAQKCVANEDAPECSRPLPXXILDEXQVEKLR
Pig         46 LVLIAFSQHLQQCPXEEHVKLVXEVTEFAKTCVADESAENCDKSXHTLFGDKLCAXPLR Human       82 ETYGEMADCCAKQEPERNECFLHKDDNPNLPPLVRPEVDVXCTAFXNEETFLKKYLY
Mouse       82 ENYGXMADCCXKQEPERNECFLHKDDNPSL-PEFERPEAXACTSXXMPTTXLGHYLH
Sheep       82 ETYGXMADCCEKQEPERNECFLHKDDSPDXPELXPEPDTXCAEFXADEKKEVGRYLY
Rabbit      82 XTYGXMADCCEKXEPERNECFLHKDEKPDLXPEFARPEADVXKAFXXDEKAPFGHYLY
Goat        82 ETYGXMADCCEKQEPERNECFLHKDDSPDXPKLXXPEPDTXCAEFXADEKKEWGKYLY
Chimp      118 EKYGEMADCCAKQEPERNECFLHKDDNPNLPPLVRPEVDVXCTAFXNEGTFLKKYLY
Macaque    106 ETYGEMADCCAKQEPERNECFLHKDDNPNLPPLVRPEVDVXCTAFXNEATLKKYLY
Hamster    106 XXYGEXADCCAKXEPERNECFLHKDDHPNLPPFVRPXAXAXTSFQXNAVTXLGHYLH
Guinea_Pig 106 ETYGEXADCCAKXXPRVECFLHKDDNPNLPPFERPEEXAXCTAFXNDRXLGHYLY
Rat        106 XNYGEXADCCAKQEPERNECFLHKDDNPNLPPFQRPEAXAXXTSFQXMPTSFLGHYLH
Cow        106 ETYGXMADCCEKQEPERNECFLHKDDSPDXPELXXPNTXCDEFXADEKKEWGKYLY
Horse      106 AXYGEXADCCAKQEPERNECFLHKDDHPNLPKLXXPEPDACCAAFQXDPDKFLGKYLY
Donkey     106 AXYGEXADCCEKQEPERNECFLHKDDHPNLPKLXXPEPDACCAAFQXDPDKFLGKYLY
Dog        106 AKYGXMADCCEKQEPXRNECFLHKDDNPGFPPLVAPEPDAXCAAFQXNEQLFLGKYLY
Chicken    109 XXYGAMADCCSKAYPERNECFLSEFVSXPDFVQEYQRPASDVXCQEXQXNRVSPLGHXX
Pig        106 EHYGXXADCCEKXEPERNECFLHKNDNPDXPKLXXPVAXCADFQXDEQKEWGRYLY
```

Figure 5 (continued)

```
Human       141 E ARRHPYFYAPELL   AK  YK A TECCQAADKAACL PKLD LR  E K SSAKQRLKC
Mouse       141 EVARRHPYFYAPELLYYAE YNE L QCCAEADR SC  PKLD    EK  VSS  QR KC
Sheep       140 EVARRHPYFYAPELLYYAN  N  F QECCQAE D ACL PK DA REKV  SSA QRL C
Rabbit      141 EVARRHPYFYAPELLYYAQ YK  L TECC AADK ACL PKLDALE   SL SAA ERL C
Goat        140 EVARRHPYFYAPELLYYAN  N  F QECCQAE DK ACL PK     REKV  SSA QRL C
Chimp       177 EVARRHPYFYAPELL   AE YF A TECCQAADKAACL PKLD LR  E K SSAKQRLKC
Macaque     165 EVARRHPYFYAPELL   AK YK A A ECCQAADKAACL PKLD LF  E K SSAKQRLKC
Hamster     165 EVARRHPYFYAPELLYYAE  G  M TECC GEADKAAC  PKLDAI EK  L SS VNQRLKC
Guinea_Pig  165 EV SRHPYFYAPELLYYAE  YRNAL TECC EAADKAACL TPKLDA  EK  L VSSA QRLKC
Rat         165 EVARRHPYFYAPELLYYAE  NE  L QCC TESD KAACLTPKLDA  EK  L VAAV QR KC
Cow         164 E ARRHPYFYAPELLYYAN  N  F QECCQAE DK ACL PK  T REKV  SSA QRL C
Horse       164 EVARRHPYFY PELL HAEE YK D TECC PADDR ACL PKLDAL E I LLSSAR ERLKC
Donkey      164 EVARRHPYFY PELL HAEE YK L TECC AD KA CL PKLDAI E I LLSAR ERLKC
Dog         165 E ARRHPYFYAPELLYYAQQ YK  F A ECCQAADKAACL PK  ALREK V LLSSAK ERFKC
Chicken     169 SVARRHP LYAPA LS  AVD EHALQSC CKES V  ACLDT EIV  REK  K  VS VKQQYFC
Pig         164 E ARRHPYFYAPELLYYA I IYK D  F ECCQAADKAACL PK   HLREKV TSA AKQRLKC
                                                                    ↑              ↑
                                                                (D2-Start)    (D1-End)

Human       201 AS QKFGERAFKAWAVARLSQ FPKA FAEVSK VTDLTKV H ECCHGDLLECADDRADL
Mouse       201 SS QKFGERAFKAWAVARLSQ FF  NADFAE     ATDLTKV NKECCHGDLLECADDRA  L
Sheep       200 AS QKFGERA  KAWSVARLSQ FPKADF  V    VTDLTKVHKECCHGDLLECADDRADL
Rabbit      201 AS QKFG RA KAWA V RLSQ FPKADF   SF   VTDLTKVHKECCHGDLLECADDRADL
Goat        200 AS QKFGERA  KAWSVARLSQ FPKADF  V    VTDLTKVHKECCHGDLLECADDRADL
Chimp       237 AS QKFGERAFKAWAVARLSQ FPKA FAEVSK VTDLTKV H ECCHGDLLECADDRADL
Macaque     225 AS QKFG RAFKAWAVARLSQKFPKA FAEVSK VTDLTKVH ECCHGDLLECADDRADL
Hamster     225 SS Q FG QRAFKAWAVAR SQKFPKADFAE     ATDLTK  TECCHGDLLECADDRA  L
Guinea_Pig  225 AS QKFGERAFKAWSVARLSQKFPKA FAE  T   VTSLTKV KECCHGDLLECADDR  L
Rat         225 SS Q KFGERAFKAWA VAR SQ FPNA FAE     ATD TK NKECCHGDLLECADDR A  L
Cow         224 AS QKFGERA  KAWSVARLSQKFPKA FAEV EV   VTDLTKVHKECCHGDLLECADDRADL
Horse       224 SS Q NFGERA KAWSVARLSQKFPKADFAEVSK VTDLTKVHKECCHGDLLECADDRADL
Donkey      224 SS  QKFGERAFKAWSVARLSQKFPKADFAEVSK VTDLTKVHKECCHGDLLECADDRADL
Dog         225 AS QKFG RAFKAWSVARLSQ FPKADFAE  SK  VTDLTKVHKECCHGDLLECADDRADL
Chicken     229  I  KQFG RV QARQ IYLSQK FPKAFF SEVSP V HDSIG VHKECC GD  ECMDDMAR
Pig         224 AS QKFGERAFKAWS  ARLSQ FPKADF  SK  VTDL AKVHKECCHGDLLECADDRADL Human       261 AKYICENQDSISSKLKECC KPLLEKSHCIAEVENDE PADLP SLAADFVES K VCKNYA
Mouse       261 AKY ICENQ A ISSKL QT CCDKPLL K AHC SEVE DT  PADLP  AADFVED  EVCKNYA
Sheep       260 AKYIC HQD A SSKLKECCDKP LEKSHCIAEV   DA PENLP  TADF AEDKEVCKNYQ
Rabbit      261 AKYIC HQ  ISS HLKECCDKP LEK AHCIYG HNDE PA LP A   FVEDK VCKNYE
Goat        260 AKYIC HQD A SSKLKECCDKP LEKSHCIAE    DA PEN LP  TADF AEDKEVCKNYQ
Chimp       297 AKYICENQDSISSKLKECC RPLLEKSHC AEVENDE PADLP SLAADFVES K VCKNYA
Macaque     285 AKY CENQDSISSKLKECCDKPLLEKSHC AEVENDE  PADLP SLAAD  VES K VCKNYA
Hamster     285 AKY CENQA SISSKL QA CCDKP L RSHC SEVE D   PADLP SLAADFVEDKEVCKNYA
Guinea_Pig  285 AKY CE HQDSISSKLKECC KPT  QA  CI  C DE  P T  LPD AVDFVEDKEVCKN A
Rat         285 AKY CENQA  ISSKLQA CCDR  LQKS C AE  DN  PADLP  AADFVEDKEVCKNYA
Cow         284 AKYIC NQD  ISSKLRECCDKPLLEKSHCIAEVE DA PEN LP  TADF AEDK VCKNYQ
Horse       284 AKYICEHQDS IS GKLKA CCDKPLI QKSHCIAEVKED  BSDLP ALAADF AEDKE CH YK
Donkey      284 TKYICEHQDS IS GKLKA CCDKPLL QKSHCIAEVKED  PSDLP ALAADFAEDKE CKHYK
Dog         285 AKY CENQDSISSKLKECCDKP LEKS C AEVE DE P DLP SLAADFVEDKEVCKNYQ
Chicken     289 MSN  CS  QDVES K  KCC KP  E SS C MDAE FDR PADLE  VEK  EDKEVCKS E
Pig         284 AKYICENQD IS  KLKECCDKPLLEKSHCIAEAK DE  PADINP EHDFVEDKEVCKNYK
```

Figure 5 (continued)

```
Human        321 EAKDVFLGMFLYEYARRHPDYSVVLLLRLAKTYETTLEKCCAAADPHECYAKVFDEFKPL
Mouse        321 EAKDVFLGTFLYEYSRRHPDYSVSLLLRLAKKYEATLEKCCAEANPEACYTTVLAEFTPL
Sheep        320 EAKDVFLGTFLYEYSRRHPVAVSLLLRLAKEYEATLEDCCAKEDPHACYATVFDKLKHL
Rabbit       321 EAKDVFLGKFLYEYSRRHPDYSVVLLRLKAYEATLKKCCATDDPHACYAKVLDEFKPL
Goat         320 EAKDVFLGTFLYEYSRRHPVAVSLLLRLAKEYEATLEDCCAKEDPHACYATVFDKLKHL
Chimp        357 EAKDVFLGMFLYEYARRHPDYSVVLLLRLAKTYETTLEKCCAAADPHECYAKVFDEFKPL
Macaque      345 EAKDVFLGMFLYEYARRHPDYSVMLLLRLAKAYEATLEKCCAAADPEECYAKVFDEFKPL
Hamster      345 EAKDVFLGTFLYEYARRHPDYSVLLAKKYEATLEKCCAEADPSACYLKVLDEFKPL
Guinea_Pig   345 EAKDVFLGTFLYEYSRRHPYSGLLRAKGYEAKLEKCCAEADPHACYAKVFDELKPL
Rat          345 EAKDVFLGTFLYEYSRRHPDYSVSLLLRLAKYEATLEKCCAEKDPFACYTTVLAEFKPL
Cow          344 EAKDAFLGKFLYEYSRRHPVAVSLLLRLAKEYEATLEECCAKDDPHACYSTVFDKLKHL
Horse        344 RAKDVFLGTFLYEYSRRHPDYSVSLLLRLAKTYEATLEKCCAEADPFACYRTVFDQFTPL
Donkey       344 RAKDVFLGTFLYEYSRRHPDYSVSLLLRLAKTYEATLEKCCAEADPFACYATVFDQFTPL
Dog          345 EAKDVFLGTFLYEYARRHPDYSVSLLLRLAKEYEATLEKCCATDDPPTCYAKVLDEFKPL
Chicken      349 AKHQAFLEYFLYEYSRRHPLGQLLRAKGYESLLEKCCKTDNPAECYANAQLQLSQH
Pig          344 EAKHVFLGTFLYEYSRRHPDYSVSLLLRAKIYEATLEDCCAKEDPACYATVFDKFPL Human        381 VEEPQNLIKQNCELFEQLGEYKFQNALLVRYTKKVPQVSTPTLVESRNLGKVGKCCKH
Mouse        381 VEEPKNLVKTNCDLYEKLGEYGFQNAILVRYTKAPQVSTPTLVEAARNLGKVGTKCCTL
Sheep        380 VEEPQNLKKNCELFEKHGEYGFQNALVRYTKAPQVSTPTLVESRSLGKVGTKCCAK
Rabbit       381 VEEPKNLVRQNCELFEQLGEYKFQNALLVRYTKKVPQVSTPTLVESRSLGKVGKCCKH
Goat         380 VEEPQNLKKNCELFEKHGEYGFQNALVRYTKAPQVSTPTLVESRSLGKVGTKCCAK
Chimp        417 VEEPQNLIKQNCELFEQLGEYKFQNALLVRYTKKVPQVSTPTLVESRNLGKVGKCCKH
Macaque      405 VEEPQNLVRQNCELFEQLGEYKFQNALLVRYTKKVPQVSTPTLVESRNLGKVGAKCCKL
Hamster      405 VEEPKNLVKANCELFEKLGEYGFQNALVRYTQKAPQVSTPTLVEAARNLGKVGKCCVL
Guinea_Pig   405 VEEPKKLVQQNCELFKLGEYGFQNALAVRYTQKAPQVSTPTLVEYARLGSVGTKCCSL
Rat          405 VEEPKNLVKTNCELEEKLGEYGFQNALLVRYTQKAPQVSTPTLVEAARNLGKVGTKCCTL
Cow          404 VEEPQNLKQNCQFEKLGEYGFQNAMVRYTKKVPQVSTPTLVESRSLGKVGTCCTK
Horse        404 VEEPKSLVKKNCLFEEGEYDFQNAIVRYTKKAPQVSTPTLVEGRTLGKVGCCKL
Donkey       404 VEEPKSLVRKNCLFEEGEYDFQNALVRYTKKAPQVSTPTLVEGRTLGKVGCCKL
Dog          405 VEEPQNLVKTNCELFEKLGEYGFQNALLVRYTKKAPQVSTPTLVESRKLGKVGTKCCKK
Chicken      409 RETQDLVKTNCELLHDEGEADFLKSLLRYTKKMPQVETDLLTGKKTTGTKCCQL
Pig          404 VEEKNLMKQNCELFEKLGEYGFQNALVRYTKKVPQVSTPTLVEARKLGIVGCCKR
                  ↑          ↑
              (D3-Start) (D2-End)

Human        441 PEAKRMPCAEDYLSLLNQLCVLHEKTPVSSVTKCCTESLVNRRPCFSALEVDETYVPK
Mouse        441 PEDQRMPCVEDYLSALNRLHERTPVSEVTKCCSESLVERRPCFSALTVDETYVPK
Sheep        440 PESERPCTEDYLSLLNRLCVLHEKTPVSEKVTKCCESLVNRRPCFSDLTVDETYVPR
Rabbit       441 PEAERPCVEDYLSLLNRLCVLHEKTPVSEKVTKCCESLVDRRPCFSALGPDETYVPK
Goat         440 PESERPCTEDYLSLLNRLCVLHEKTPVSEKVTKCCTESLVNRRPCFSDLTVDETYVPK
Chimp        477 PEAKRPCAEDYLSLLNQLCVLHEKTPVSSVTKCCTESLVNRRPCFSALEVDETYVPK
Macaque      465 PEAKRPCAEDYLSLLNRLCVLHEKTPVSEKVTKCCTESLVNRRPCFSALEDEAYVPK
Hamster      465 PEAQRPCVEDYLSALNRCVLHEKTPVSEDVTKCCTERVERRPCFSALEVDETYVPK
Guinea_Pig   465 PETERSCTENYLALNRLHEKTPVSEKVTKCCTESLVNRRPCFSALEHVDETYVPK
Rat          465 PEAQRPCVEDYLSALNRLCVLHEKTPVSEKVTKCCESLVERRPCFSALTVDETYVPK
Cow          464 PESERPCTEDYLSLLNRLCVLHEKTPVSEKVTKCCTESLVNRRPCFSALTPDETYVPK
Horse        464 PESERPCSENHLAALNRLCVLHEKTPVSEKVTKCCSIAERRPCFSALEDEGYVPK
Donkey       464 PESERPCSENHLAALNRLCVLHEKTPVSEKVTKCCSIAERRPCFSALEDEGYVPK
Dog          465 PESERSCAEDYLSLLNRLCVLHEKTPVSEVTKCCESLVNRRPCFSALEVDETYVPK
Chicken      469 GPDRRACSEDYLSHDTRKQETTENVQCCQLYANRPCFAGVDTKYVPP
Pig          464 PEERSCAEDYLSLLNRLCVLHEKTPVSEKVTKCCTESLVNRRPCFSALTPDETYRPK
```

Figure 5 (continued)

```
Human       501 EENAETFTFHADICTLSEKE QIKKQTALVELVKHKPKATKEQLRAVMD F AFV KCCK
Mouse       501 EEKAETFTFH SDICTLPEKEKQIKKQTALA ELVKHKPKATAEQLKTVMD    CCK
Sheep       500 P DEKF FTFHADICTLP TEKQIKKQTALVEL KHRPKAT EQLKTVMENF VAFVDKCCA
Rabbit      501 EENAETFTFHADICTLPET  IKKQTALVELVKHKP ATN QLKTV G FTA DKCC
Goat        500 P D E FTFHADICTLP TEKQIKKQTALVEL KHKPKAT EQLKTVMENF VAFVDKCCA
Chimp       537 EENAETFTFHADICTLSEKE QIKKQTALVELVKHKPRATKEQLRAVMD F AFV KCCK
Macaque     525 A NAETFTFHAD CTLSEKEKQ KKQTALVELVKHKPKATKEQLK VMDNF AFV KCCK
Hamster     525 EEKAETFTFHADIC LPEKEKQ KKQAALVELVKHKPKATGPQ TV G FTA DKCCK
Guinea_Pig  525 P HA FTFHADICTLP EKEKQ RKQMALVELVKHKPKA EQLKTVMG F A  KCCD
Rat         525 EEKAETFTFH SDICTLP EKEKQIKKQTALA ELVKHKPKAT QLKTVMG F CFVDKCCK
Cow         524 A DEKL FTFHADICTLP TEKQIKKQTALVEL KHKPKAT EQLKTVMENF VAFVDKCCA
Horse       524 EEKAETFTFHADICTLPEDEKQIKKQ ALA ELVKHKPKATKEQLKTV GNF SAFVAKCCG
Donkey      524 EEKAETFTFHADICTLPEDEKQIKKQ ALA ELVKHRPKAT EQLKTV GNF SAFVAKCCG
Dog         525 EENAETFTFHAD CTLPEA EKQ KKQTALVEL KHKPKAT EQLKTVMG F AFV KCCA
Chicken     529 P NP M EDEK  A AEE  GQMKLL N  RKPQM  EQ RT ADGF TAMVDKCCK
Pig         524 E VEG TFTFHAD CTLPEDEKQIKKQTALVEL KHRPAT EQL TV GNF AFVKCCA Human       561 A DKETCFAEEGKKLVAASQAAL L-- (SEQ ID NO. 1)
Mouse       561 AADK TC STEGP LVTRCKDALA --- (SEQ ID NO. 9)
Sheep       560 A DKE CFVLEGPKLVAS QAALA --- (SEQ ID NO. 16)
Rabbit      561 A DKEACFAVEGPKLVES KAT  --- (SEQ ID NO. 14)
Goat        560 A DKE CF L EGPKLVAS QAALA --- (SEQ ID NO. 15)
Chimp       597 A DKETCFAEEG KLVAASQAAL L-- (SEQ ID NO. 5)
Macaque     585 A DKEACFAEEGPK VAASQAALA --- (SEQ ID NO. 6)
Hamster     585 A DKEACFSE GPKLVAS SQAALA --- (SEQ ID NO. 7)
Guinea_Pig  565 A NKEAC  E GPKLVAKC A LA --- (SEQ ID NO. 8)
Rat         585 AADK NCFA EGP LVAP KEALA --- (SEQ ID NO. 10)
Cow         584 A DKEACFA EGPKLVVS  TALA --- (SEQ ID NO. 11)
Horse       584 R DKEACFAEEGPKLVAS SQ ALA --- (SEQ ID NO. 12)
Donkey      584 A DKEACFAEEGPKLVAS SQ ALA --- (SEQ ID NO. 13)
Dog         585 A NKE CF SEEGPKLVAAAQAAL V-- (SEQ ID NO. 17)
Chicken     589 QS INTC  EEC AN  VQ RAT  IGA (SEQ ID NO. 18)
Pig         584 AP  EACFA EGPK  VIEIR  L A --- (SEQ ID NO. 19)
                                        ↑
                                    (D3-End)
```

| 1 | Wt HSA |
| 2 | DI + DIII K573P-F5M |
| 3 | Wt DI + DIII-F5M |
| 4 | DI + DIII K500A-F5M |

```
SEQUENCE LISTING

<160> NUMBER OF SEQ ID NOS: 35

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

```
Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Lys Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 2
<211> LENGTH: 1758
```

<212> TYPE: DNA
<213> ORGANISM: Homo sapiens
<220> FEATURE:
<221> NAME/KEY: misc_feature
<222> LOCATION: (1)..(1758)
<223> OTHER INFORMATION: cDNA encoding HSA

<400> SEQUENCE: 2

```
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca aatcacttca tacccttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tccttttctt tgctaaaagg     480
tataaagctg cttttacaga atgttgccaa gctgctgata agctgcctg cctgttgcca     540
aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag ggcggacctt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgtttgcaa aaactatgct     960
gaggcaaagg atgtcttcct gggcatgttt ttgtatgaat atgcaagaag gcatcctgat    1020
tactctgtcg tgctgctgct gagacttgcc aagacatatg aaaccactct agagaagtgc    1080
tgtgccgctg cagatcctca tgaatgctat gccaaagtgt tcgatgaatt taaacctctt    1140
gtggaagagc tcagaatttt aatcaaacaa aattgtgagc ttttttgagca gcttggagag    1200
tacaaattcc agaatgcgct attagttcgt tacaccaaga aagtacccca gtgtcaact     1260
ccaactcttg tagaggtctc aagaaaccta ggaaaagtgg gcagcaaatg ttgtaaacat    1320
cctgaagcaa aaagaatgcc ctgtgcagaa gactatctat ccgtggtcct gaaccagtta    1380
tgtgtgttgc atgagaaaac gccagtaagt gacagagtca ccaaatgctg cacagaatcc    1440
ttggtgaaca ggcgaccatg cttttcagct ctggaagtcg atgaaacata cgttcccaaa    1500
gagtttaatg ctgaaacatt caccttccat gcagatatat gcacactttc tgagaaggag    1560
agacaaatca gaaacaaac tgcacttgtt gagctcgtga acacaagcc caaggcaaca    1620
aaagagcaac tgaaagctgt tatggatgat ttcgcagctt ttgtagagaa gtgctgcaag    1680
gctgacgata aggagacctg ctttgccgag agggtaaaa aacttgttgc tgcaagtcaa    1740
gctgccttag gcttataa                                                 1758
```

<210> SEQ ID NO 3
<211> LENGTH: 2264
<212> TYPE: DNA
<213> ORGANISM: Homo sapiens
<220> FEATURE:
<221> NAME/KEY: misc_feature
<222> LOCATION: (1)..(2264)
<223> OTHER INFORMATION: Genomic nucleotide sequence encoding HSA

<400> SEQUENCE: 3

```
agtatattag tgctaatttc cctccgtttg tcctagcttt tctcttctgt caacccaca      60
cgcctttggc acaatgaagt gggtaacctt tatttccctt cttttttctct ttagctcggc   120
ttattccagg ggtgtgtttc gtcgagatgc acacaagagt gaggttgctc atcggtttaa   180
agatttggga gaagaaaatt tcaaagcctt ggtgttgatt gcctttgctc agtatcttca   240
gcagtgtcca tttgaagatc atgtaaaatt agtgaatgaa gtaactgaat ttgcaaaaac   300
atgtgttgct gatgagtcag ctgaaaattg tgacaaatca cttcataccc tttttggaga   360
caaattatgc acagttgcaa ctcttcgtga aacctatggt gaaatggctg actgctgtgc   420
aaaacaagaa cctgagagaa atgaatgctt cttgcaacac aaagatgaca acccaaacct   480
ccccgattg gtgagaccag aggttgatgt gatgtgcact gcttttcatg acaatgaaga    540
gacattttg aaaaaatact tatatgaaat tgccagaaga catccttact tttatgcccc    600
ggaactcctt ttctttgcta aaaggtataa agctgctttt acagaatgtt gccaagctgc   660
tgataaagct gcctgcctgt tgccaaagct cgatgaactt cgggatgaag ggaaggcttc   720
gtctgccaaa cagagactca gtgtgccag tctccaaaaa tttggagaaa gagcttttcaa  780
agcatgggca gtagctcgcc tgagccgag atttcccaaa gctgagtttg cagaagtttc    840
caagttagtg acagatctta ccaaagtcca cacggaatgc tgccatggag atctgcttga   900
atgtgctgat gacagggcgg accttgccaa gtatatctgt gaaaatcaag attcgatctc   960
cagtaaactg aaggaatgct gtgaaaaacc tctgttggaa aaatcccact gcattgccga  1020
agtggaaaat gatgagatgc ctgctgactt gccttcatta gctgctgatt ttgttgaaag  1080
taaggatgtt tgcaaaaact atgctgaggc aaaggatgtc ttcctgggca tgttttgta   1140
tgaatatgca agaaggcatc ctgattactc tgtcgtgctg ctgctgagac ttgccaagac  1200
atatgaaacc actctagaga agtgctgtgc cgctgcagat cctcatgaat gctatgccaa  1260
agtgttcgat gaatttaaac ctcttgtgga agagcctcag aatttaatca aacaaaattg  1320
tgagcttttt gagcagcttg gagagtacaa attccagaat gcgctattag ttcgttacac  1380
caagaaagta ccccaagtgt caactccaac tcttgtagag gtctcaagaa acctaggaaa  1440
agtgggcagc aaatgttgta acatcctga agcaaaaaga atgccctgtg cagaagacta   1500
tctatccgtg gtcctgaacc agttatgtgt gttgcatgag aaaacgccag taagtgacag  1560
agtcaccaaa tgctgcacag aatccttggt gaacaggcga ccatgctttt cagctctgga  1620
agtcgatgaa acatacgttc ccaaagagtt taatgctgaa acattcaccct tccatgcaga  1680
tatatgcaca ctttctgaga aggagagaca aatcaagaaa caaactgcac ttgttgagct  1740
cgtgaaacac aagcccaagg caacaaaaga gcaactgaaa gctgttatgg atgatttcgc  1800
agcttttgta gagaagtgct gcaaggctga cgataaggag acctgctttg ccgaggaggg  1860
taaaaaactt gttgctgcaa gtcaagctgc cttaggctta aacatcaca tttaaaagca   1920
tctcagccta ccatgagaat aagagaaaga aaatgaagat caaaagctta ttcatctgtt  1980
tttcttttc gttggtgtaa agccaacacc ctgtctaaaa aacataaatt tctttaatca   2040
ttttgcctct tttctctgtg cttcaattaa taaaaaatgg aaagaatcta atagagtggt  2100
acagcactgt tattttttcaa agatgtgttg ctatcctgaa aattctgtag gttctgtgga  2160
agttccagtg ttctctctta ttccacttcg gtagaggatt tctagtttct tgtgggctaa  2220
ttaaataaat cattaatact cttctaaaaa aaaaaaaaaa aaaa                   2264
```

```
<210> SEQ ID NO 4
<211> LENGTH: 609
<212> TYPE: PRT
<213> ORGANISM: Homo sapiens

<400> SEQUENCE: 4

Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380
```

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 5
<211> LENGTH: 621
<212> TYPE: PRT
<213> ORGANISM: Pan troglodytes

<400> SEQUENCE: 5

Met Asn Glu Ser Ser Cys Cys Ser Thr Ser Leu Pro Ala Phe Gly Val
1               5                   10                  15

Ser Val Leu Asp Ser Gly His Ser Ser Ser Ala Tyr Ser Arg Gly
            20                  25                  30

Val Phe Arg Arg Asp Ala His Lys Ser Glu Val Ala His Arg Phe Lys
        35                  40                  45

Asp Leu Gly Glu Glu Asn Phe Lys Ala Leu Val Leu Val Ala Phe Ala
    50                  55                  60

Gln Tyr Leu Gln Gln Cys Pro Phe Glu Asp His Val Lys Leu Val Asn
65                  70                  75                  80

Glu Val Thr Glu Phe Ala Lys Thr Cys Val Ala Asp Glu Ser Ala Glu
                85                  90                  95

Asn Cys Asp Lys Ser Leu His Thr Leu Phe Gly Asp Lys Leu Cys Thr
            100                 105                 110

Val Ala Thr Leu Arg Glu Lys Tyr Gly Glu Met Ala Asp Cys Cys Ala
        115                 120                 125

Lys Gln Glu Pro Glu Arg Asn Glu Cys Phe Leu Gln His Lys Asp Asp
    130                 135                 140

```
Asn Pro Asn Leu Pro Arg Leu Val Arg Pro Glu Val Asp Val Met Cys
145                 150                 155                 160

Thr Ala Phe His Asp Asn Glu Gly Thr Phe Leu Lys Lys Tyr Leu Tyr
            165                 170                 175

Glu Val Ala Arg Arg His Pro Tyr Phe Tyr Ala Pro Glu Leu Leu Phe
        180                 185                 190

Phe Ala Glu Arg Tyr Lys Ala Ala Phe Thr Glu Cys Cys Gln Ala Ala
    195                 200                 205

Asp Lys Ala Ala Cys Leu Leu Pro Lys Leu Asp Glu Leu Arg Asp Glu
210                 215                 220

Gly Lys Ala Ser Ser Ala Lys Gln Arg Leu Lys Cys Ala Ser Leu Gln
225                 230                 235                 240

Lys Phe Gly Glu Arg Ala Phe Lys Ala Trp Ala Val Ala Arg Leu Ser
            245                 250                 255

Gln Arg Phe Pro Lys Ala Glu Phe Ala Glu Val Ser Lys Leu Val Thr
        260                 265                 270

Asp Leu Thr Lys Val His Thr Glu Cys Cys His Gly Asp Leu Leu Glu
    275                 280                 285

Cys Ala Asp Asp Arg Ala Asp Leu Ala Lys Tyr Ile Cys Glu Asn Gln
290                 295                 300

Asp Ser Ile Ser Ser Lys Leu Lys Glu Cys Cys Glu Lys Pro Leu Leu
305                 310                 315                 320

Glu Lys Ser His Cys Leu Ala Glu Val Glu Asn Asp Glu Met Pro Ala
            325                 330                 335

Asp Leu Pro Ser Leu Ala Ala Asp Phe Val Glu Ser Lys Glu Val Cys
        340                 345                 350

Lys Asn Tyr Ala Glu Ala Lys Asp Val Phe Leu Gly Met Phe Leu Tyr
    355                 360                 365

Glu Tyr Ala Arg Arg His Pro Asp Tyr Ser Val Val Leu Leu Leu Arg
370                 375                 380

Leu Ala Lys Thr Tyr Glu Thr Thr Leu Glu Lys Cys Cys Ala Ala Ala
385                 390                 395                 400

Asp Pro His Glu Cys Tyr Ala Lys Val Phe Asp Glu Phe Lys Pro Leu
            405                 410                 415

Val Glu Glu Pro Gln Asn Leu Ile Lys Gln Asn Cys Glu Leu Phe Glu
        420                 425                 430

Gln Leu Gly Glu Tyr Lys Phe Gln Asn Ala Leu Leu Val Arg Tyr Thr
    435                 440                 445

Lys Lys Val Pro Gln Val Ser Thr Pro Thr Leu Val Glu Val Ser Arg
450                 455                 460

Asn Leu Gly Lys Val Gly Ser Lys Cys Cys Lys His Pro Glu Ala Lys
465                 470                 475                 480

Arg Met Pro Cys Ala Glu Asp Tyr Leu Ser Val Val Leu Asn Gln Leu
            485                 490                 495

Cys Val Leu His Glu Lys Thr Pro Val Ser Asp Arg Val Thr Lys Cys
        500                 505                 510

Cys Thr Glu Ser Leu Val Asn Arg Arg Pro Cys Phe Ser Ala Leu Glu
    515                 520                 525

Val Asp Glu Thr Tyr Val Pro Lys Glu Phe Asn Ala Glu Thr Phe Thr
530                 535                 540

Phe His Ala Asp Ile Cys Thr Leu Ser Glu Lys Glu Arg Gln Ile Lys
545                 550                 555                 560

Lys Gln Thr Ala Leu Val Glu Leu Val Lys His Lys Pro Lys Ala Thr
```

```
                    565                 570                 575
Lys Glu Gln Leu Lys Ala Val Met Asp Asp Phe Ala Ala Phe Val Glu
            580                 585                 590

Lys Cys Cys Lys Ala Asp Asp Lys Glu Thr Cys Phe Ala Glu Glu Gly
            595                 600                 605

Lys Lys Leu Val Ala Ala Ser Gln Ala Ala Leu Gly Leu
            610                 615                 620

<210> SEQ ID NO 6
<211> LENGTH: 608
<212> TYPE: PRT
<213> ORGANISM: Macaca mulatta

<400> SEQUENCE: 6

Met Lys Trp Val Thr Phe Ile Ser Leu Leu Phe Leu Phe Ser Ser Ala
1               5                   10                  15

Tyr Ser Arg Gly Val Phe Arg Arg Asp Thr His Lys Ser Glu Val Ala
            20                  25                  30

His Arg Phe Lys Asp Leu Gly Glu Glu His Phe Lys Gly Leu Val Leu
        35                  40                  45

Val Ala Phe Ser Gln Tyr Leu Gln Gln Cys Pro Phe Glu Glu His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Pro Leu Val Arg Pro Glu Val
    130                 135                 140

Asp Val Met Cys Thr Ala Phe His Asp Asn Glu Ala Thr Phe Leu Lys
145                 150                 155                 160

Lys Tyr Leu Tyr Glu Val Ala Arg Arg His Pro Tyr Phe Tyr Ala Pro
                165                 170                 175

Glu Leu Leu Phe Phe Ala Ala Arg Tyr Lys Ala Ala Phe Ala Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Asp Arg Ala Phe Lys Ala Trp Ala Val
225                 230                 235                 240

Ala Arg Leu Ser Gln Lys Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Ser Lys Leu Lys Glu Cys Cys Asp
    290                 295                 300

Lys Pro Leu Leu Glu Lys Ser His Cys Leu Ala Glu Val Glu Asn Asp
305                 310                 315                 320
```

-continued

```
Glu Met Pro Ala Asp Leu Pro Ser Leu Ala Asp Tyr Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Met
            355                 360                 365

Leu Leu Leu Arg Leu Ala Lys Ala Tyr Glu Ala Thr Leu Glu Lys Cys
    370                 375                 380

Cys Ala Ala Ala Asp Pro His Glu Cys Tyr Ala Lys Val Phe Asp Glu
385                 390                 395                 400

Phe Gln Pro Leu Val Glu Pro Gln Asn Leu Val Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ala Lys Cys Cys Lys Leu
        450                 455                 460

Pro Glu Ala Lys Arg Met Pro Cys Ala Glu Asp Tyr Leu Ser Val Val
465                 470                 475                 480

Leu Asn Arg Leu Cys Val Leu His Glu Lys Thr Pro Val Ser Glu Lys
            485                 490                 495

Val Thr Lys Cys Cys Thr Glu Ser Leu Val Asn Arg Arg Pro Cys Phe
            500                 505                 510

Ser Ala Leu Glu Leu Asp Glu Ala Tyr Val Pro Lys Ala Phe Asn Ala
            515                 520                 525

Glu Thr Phe Thr Phe His Ala Asp Met Cys Thr Leu Ser Glu Lys Glu
            530                 535                 540

Lys Gln Val Lys Gln Thr Ala Leu Val Glu Leu Val Lys His Lys
545                 550                 555                 560

Pro Lys Ala Thr Lys Glu Gln Leu Lys Gly Val Met Asp Asn Phe Ala
            565                 570                 575

Ala Phe Val Glu Lys Cys Cys Lys Ala Asp Asp Lys Glu Ala Cys Phe
            580                 585                 590

Ala Glu Glu Gly Pro Lys Phe Val Ala Ala Ser Gln Ala Ala Leu Ala
            595                 600                 605

<210> SEQ ID NO 7
<211> LENGTH: 608
<212> TYPE: PRT
<213> ORGANISM: Mesocricetus auratus

<400> SEQUENCE: 7

Met Lys Trp Val Thr Phe Leu Leu Leu Leu Phe Val Ser Asp Ser Ala
1               5                   10                  15

Phe Ser Arg Gly Leu Phe Arg Arg Asp Ala His Lys Ser Glu Ile Ala
            20                  25                  30

His Arg Phe Lys Asp Leu Gly Glu Gln His Phe Lys Gly Leu Val Leu
        35                  40                  45

Ile Ala Phe Ser Gln Phe Leu Gln Lys Cys Pro Tyr Glu Glu His Val
    50                  55                  60

Lys Leu Val Asn Glu Val Thr Asp Phe Ala Lys Thr Cys Val Ala Asp
65                  70                  75                  80

Glu Ser Ala Glu Asn Cys Asp Lys Ser Leu His Thr Leu Phe Gly Asp
            85                  90                  95
```

```
Lys Leu Cys Ala Ile Pro Thr Leu Arg Asp Ser Tyr Gly Glu Leu Ala
            100                 105                 110

Asp Cys Cys Ala Lys Lys Glu Pro Glu Arg Asn Glu Cys Phe Leu Lys
            115                 120                 125

His Lys Asp Asp His Pro Asn Leu Pro Pro Phe Val Arg Pro Asp Ala
            130                 135                 140

Glu Ala Met Cys Thr Ser Phe Gln Glu Asn Ala Val Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Ser Ala Ile Met Thr Glu Cys
            180                 185                 190

Cys Gly Glu Ala Asp Lys Ala Ala Cys Ile Thr Pro Lys Leu Asp Ala
            195                 200                 205

Leu Lys Glu Lys Ala Leu Ala Ser Ser Val Asn Gln Arg Leu Lys Cys
            210                 215                 220

Ser Ser Leu Gln Arg Phe Gly Gln Arg Ala Phe Lys Ala Trp Ala Val
225                 230                 235                 240

Ala Arg Met Ser Gln Lys Phe Pro Lys Ala Asp Phe Ala Glu Ile Thr
                245                 250                 255

Lys Leu Ala Thr Asp Leu Thr Lys Leu Thr Glu Glu Cys Cys His Gly
            260                 265                 270

Asp Leu Leu Glu Cys Ala Asp Asp Arg Ala Glu Leu Ala Lys Tyr Met
            275                 280                 285

Cys Glu Asn Gln Ala Ser Ile Ser Ser Lys Leu Gln Ala Cys Cys Asp
            290                 295                 300

Lys Pro Val Leu Lys Lys Ser His Cys Leu Ser Glu Val Glu Asn Asp
305                 310                 315                 320

Asp Leu Pro Ala Asp Leu Pro Ser Leu Ala Ala Asp Phe Val Glu Asp
                325                 330                 335

Lys Glu Val Cys Lys Asn Tyr Ala Glu Ala Lys Asp Val Phe Leu Gly
            340                 345                 350

Thr Phe Leu Tyr Glu Tyr Ala Arg Arg His Pro Asp Tyr Ser Val Ala
            355                 360                 365

Leu Leu Leu Arg Leu Ala Lys Lys Tyr Glu Ala Thr Leu Glu Lys Cys
            370                 375                 380

Cys Ala Glu Ala Asp Pro Ser Ala Cys Tyr Gly Lys Val Leu Asp Glu
385                 390                 395                 400

Phe Gln Pro Leu Val Glu Glu Pro Lys Asn Leu Val Lys Ala Asn Cys
                405                 410                 415

Glu Leu Phe Glu Lys Leu Gly Glu Tyr Gly Phe Gln Asn Ala Leu Ile
            420                 425                 430

Val Arg Tyr Thr Gln Lys Ala Pro Gln Val Ser Thr Pro Thr Leu Val
            435                 440                 445

Glu Ala Ala Arg Asn Leu Gly Lys Val Gly Ser Lys Cys Cys Val Leu
            450                 455                 460

Pro Glu Ala Gln Arg Leu Pro Cys Val Glu Asp Tyr Ile Ser Ala Ile
465                 470                 475                 480

Leu Asn Arg Val Cys Val Leu His Glu Lys Thr Pro Val Ser Glu Gln
                485                 490                 495

Val Thr Lys Cys Cys Thr Gly Ser Val Val Glu Arg Arg Pro Cys Phe
            500                 505                 510
```

```
Ser Ala Leu Pro Val Asp Glu Thr Tyr Val Pro Lys Glu Phe Lys Ala
            515                 520                 525

Glu Thr Phe Thr Phe His Ala Asp Ile Cys Ser Leu Pro Lys Glu
530                 535                 540

Lys Gln Met Lys Lys Gln Ala Ala Leu Val Glu Leu Val Lys His Lys
545                 550                 555                 560

Pro Lys Ala Thr Gly Pro Gln Leu Arg Thr Val Leu Gly Glu Phe Thr
                565                 570                 575

Ala Phe Leu Asp Lys Cys Cys Lys Ala Glu Asp Lys Glu Ala Cys Phe
                580                 585                 590

Ser Glu Asp Gly Pro Lys Leu Val Ala Ser Ser Gln Ala Ala Leu Ala
                595                 600                 605

<210> SEQ ID NO 8
<211> LENGTH: 608
<212> TYPE: PRT
<213> ORGANISM: Cavia porcellus

<400> SEQUENCE: 8

Met Lys Trp Val Thr Phe Ile Ser Leu Leu Phe Leu Phe Ser Ser Val
1               5                   10                  15

Tyr Ser Arg Gly Val Phe Arg Arg Glu Ala His Lys Ser Glu Ile Ala
                20                  25                  30

His Arg Phe Asn Asp Leu Gly Glu Gly His Phe Lys Gly Leu Val Leu
            35                  40                  45

Ile Thr Leu Ser Gln His Leu Gln Lys Ser Pro Phe Glu Glu His Val
    50                  55                  60

Lys Leu Val Asn Glu Val Thr Asp Phe Ala Lys Ala Cys Val Ala Asp
65                  70                  75                  80

Glu Ser Ala Gln Asn Cys Gly Lys Ala Ile Ala Thr Leu Phe Gly Asp
                85                  90                  95

Lys Val Cys Ala Ile Pro Ser Leu Arg Glu Thr Tyr Gly Glu Leu Ala
            100                 105                 110

Asp Cys Cys Ala Lys Glu Asp Pro Asp Arg Val Glu Cys Phe Leu Gln
        115                 120                 125

His Lys Asp Asp Asn Pro Asn Leu Pro Pro Phe Glu Arg Pro Glu Pro
    130                 135                 140

Glu Ala Leu Cys Thr Ala Phe Lys Glu Asn Asn Asp Arg Phe Ile Gly
145                 150                 155                 160

His Tyr Leu Tyr Glu Val Ser Arg Arg His Pro Tyr Phe Tyr Ala Pro
                165                 170                 175

Glu Leu Leu Tyr Tyr Ala Glu Lys Tyr Lys Asn Ala Leu Thr Glu Cys
            180                 185                 190

Cys Glu Ala Ala Asp Lys Ala Ala Cys Leu Thr Pro Lys Leu Asp Ala
        195                 200                 205

Ile Lys Glu Lys Ala Leu Val Ser Ser Ala Gln Gln Arg Leu Lys Cys
    210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
                245                 250                 255

Thr Ile Val Thr Ser Leu Thr Lys Val Thr Lys Glu Cys Cys His Gly
            260                 265                 270

Asp Leu Leu Glu Cys Ala Asp Asp Arg Gln Glu Leu Ala Lys Tyr Met
        275                 280                 285
```

Cys Glu His Gln Asp Ser Ile Ser Ser Lys Leu Lys Glu Cys Cys Val
            290                 295                 300

Lys Pro Thr Leu Gln Lys Ala His Cys Ile Leu Glu Ile Gln Arg Asp
305                 310                 315                 320

Glu Leu Pro Thr Glu Leu Pro Asp Leu Ala Val Asp Phe Val Glu Asp
                325                 330                 335

Lys Glu Val Cys Lys Asn Phe Ala Glu Ala Lys Asp Val Phe Leu Gly
            340                 345                 350

Thr Phe Leu Tyr Glu Tyr Ser Arg Arg His Pro Glu Tyr Ser Ile Gly
        355                 360                 365

Met Leu Leu Arg Ile Ala Lys Gly Tyr Glu Ala Lys Leu Glu Lys Cys
    370                 375                 380

Cys Ala Glu Ala Asp Pro His Ala Cys Tyr Ala Lys Val Phe Asp Glu
385                 390                 395                 400

Leu Gln Pro Leu Ile Asp Glu Pro Lys Lys Leu Val Gln Gln Asn Cys
                405                 410                 415

Glu Leu Phe Asp Lys Leu Gly Glu Tyr Gly Phe Gln Asn Ala Leu Ala
            420                 425                 430

Val Arg Tyr Thr Gln Lys Ala Pro Gln Val Ser Thr Pro Thr Leu Val
        435                 440                 445

Glu Tyr Ala Arg Lys Leu Gly Ser Val Gly Thr Lys Cys Cys Ser Leu
    450                 455                 460

Pro Glu Thr Glu Arg Leu Ser Cys Thr Glu Asn Tyr Leu Ala Leu Ile
465                 470                 475                 480

Leu Asn Arg Leu Cys Ile Leu His Glu Lys Thr Pro Val Ser Glu Arg
                485                 490                 495

Val Thr Lys Cys Cys Thr Glu Ser Leu Val Asn Arg Arg Pro Cys Phe
            500                 505                 510

Ser Ala Leu His Val Asp Glu Thr Tyr Val Pro Lys Pro Phe His Ala
        515                 520                 525

Asp Ser Phe Thr Phe His Ala Asp Ile Cys Thr Leu Pro Glu Lys Glu
    530                 535                 540

Lys Gln Val Lys Lys Gln Met Ala Leu Val Glu Leu Val Lys His Lys
545                 550                 555                 560

Pro Lys Ala Ser Glu Glu Gln Met Lys Thr Val Met Gly Asp Phe Ala
                565                 570                 575

Ala Phe Leu Lys Lys Cys Cys Asp Ala Asp Asn Lys Glu Ala Cys Phe
            580                 585                 590

Thr Glu Asp Gly Pro Lys Leu Val Ala Lys Cys Gln Ala Thr Leu Ala
        595                 600                 605

```
<210> SEQ ID NO 9
<211> LENGTH: 608
<212> TYPE: PRT
<213> ORGANISM: Mus musculus

<400> SEQUENCE: 9
```

Met Lys Trp Val Thr Phe Leu Leu Leu Leu Phe Val Ser Gly Ser Ala
1               5                   10                  15

Phe Ser Arg Gly Val Phe Arg Arg Glu Ala His Lys Ser Glu Ile Ala
            20                  25                  30

His Arg Tyr Asn Asp Leu Gly Glu Gln His Phe Lys Gly Leu Val Leu
        35                  40                  45

Ile Ala Phe Ser Gln Tyr Leu Gln Lys Cys Ser Tyr Asp Glu His Ala

```
            50                  55                  60
Lys Leu Val Gln Glu Val Thr Asp Phe Ala Lys Thr Cys Val Ala Asp
 65                  70                  75                  80

Glu Ser Ala Ala Asn Cys Asp Lys Ser Leu His Thr Leu Phe Gly Asp
                 85                  90                  95

Lys Leu Cys Ala Ile Pro Asn Leu Arg Glu Asn Tyr Gly Glu Leu Ala
                100                 105                 110

Asp Cys Cys Thr Lys Gln Glu Pro Glu Arg Asn Glu Cys Phe Leu Gln
                115                 120                 125

His Lys Asp Asp Asn Pro Ser Leu Pro Pro Phe Glu Arg Pro Glu Ala
                130                 135                 140

Glu Ala Met Cys Thr Ser Phe Lys Glu Asn Pro Thr Thr Phe Met Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Gln Tyr Asn Glu Ile Leu Thr Gln Cys
                180                 185                 190

Cys Ala Glu Ala Asp Lys Glu Ser Cys Leu Thr Pro Lys Leu Asp Gly
                195                 200                 205

Val Lys Glu Lys Ala Leu Val Ser Ser Val Arg Gln Arg Met Lys Cys
                210                 215                 220

Ser Ser Met Gln Lys Phe Gly Glu Arg Ala Phe Lys Ala Trp Ala Val
225                 230                 235                 240

Ala Arg Leu Ser Gln Thr Phe Pro Asn Ala Asp Phe Ala Glu Ile Thr
                245                 250                 255

Lys Leu Ala Thr Asp Leu Thr Lys Val Asn Lys Glu Cys Cys His Gly
                260                 265                 270

Asp Leu Leu Glu Cys Ala Asp Asp Arg Ala Glu Leu Ala Lys Tyr Met
                275                 280                 285

Cys Glu Asn Gln Ala Thr Ile Ser Ser Lys Leu Gln Thr Cys Cys Asp
                290                 295                 300

Lys Pro Leu Leu Lys Lys Ala His Cys Leu Ser Glu Val Glu His Asp
305                 310                 315                 320

Thr Met Pro Ala Asp Leu Pro Ala Ile Ala Ala Asp Phe Val Glu Asp
                325                 330                 335

Gln Glu Val Cys Lys Asn Tyr Ala Glu Ala Lys Asp Val Phe Leu Gly
                340                 345                 350

Thr Phe Leu Tyr Glu Tyr Ser Arg Arg His Pro Asp Tyr Ser Val Ser
                355                 360                 365

Leu Leu Leu Arg Leu Ala Lys Lys Tyr Glu Ala Thr Leu Glu Lys Cys
                370                 375                 380

Cys Ala Glu Ala Asn Pro Pro Ala Cys Tyr Gly Thr Val Leu Ala Glu
385                 390                 395                 400

Phe Gln Pro Leu Val Glu Glu Pro Lys Asn Leu Val Lys Thr Asn Cys
                405                 410                 415

Asp Leu Tyr Glu Lys Leu Gly Glu Tyr Gly Phe Gln Asn Ala Ile Leu
                420                 425                 430

Val Arg Tyr Thr Gln Lys Ala Pro Gln Val Ser Thr Pro Thr Leu Val
                435                 440                 445

Glu Ala Ala Arg Asn Leu Gly Arg Val Gly Thr Lys Cys Cys Thr Leu
                450                 455                 460

Pro Glu Asp Gln Arg Leu Pro Cys Val Glu Asp Tyr Leu Ser Ala Ile
465                 470                 475                 480
```

```
Leu Asn Arg Val Cys Leu Leu His Glu Lys Thr Pro Val Ser Glu His
                485                 490                 495

Val Thr Lys Cys Cys Ser Gly Ser Leu Val Glu Arg Arg Pro Cys Phe
                500                 505                 510

Ser Ala Leu Thr Val Asp Glu Thr Tyr Val Pro Lys Glu Phe Lys Ala
                515                 520                 525

Glu Thr Phe Thr Phe His Ser Asp Ile Cys Thr Leu Pro Glu Lys Glu
                530                 535                 540

Lys Gln Ile Lys Lys Gln Thr Ala Leu Ala Glu Leu Val Lys His Lys
545                 550                 555                 560

Pro Lys Ala Thr Ala Glu Gln Leu Lys Thr Val Met Asp Asp Phe Ala
                565                 570                 575

Gln Phe Leu Asp Thr Cys Cys Lys Ala Ala Asp Lys Asp Thr Cys Phe
                580                 585                 590

Ser Thr Glu Gly Pro Asn Leu Val Thr Arg Cys Lys Asp Ala Leu Ala
                595                 600                 605

<210> SEQ ID NO 10
<211> LENGTH: 608
<212> TYPE: PRT
<213> ORGANISM: Rattus norvegicus

<400> SEQUENCE: 10

Met Lys Trp Val Thr Phe Leu Leu Leu Phe Ile Ser Gly Ser Ala
1               5                   10                  15

Phe Ser Arg Gly Val Phe Arg Arg Glu Ala His Lys Ser Glu Ile Ala
                20                  25                  30

His Arg Phe Lys Asp Leu Gly Glu Gln His Phe Lys Gly Leu Val Leu
                35                  40                  45

Ile Ala Phe Ser Gln Tyr Leu Gln Lys Cys Pro Tyr Glu Glu His Ile
            50                  55                  60

Lys Leu Val Gln Glu Val Thr Asp Phe Ala Lys Thr Cys Val Ala Asp
65                  70                  75                  80

Glu Asn Ala Glu Asn Cys Asp Lys Ser Ile His Thr Leu Phe Gly Asp
                85                  90                  95

Lys Leu Cys Ala Ile Pro Lys Leu Arg Asp Asn Tyr Gly Glu Leu Ala
                100                 105                 110

Asp Cys Cys Ala Lys Gln Glu Pro Glu Arg Asn Glu Cys Phe Leu Gln
                115                 120                 125

His Lys Asp Asp Asn Pro Asn Leu Pro Pro Phe Gln Arg Pro Glu Ala
                130                 135                 140

Glu Ala Met Cys Thr Ser Phe Gln Glu Asn Pro Thr Ser Phe Leu Gly
145                 150                 155                 160

His Tyr Leu His Glu Val Ala Arg Arg His Pro Tyr Phe Tyr Ala Pro
                165                 170                 175

Glu Leu Leu Tyr Tyr Ala Glu Lys Tyr Asn Glu Val Leu Thr Gln Cys
                180                 185                 190

Cys Thr Glu Ser Asp Lys Ala Ala Cys Leu Thr Pro Lys Leu Asp Ala
                195                 200                 205

Val Lys Glu Lys Ala Leu Val Ala Ala Val Arg Gln Arg Met Lys Cys
                210                 215                 220

Ser Ser Met Gln Arg Phe Gly Glu Arg Ala Phe Lys Ala Trp Ala Val
225                 230                 235                 240

Ala Arg Met Ser Gln Arg Phe Pro Asn Ala Glu Phe Ala Glu Ile Thr
```

```
                    245                 250                 255
Lys Leu Ala Thr Asp Val Thr Lys Ile Asn Lys Glu Cys Cys His Gly
                260                 265                 270

Asp Leu Glu Cys Ala Asp Arg Ala Glu Leu Ala Lys Tyr Met
            275                 280                 285

Cys Glu Asn Gln Ala Thr Ile Ser Ser Lys Leu Gln Ala Cys Cys Asp
    290                 295                 300

Lys Pro Val Leu Gln Lys Ser Gln Cys Leu Ala Glu Ile Glu His Asp
305                 310                 315                 320

Asn Ile Pro Ala Asp Leu Pro Ser Ile Ala Ala Asp Phe Val Glu Asp
                325                 330                 335

Lys Glu Val Cys Lys Asn Tyr Ala Glu Ala Lys Asp Val Phe Leu Gly
                340                 345                 350

Thr Phe Leu Tyr Glu Tyr Ser Arg Arg His Pro Asp Tyr Ser Val Ser
            355                 360                 365

Leu Leu Leu Arg Leu Ala Lys Lys Tyr Glu Ala Thr Leu Glu Lys Cys
        370                 375                 380

Cys Ala Glu Gly Asp Pro Pro Ala Cys Tyr Gly Thr Val Leu Ala Glu
385                 390                 395                 400

Phe Gln Pro Leu Val Glu Pro Lys Asn Leu Val Lys Thr Asn Cys
                405                 410                 415

Glu Leu Tyr Glu Lys Leu Gly Glu Tyr Gly Phe Gln Asn Ala Val Leu
            420                 425                 430

Val Arg Tyr Thr Gln Lys Ala Pro Gln Val Ser Thr Pro Thr Leu Val
        435                 440                 445

Glu Ala Ala Arg Asn Leu Gly Arg Val Gly Thr Lys Cys Cys Thr Leu
    450                 455                 460

Pro Glu Ala Gln Arg Leu Pro Cys Val Glu Asp Tyr Leu Ser Ala Ile
465                 470                 475                 480

Leu Asn Arg Leu Cys Val Leu His Glu Lys Thr Pro Val Ser Glu Lys
                485                 490                 495

Val Thr Lys Cys Cys Ser Gly Ser Leu Val Glu Arg Arg Pro Cys Phe
            500                 505                 510

Ser Ala Leu Thr Val Asp Glu Thr Tyr Val Pro Lys Glu Phe Lys Ala
        515                 520                 525

Glu Thr Phe Thr Phe His Ser Asp Ile Cys Thr Leu Pro Asp Lys Glu
    530                 535                 540

Lys Gln Ile Lys Lys Gln Thr Ala Leu Ala Glu Leu Val Lys His Lys
545                 550                 555                 560

Pro Lys Ala Thr Glu Asp Gln Leu Lys Thr Val Met Gly Asp Phe Ala
                565                 570                 575

Gln Phe Val Asp Lys Cys Cys Lys Ala Ala Asp Lys Asp Asn Cys Phe
            580                 585                 590

Ala Thr Glu Gly Pro Asn Leu Val Ala Arg Ser Lys Glu Ala Leu Ala
        595                 600                 605

<210> SEQ ID NO 11
<211> LENGTH: 607
<212> TYPE: PRT
<213> ORGANISM: Bos taurus

<400> SEQUENCE: 11

Met Lys Trp Val Thr Phe Ile Ser Leu Leu Leu Phe Ser Ser Ala
1               5                   10                  15
```

-continued

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
            115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
        355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu

```
                435                 440                 445
Val Ser Arg Ser Leu Gly Lys Val Gly Thr Arg Cys Cys Thr Lys Pro
    450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
        515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 12
<211> LENGTH: 607
<212> TYPE: PRT
<213> ORGANISM: Equus caballus

<400> SEQUENCE: 12

Met Lys Trp Val Thr Phe Val Ser Leu Leu Phe Leu Phe Ser Ser Ala
1               5                   10                  15

Tyr Ser Arg Gly Val Leu Arg Arg Asp Thr His Lys Ser Glu Ile Ala
                20                  25                  30

His Arg Phe Asn Asp Leu Gly Glu Lys His Phe Lys Gly Leu Val Leu
            35                  40                  45

Val Ala Phe Ser Gln Tyr Leu Gln Gln Cys Pro Phe Glu Asp His Val
        50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Leu Ala Cys Leu Ile Pro Lys Leu Asp Ala Leu
        195                 200                 205
```

Lys Glu Arg Ile Leu Leu Ser Ser Ala Lys Glu Arg Leu Lys Cys Ser
    210                 215                 220

Ser Phe Gln Asn Phe Gly Glu Arg Ala Val Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys
    370                 375                 380

Ala Glu Ala Asp Pro Pro Ala Cys Tyr Arg Thr Val Phe Asp Gln Phe
385                 390                 395                 400

Thr Pro Leu Val Glu Glu Pro Lys Ser Leu Val Lys Lys Asn Cys Asp
                405                 410                 415

Leu Phe Glu Glu Val Gly Glu Tyr Asp Phe Gln Asn Ala Leu Ile Val
            420                 425                 430

Arg Tyr Thr Lys Lys Ala Pro Gln Val Ser Thr Pro Thr Leu Val Glu
        435                 440                 445

Ile Gly Arg Thr Leu Gly Lys Val Gly Ser Arg Cys Cys Lys Leu Pro
    450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
            500                 505                 510

Ala Leu Glu Leu Asp Glu Gly Tyr Val Pro Lys Glu Phe Lys Ala Glu
        515                 520                 525

Thr Phe Thr Phe His Ala Asp Ile Cys Thr Leu Pro Glu Asp Glu Lys
    530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Arg Glu Asp Lys Glu Ala Cys Phe Ala
            580                 585                 590

Glu Glu Gly Pro Lys Leu Val Ala Ser Ser Gln Leu Ala Leu Ala
        595                 600                 605

<210> SEQ ID NO 13
<211> LENGTH: 607
<212> TYPE: PRT

<213> ORGANISM: Equus asinus

<400> SEQUENCE: 13

Met Lys Trp Val Thr Phe Val Ser Leu Leu Phe Leu Phe Ser Ser Ala
1               5                   10                  15

Tyr Phe Arg Gly Val Leu Arg Arg Asp Thr His Lys Ser Glu Ile Ala
            20                  25                  30

His Arg Phe Asn Asp Leu Gly Glu Lys His Phe Lys Gly Leu Val Leu
        35                  40                  45

Val Ala Phe Ser Gln Tyr Leu Gln Gln Cys Pro Phe Glu Asp His Val
    50                  55                  60

Lys Leu Val Asn Glu Val Thr Glu Phe Ala Lys Lys Cys Ala Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Ala Thr Tyr Gly Glu Leu Ala
            100                 105                 110

Asp Cys Cys Glu Lys Gln Glu Pro Glu Arg Asn Glu Cys Phe Leu Thr
        115                 120                 125

His Lys Asp Asp His Pro Asn Leu Pro Lys Leu Lys Pro Glu Pro Asp
    130                 135                 140

Ala Gln Cys Ala Ala Phe Gln Glu Asp Pro Asp Lys Phe Leu Gly Lys
145                 150                 155                 160

Tyr Leu Tyr Glu Val Ala Arg Arg His Pro Tyr Phe Tyr Gly Pro Glu
                165                 170                 175

Leu Leu Phe His Ala Glu Glu Tyr Lys Ala Asp Phe Thr Glu Cys Cys
            180                 185                 190

Pro Ala Asp Asp Lys Ala Gly Cys Leu Ile Pro Lys Leu Asp Ala Leu
        195                 200                 205

Lys Glu Arg Ile Leu Leu Ser Ser Ala Lys Glu Arg Leu Lys Cys Ser
    210                 215                 220

Ser Phe Gln Lys Phe Gly Glu Arg Ala Phe Lys Ala Trp Ser Val Ala
225                 230                 235                 240

Arg Leu Ser Gln Lys Phe Pro Lys Ala Asp Phe Ala Glu Val Ser Lys
                245                 250                 255

Ile Val Thr Asp Leu Thr Lys Val His Lys Glu Cys Cys His Gly Asp
            260                 265                 270

Leu Leu Glu Cys Ala Asp Asp Arg Ala Asp Leu Thr Lys Tyr Ile Cys
        275                 280                 285

Glu His Gln Asp Ser Ile Ser Gly Lys Leu Lys Ala Cys Cys Asp Lys
    290                 295                 300

Pro Leu Leu Gln Lys Ser His Cys Ile Ala Glu Val Lys Glu Asp Asp
305                 310                 315                 320

Leu Pro Ser Asp Leu Pro Ala Leu Ala Ala Asp Phe Ala Glu Asp Lys
                325                 330                 335

Glu Ile Cys Lys His Tyr Lys Asp Ala Lys Asp Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Thr Tyr Glu Ala Thr Leu Glu Lys Cys Cys
    370                 375                 380

Ala Glu Ala Asp Pro Pro Ala Cys Tyr Ala Thr Val Phe Asp Gln Phe
385                 390                 395                 400

```
Thr Pro Leu Val Glu Glu Pro Lys Ser Leu Val Lys Asn Cys Asp
                405                 410                 415

Leu Phe Glu Glu Val Gly Glu Tyr Asp Phe Gln Asn Ala Leu Ile Val
            420                 425                 430

Arg Tyr Thr Lys Lys Ala Pro Gln Val Ser Thr Pro Thr Leu Val Glu
            435                 440                 445

Ile Gly Arg Thr Leu Gly Lys Val Gly Ser Arg Cys Cys Lys Leu Pro
450                 455                 460

Glu Ser Glu Arg Leu Pro Cys Ser Glu Asn His Leu Ala Leu Ala Leu
465                 470                 475                 480

Asn Arg Leu Cys Val Leu His Glu Lys Thr Pro Val Ser Glu Lys Ile
                485                 490                 495

Thr Lys Cys Cys Thr Asp Ser Leu Ala Glu Arg Arg Pro Cys Phe Ser
            500                 505                 510

Ala Leu Glu Leu Asp Glu Gly Tyr Ile Pro Lys Glu Phe Lys Ala Glu
            515                 520                 525

Thr Phe Thr Phe His Ala Asp Ile Cys Thr Leu Pro Glu Asp Glu Lys
            530                 535                 540

Gln Ile Lys Lys Gln Ser Ala Leu Ala Glu Leu Val Lys His Lys Pro
545                 550                 555                 560

Lys Ala Thr Lys Glu Gln Leu Lys Thr Val Leu Gly Asn Phe Ser Ala
                565                 570                 575

Phe Val Ala Lys Cys Cys Gly Ala Glu Asp Lys Glu Ala Cys Phe Ala
            580                 585                 590

Glu Glu Gly Pro Lys Leu Val Ala Ser Ser Gln Leu Ala Leu Ala
            595                 600                 605

<210> SEQ ID NO 14
<211> LENGTH: 608
<212> TYPE: PRT
<213> ORGANISM: Oryctolagus cuniculus

<400> SEQUENCE: 14

Met Lys Trp Val Thr Phe Ile Ser Leu Leu Phe Leu Phe Ser Ser Ala
1               5                   10                  15

Tyr Ser Arg Gly Val Phe Arg Arg Glu Ala His Lys Ser Glu Ile Ala
            20                  25                  30

His Arg Phe Asn Asp Val Gly Glu Glu His Phe Ile Gly Leu Val Leu
        35                  40                  45

Ile Thr Phe Ser Gln Tyr Leu Gln Lys Cys Pro Tyr Glu Glu His Ala
    50                  55                  60

Lys Leu Val Lys Glu Val Thr Asp Leu Ala Lys Ala Cys Val Ala Asp
65                  70                  75                  80

Glu Ser Ala Ala Asn Cys Asp Lys Ser Leu His Asp Ile Phe Gly Asp
                85                  90                  95

Lys Ile Cys Ala Leu Pro Ser Leu Arg Asp Thr Tyr Gly Asp Val Ala
            100                 105                 110

Asp Cys Cys Glu Lys Lys Glu Pro Glu Arg Asn Glu Cys Phe Leu His
        115                 120                 125

His Lys Asp Asp Lys Pro Asp Leu Pro Pro Phe Ala Arg Pro Glu Ala
    130                 135                 140

Asp Val Leu Cys Lys Ala Phe His Asp Glu Lys Ala Phe Phe Gly
145                 150                 155                 160

His Tyr Leu Tyr Glu Val Ala Arg Arg His Pro Tyr Phe Tyr Ala Pro
                165                 170                 175
```

```
Glu Leu Leu Tyr Tyr Ala Gln Lys Tyr Lys Ala Ile Leu Thr Glu Cys
            180                 185                 190

Cys Glu Ala Ala Asp Lys Gly Ala Cys Leu Thr Pro Lys Leu Asp Ala
        195                 200                 205

Leu Glu Gly Lys Ser Leu Ile Ser Ala Ala Gln Glu Arg Leu Arg Cys
    210                 215                 220

Ala Ser Ile Gln Lys Phe Gly Asp Arg Ala Tyr Lys Ala Trp Ala Leu
225                 230                 235                 240

Val Arg Leu Ser Gln Arg Phe Pro Lys Ala Asp Phe Thr Asp Ile Ser
                245                 250                 255

Lys Ile Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
        275                 280                 285

Cys Glu His Gln Glu Thr Ile Ser Ser His Leu Lys Glu Cys Cys Asp
    290                 295                 300

Lys Pro Ile Leu Glu Lys Ala His Cys Ile Tyr Gly Leu His Asn Asp
305                 310                 315                 320

Glu Thr Pro Ala Gly Leu Pro Ala Val Ala Glu Glu Phe Val Glu Asp
                325                 330                 335

Lys Asp Val Cys Lys Asn Tyr Glu Glu Ala Lys Asp Leu Phe Leu Gly
            340                 345                 350

Lys Phe Leu Tyr Glu Tyr Ser Arg Arg His Pro Asp Tyr Ser Val Val
        355                 360                 365

Leu Leu Leu Arg Leu Gly Lys Ala Tyr Glu Ala Thr Leu Lys Lys Cys
    370                 375                 380

Cys Ala Thr Asp Asp Pro His Ala Cys Tyr Ala Lys Val Leu Asp Glu
385                 390                 395                 400

Phe Gln Pro Leu Val Asp Glu Pro Lys Asn Leu Val Lys Gln Asn Cys
                405                 410                 415

Glu Leu Tyr Glu Gln Leu Gly Asp Tyr Asn Phe Gln Asn Ala Leu Leu
            420                 425                 430

Val Arg Tyr Thr Lys Lys Val Pro Gln Val Ser Thr Pro Thr Leu Val
        435                 440                 445

Glu Ile Ser Arg Ser Leu Gly Lys Val Gly Ser Lys Cys Cys Lys His
    450                 455                 460

Pro Glu Ala Glu Arg Leu Pro Cys Val Glu Asp Tyr Leu Ser Val Val
465                 470                 475                 480

Leu Asn Arg Leu Cys Val Leu His Glu Lys Thr Pro Val Ser Glu Lys
                485                 490                 495

Val Thr Lys Cys Cys Ser Glu Ser Leu Val Asp Arg Arg Pro Cys Phe
            500                 505                 510

Ser Ala Leu Gly Pro Asp Glu Thr Tyr Val Pro Lys Glu Phe Asn Ala
        515                 520                 525

Glu Thr Phe Thr Phe His Ala Asp Ile Cys Thr Leu Pro Glu Thr Glu
    530                 535                 540

Arg Lys Ile Lys Lys Gln Thr Ala Leu Val Glu Leu Val Lys His Lys
545                 550                 555                 560

Pro His Ala Thr Asn Asp Gln Leu Lys Thr Val Val Gly Glu Phe Thr
                565                 570                 575

Ala Leu Leu Asp Lys Cys Cys Ser Ala Glu Asp Lys Glu Ala Cys Phe
            580                 585                 590
```

Ala Val Glu Gly Pro Lys Leu Val Glu Ser Ser Lys Ala Thr Leu Gly
    595                    600                  605

<210> SEQ ID NO 15
<211> LENGTH: 583
<212> TYPE: PRT
<213> ORGANISM: Capra hircus

<400> SEQUENCE: 15

Asp Thr His Lys Ser Glu Ile Ala His Arg Phe Asn Asp Leu Gly Glu
1               5                 10               15

Glu Asn Phe Gln Gly Leu Val Leu Ile Ala Phe Ser Gln Tyr Leu Gln
             20                 25               30

Gln Cys Pro Phe Asp Glu His Val Lys Leu Val Lys Glu Leu Thr Glu
        35                40               45

Phe Ala Lys Thr Cys Val Ala Asp Glu Ser His Ala Gly Cys Asp Lys
    50                  55                  60

Ser Leu His Thr Leu Phe Gly Asp Glu Leu Cys Lys Val Ala Thr Leu
65              70                75               80

Arg Glu Thr Tyr Gly Asp Met Ala Asp Cys Cys Glu Lys Gln Glu Pro
             85                 90               95

Glu Arg Asn Glu Cys Phe Leu Lys His Lys Asp Asp Ser Pro Asp Leu
            100               105             110

Pro Lys Leu Lys Pro Glu Pro Asp Thr Leu Cys Ala Glu Phe Lys Ala
        115                120               125

Asp Glu Lys Lys Phe Trp Gly Lys Tyr Leu Tyr Glu Val Ala Arg Arg
    130                 135               140

His Pro Tyr Phe Tyr Ala Pro Glu Leu Leu Tyr Tyr Ala Asn Lys Tyr
145             150                155             160

Asn Gly Val Phe Gln Glu Cys Cys Gln Ala Glu Asp Lys Gly Ala Cys
               165               170             175

Leu Leu Pro Lys Ile Glu Thr Met Arg Glu Lys Val Leu Ala Ser Ser
        180                185               190

Ala Arg Gln Arg Leu Arg Cys Ala Ser Ile Gln Lys Phe Gly Glu Arg
    195                 200               205

Ala Leu Lys Ala Trp Ser Val Ala Arg Leu Ser Gln Lys Phe Pro Lys
    210                 215               220

Ala Asp Phe Thr Asp Val Thr Lys Ile Val Thr Asp Leu Thr Lys Val
225             230                235             240

His Lys Glu Cys Cys His Gly Asp Leu Leu Glu Cys Ala Asp Asp Arg
               245               250             255

Ala Asp Leu Ala Lys Tyr Ile Cys Asp His Gln Asp Thr Leu Ser Ser
            260               265             270

Lys Leu Lys Glu Cys Cys Asp Lys Pro Val Leu Glu Lys Ser His Cys
    275                 280               285

Ile Ala Glu Ile Asp Lys Asp Ala Val Pro Glu Asn Leu Pro Pro Leu
    290                 295               300

Thr Ala Asp Phe Ala Glu Asp Lys Glu Val Cys Lys Asn Tyr Gln Glu
305             310                315             320

Ala Lys Asp Val Phe Leu Gly Ser Phe Leu Tyr Glu Tyr Ser Arg Arg
               325               330             335

His Pro Glu Tyr Ala Val Ser Val Leu Leu Arg Leu Ala Lys Glu Tyr
            340               345             350

Glu Ala Thr Leu Glu Asp Cys Cys Ala Lys Glu Asp Pro His Ala Cys
    355                 360               365

Tyr Ala Thr Val Phe Asp Lys Leu Lys His Leu Val Asp Glu Pro Gln
            370                 375                 380

Asn Leu Ile Lys Lys Asn Cys Glu Leu Phe Glu Lys His Gly Glu Tyr
385                 390                 395                 400

Gly Phe Gln Asn Ala Leu Ile Val Arg Tyr Thr Arg Lys Ala Pro Gln
                405                 410                 415

Val Ser Thr Pro Thr Leu Val Glu Ile Ser Arg Ser Leu Gly Lys Val
                420                 425                 430

Gly Thr Lys Cys Cys Ala Lys Pro Glu Ser Glu Arg Met Pro Cys Thr
            435                 440                 445

Glu Asp Tyr Leu Ser Leu Ile Leu Asn Arg Leu Cys Val Leu His Glu
            450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Asp Leu Thr Leu Asp Glu Thr Tyr
                485                 490                 495

Val Pro Lys Pro Phe Asp Gly Glu Ser Phe Thr Phe His Ala Asp Ile
                500                 505                 510

Cys Thr Leu Pro Asp Thr Glu Lys Gln Ile Lys Lys Gln Thr Ala Leu
            515                 520                 525

Val Glu Leu Leu Lys His Lys Pro Lys Ala Thr Asp Glu Gln Leu Lys
            530                 535                 540

Thr Val Met Glu Asn Phe Val Ala Phe Val Asp Lys Cys Cys Ala Ala
545                 550                 555                 560

Asp Asp Lys Glu Gly Cys Phe Leu Leu Glu Gly Pro Lys Leu Val Ala
                565                 570                 575

Ser Thr Gln Ala Ala Leu Ala
            580

<210> SEQ ID NO 16
<211> LENGTH: 607
<212> TYPE: PRT
<213> ORGANISM: Ovis aries

<400> SEQUENCE: 16

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Asn Asp Leu Gly Glu Glu Asn Phe Gln Gly Leu Val Leu
            35                  40                  45

Ile Ala Phe Ser Gln Tyr Leu Gln Gln Cys Pro Phe Asp Glu His Val
        50                  55                  60

Lys Leu Val Lys Glu Leu Thr Glu Phe Ala Lys Thr Cys Val Ala Asp
65                  70                  75                  80

Glu Ser His Ala Gly Cys Asp Lys Ser Leu His Thr Leu Phe Gly Asp
                85                  90                  95

Glu Leu Cys Lys Val Ala Thr Leu Arg Glu Thr Tyr Gly Asp Met Ala
                100                 105                 110

Asp Cys Cys Glu Lys Gln Glu Pro Glu Arg Asn Glu Cys Phe Leu Asn
            115                 120                 125

His Lys Asp Asp Ser Pro Asp Leu Pro Lys Leu Lys Pro Glu Pro Asp
130                 135                 140

Thr Leu Cys Ala Glu Phe Lys Ala Asp Glu Lys Lys Phe Trp Gly Lys

```
                145                 150                 155                 160
            Tyr Leu Tyr Glu Val Ala Arg Arg His Pro Tyr Phe Tyr Ala Pro Glu
                            165                 170                 175
            Leu Leu Tyr Tyr Ala Asn Lys Tyr Asn Gly Val Phe Gln Glu Cys Cys
                            180                 185                 190
            Gln Ala Glu Asp Lys Gly Ala Cys Leu Leu Pro Lys Ile Asp Ala Met
                            195                 200                 205
            Arg Glu Lys Val Leu Ala Ser Ser Ala Arg Gln Arg Leu Arg Cys Ala
                    210                 215                 220
            Ser Ile Gln Lys Phe Gly Glu Arg Ala Leu Lys Ala Trp Ser Val Ala
            225                 230                 235                 240
            Arg Leu Ser Gln Lys Phe Pro Lys Ala Asp Phe Thr Asp Val Thr Lys
                            245                 250                 255
            Ile Val Thr Asp Leu Thr Lys Val His Lys Glu Cys Cys His Gly Asp
                            260                 265                 270
            Leu Leu Glu Cys Ala Asp Asp Arg Ala Asp Leu Ala Lys Tyr Ile Cys
                            275                 280                 285
            Asp His Gln Asp Ala Leu Ser Ser Lys Leu Lys Glu Cys Cys Asp Lys
                    290                 295                 300
            Pro Val Leu Glu Lys Ser His Cys Ile Ala Glu Val Asp Lys Asp Ala
            305                 310                 315                 320
            Val Pro Glu Asn Leu Pro Pro Leu Thr Ala Asp Phe Ala Glu Asp Lys
                            325                 330                 335
            Glu Val Cys Lys Asn Tyr Gln Glu Ala Lys Asp Val Phe Leu Gly Ser
                            340                 345                 350
            Phe Leu Tyr Glu Tyr Ser Arg Arg His Pro Glu Tyr Ala Val Ser Val
                            355                 360                 365
            Leu Leu Arg Leu Ala Lys Glu Tyr Glu Ala Thr Leu Glu Asp Cys Cys
                    370                 375                 380
            Ala Lys Glu Asp Pro His Ala Cys Tyr Ala Thr Val Phe Asp Lys Leu
            385                 390                 395                 400
            Lys His Leu Val Asp Glu Pro Gln Asn Leu Ile Lys Lys Asn Cys Glu
                            405                 410                 415
            Leu Phe Glu Lys His Gly Glu Tyr Gly Phe Gln Asn Ala Leu Ile Val
                            420                 425                 430
            Arg Tyr Thr Arg Lys Ala Pro Gln Val Ser Thr Pro Thr Leu Val Glu
                            435                 440                 445
            Ile Ser Arg Ser Leu Gly Lys Val Gly Thr Lys Cys Cys Ala Lys Pro
                    450                 455                 460
            Glu Ser Glu Arg Met Pro Cys Thr Glu Asp Tyr Leu Ser Leu Ile Leu
            465                 470                 475                 480
            Asn Arg Leu Cys Val Leu His Glu Lys Thr Pro Val Ser Glu Lys Val
                            485                 490                 495
            Thr Lys Cys Cys Thr Glu Ser Leu Val Asn Arg Arg Pro Cys Phe Ser
                            500                 505                 510
            Asp Leu Thr Leu Asp Glu Thr Tyr Val Pro Lys Pro Phe Asp Glu Lys
                            515                 520                 525
            Phe Phe Thr Phe His Ala Asp Ile Cys Thr Leu Pro Asp Thr Glu Lys
                            530                 535                 540
            Gln Ile Lys Lys Gln Thr Ala Leu Val Glu Leu Leu Lys His Lys Pro
            545                 550                 555                 560
            Lys Ala Thr Asp Glu Gln Leu Lys Thr Val Met Glu Asn Phe Val Ala
                            565                 570                 575
```

Phe Val Asp Lys Cys Cys Ala Ala Asp Asp Lys Glu Gly Cys Phe Val
            580                 585                 590

Leu Glu Gly Pro Lys Leu Val Ala Ser Thr Gln Ala Ala Leu Ala
        595                 600                 605

<210> SEQ ID NO 17
<211> LENGTH: 608
<212> TYPE: PRT
<213> ORGANISM: canis lupus familiaris

<400> SEQUENCE: 17

Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
                20                  25                  30

His Arg Tyr Asn Asp Leu Gly Glu Glu His Phe Arg Gly Leu Val Leu
            35                  40                  45

Val Ala Phe Ser Gln Tyr Leu Gln Gln Cys Pro Phe Glu Asp His Val
    50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
            100                 105                 110

Asp Cys Cys Glu Lys Gln Glu Pro Asp Arg Asn Glu Cys Phe Leu Ala
        115                 120                 125

His Lys Asp Asp Asn Pro Gly Phe Pro Pro Leu Val Ala Pro Glu Pro
    130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
            180                 185                 190

Cys Gln Ala Ala Asp Lys Ala Ala Cys Leu Gly Pro Lys Ile Glu Ala
        195                 200                 205

Leu Arg Glu Lys Val Leu Leu Ser Ser Ala Lys Glu Arg Phe Lys Cys
    210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
                245                 250                 255

Lys Val Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
        275                 280                 285

Cys Glu Asn Gln Asp Ser Ile Ser Thr Lys Leu Lys Glu Cys Cys Asp
    290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly

```
                    340                 345                 350
Thr Phe Leu Tyr Glu Tyr Ala Arg Arg His Pro Glu Tyr Ser Val Ser
        355                 360                 365

Leu Leu Leu Arg Leu Ala Lys Glu Tyr Glu Ala Thr Leu Glu Lys Cys
        370                 375                 380

Cys Ala Thr Asp Asp Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                    405                 410                 415

Glu Leu Phe Glu Lys Leu Gly Glu Tyr Gly Phe Gln Asn Ala Leu Leu
            420                 425                 430

Val Arg Tyr Thr Lys Lys Ala Pro Gln Val Ser Thr Pro Thr Leu Val
        435                 440                 445

Glu Val Ser Arg Lys Leu Gly Lys Val Gly Thr Lys Cys Cys Lys Lys
        450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
                500                 505                 510

Ser Gly Leu Glu Val Asp Glu Thr Tyr Val Pro Lys Glu Phe Asn Ala
            515                 520                 525

Glu Thr Phe Thr Phe His Ala Asp Leu Cys Thr Leu Pro Glu Ala Glu
        530                 535                 540

Lys Gln Val Lys Gln Thr Ala Leu Val Glu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
            580                 585                 590

Ser Glu Glu Gly Pro Lys Leu Val Ala Ala Gln Ala Ala Leu Val
        595                 600                 605

<210> SEQ ID NO 18
<211> LENGTH: 615
<212> TYPE: PRT
<213> ORGANISM: Gallus gallus

<400> SEQUENCE: 18

Met Lys Trp Val Thr Leu Ile Ser Phe Ile Phe Leu Phe Ser Ser Ala
1               5                   10                  15

Thr Ser Arg Asn Leu Gln Arg Phe Ala Arg Asp Ala Glu His Lys Ser
            20                  25                  30

Glu Ile Ala His Arg Tyr Asn Asp Leu Lys Glu Glu Thr Phe Lys Ala
        35                  40                  45

Val Ala Met Ile Thr Phe Ala Gln Tyr Leu Gln Arg Cys Ser Tyr Glu
    50                  55                  60

Gly Leu Ser Lys Leu Val Lys Asp Val Asp Leu Ala Gln Lys Cys
65                  70                  75                  80

Val Ala Asn Glu Asp Ala Pro Glu Cys Ser Lys Pro Leu Pro Ser Ile
                85                  90                  95

Ile Leu Asp Glu Ile Cys Gln Val Glu Lys Leu Arg Asp Ser Tyr Gly
            100                 105                 110
```

```
Ala Met Ala Asp Cys Cys Ser Lys Ala Asp Pro Glu Arg Asn Glu Cys
            115                 120                 125
Phe Leu Ser Phe Lys Val Ser Gln Pro Asp Phe Val Gln Pro Tyr Gln
    130                 135                 140
Arg Pro Ala Ser Asp Val Ile Cys Gln Glu Tyr Gln Asp Asn Arg Val
145                 150                 155                 160
Ser Phe Leu Gly His Phe Ile Tyr Ser Val Ala Arg Arg His Pro Phe
                165                 170                 175
Leu Tyr Ala Pro Ala Ile Leu Ser Phe Ala Val Asp Phe Glu His Ala
            180                 185                 190
Leu Gln Ser Cys Cys Lys Glu Ser Asp Val Gly Ala Cys Leu Asp Thr
        195                 200                 205
Lys Glu Ile Val Met Arg Glu Lys Ala Lys Gly Val Ser Val Lys Gln
210                 215                 220
Gln Tyr Phe Cys Gly Ile Leu Lys Gln Phe Gly Asp Arg Val Phe Gln
225                 230                 235                 240
Ala Arg Gln Leu Ile Tyr Leu Ser Gln Lys Tyr Pro Lys Ala Pro Phe
                245                 250                 255
Ser Glu Val Ser Lys Phe Val His Asp Ser Ile Gly Val His Lys Glu
            260                 265                 270
Cys Cys Glu Gly Asp Met Val Glu Cys Met Asp Asp Met Ala Arg Met
        275                 280                 285
Met Ser Asn Leu Cys Ser Gln Gln Asp Val Phe Ser Gly Lys Ile Lys
    290                 295                 300
Asp Cys Cys Glu Lys Pro Ile Val Glu Arg Ser Gln Cys Ile Met Glu
305                 310                 315                 320
Ala Glu Phe Asp Glu Lys Pro Ala Asp Leu Pro Ser Leu Val Glu Lys
                325                 330                 335
Tyr Ile Glu Asp Lys Glu Val Cys Lys Ser Phe Glu Ala Gly His Asp
            340                 345                 350
Ala Phe Met Ala Glu Phe Val Tyr Glu Tyr Ser Arg Arg His Pro Glu
        355                 360                 365
Phe Ser Ile Gln Leu Ile Met Arg Ile Ala Lys Gly Tyr Glu Ser Leu
    370                 375                 380
Leu Glu Lys Cys Cys Lys Thr Asp Asn Pro Ala Glu Cys Tyr Ala Asn
385                 390                 395                 400
Ala Gln Glu Gln Leu Asn Gln His Ile Lys Glu Thr Gln Asp Val Val
                405                 410                 415
Lys Thr Asn Cys Asp Leu Leu His Asp His Gly Glu Ala Asp Phe Leu
            420                 425                 430
Lys Ser Ile Leu Ile Arg Tyr Thr Lys Lys Met Pro Gln Val Pro Thr
        435                 440                 445
Asp Leu Leu Leu Glu Thr Gly Lys Lys Met Thr Thr Ile Gly Thr Lys
    450                 455                 460
Cys Cys Gln Leu Gly Glu Asp Arg Arg Met Ala Cys Ser Glu Gly Tyr
465                 470                 475                 480
Leu Ser Ile Val Ile His Asp Thr Cys Arg Lys Gln Glu Thr Thr Pro
                485                 490                 495
Ile Asn Asp Asn Val Ser Gln Cys Cys Ser Gln Leu Tyr Ala Asn Arg
            500                 505                 510
Arg Pro Cys Phe Thr Ala Met Gly Val Asp Thr Lys Tyr Val Pro Pro
        515                 520                 525
Pro Phe Asn Pro Asp Met Phe Ser Phe Asp Glu Lys Leu Cys Ser Ala
```

```
Pro Ala Glu Glu Arg Glu Val Gly Gln Met Lys Leu Leu Ile Asn Leu
545                 550                 555                 560

Ile Lys Arg Lys Pro Gln Met Thr Glu Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Glu Gly Ala Asn Leu Ile Val Gln Ser Arg
        595                 600                 605

Ala Thr Leu Gly Ile Gly Ala
        610                 615

<210> SEQ ID NO 19
<211> LENGTH: 607
<212> TYPE: PRT
<213> ORGANISM: Sus scrofa

<400> SEQUENCE: 19

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys Cys Ala
    210                 215                 220

Ser Ile Gln Lys Phe Gly Glu Arg Ala Phe Lys Ala Trp Ser Leu Ala
225                 230                 235                 240

Arg Leu Ser Gln Arg Phe Pro Lys Ala Asp Phe Thr Glu Ile Ser Lys
                245                 250                 255

Ile Val Thr Asp Leu Ala Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285
```

Glu Asn Gln Asp Thr Ile Ser Thr Lys Leu Lys Glu Cys Cys Asp Lys
            290                 295                 300

Pro Leu Glu Lys Ser His Cys Ile Ala Glu Ala Lys Arg Asp Glu
305                 310                 315                 320

Leu Pro Ala Asp Leu Asn Pro Leu Glu His Asp Phe Val Asp Lys
                325                 330                 335

Glu Val Cys Lys Asn Tyr Lys Glu Ala Lys His Val Phe Leu Gly Thr
                340                 345                 350

Phe Leu Tyr Glu Tyr Ser Arg Arg His Pro Asp Tyr Ser Val Ser Leu
            355                 360                 365

Leu Leu Arg Ile Ala Lys Ile Tyr Glu Ala Thr Leu Glu Asp Cys Cys
370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                405                 410                 415

Leu Phe Glu Lys Leu Gly Glu Tyr Gly Phe Gln Asn Ala Leu Ile Val
                420                 425                 430

Arg Tyr Thr Lys Lys Val Pro Gln Val Ser Thr Pro Thr Leu Val Glu
            435                 440                 445

Val Ala Arg Lys Leu Gly Leu Val Gly Ser Arg Cys Cys Lys Arg Pro
450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
                500                 505                 510

Ala Leu Thr Pro Asp Glu Thr Tyr Lys Pro Lys Glu Phe Val Glu Gly
            515                 520                 525

Thr Phe Thr Phe His Ala Asp Leu Cys Thr Leu Pro Glu Asp Glu Lys
            530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
                580                 585                 590

Val Glu Gly Pro Lys Phe Val Ile Glu Ile Arg Gly Ile Leu Ala
            595                 600                 605

<210> SEQ ID NO 20
<211> LENGTH: 387
<212> TYPE: PRT
<213> ORGANISM: Artificial sequence
<220> FEATURE:
<223> OTHER INFORMATION: Artificial albumin variant: human serum albumin
      domain 1 and human serum albumin domain 2

<400> SEQUENCE: 20

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

```
Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu
385

<210> SEQ ID NO 21
<211> LENGTH: 403
<212> TYPE: PRT
<213> ORGANISM: Artificial sequence
<220> FEATURE:
<223> OTHER INFORMATION: Artificial albumin variant: human serum albumin
      domain 2 and human serum albumin domain 3

<400> SEQUENCE: 21

Asp Glu Leu Arg Asp Glu Gly Lys Ala Ser Ser Ala Lys Gln Arg Leu
```

```
              1               5                   10                  15
            Lys Cys Ala Ser Leu Gln Lys Phe Gly Glu Arg Ala Phe Lys Ala Trp
                         20                  25                  30
            Ala Val Ala Arg Leu Ser Gln Arg Phe Pro Lys Ala Glu Phe Ala Glu
                         35                  40                  45
            Val Ser Lys Leu Val Thr Asp Leu Thr Lys Val His Thr Glu Cys Cys
             50                  55                  60
            His Gly Asp Leu Leu Glu Cys Ala Asp Asp Arg Ala Asp Leu Ala Lys
             65                  70                  75                  80
            Tyr Ile Cys Glu Asn Gln Asp Ser Ile Ser Ser Lys Leu Lys Glu Cys
                         85                  90                  95
            Cys Glu Lys Pro Leu Leu Glu Lys Ser His Cys Ile Ala Glu Val Glu
                         100                 105                 110
            Asn Asp Glu Met Pro Ala Asp Leu Pro Ser Leu Ala Ala Asp Phe Val
                         115                 120                 125
            Glu Ser Lys Asp Val Cys Lys Asn Tyr Ala Glu Ala Lys Asp Val Phe
                         130                 135                 140
            Leu Gly Met Phe Leu Tyr Glu Tyr Ala Arg Arg His Pro Asp Tyr Ser
            145                 150                 155                 160
            Val Val Leu Leu Leu Arg Leu Ala Lys Thr Tyr Glu Thr Thr Leu Glu
                         165                 170                 175
            Lys Cys Cys Ala Ala Ala Asp Pro His Glu Cys Tyr Ala Lys Val Phe
                         180                 185                 190
            Asp Glu Phe Lys Pro Leu Val Glu Glu Pro Gln Asn Leu Ile Lys Gln
                         195                 200                 205
            Asn Cys Glu Leu Phe Glu Gln Leu Gly Glu Tyr Lys Phe Gln Asn Ala
            210                 215                 220
            Leu Leu Val Arg Tyr Thr Lys Lys Val Pro Gln Val Ser Thr Pro Thr
            225                 230                 235                 240
            Leu Val Glu Val Ser Arg Asn Leu Gly Lys Val Gly Ser Lys Cys Cys
                         245                 250                 255
            Lys His Pro Glu Ala Lys Arg Met Pro Cys Ala Glu Asp Tyr Leu Ser
                         260                 265                 270
            Val Val Leu Asn Gln Leu Cys Val Leu His Glu Lys Thr Pro Val Ser
                         275                 280                 285
            Asp Arg Val Thr Lys Cys Cys Thr Glu Ser Leu Val Asn Arg Arg Pro
                         290                 295                 300
            Cys Phe Ser Ala Leu Glu Val Asp Glu Thr Tyr Val Pro Lys Glu Phe
            305                 310                 315                 320
            Asn Ala Glu Thr Phe Thr Phe His Ala Asp Ile Cys Thr Leu Ser Glu
                         325                 330                 335
            Lys Glu Arg Gln Ile Lys Lys Gln Thr Ala Leu Val Glu Leu Val Lys
                         340                 345                 350
            His Lys Pro Lys Ala Thr Lys Glu Gln Leu Lys Ala Val Met Asp Asp
                         355                 360                 365
            Phe Ala Ala Phe Val Glu Lys Cys Cys Lys Ala Asp Asp Lys Glu Thr
            370                 375                 380
            Cys Phe Ala Glu Glu Gly Lys Lys Leu Val Ala Ala Ser Gln Ala Ala
            385                 390                 395                 400
            Leu Gly Leu

<210> SEQ ID NO 22
<211> LENGTH: 399
```

<212> TYPE: PRT
<213> ORGANISM: Artificial sequence
<220> FEATURE:
<223> OTHER INFORMATION: Artificial albumin variant: human serum albumin
      domain 1 and human serum albumin domain 3

<400> SEQUENCE: 22

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Val Glu Glu Pro Gln Asn Leu Ile Lys Gln Asn Cys Glu Leu
        195                 200                 205

Phe Glu Gln Leu Gly Glu Tyr Lys Phe Gln Asn Ala Leu Leu Val Arg
    210                 215                 220

Tyr Thr Lys Lys Val Pro Gln Val Ser Thr Pro Thr Leu Val Glu Val
225                 230                 235                 240

Ser Arg Asn Leu Gly Lys Val Gly Ser Lys Cys Cys Lys His Pro Glu
                245                 250                 255

Ala Lys Arg Met Pro Cys Ala Glu Asp Tyr Leu Ser Val Val Leu Asn
            260                 265                 270

Gln Leu Cys Val Leu His Glu Lys Thr Pro Val Ser Asp Arg Val Thr
        275                 280                 285

Lys Cys Cys Thr Glu Ser Leu Val Asn Arg Arg Pro Cys Phe Ser Ala
    290                 295                 300

Leu Glu Val Asp Glu Thr Tyr Val Pro Lys Glu Phe Asn Ala Glu Thr
305                 310                 315                 320

Phe Thr Phe His Ala Asp Ile Cys Thr Leu Ser Glu Lys Glu Arg Gln
                325                 330                 335

Ile Lys Lys Gln Thr Ala Leu Val Glu Leu Val Lys His Lys Pro Lys
            340                 345                 350

Ala Thr Lys Glu Gln Leu Lys Ala Val Met Asp Asp Phe Ala Ala Phe
        355                 360                 365

Val Glu Lys Cys Cys Lys Ala Asp Asp Lys Glu Thr Cys Phe Ala Glu
    370                 375                 380
```

```
Glu Gly Lys Lys Leu Val Ala Ala Ser Gln Ala Ala Leu Gly Leu
385                 390                 395

<210> SEQ ID NO 23
<211> LENGTH: 205
<212> TYPE: PRT
<213> ORGANISM: Artificial sequence
<220> FEATURE:
<223> OTHER INFORMATION: Artificial albumin variant: human serum albumin
      domain 3

<400> SEQUENCE: 23

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu
        195                 200                 205

<210> SEQ ID NO 24
<211> LENGTH: 410
<212> TYPE: PRT
<213> ORGANISM: Artificial sequence
<220> FEATURE:
<223> OTHER INFORMATION: Artificial albumin variant: two consecutive
      copies of human serum albumin domain 3

<400> SEQUENCE: 24

Val Glu Glu Pro Gln Asn Leu Ile Lys Gln Asn Cys Glu Leu Phe Glu
1               5                   10                  15

Gln Leu Gly Glu Tyr Lys Phe Gln Asn Ala Leu Leu Val Arg Tyr Thr
            20                  25                  30

Lys Lys Val Pro Gln Val Ser Thr Pro Thr Leu Val Glu Val Ser Arg
        35                  40                  45

Asn Leu Gly Lys Val Gly Ser Lys Cys Cys Lys His Pro Glu Ala Lys
    50                  55                  60

Arg Met Pro Cys Ala Glu Asp Tyr Leu Ser Val Val Leu Asn Gln Leu
65                  70                  75                  80
```

Cys Val Leu His Glu Lys Thr Pro Val Ser Asp Arg Val Thr Lys Cys
                85                  90                  95

Cys Thr Glu Ser Leu Val Asn Arg Arg Pro Cys Phe Ser Ala Leu Glu
            100                 105                 110

Val Asp Glu Thr Tyr Val Pro Lys Glu Phe Asn Ala Glu Thr Phe Thr
        115                 120                 125

Phe His Ala Asp Ile Cys Thr Leu Ser Glu Lys Glu Arg Gln Ile Lys
    130                 135                 140

Lys Gln Thr Ala Leu Val Glu Leu Val Lys His Lys Pro Lys Ala Thr
145                 150                 155                 160

Lys Glu Gln Leu Lys Ala Val Met Asp Asp Phe Ala Ala Phe Val Glu
                165                 170                 175

Lys Cys Cys Lys Ala Asp Asp Lys Glu Thr Cys Phe Ala Glu Glu Gly
            180                 185                 190

Lys Lys Leu Val Ala Ala Ser Gln Ala Ala Leu Gly Leu Val Glu Glu
        195                 200                 205

Pro Gln Asn Leu Ile Lys Gln Asn Cys Glu Leu Phe Glu Gln Leu Gly
    210                 215                 220

Glu Tyr Lys Phe Gln Asn Ala Leu Leu Val Arg Tyr Thr Lys Lys Val
225                 230                 235                 240

Pro Gln Val Ser Thr Pro Thr Leu Val Glu Val Ser Arg Asn Leu Gly
                245                 250                 255

Lys Val Gly Ser Lys Cys Cys Lys His Pro Glu Ala Lys Arg Met Pro
            260                 265                 270

Cys Ala Glu Asp Tyr Leu Ser Val Val Leu Asn Gln Leu Cys Val Leu
        275                 280                 285

His Glu Lys Thr Pro Val Ser Asp Arg Val Thr Lys Cys Cys Thr Glu
    290                 295                 300

Ser Leu Val Asn Arg Arg Pro Cys Phe Ser Ala Leu Glu Val Asp Glu
305                 310                 315                 320

Thr Tyr Val Pro Lys Glu Phe Asn Ala Glu Thr Phe Thr Phe His Ala
                325                 330                 335

Asp Ile Cys Thr Leu Ser Glu Lys Glu Arg Gln Ile Lys Lys Gln Thr
            340                 345                 350

Ala Leu Val Glu Leu Val Lys His Lys Pro Lys Ala Thr Lys Glu Gln
        355                 360                 365

Leu Lys Ala Val Met Asp Asp Phe Ala Ala Phe Val Glu Lys Cys Cys
    370                 375                 380

Lys Ala Asp Asp Lys Glu Thr Cys Phe Ala Glu Glu Gly Lys Lys Leu
385                 390                 395                 400

Val Ala Ala Ser Gln Ala Ala Leu Gly Leu
                405                 410

<210> SEQ ID NO 25
<211> LENGTH: 584
<212> TYPE: PRT
<213> ORGANISM: Artificial sequence
<220> FEATURE:
<223> OTHER INFORMATION: Artificial albumin variant: human serum albumin
      domain 1, human serum albumin domain 2 and rabbit serum albumin
      domain 3

<400> SEQUENCE: 25

Asp Ala His Lys Ser Glu Val Ala His Arg Phe Lys Asp Leu Gly Glu
1               5                   10                  15

-continued

```
Glu Asn Phe Lys Ala Leu Val Leu Ile Ala Phe Ala Gln Tyr Leu Gln
                 20                  25                  30
Gln Cys Pro Phe Glu Asp His Val Lys Leu Val Asn Glu Val Thr Glu
         35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
        100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Asp Glu Pro
370                 375                 380
Lys Asn Leu Val Lys Gln Asn Cys Glu Leu Tyr Glu Gln Leu Gly Asp
385                 390                 395                 400
Tyr Asn Phe Gln Asn Ala Leu Leu Val Arg Tyr Thr Lys Lys Val Pro
                405                 410                 415
Gln Val Ser Thr Pro Thr Leu Val Glu Ile Ser Arg Ser Leu Gly Lys
        420                 425                 430
Val Gly Ser Lys Cys Cys Lys His Pro Glu Ala Glu Arg Leu Pro Cys
```

```
                435                 440                 445
Val Glu Asp Tyr Leu Ser Val Val Leu Asn Arg Leu Cys Val Leu His
    450                 455                 460

Glu Lys Thr Pro Val Ser Glu Lys Val Thr Lys Cys Cys Ser Glu Ser
465                 470                 475                 480

Leu Val Asp Arg Arg Pro Cys Phe Ser Ala Leu Gly Pro Asp Glu Thr
                485                 490                 495

Tyr Val Pro Lys Glu Phe Asn Ala Glu Thr Phe Thr Phe His Ala Asp
                500                 505                 510

Ile Cys Thr Leu Pro Glu Thr Glu Arg Lys Ile Lys Lys Gln Thr Ala
                515                 520                 525

Leu Val Glu Leu Val Lys His Lys Pro His Ala Thr Asn Asp Gln Leu
            530                 535                 540

Lys Thr Val Val Gly Glu Phe Thr Ala Leu Leu Asp Lys Cys Cys Ser
545                 550                 555                 560

Ala Glu Asp Lys Glu Ala Cys Phe Ala Val Glu Gly Pro Lys Leu Val
                565                 570                 575

Glu Ser Ser Lys Ala Thr Leu Gly
            580

<210> SEQ ID NO 26
<211> LENGTH: 585
<212> TYPE: PRT
<213> ORGANISM: Artificial sequence
<220> FEATURE:
<223> OTHER INFORMATION: Artificial albumin variant: rabbit serum
      albumin domain 1, rabbit serum albumin domain 2 and human serum
      albumin domain 3

<400> SEQUENCE: 26

Glu Ala His Lys Ser Glu Ile Ala His Arg Phe Asn Asp Val Gly Glu
1               5                   10                  15

Glu His Phe Ile Gly Leu Val Leu Ile Thr Phe Ser Gln Tyr Leu Gln
            20                  25                  30

Lys Cys Pro Tyr Glu Glu His Ala Lys Leu Val Lys Glu Val Thr Asp
        35                  40                  45

Leu Ala Lys Ala Cys Val Ala Asp Glu Ser Ala Ala Asn Cys Asp Lys
    50                  55                  60

Ser Leu His Asp Ile Phe Gly Asp Lys Ile Cys Ala Leu Pro Ser Leu
65                  70                  75                  80

Arg Asp Thr Tyr Gly Asp Val Ala Asp Cys Cys Glu Lys Lys Glu Pro
                85                  90                  95

Glu Arg Asn Glu Cys Phe Leu His His Lys Asp Asp Lys Pro Asp Leu
            100                 105                 110

Pro Pro Phe Ala Arg Pro Glu Ala Asp Val Leu Cys Lys Ala Phe His
        115                 120                 125

Asp Asp Glu Lys Ala Phe Phe Gly His Tyr Leu Tyr Glu Val Ala Arg
    130                 135                 140

Arg His Pro Tyr Phe Tyr Ala Pro Glu Leu Leu Tyr Tyr Ala Gln Lys
145                 150                 155                 160

Tyr Lys Ala Ile Leu Thr Glu Cys Cys Glu Ala Ala Asp Lys Gly Ala
                165                 170                 175

Cys Leu Thr Pro Lys Leu Asp Ala Leu Glu Gly Lys Ser Leu Ile Ser
            180                 185                 190

Ala Ala Gln Glu Arg Leu Arg Cys Ala Ser Ile Gln Lys Phe Gly Asp
        195                 200                 205
```

-continued

Arg Ala Tyr Lys Ala Trp Ala Leu Val Arg Leu Ser Gln Arg Phe Pro
            210                 215                 220

Lys Ala Asp Phe Thr Asp Ile Ser Lys Ile Val Thr Asp Leu Thr Lys
225                 230                 235                 240

Val His Lys Glu Cys Cys His Gly Asp Leu Leu Glu Cys Ala Asp Asp
                    245                 250                 255

Arg Ala Asp Leu Ala Lys Tyr Met Cys Glu His Gln Glu Thr Ile Ser
            260                 265                 270

Ser His Leu Lys Glu Cys Cys Asp Lys Pro Ile Leu Glu Lys Ala His
        275                 280                 285

Cys Ile Tyr Gly Leu His Asn Asp Glu Thr Pro Ala Gly Leu Pro Ala
290                 295                 300

Val Ala Glu Glu Phe Val Glu Asp Lys Asp Val Cys Lys Asn Tyr Glu
305                 310                 315                 320

Glu Ala Lys Asp Leu Phe Leu Gly Lys Phe Leu Tyr Glu Tyr Ser Arg
                325                 330                 335

Arg His Pro Asp Tyr Ser Val Val Leu Leu Arg Leu Gly Lys Ala
            340                 345                 350

Tyr Glu Ala Thr Leu Lys Lys Cys Cys Ala Thr Asp Asp Pro His Ala
            355                 360                 365

Cys Tyr Ala Lys Val Leu Asp Glu Phe Gln Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 27
<211> LENGTH: 585
<212> TYPE: PRT
<213> ORGANISM: Artificial sequence
<220> FEATURE:

<223> OTHER INFORMATION: Artificial albumin variant: sheep serum albumin
domain 1, sheep serum albumin domain 2 and human serum albumin
domain 3

<400> SEQUENCE: 27

```
Asp Thr His Lys Ser Glu Ile Ala His Arg Phe Asn Asp Leu Gly Glu
1               5                   10                  15

Glu Asn Phe Gln Gly Leu Val Leu Ile Ala Phe Ser Gln Tyr Leu Gln
            20                  25                  30

Gln Cys Pro Phe Asp Glu His Val Lys Leu Val Lys Glu Leu Thr Glu
        35                  40                  45

Phe Ala Lys Thr Cys Val Ala Asp Glu Ser His Ala Gly Cys Asp Lys
50                  55                  60

Ser Leu His Thr Leu Phe Gly Asp Glu Leu Cys Lys Val Ala Thr Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Asn His Lys Asp Asp Ser Pro Asp Leu
            100                 105                 110

Pro Lys Leu Lys Pro Glu Pro Asp Thr Leu Cys Ala Glu Phe Lys Ala
        115                 120                 125

Asp Glu Lys Lys Phe Trp Gly Lys Tyr Leu Tyr Glu Val Ala Arg Arg
130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Asp Ala Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
210                 215                 220

Ala Asp Phe Thr Asp Val Thr Lys Ile Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp His Gln Asp Ala Leu Ser Ser
            260                 265                 270

Lys Leu Lys Glu Cys Cys Asp Lys Pro Val Leu Glu Lys Ser His Cys
        275                 280                 285

Ile Ala Glu Val Asp Lys Asp Ala Val Pro Glu Asn Leu Pro Pro Leu
290                 295                 300

Thr Ala Asp Phe Ala Glu Asp Lys Glu Val Cys Lys Asn Tyr Gln Glu
305                 310                 315                 320

Ala Lys Asp Val Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350

Glu Ala Thr Leu Glu Asp Cys Cys Ala Lys Glu Asp Pro His Ala Cys
        355                 360                 365

Tyr Ala Thr Val Phe Asp Lys Leu Lys His Leu Val Val Glu Glu Pro
370                 375                 380

Gln Asn Leu Ile Lys Gln Asn Cys Glu Leu Phe Glu Gln Leu Gly Glu
```

```
                385                 390                 395                 400
Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 28
<211> LENGTH: 583
<212> TYPE: PRT
<213> ORGANISM: Artificial sequence
<220> FEATURE:
<223> OTHER INFORMATION: Artificial albumin variant: human serum albumin
      domain 1, human serum albumin domain 2 and sheep serum albumin
      domain 3

<400> SEQUENCE: 28

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160
```

```
Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Asp Glu Pro Gln
    370                 375                 380

Asn Leu Ile Lys Lys Asn Cys Glu Leu Phe Glu Lys His Gly Glu Tyr
385                 390                 395                 400

Gly Phe Gln Asn Ala Leu Ile Val Arg Tyr Thr Arg Lys Ala Pro Gln
                405                 410                 415

Val Ser Thr Pro Thr Leu Val Glu Ile Ser Arg Ser Leu Gly Lys Val
            420                 425                 430

Gly Thr Lys Cys Cys Ala Lys Pro Glu Ser Glu Arg Met Pro Cys Thr
        435                 440                 445

Glu Asp Tyr Leu Ser Leu Ile Leu Asn Arg Leu Cys Val Leu His Glu
    450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Asp Leu Thr Leu Asp Glu Thr Tyr
                485                 490                 495

Val Pro Lys Pro Phe Asp Glu Lys Phe Phe Thr Phe His Ala Asp Ile
            500                 505                 510

Cys Thr Leu Pro Asp Thr Glu Lys Gln Ile Lys Lys Gln Thr Ala Leu
        515                 520                 525

Val Glu Leu Leu Lys His Lys Pro Lys Ala Thr Asp Glu Gln Leu Lys
    530                 535                 540

Thr Val Met Glu Asn Phe Val Ala Phe Val Asp Lys Cys Cys Ala Ala
545                 550                 555                 560

Asp Asp Lys Glu Gly Cys Phe Val Leu Glu Gly Pro Lys Leu Val Ala
                565                 570                 575
```

Ser Thr Gln Ala Ala Leu Ala
        580

<210> SEQ ID NO 29
<211> LENGTH: 584
<212> TYPE: PRT
<213> ORGANISM: Artificial sequence
<220> FEATURE:
<223> OTHER INFORMATION: Artificial albumin variant: human serum albumin
      domain 1, human serum albumin domain 2 and mouse serum albumin
      domain 3

<400> SEQUENCE: 29

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr

```
                     340                 345                 350
Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580

<210> SEQ ID NO 30
<211> LENGTH: 585
<212> TYPE: PRT
<213> ORGANISM: Artificial sequence
<220> FEATURE:
<223> OTHER INFORMATION: Artificial albumin variant: mouse serum albumin
      domain 1, mouse serum albumin domain 2 and human serum albumin
      domain 3

<400> SEQUENCE: 30

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110
```

-continued

```
Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
        130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
                180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
        260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
        340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525
```

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 31
<211> LENGTH: 585
<212> TYPE: PRT
<213> ORGANISM: Homo sapiens

<400> SEQUENCE: 31

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

```
Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 32
<211> LENGTH: 290
<212> TYPE: PRT
<213> ORGANISM: Homo sapiens
<220> FEATURE:
<221> NAME/KEY: misc_feature
<222> LOCATION: (1)..(290)
<223> OTHER INFORMATION: Truncated heavy chain of the major
      histocompatibility complex class I-like Fc receptor (FCGRT)
      (together, SEQ ID No. 32 and SEQ ID No. 33 form FcRN)

<400> SEQUENCE: 32

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
```

-continued

```
                65                  70                  75                  80
Ser Trp Tyr Trp Glu Lys Glu Thr Thr Asp Leu Arg Ile Lys Glu Lys
                    85                  90                  95

Leu Phe Leu Glu Ala Phe Lys Ala Leu Gly Lys Gly Pro Tyr Thr
            100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
        130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
            195                 200                 205

Ala Arg Pro Ser Ser Pro Gly Phe Ser Val Leu Thr Cys Ser Ala Phe
        210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
            275                 280                 285

Glu Leu
    290
```

<210> SEQ ID NO 33
<211> LENGTH: 119
<212> TYPE: PRT
<213> ORGANISM: Homo sapiens
<220> FEATURE:
<221> NAME/KEY: misc_feature
<222> LOCATION: (1)..(119)
<223> OTHER INFORMATION: Beta-2-microglobulin (together, SEQ ID No. 32
      and SEQ ID No. 33 form FcRN)

<400> SEQUENCE: 33

```
Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
```

```
            115

<210> SEQ ID NO 34
<211> LENGTH: 152
<212> TYPE: PRT
<213> ORGANISM: Artificial sequence
<220> FEATURE:
<223> OTHER INFORMATION: Human IL-1ra (N84Q)

<400> SEQUENCE: 34

Arg Pro Ser Gly Arg Lys Ser Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Gln Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 35
<211> LENGTH: 244
<212> TYPE: PRT
<213> ORGANISM: Artificial sequence
<220> FEATURE:
<223> OTHER INFORMATION: scFv (FITC8)

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ser Gly Ile Ser Gly Asn Gly Gly Tyr Thr Tyr Phe Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Asp Gly Ser Gly Trp Ser Phe Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140
```

-continued

```
Thr Pro Gly Gln Arg Val Thr Ile Ser Cys Thr Gly Ser Ser Ser Asn
145                 150                 155                 160

Ile Gly Ala Gly Tyr Asp Val His Trp Tyr Gln Gln Leu Pro Gly Thr
                165                 170                 175

Ala Pro Lys Leu Leu Ile Tyr Gly Asn Asn Asn Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Arg Ser Glu Asp Glu Ala Asp Tyr Tyr Cys Ala Ala
        210                 215                 220

Trp Asp Asp Ser Leu Ser Gly Arg Val Phe Gly Gly Gly Thr Lys Leu
225                 230                 235                 240

Thr Val Leu Gly
```

ALBUMIN DERIVATIVES AND VARIANTS

CROSS-REFERENCE TO RELATED APPLICATIONS

This application is a 35 U.S.C. 371 national application of PCT/EP2011/055577 filed Apr. 8, 2011, which claims priority or the benefit under 35 U.S.C. 119 of European application nos. 10159450.5, 10174164.3 and 11158921.4 filed on Apr. 9, 2010, Aug. 26, 2010 and Mar. 18, 2011, respectively, and U.S. provisional application Nos. 61/326,952, 61/381,255 and 61/468,149 filed on Apr. 22, 2010, Sep. 9, 2010 and Mar. 28, 2011, respectively, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The invention relates to albumin derivatives and variants and/or fusion polypeptides comprising such albumin derivatives and variants.

The invention further relates to the use of albumin derivatives and variants and/or fusion polypeptides comprising such albumin derivative or variant as a tool for drug delivery, polypeptide stability and in vivo half-life extension or modulation.

BACKGROUND OF THE INVENTION

Albumin is a protein naturally found in the blood plasma of mammals, where it is the most abundant protein. It has important roles in maintaining the desired osmotic pressure of the blood and also has a role in the transport of various substances within the blood stream.

Albumin binds in vivo to its receptor, the neonatal Fc receptor (FcRn) "Brambell" and this interaction is known to be important for increasing the plasma half-life of albumin. FcRn is a membrane bound protein, expressed in many cell and tissue types, and has been found to reduce the rate of intracellular degradation of albumin (Roopenian, D. C. and Akilesh, S. (2007), *Nat. Rev. Immunol* 7, 715-725.). FcRn contributes to maintaining both the high level of IgG and albumin in the serum of mammals, such as human beings.

Whilst the FcRn-immunoglobulin G (IgG) interaction has been characterized in the prior art, the FcRn-albumin interaction is less well characterized or understood. The major albumin-FcRn binding-site is localized within domain III (DIII: 381-585) (Andersen et al (2010) Clinical Biochemistry 43, 367-372). However, it is known within the art that both IgG and albumin bind non-cooperatively to distinct sites on FcRn (Andersen, et al. (2006), *Eur. J. Immunol* 36, 3044-3051; Chaudhury, et al. (2006), *Biochemistry* 45, 4983-4990.).

Human serum albumin (HSA) has been characterized as a polypeptide of 585 amino acids, the sequence of which can be found in Peters, T., Jr. (1996) *All about Albumin: Biochemistry, Genetics and Medical, Applications*, pp 10, Academic Press, Inc., Orlando (ISBN 0-12-552110-3). Albumin has a characteristic pH-dependent binding to FcRn, where it binds at an acidic pH, such as pH 6.0 but not at a pH above neutral, such as pH 7.4.

The plasma half-life of HSA has been found to be approximately 19 days (Peters, T., Jr. (1985) Adv. Protein Chem. 37, 161-245; Peters, T., Jr. (1996) All about Albumin, Academic Press, Inc., San Diego, Calif. (page 245-246)); Benotti P, Blackburn GL: Crit Care Med (1979) 7:520-525). A naturally occurring point mutant, having the substitution D494N has a lower plasma half-life (*Biochim Biophys Acta.* 1991, 1097:49-54). This single substitution creates an N-linked glycosylation site in this variant/mutant, which is not present in wild-type (wt) HSA. It is not known whether the potential glycosylation at this site or the amino acid change itself is responsible for the change in plasma half-life observed.

Albumin is a plasma protein considered to have a long plasma half-life and because of this property it has been suggested to be used in drug delivery. Albumin has been conjugated to pharmaceutically beneficial compounds (WO0069902A). Hence, the resultant plasma half-life of the conjugates has generally been found to be considerably longer than the plasma half-life of the beneficial compounds alone.

Further, albumin has been fused to therapeutically beneficial peptides (WO 01/79271 A and WO 03/59934 A), with the typical result that the fusion polypeptides have the activities of the therapeutically beneficial peptides and a long plasma half-life, which is considerably greater than the plasma half-life of the therapeutically beneficial peptides alone.

Otagiri et al (2009), Biol. Pharm, Bull. 32(4), 527-534, discloses that 77 albumin variants are known, of these 25 are found in domain III. A natural variant lacking the last 175 amino acids at the carboxy terminus has been shown to have reduced half-life (Andersen et al (2010), Clinical Biochemistry 43, 367-372). Iwao et al. (2007) studied the half-life of naturally occurring human albumin variants using a mouse model, and found that K541E and K560E had reduced half-life, E501K and E570K had increased half-life and K573E had almost no effect on half-life (Iwao, et. al. (2007) B.B.A. Proteins and Proteomics 1774, 1582-1590).

Galliano et al (1993) Biochim. Biophys. Acta 1225, 27-32 discloses a natural variant E505K. Minchiotti et al. (1990) discloses a natural variant K536E. Minchiotti et al (1987) Biochim. Biophys. Acta 916, 411-418 discloses a natural variant K574N. Takahashi et al (1987) Proc. Natl. Acad. Sci. USA 84, 4413-4417, discloses a natural variant D550G. Carlson et al (1992). Proc. Nat. Acad. Sci. USA 89, 8225-8229, discloses a natural variant D550A.

WO 2007112940 discloses constructs comprising at least one albumin domain III and at least one therapeutic moiety and the use of such constructs for half-life extension of drugs.

Albumin has the inherent ability to allow the binding of a number of ligands, and these become associated (associates) with albumin. This property has been utilized to extend the plasma half-life of such aforementioned ligands, e.g. to extend the plasma half-life of drugs having the ability to non-covalently bind to albumin. This can also be achieved by binding a pharmaceutically beneficial compound, which has little or no albumin binding properties, to a moiety having albumin-binding properties. See review article and reference therein: Kratz (2008). Journal of Controlled Release 132, 171-183.

U.S. Pat. No. 7,253,259 discloses a protein produced by gene recombinant technology including at least one domain selected from domains I, II and III of serum albumin but having a different structure from that of native albumin; and a method of producing the protein.

Albumin is used in preparations of pharmaceutically beneficial compounds, in which such a preparation maybe for example, but not limited to, a nano particle or micro particle of albumin. In these examples the delivery of a pharmaceutically beneficial compound or mixture of compounds may benefit from alteration in the albumins affinity to the FcRn receptor where the beneficial compound has been shown to associate with albumin for the means of delivery.

The exact nature or associated properties that influences the extension to the plasma half-life of the formed conjugates or fusion polypeptides is unclear (for example, but not limited to, Levemir®, Kurtzhals P et al. Biochem. J. 1995; 312:725-731), but it appears to be directly related to the albumin moiety and the selected pharmaceutically beneficial compound/peptide they are composed of. It would be desirable to be able to control the plasma half-life of a given albumin domain III derivative, fragments, or variants thereof with a conjugated or fusion or association such that a longer or shorter plasma half-life, than given by the components of the conjugate/fusion alone, can be achieved. This would allow the custom design of a particular drug according to the particulars of the indication intended to be treated.

Albumin is known to accumulate and be catabolised in tumours, it has also been shown to accumulate in inflamed joints of rheumatoid arthritis sufferers. See review article and reference therein, Kratz (2008). Journal of Controlled Release 132, 171-183. It is envisaged that HSA variants with increased affinity for FcRn would be advantageous for the delivery and/or targeting (such as passive targeting) of pharmaceutically beneficial compounds.

It may be desirable to have variants of albumin that have little or no binding to FcRn in order to provide shorter half-lives or controlled serum pharmacokinetics as described by Vania Kenanova, Tove Olafsen, Felix Bergara and Anna Wu (2009) J Nucl Med.; 50 (Supplement 2):1582).

SUMMARY OF THE INVENTION

The first aspect of the invention provides an albumin derivative or variant, fragment thereof or fusion polypeptide comprising or consisting of said albumin derivative or variant or fragment thereof, where the albumin derivative or variant or fragment thereof comprises or consists of albumin domain III or derivative or variant thereof, and at least one additional albumin domain, fragment or derivative or variant thereof. Preferably, the first aspect does not include wild-type albumin itself. However, the first aspect may include wild-type albumin modified such that it comprises or consists of wild-type albumin and an alteration such as addition of one or more (several) domains from any albumin, one or more (several) point mutations, fusion to a beneficial moiety, conjugation to a beneficial moiety and/or association with a beneficial moiety.

In a preferred embodiment the albumin derivative or variant, fragment thereof or fusion polypeptide comprising or consisting of said albumin derivative or variant or fragment thereof comprises or consists of one or more (several) substitutions, insertions or deletions, most preferably substitutions, in positions corresponding to the positions in SEQ ID NO: 31 or SEQ ID NO: 1 (HSA) selected from the group consisting of one or more of (several) positions: 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584.

In a second aspect, the invention relates to isolated polynucleotides that encode any of the derivatives or variants of the invention, for example: (i) nucleic acids encoding the albumin derivative, fragment thereof or fusion polypeptide comprising or consisting of said albumin derivative or fragment thereof, (ii) plasmids comprising said nucleic acids and (iii) host cells comprising said plasmid.

Conjugates comprising an albumin derivative or variant, or fragment thereof, according to the invention and at least one therapeutic or diagnostic moiety form a third aspect of the invention.

A fourth aspect of the invention provides fusion polypeptides comprising or consisting of said albumin derivative or variant or fragment thereof and at least one therapeutic protein or peptide. A fifth aspect of the invention relates to 'associates' of the derivatives or variants of albumin or fragments thereof with another compound bound or associated to the derivative albumin, variant albumin or fragment thereof by non-covalent binding.

The sixth aspect of the invention relates to a composition, preferably a pharmaceutical composition, comprising or consisting of an albumin derivative, fragment, variant thereof or fusion polypeptide comprising or consisting of the albumin derivative, fragment, variant thereof conjugated, fused or associated with a therapeutic, pharmaceutical or other beneficial polypeptide.

A seventh aspect of the invention relates to methods of production of the derivatives or variants.

An eighth aspect of the invention relates to use of the derivatives and/or variants in imaging, for example use of a conjugate, associate or fusion polypeptide for imaging purposes in animals or human beings.

A ninth aspect of the invention relates to a method of treatment and/or use of a polypeptide sequence or nucleotide sequence of the present invention in a method of treatment.

A tenth aspect, the invention relates to compositions comprising the derivative albumin, variant albumin, associates thereof or fragment thereof, derivative or variant albumin fragment or associates thereof or fusion polypeptide comprising derivative or variant albumin or fragment thereof according to the invention.

BRIEF DESCRIPTION OF DRAWINGS

FIG. 1, A) Binding of shFcRn-GST to wt HSA and wt HSA derivatives (2000-0.9 nM) at (A) pH 6.0 and (B) pH 7.4. The ELISA values represent the mean of duplicates.

FIG. 2. Representative sensorgrams showing binding of 1 µM of wt HSA and wt HSA derivatives to immobilized shFcRn-GST (~1400 RU) at pH 6.0 and pH 7.4. (A) DI-DII (B) DI-DIII, (C) DII-DIII, (D) DIII, (E) DIII-DIII and (F) wt HSA.

FIG. 4, Multiple alignment of amino acid sequences of (i) full length mature HSA (Hu_1_2_3), (ii) an albumin variant comprising domain I and domain III of HSA (Hu_1_3), (iii) an albumin variant comprising domain II and domain III of HSA (Hu_2_3), (iv) full-length *Macaca mulatta* albumin (Mac_mul), (v) full-length *Rattus norvegicus* albumin (Rat) and (vi) full-length *Mus musculus* albumin (Mouse). Positions 500, 550 and 573 (relative to full length HSA) are indicated by arrows. In FIG. 4, Domains I, II and III are referred to as 1, 2 and 3 (respectively).

FIG. 5, Multiple alignment of amino acid sequence of mature serum albumin from human, sheep, mouse, rabbit and goat and immature albumins from chimpanzee ("Chimp"), macaque, hamster, guinea pig, rat, cow, horse, donkey, dog, chicken, and pig. The Start and End amino acids of domains 1, 2 and 3 (as defined by Dockal et al (The Journal of Biological Chemistry, 1999, Vol. 274(41): 29303-29310)) are indicated with respect to mature human serum albumin.

FIG. 8, Representative sensorgrams showing binding of 10 µM of HSA Domain III and variants thereof to immobilized shFcRn-HIS (~2100RU) at pH 5.5.

DETAILED DESCRIPTION OF THE INVENTION

Figure 3:
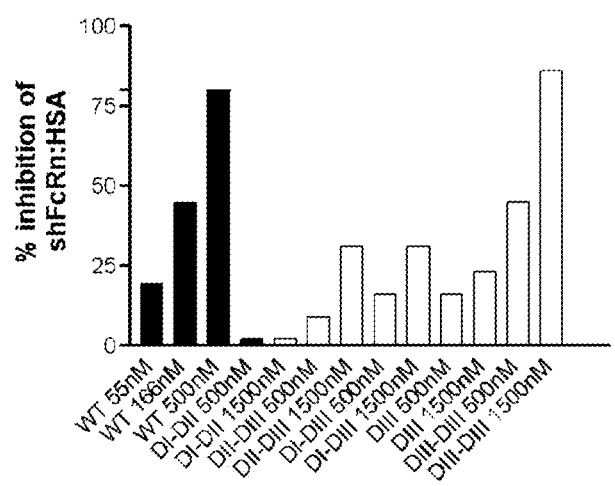
FIG. 3, Serial dilutions of wt HSA and wt HSA domain constructs to give final sample concentration at 55 nM, 166 nM and 500 nM, and 500 nM and 1500 nM, respectively, were pre-incubated shFcRn (50 nM) and injected over immobilized HSA (~2600 RU). Injections were performed at 25° C. at a flow rate of 50 µl/min at pH 6.0.

A first aspect of the invention relates to an albumin derivative or variant, fragment thereof or fusion polypeptide comprising or consisting of said albumin derivative or variant or fragment thereof, where the albumin derivative or variant or fragment thereof comprises or consists of a first albumin domain III, fragment or derivative or variant thereof, and at least one second albumin domain, fragment or derivative or variant thereof. Preferably, the derivative or variant is not a naturally occurring derivative or variant such as a wild-type albumin from one of human; primate, such as chimpanzee, gorilla or macaque; rabbit; rodent such as mouse, rat and hamster; bovine; equine such as horse or donkey; goat; sheep; dog; guinea pig; chicken and pig. The first aspect may or may not include an albumin derivative or variant comprising or consisting of domains I, II and III (or fragments thereof) of a wild-type albumin and one or more (several) additional domains (or fragments thereof) from any albumin, such as albumin from human or other species disclosed herein.

Some albumin derivatives or variants, fragments thereof or fusion poylpeptides according to the first aspect of the invention do not comprise domain I (or fragment thereof) of an albumin. Some albumin derivatives or variants, fragments thereof or fusion poylpeptides according to the first aspect of the invention do not comprise domain II (or fragment thereof) of an albumin. Other albumin derivatives or variants, fragments thereof or fusion poylpeptides according to the first aspect of the invention comprise domain III of an albumin and one or both of domain I (or fragment thereof) or domain II (or fragment thereof) of an albumin.

The invention is based on the discovery that a polypeptide comprising a first albumin domain III and at least one second albumin domain fragment or derivative or variant thereof, has a stronger binding to FcRn than the corresponding domain III alone. This is surprising in view of the prior art, in particular WO 2007112940, where it appears that amino residues of domain III are involved in the interaction of albumin with the FcRn receptor which is involved in prolonging the life-span of albumin in circulation, for example in plasma. It is known that domain III is responsible for binding of albumin to FcRn. According to the invention, the term "albumin" means a protein having the same and/or very similar three dimensional structure as HSA and having a long plasma half-life. HSA as disclosed in SEQ ID NO: 31 or SEQ ID NO: 1 or any naturally occurring allele thereof, is the preferred albumin according to the invention. Those skilled in the art would also appreciate that the described characteristics of HSA domain III derivative, fragment, variant thereof would also be probable for other non-human albumins, in accordance to the current invention described.

Thus, the albumin derivative or variant, fragment thereof or fusion polypeptide comprising or consisting of said albumin derivative or variant or fragment thereof according to the invention has the benefit of a long plasma half-life, similar to albumin.

The size of the albumin derivative or variant, fragment thereof or fusion polypeptide comprising or consisting of said albumin derivative or variant or fragment thereof of the invention may vary depending on the size of the fragment, number of domains, the size of the non-albumin part of the fusion polypeptide etc. In principle, the size may vary from slightly above the size of the domain III and upward but in practise it is preferred that the size is around the size of natural albumin. Without wishing to be bound by any theory it is believed that the size above the kidney threshold value, such as the size of natural albumin, is ideal for high plasma half-life. Thus, it is preferred that the albumin derivative or variant, fragment thereof or fusion polypeptide comprising or consisting of said albumin derivative or variant or fragment thereof of the invention and/or a conjugate comprising or consisting of the albumin derivative or variant or fragment thereof has a size in the range of 40-80 kDa, preferably in the range of 50-70 kDa, more preferred in the range of 55-65 kDa and most preferred around 60 kDa.

HSA is a preferred albumin according to the invention and is a protein consisting of 585 amino acid residues and has a molecular weight of 67 kDa. In its natural form it is not glycosylated. The amino acid sequence of HSA is shown in SEQ ID NO: 31 or SEQ ID NO: 1. The skilled person will appreciate that natural alleles may exist having essentially the same properties as HSA but having one or more (several) amino acid changes compared to SEQ ID NO: 31 or SEQ ID NO: 1, and the inventors also contemplate the use of such natural alleles as parent albumin according to the invention.

Albumins have generally a long plasma half-life of approximately 20 days or longer, e.g., HSA has a plasma half-life of 19 days. It is known that the long plasma half-life of HSA is mediated via interaction with its receptor FcRn, however, an understanding or knowledge of the exact mechanism behind the long half-life of HSA is not essential for the invention.

According to the invention the term "albumin" means a protein having the same, or very similar three dimensional structure as HSA and having a long plasma half-life. As examples of albumin proteins according to the invention can be mentioned human serum albumin (e.g. AAA98797 or P02768-1, SEQ ID NO: 31 or SEQ ID NO: 1 (mature), SEQ ID NO: 4 (immature)), primate serum albumin, (such as chimpanzee serum albumin (e.g. predicted sequence XP_517233.2 SEQ ID NO: 5), gorilla serum albumin or macaque serum albumin (e.g. NP_001182578, SEQ ID NO: 6), rodent serum albumin (such as hamster serum albumin (e.g. A6YF56, SEQ ID NO: 7), guinea pig serum albumin (e.g. Q6WDN9-1, SEQ ID NO: 8), mouse serum albumin (e.g. AAH49971 or P07724-1 Version 3, SEQ ID NO: 9) and rat serum albumin (e.g. AAH85359 or P02770-1 Version 2, SEQ ID NO: 10))), bovine serum albumin (e.g. cow serum albumin P02769-1, SEQ ID NO: 11), equine serum albumin such as horse serum albumin (e.g. P35747-1, SEQ ID NO: 12) or donkey serum albumin (e.g. Q5XLE4-1, SEQ ID NO: 13), rabbit serum albumin (e.g. P49065-1 Version 2, SEQ ID NO: 14), goat serum albumin (e.g. ACF10391, SEQ ID NO: 15), sheep serum albumin (e.g. P14639-1, SEQ ID NO: 16), dog serum albumin (e.g. P49822-1, SEQ ID NO: 17), chicken serum albumin (e.g. P19121-1 Version 2, SEQ ID NO: 18) and pig serum albumin (e.g. P08835-1 Version 2, SEQ ID NO: 19). HSA as disclosed in SEQ ID NO: 31 or SEQ ID NO: 1 or any naturally occurring allele thereof, is the preferred albumin according to the invention.

The parent albumin, a fragment thereof, or albumin part of a fusion polypeptide comprising or consisting of albumin or a fragment thereof according to the invention has generally a sequence identity to the sequence of HSA shown in SEQ ID NO: 31 or SEQ ID NO: 1 of at least 60%, preferably at least 70%, preferably at least 80%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, more preferred at least 96%, more preferred at least 97%, more preferred at least 98% and most preferred at least 99%.

The parent preferably comprises or consists of at least a part of the amino acid sequence of SEQ ID NO: 31 or SEQ ID NO: 1. In another embodiment, the parent comprises or consists of at least a part of the mature polypeptide of SEQ ID NO: 31 or SEQ ID NO: 1.

In another embodiment, the parent is an allelic derivative or variant of at least a part of the mature polypeptide of SEQ ID NO: 31 or SEQ ID NO: 1.

The term "isolated derivative" or "isolated variant" means a derivative or variant that is modified by the hand of man. In one embodiment, the derivative or variant is at least 1% pure, e.g., at least 5% pure, at least 10% pure, at least 20% pure, at least 40% pure, at least 60% pure, at least 80% pure, and at least 90% pure, as determined by SDS-PAGE or GP-HPLC.

The term "substantially pure derivative" or "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the derivative or variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The derivatives or variants of the present are preferably in a substantially pure form. This can be accomplished, for example, by preparing the derivative or variant by well known recombinant methods or by classical purification methods.

The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 1 to 585.

The term "mature polypeptide coding sequence" means a polynucleotide that encodes a mature polypeptide. In one embodiment, the mature polypeptide coding sequence is nucleotides 1 to 1758 of SEQ ID NO: 2.

The term "FcRn" means the human neonatal Fc receptor (FcRn). 'shFcRn' is a soluble recombinant form of FcRn. The term "smFcRn" is a soluble recombinant form of the mouse neonatal Fc Receptor.

According to the invention the term "albumin derivative, fragment thereof or fusion polypeptide comprising or consisting of said albumin derivative or fragment thereof" means a non-natural, engineered molecule comprising or consisting of albumin domains as specified. Thus, the term does not include natural full-length albumin or a fusion polypeptide comprising full-length albumin. The term "derivative" includes an albumin polypeptide comprising an alteration, e.g. a substitution, insertion, and/or deletion, at one or more (several) positions. A substitution means a replacement of an amino acid occupying a position with a different amino acid; a deletion means removal of an amino acid occupying a position; and an insertion means adding 1, 2 or 3, or more, amino acids adjacent to an amino acid occupying a position, an insertion can be at the C- or N-side of an amino acid, but is typically at the C-side of an amino acid.

The term "variant" includes an albumin or albumin derivative or fusion protein thereof in which the albumin derivative or fusion is altered by chemical means such as post-translational derivitisation or modification of the polypeptide, e.g. PEGylation and/or conjugation of a desirable moiety (such as a therapeutic moiety) to a thiol group, such as provided by an unpaired cysteine. The term "variant" also includes a fusion protein of an albumin derivative according to the invention in which the derivative is not altered by chemical means.

The terms "derivative" and "variant" may or may not be used interchangeably.

Albumins are proteins and constitute the most abundant protein in plasma in mammals and albumins from a large and diverse number of mammals have been characterized by biochemical methods and/or by sequence information. Several albumins e.g. HSA, have also been characterized crystallographically and the structure determined, and it has been shown that albumins consists of three distinct domains called Domain I, Domain II and Domain III.

The domains of the invention may in principle be derived from any albumin, however, it is preferred that the domains are derived from human serum albumin, primate serum albumin, such as chimpanzee serum albumin, gorilla serum albumin or or macaque serum albumin, rodent serum albumin such as rabbit serum albumin, mouse serum albumin and rat serum albumin, bovine serum albumin, equine serum albumin, donkey serum albumin, hamster serum albumin, goat serum albumin, sheep serum albumin, dog serum albumin, guinea pig serum albumin, chicken serum albumin and pig serum albumin.

A particularly preferred albumin according to the invention is HSA having the sequence shown in SEQ ID NO: 31 or SEQ ID NO: 1 and preferred albumin domains of the invention are HSA domain I consisting of amino acid residues 1 to 194±1 to 15 amino acids of SEQ ID NO: 31 or SEQ ID NO: 1; HSA domain II consisting of amino acid residues 192 to 387±1 to 15 amino acids of SEQ ID NO: 31 or SEQ ID NO: 1 and HSA domain III consisting of amino acid residues 381 to 585±1 to 15 amino acids of SEQ ID NO: 31 or SEQ ID NO: 1 or a combination of one or more (several) of these domains, e.g. domain 1 and 2, domain 2 and 3 or domain 1 and 3 fused together. No generally accepted convention for the exact borders of the albumin domains exists and the overlap in the above mentioned ranges and the allowance of a varying length of plus or minus 1, 2, 3, 4, 5, 6, 7, 8, 9, 10, 11, 12, 13, 14 or 15 from amino acids, preferably from 1 to 15 amino acids, more preferably from 1 to 10 amino acids, most preferably from 1 to 5 amino acids, at the N-terminal and/or C-terminal of the domains, allowing for a total variance in length of up to 30 amino acids, preferably up to 20 amino acids, more preferably up to 10 amino acids for each domain reflects this fact and that there may be some diverging opinions on the amino acid residues in the border between the domains belongs to one or the other domain. For the same reason it may be possible to find references to the amino acid residues of albumin domains that diverge from the numbers above, however, the skilled person will appreciate how to identify the albumin domains based on the teaching in the literature and the teaching above. Corresponding domains of non-human albumins can be identified by alignment with HSA using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. Alternative alignment tools can also be used, for example MUSCLE as described herein.

The domains may also be defined according to Dockal or Kjeldsen: Dockal et al (The Journal of Biological Chemistry, 1999, Vol. 274(41): 29303-29310) defines the domains of HSA as: Domain I: amino acids 1 to 197, Domain II: amino acids 189 to 385, Domain III: amino acids 381 to 585. Kjeldsen et al (Protein Expression and Purification, 1998, Vol 13: 163-169) defines the domains as: Domain I: amino acids 1 to 192, Domain II: amino acids 193 to 382, Domain III: amino acids 383 to 585.

Therefore, in this invention, the following domain definitions are preferred. The amino acid numbers correspond to those of SEQ ID NO: 31 or SEQ ID NO: 1 (HSA). However, using these numbers, the skilled person can identify corresponding domains in other albumin sequences.

Domain I may or may not start at amino acid 1 and may or may not end at any of amino acids 192, 193, 194, 195, 196 or 197, preferably any of amino acids 192, 194 or 197.

Domain II may or may not start at amino acid 189, 190, 191, 192 or 193, preferably any of amino acids 189, 192 or 193, and may or may not end at amino acid 382, 383, 384, 385, 386 or 387, preferably any of amino acids 382, 285 or 387.

Domain III may or may not start at amino acid 381, 382 or 383, preferably amino acid 381 or 383, and may or may not end at amino acid 585.

Domains in non-human albumins may have the same or different amino acid lengths and/or residue numbers as HSA. For example, a multiple alignment or pair-wise alignment may be prepared using HSA and one or more (several) other albumins, fragments, derivatives, variants and/or fusions in order to identify domains corresponding to domains 1, 2 and/or 3 of HSA. An example of a suitable alignment is given in FIG. 5. FIG. 5 was created using MUSCLE and Boxshade in the same manner as described for FIG. 4. For clarity, the mature sequence of HSA, sheep, mouse, rabbit and goat albumins are provided (i.e. numbering starts at the first amino acid after the leader sequence and pro-sequence) and all other albumin sequences provided are immature sequences (i.e. include leader sequence, pro-sequence (if present) and mature albumin sequence). Examples of domain coordinates for human, sheep, rabbit and mouse albumins are given in the Examples. These coordinates can be applied to any aspect of the invention. Domain coordinates for all albumins can be identified or extrapolated from a suitable alignment, such as FIG. 5, by identifying amino acids corresponding to one or more (several) of the domain coordinates of HSA (as disclosed herein). Typically, domain coordinates are designated using the first amino acid of the mature albumin as position 1, therefore the amino acid sequence of a leader sequence and/or a pro-peptide is usually ignored in this respect.

The first albumin domain III, fragment or derivative or variant thereof may in principle be any albumin domain III, however, HSA domain III (e.g. SEQ ID NO: 23), fragment or derivatives or variants thereof are preferred.

Throughout this specification, a molecule comprising domain I and domain II may be referred to as 'DI-DII' or as 'DI+DII' or as 'D1+D2' or as 'D1-D2'. Likewise, a molecule comprising domain I and domain III may be referred to as any of 'DI-DIII' or as 'DI+DIII' or as 'D1+D3' or as D1-D3'. Therefore, a molecule comprising domain II and domain III may be referred to as 'DII-DIII' or as 'DII+DIII' or as 'D2+D3' or as D2-D3'. Furthermore, a designation such as "HSA 1/2-RSA 3" means that the molecule comprises HSA domain 1, HSA domain 2 and RSA domain 3 which is the same as HSA domain I, HSA domain II and RSA domain III.

The term "derivative" in relation to an albumin domain means a polypeptide having a similar primary and/or tertiary structure to said albumin domain in its natural form, in the following called the parent domain, but which differs from said parent domain with one or more (several) substitutions, insertions, and/or deletions, of one or more (several) amino acid residues at one or more (several) positions. The derivative can be obtained through human intervention by modification of the nucleic acid sequence encoding the parent domain and expression of the modified nucleic acid sequence in a suitable host organism using techniques known in the art.

The term "fragment" means a polypeptide having one or more (several) amino acids deleted from the amino and/or carboxyl terminus of an albumin and/or an internal region of albumin that has retained the ability to bind to FcRn. Fragments may comprise or consist of one uninterrupted sequence derived from HSA or it may comprise or consist of two or more sequences derived from HSA. The fragments according to the invention have a size of at least or more than approximately 20 amino acid residues, preferably at least or more than 30 amino acid residues, more preferred at least or more than 40 amino acid residues, more preferred at least or more than 50 amino acid residues, more preferred at least or more than 75 amino acid residues, more preferred at least or more than 100 amino acid residues, more preferred at least or more than 200 amino acid residues, more preferred at least or more than 300 amino acid residues, even more preferred at least or more than 400 amino acid residues and most preferred at least or more than 500 amino acid residues.

The term "fragment" in relation to the first albumin domain III of this invention means a part of the particular relevant albumin domain having retained the ability to bind FcRn. Fragments may consist of one uninterrupted sequence derived from a parent domain or may comprise of consist of two or more sequences derived from the parent domain. The fragments according to the invention have a size of at least or more than approximately 20 amino acid residues, preferably at least or more than 30 amino acid residues, more preferred at least or more than 40 amino acid residues, more preferred at least or more than 50 amino acid residues, more preferred at least or more than 75 amino acid residues, and most preferred at least or more than 100 amino acid residues.

The at least one second albumin domain, fragment or derivative or variant thereof may in principle be any albumin domain, fragment or derivative or variant thereof.

The term "fragment" in the relation to the second albumin domain of this invention means a part of the particular relevant albumin domain. Fragments may consist of one uninterrupted sequence derived from the parent domain or it may comprise or consist of two or more sequences derived from the parent domain. The fragments according to the invention have a size of at least or more than approximately 20 amino acid residues, preferably at least or more than 30 amino acid residues, more preferred at least or more than 40 amino acid residues, more preferred at least or more than 50 amino acid residues, more preferred at least or more than 75 amino acid residues, and most preferred at least or more than 100 amino acid residues.

The first albumin domain III, fragment or derivative or variant thereof and the at least one second albumin domain, fragment or derivative or variant thereof may be derived from same species or they may be derived from different species. For example, the first albumin domain III, fragment or derivative or variant thereof may be HSA domain III and the at least one second albumin domain, fragment of derivative or variant thereof be mouse serum albumin domain II, or the first albumin domain III, fragment or derivative or variant thereof may be rabbit serum albumin domain III and the at least one second albumin domain, fragment of derivative or variant thereof be human serum albumin domain I.

The albumin derivative or variant, fragment thereof or fusion polypeptide comprising or consisting of said albumin derivative or variant or fragment thereof comprises or consists of at least two albumin domains or fragments thereof and it may comprise or consist of more than two domains. In principle there is no upper limit for the number of albumin domains or fragments thereof that may be combined in the albumin derivative or variant, fragment thereof or fusion polypeptide comprising or consisting of said albumin derivative or variant or fragment thereof according to the invention, however, it is preferred that the albumin derivative or variant, fragment thereof or fusion polypeptide comprising or consisting of said albumin derivative or variant or fragment thereof according to the invention comprises or consist of 2 or 3 albumin domains, most preferred 2 domains.

As examples of preferred albumin derivative or variant, fragment thereof or fusion polypeptide comprising or consisting of said albumin derivative or variant or fragment thereof according to the invention can be mentioned albumin domain I+albumin domain III (e.g. SEQ ID NO: 22), albumin domain II+albumin domain III (e.g. SEQ ID NO: 21), albumin domain III+albumin domain III (e.g. SEQ ID NO: 24), albumin domain III+albumin domain I and albumin domain III+albumin domain II.

Preferred albumin derivative or variant, fragment thereof or fusion polypeptide comprising or consisting of said albumin derivative or variant, comprises or consists of an albumin domain III derived from one species and albumin domain I and II derived from a different species. Examples include an albumin derivative consisting of Domain I and II derived from human serum albumin and domain III derived from rabbit serum albumin (e.g. SEQ ID NO: 25), a derivative consisting of Domain I and II derived from rabbit serum albumin and domain III derived from human serum albumin (e.g. SEQ ID NO: 26), a derivative consisting of Domain I and II derived from sheep serum albumin and domain III derived from human serum albumin (e.g. SEQ ID NO: 27), and a derivative consisting of domain I and domain II derived from human serum albumin and domain III derived from mouse serum albumin (e.g. SEQ ID NO: 29). These derivatives have surprisingly different binding properties to FcRn than the complete albumin from which the domain III of the derivative is derived.

The derivative consisting of domain I and II derived from human serum albumin and domain III derived from rabbit serum albumin (e.g. SEQ ID NO: 25), the derivative consisting of domain I and II derived from sheep serum albumin and domain III derived from human serum albumin (e.g. SEQ ID NO: 27) and the derivative consisting of the domain I and II derived from human serum albumin and domain III derived from mouse serum albumin (e.g. SEQ ID NO: 29) have stronger binding to FcRn than human serum albumin. The derivative consisting of domain I and II form rabbit serum albumin and domain III from human serum albumin (e.g. SEQ ID NO: 26) has a weaker binding to FcRn than HSA. Variants of the derivatives are also envisaged and included in the invention.

In one embodiment one or more (several) albumin domain III in the albumin derivative or variant, fragment thereof or fusion polypeptide comprising or consisting of said albumin derivative or variant or fragment thereof comprises or consists of one or more (several) alteration(s) such as substitution(s), deletion(s) or insertion(s) in one or more position(s) corresponding to the positions in HSA selected from one or more (several) of: 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584. The inventors have found that these amino acid residues are important for the interaction of serum albumin and the FcRn receptor and alteration in one or more (several) of these positions will alter the binding of the albumin derivative or variant, fragment thereof or fusion polypeptide comprising or consisting of said albumin derivative or variant or fragment thereof according to the invention to the FcRn receptor and thereby alter the plasma half-life thereof. The alteration at one or more (several) position may be selected independently among substitutions, insertions and deletions. Substitutions are preferred.

The derivative or variant albumin, a fragment thereof, or albumin part of a fusion polypeptide comprising or consisting of a derivative or variant albumin or a fragment thereof according to the invention has generally a domain III which has an amino acid sequence identity to the sequence of HSA Domain III (as defined herein in relation to SEQ ID NO: 31 or SEQ ID NO: 1) of at least 60%, preferably at least 70%, preferably at least 80%, preferably at least 81%, 82%, 83%, 84%, 85%, 86%, 87%, 88% or 89%, preferably at least 90%, more preferred at least 95%, more preferred at least 96%, more preferred at least 97%, more preferred at least 98% and most preferred at least 99%. Even more preferably, the derivative or variant albumin, a fragment thereof, or albumin part of a fusion polypeptide comprising or consisting of a derivative or variant albumin or a fragment thereof according to the invention has generally a domain III which has an amino acid sequence identity amino acids 381 to 585 of an albumin, such as any of SEQ ID NO: 31 or SEQ ID NO: 1 or equivalent positions in one or more (several) of SEQ ID NO: 4, 5, 6, 7, 8, 9, 10, 11, 12, 13, 14, 15, 16, 17, 18 or 19, SEQ ID NO: 31 or SEQ ID NO: 1 (human serum albumin), of at least 60%, preferably at least 70%, preferably at least 80%, preferably at least 81%, 82%, 83%, 84%, 85%, 86%, 87%, 88% or 89%, preferably at least 90%, more preferred at least 95%, more preferred at least 96%, more preferred at least 97%, more preferred at least 98% and most preferred at least 99%.

In a further embodiment, the derivative or variants of albumin, fragments thereof or fusion polypeptides comprising or consisting of a derivative or variant albumin or a fragment thereof according to the invention have a plasma half-life that is longer than the plasma half-life of the parent albumin fragment thereof or fusion polypeptide comprising or consisting of the parent albumin or a fragment thereof. Examples according to this embodiment include derivatives or variants of albumin, fragments thereof or fusion polypeptides comprising or consisting of a derivative or variant albumin or a fragment thereof comprising or consisting of one or more (several) substitutions in one or more (several) of the position corresponding to the group consisting of E492, N503, D550 and K573 in HSA. Preferably the amino acid residue in the position corresponding to E492 in HSA is substituted with a G residue, the amino acid in the position corresponding to N503 in HSA is substituted with a H or K residues, the amino acid in the position corresponding to D550 in HSA is substituted with a E residue and the amino acid in the position corresponding to K573 in HSA is substituted with an A or a P residue. Also preferred is a derivative or variant where the amino acid corresponding to E492 in HSA is substituted from a G residue and the amino acid corresponding to K573 in HSA is substituted with an A or a P residue. Other preferred derivative or variant has a number of substitutions corresponding to E492 in HSA with an H residue, E501 in HSA with a P, N503 in HSA with an H, E505 in HSA with a D, T506 in HSA with an S, T540 in HSA with a S, K541 in HSA with a E.

In a further embodiment the derivative or variants of albumin, fragments thereof or fusion polypeptides comprising or consisting of a derivative or variant albumin or a fragment thereof according to the invention have a plasma half-life that is shorter than the plasma half-life of the parent albumin fragment thereof or fusion polypeptide comprising or consisting of the parent albumin or a fragment thereof. Examples according to this embodiment include derivatives or variants of albumin, fragments thereof or fusion polypeptides comprising or consisting of a derivative or variant albumin or a fragment thereof comprising a substitution in the position corresponding to one or more (several) of the group consisting of Q417, H440, H464, D494, E495, T496, P499, K500, E501, H510, H535, K536, P537, K538, K541, D550N, D494+T496 or E492+V493 in HSA. Preferred substitutions include the substitutions corresponding to Q417A, H440A, H464Q, D494E+Q417H, D494N, Q, A, E495Q, A, T496A, D494N+T496A or, P499A, K500A E501A, E501Q, H510Q, H535Q, K536A, P537A, K538A, K541G, K541A K541D or D550N in HSA.

In addition to the one or more (several) substitutions, insertions or deletions (where substitutions are preferred) in one or more (several) positions corresponding to the group consisting of positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of SEQ ID NO: 31 or SEQ ID NO: 1 the derivative or variant albumin, fragments thereof or fusion polypeptides comprising or consisting of a derivative or variant albumin or a fragment thereof according to the invention may contain additional substitutions, deletions or insertions in other positions of the molecules. Such additional substitutions, deletions or insertions may be useful in order to alter other properties of the molecules such as but not limited to altered glycosylation; introduction of reactive groups of the surface such a thiol groups, removing/generating a carbamylation site; etc.

Residues that might be altered in order to provide reactive residues on the surface and which advantageously could be applied to the invention has been disclosed in the unpublished patent application EP 2009 152 625 (incorporated herein by reference). Particular preferred residues include the positions corresponding to positions in HSA outside the regions interacting with FcRn.

As examples of alterations that can be made in SEQ ID NO: 31 or SEQ ID NO: 1 or in corresponding positions in other albumins (such as in SEQ ID Numbers 4 to 19) in order to provide a reactive thiol group on the surface includes: L585C, D1C, A2C, D562C, A364C, A504C, E505C, T79C, E86C, D129C, D549C, A581C, D121C, E82C, S270C, A578C, L595LC, D1DC, A2AC, D562DC, A364AC, A504AC, E505EC, T79TC, E86EC, D129DC, D549DC, A581AC, A581AC, D121DC, E82EC, S270SC, A579AC, C360*, C316*, C75*, C168*, C558*, C361*, C91*, C124*, C169* and C567*. Alternatively a cysteine residue may be added to the N- or C-terminal regions of albumin.

In one embodiment, the number of alterations in the derivatives or variants of the invention is 1 to 20 amino acids, e.g., 1 to 10 and 1 to 5, such as 1, 2, 3, 4, 5, 6, 7, 8, 9 or 10 alterations.

The derivative or variant albumin, a fragment thereof or fusion polypeptide comprising or consisting of the derivative or variant albumin or fragment thereof has altered plasma half-life compared with the corresponding parent albumin domain(s), fragment thereof, or fusion polypeptide comprising or consisting of the derivative or variant albumin domain(s) or fragment thereof.

In a particularly preferred embodiment, the parent albumin domain(s) are from HSA and the derivative or variant albumin, a fragment thereof or fusion polypeptide comprising or consisting of the derivative or variant albumin domain(s) or fragment thereof has altered plasma half-life compared with the HSA domain(s), the corresponding fragment or fusion polypeptide comprising or consisting of HSA domain(s) or fragment thereof.

One way to determine whether the affinity of a derivative or variant albumin to FcRn is higher or lower than the parent albumin is to use the Surface Plasmon Resonance assay (SPR) as described below. The skilled person will understand that other methods might be useful to determine whether the affinity of a derivative or variant albumin to FcRn is higher or lower than the affinity of the parent albumin to FcRn, e.g., determination and comparison of the binding constants KD. Thus, according to the invention derivative or variant albumins having a KD that is lower than the KD for natural HSA is considered to have a higher plasma half-life than HSA and variant albumins having a KD that is higher than the KD for natural HSA is considered to have a lower plasma half-life than HSA.

The derivatives or variants of albumin or fragments thereof or fusion polypeptides comprising or consisting of albumin or fragments thereof comprise or consist of one or more (several) alterations, such as substitutions, deletions or insertions at one or more (several) positions corresponding to the positions in HSA (SEQ ID NO: 31 or SEQ ID NO: 1) selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584. The substitution may be any substitution where the amino acid in the natural albumin sequence is substituted with a different amino acid selected among the remaining 19 natural occurring amino acids. For the avoidance of doubt, the skilled person can use the nomenclature used herein to identify the positions in a domain of HSA or in an albumin, domain or fragment of an alternative albumin.

In one embodiment, a derivative or variant comprises an alteration at one or more (several) positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1. In another embodiment, a derivative or variant comprises an alteration at two positions corresponding to any of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1. In another embodiment, a derivative or variant comprises an alteration at three positions corresponding to any of positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1. In another embodiment, a derivative or variant comprises an alteration at each position corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1.

In another embodiment, the derivative or variant comprises the substitution Q417A, H of the mature polypeptide of SEQ ID NO: 31 or SEQ ID NO: 1. In another embodiment, the derivative or variant comprises the substitution H440Q of the mature polypeptide of SEQ ID NO: 1. In another embodiment, the derivative or variant comprises the substitution H464Q of the mature polypeptide of SEQ ID NO: 31 or SEQ ID NO: 1. In another embodiment, the derivative or variant comprises the substitution A490D of the mature polypeptide of SEQ ID NO: 31 or SEQ ID NO: 1. In another embodiment, the derivative or variant comprises the substitution E492G, T, P, H of the mature polypeptide of SEQ ID NO: 31 or SEQ ID NO: 1. In another embodiment, the derivative or variant comprises the substitution V493P, L of the mature polypeptide of SEQ ID NO: 31 or SEQ ID NO: 1. In another embodiment, the derivative or variant comprises the substitution D494N, Q, A, E, P of the mature polypeptide of SEQ ID NO: 31 or SEQ ID NO: 1. In another embodiment, the derivative or variant comprises the substitution E495Q, A of the mature polypeptide of SEQ ID NO: 31 or SEQ ID NO: 1. In another embodiment, the derivative or variant comprises the substitution T496A of the mature polypeptide of SEQ ID NO: 31 or SEQ ID NO: 1. In another embodiment, the derivative or variant comprises the substitution P499A of the mature polypeptide of SEQ ID NO: 31 or SEQ ID NO: 1. In another embodiment, the derivative or variant comprises the substitution K500E, G, D, A, S, C, P, H, F, N, W, T, M, Y, V, Q, L, I, R of the mature polypeptide of SEQ ID NO: 31 or SEQ ID NO: 1. In another embodiment, the derivative or variant comprises the substitution E501A, P, Q of the mature polypeptide of SEQ ID NO: 31 or SEQ ID NO: 1. In another embodiment, the derivative or variant comprises the substitution N503K, D, H of the mature polypeptide of SEQ ID NO: 31 or SEQ ID NO: 1. In another embodiment, the derivative or variant comprises the substitution A504E of the mature polypeptide of SEQ ID NO: 31 or SEQ ID NO: 1. In another embodiment, the derivative or variant comprises the substitution E505K, D of the mature polypeptide of SEQ ID NO: 31 or SEQ ID NO: 1. In another embodiment, the derivative or variant comprises the substitution T506F, S of the mature polypeptide of SEQ ID NO: 31 or SEQ ID NO: 1. In another embodiment, the derivative or variant comprises the substitution H510Q of the mature polypeptide of SEQ ID NO: 31 or SEQ ID NO: 1. In another embodiment, the derivative or variant comprises the substitution H535Q of the mature polypeptide of SEQ ID NO: 31 or SEQ ID NO: 1. In another embodiment, the derivative or variant comprises the substitution K536A of the mature polypeptide of SEQ ID NO: 31 or SEQ ID NO: 1. In another embodiment, the derivative or variant comprises the substitution P537A of the mature polypeptide of SEQ ID NO: 31 or SEQ ID NO: 1. In another embodiment, the derivative or variant comprises the substitution K538A, H of the mature polypeptide of SEQ ID NO: 31 or SEQ ID NO: 1. In another embodiment, the derivative or variant comprises the substitution T540S of the mature polypeptide of SEQ ID NO: 31 or SEQ ID NO: 1. In another embodiment, the derivative or variant comprises the substitution K541A, D, G, N, E of the mature polypeptide of SEQ ID NO: 31 or SEQ ID NO: 1. In another embodiment, the derivative or variant comprises the substitution E542P, D of the mature polypeptide of SEQ ID NO: 31 or SEQ ID NO: 1. In another embodiment, the derivative or variant comprises the substitution D550N of the mature polypeptide of SEQ ID NO: 31 or SEQ ID NO: 1. In another embodiment, the derivative or variant comprises the substitution K573Y, W, P, H, F, V, I, T, N, S, G, M, C, A, E, Q, R, L, D of the mature polypeptide of SEQ ID NO: 31 or SEQ ID NO: 1. In another embodiment, the derivative or variant comprises the substitution K574N of the mature polypeptide of SEQ ID NO: 31 or SEQ ID NO: 1. In another embodiment, the derivative or variant comprises the substitution Q580K of the mature polypeptide of SEQ ID NO: 31 or SEQ ID NO: 1. In another embodiment, the derivative or variant comprises the substitution L575F of the mature polypeptide of SEQ ID NO: 31 or SEQ ID NO: 1. In another embodiment, the derivative or variant comprises the substitution A577T, E of the mature polypeptide of SEQ ID NO: 31 or SEQ ID NO: 1. In another embodiment, the derivative or variant comprises the substitution A578R, S of the mature polypeptide of SEQ ID NO: 31 or SEQ ID NO: 1. In another embodiment, the derivative or variant comprises the substitution S579C, T of the mature polypeptide of SEQ ID NO: 31 or SEQ ID NO: 1. In another embodiment, the derivative or variant comprises the substitution Q580K of the mature polypeptide of SEQ ID NO: 31 or SEQ ID NO: 1. In another embodiment, the derivative or variant comprises the substitution A581D of the mature polypeptide of SEQ ID NO: 31 or SEQ ID NO: 1. In another embodiment, the derivative or variant comprises the substitution A582T of the mature polypeptide of SEQ ID NO: 31 or SEQ ID NO: 1. In another embodiment, the derivative or variant comprises the substitution G584A of the mature polypeptide of SEQ ID NO: 31 or SEQ ID NO: 1.

In one embodiment, the derivative or variant comprises an alteration at a position corresponding to position 417. In another embodiment, the amino acid at a position corresponding to position 417 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala or His. In another embodiment, the derivative or variant comprises the substitution Q417A, H of the mature polypeptide of SEQ ID NO: 31 or SEQ ID NO: 1.

In another embodiment, the derivative or variant comprises an alteration at a position corresponding to position 440. In another embodiment, the amino acid at a position corresponding to position 440 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution H440Q of the mature polypeptide of SEQ ID NO: 31 or SEQ ID NO: 1.

In another embodiment, the derivative or variant comprises an alteration at a position corresponding to position 464. In another embodiment, the amino acid at a position corresponding to position 464 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution H464Q of the mature polypeptide of SEQ ID NO: 31 or SEQ ID NO: 1.

In another embodiment, the derivative or variant comprises an alteration at a position corresponding to position 490 In another embodiment, the amino acid at a position corresponding to position 490 is substituted with Ala, Arg, Asn, Asp, Cys, Gln, Glu, Gly, His, Ile, Leu, Lys, Met, Phe, Pro, Ser, Thr, Trp, Tyr, or Val. In another embodiment, the derivative or variant comprises the substitution A490G of the mature polypeptide of SEQ ID NO: 31 or SEQ ID NO: 1.

In another embodiment, the derivative or variant comprises an alteration at a position corresponding to position 492. In another embodiment, the amino acid at a position corresponding to position 492 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gly. In another embodiment, the derivative or variant comprises the substitution E492G of the mature polypeptide of SEQ ID NO: 31 or SEQ ID NO: 1.

In another embodiment, the derivative or variant comprises an alteration at a position corresponding to position 493. In another aspect, the amino acid at a position corresponding to position 493 is substituted with Ala, Arg, Asn, Asp, Cys, Gln, Glu, Gly, His, Ile, Leu, Lys, Met, Phe, Pro, Ser, Thr, Trp, Tyr, or Val, preferably with Pro. In another embodiment, the derivative or variant comprises the substitution V493P of the mature polypeptide of SEQ ID NO: 31 or SEQ ID NO: 1.

In another embodiment, the derivative or variant comprises an alteration at a position corresponding to position 494. In another embodiment, the amino acid at a position corresponding to position 494 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn, Gln or Ala. In another embodiment, the derivative or variant comprises the substitution D494N, Q, A of the mature polypeptide of SEQ ID NO: 31 or SEQ ID NO: 1.

In another embodiment, the derivative or variant comprises an alteration at a position corresponding to position 495. In another embodiment, the amino acid at a position corresponding to position 495 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln or Ala. In another embodiment, the derivative or variant comprises the substitution E495Q or A of the mature polypeptide of SEQ ID NO: 31 or SEQ ID NO: 1.

In another embodiment, the derivative or variant comprises an alteration at a position corresponding to position 496. In another embodiment, the amino acid at a position corresponding to position 496 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution T496A of the mature polypeptide of SEQ ID NO: 31 or SEQ ID NO: 1.

In another embodiment, the derivative or variant comprises an alteration at a position corresponding to position 499. In another embodiment, the amino acid at a position corresponding to position 499 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution P499A of the mature polypeptide of SEQ ID NO: 31 or SEQ ID NO: 1.

In another embodiment, the derivative or variant comprises an alteration at a position corresponding to position 500. In another embodiment, the amino acid at a position corresponding to position 500 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution K500E, G, D, A, S, C, P, H, F, N, W, T, M, Y, V, Q, L, I, R of the mature polypeptide of SEQ ID NO: 31 or SEQ ID NO: 1.

In another embodiment, the derivative or variant comprises an alteration at a position corresponding to position 501. In another embodiment, the amino acid at a position corresponding to position 501 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala or Gin to reduce affinity and Pro to increase affinity. In another embodiment, the derivative or variant comprises the substitution E501A, Q, P of the mature polypeptide of SEQ ID NO: 31 or SEQ ID NO: 1.

In another embodiment, the derivative or variant comprises an alteration at a position corresponding to position 503. In another embodiment, the amino acid at a position corresponding to position 503 is substituted with Ala, Arg, Asn, Asp, Cys, Gin, Glu, Gly, His, Ile, Leu, Lys, Met, Phe, Pro, Ser, Thr, Trp, Tyr, or Val, preferably with Asp or Lys or His. In another embodiment, the derivative or variant comprises the substitution N503D, K, H of the mature polypeptide of SEQ ID NO: 31 or SEQ ID NO: 1.

In another embodiment, the derivative or variant comprises an alteration at a position corresponding to position 504. In another embodiment, the amino acid at a position corresponding to position 504 is substituted with Ala, Arg, Asn, Asp, Cys, Gin, Glu, Gly, His, Ile, Leu, Lys, Met, Phe, Pro, Ser, Thr, Trp, Tyr, or Val. In another embodiment, the derivative or variant comprises the substitution A504 of the mature polypeptide of SEQ ID NO: 31 or SEQ ID NO: 1.

In another embodiment, the derivative or variant comprises an alteration at a position corresponding to position 505. In another embodiment, the amino acid at a position corresponding to position 505 is substituted with Ala, Arg, Asn, Asp, Cys, Gln, Glu, Gly, His, Ile, Leu, Lys, Met, Phe, Pro, Ser, Thr, Trp, Tyr, or Val. In another embodiment, the derivative or variant comprises the substitution E505D of the mature polypeptide of SEQ ID NO: 31 or SEQ ID NO: 1.

In another embodiment, the derivative or variant comprises an alteration at a position corresponding to position 506. In another embodiment, the amino acid at a position corresponding to position 506 is substituted with Ala, Arg, Asn, Asp, Cys, Gln, Glu, Gly, His, Ile, Leu, Lys, Met, Phe, Pro, Ser, Thr, Trp, Tyr, or Val. In another embodiment, the derivative or variant comprises the substitution T506S, F of the mature polypeptide of SEQ ID NO: 31 or SEQ ID NO: 1.

In another embodiment, the derivative or variant comprises an alteration at a position corresponding to position 510. In another embodiment, the amino acid at a position corresponding to position 510 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another embodiment, the derivative or variant comprises the substitution H510Q of the mature polypeptide of SEQ ID NO: 31 or SEQ ID NO: 1.

In another embodiment, the derivative or variant comprises an alteration at a position corresponding to position 535. In another embodiment, the amino acid at a position corresponding to position 535 is substituted with Ala, Arg, Asn, Asp, Cys, Gin, Glu, Gly, His, Ile, Leu, Lys, Met, Phe, Pro, Ser, Thr, Trp, Tyr, or Val, preferably with Gln. In another embodiment, the derivative or variant comprises the substitution H535Q of the mature polypeptide of SEQ ID NO: 31 or SEQ ID NO: 1.

In another embodiment, the derivative or variant comprises an alteration at a position corresponding to position 536. In another embodiment, the amino acid at a position corresponding to position 536 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala. In another embodiment, the derivative or variant comprises the substitution K536A of the mature polypeptide of SEQ ID NO: 31 or SEQ ID NO: 1.

In another embodiment, the derivative or variant comprises an alteration at a position corresponding to position 537. In another embodiment, the amino acid at a position corresponding to position 537 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala. In another embodiment, the derivative or variant comprises the substitution P537A of the mature polypeptide of SEQ ID NO: 31 or SEQ ID NO: 1.

In another embodiment, the derivative or variant comprises an alteration at a position corresponding to position 538. In another embodiment, the amino acid at a position corresponding to position 538 is substituted with Ala, Arg, Asn, Asp, Cys, Gin, Glu, Gly, His, Ile, Leu, Lys, Met, Phe, Pro, Ser, Thr, Trp, Tyr, or Val, preferably with Ala. In another embodiment, the derivative or variant comprises the substitution K538H, A of the mature polypeptide of SEQ ID NO: 31 or SEQ ID NO: 1.

In another embodiment, the derivative or variant comprises an alteration at a position corresponding to position 540. In another embodiment, the amino acid at a position corresponding to position 540 is substituted with Ala, Arg, Asn, Asp, Cys, Gin, Glu, Gly, His, Ile, Leu, Lys, Met, Phe, Pro, Ser, Thr, Trp, Tyr, or Val. In another embodiment, the derivative or variant comprises the substitution T540S of the mature polypeptide of SEQ ID NO: 31 or SEQ ID NO: 1.

In another embodiment, the derivative or variant comprises an alteration at a position corresponding to position 541. In another embodiment, the amino acid at a position corresponding to position 541 is substituted with Ala, Arg, Asn, Asp, Cys, Gin, Glu, Gly, His, Ile, Leu, Lys, Met, Phe, Pro, Ser, Thr, Trp, Tyr, or Val, preferably with Gly, Asp or Ala. In another embodiment, the derivative or variant comprises the substitution K541 G, D A, N of the mature polypeptide of SEQ ID NO: 31 or SEQ ID NO: 1.

In another embodiment, the derivative or variant comprises an alteration at a position corresponding to position 542. In another embodiment, the amino acid at a position corresponding to position 542 is substituted with Ala, Arg, Asn, Asp, Cys, Gin, Glu, Gly, His, Ile, Leu, Lys, Met, Phe, Pro, Ser, Thr, Trp, Tyr, or Val, preferably with Asp or Pro. In another embodiment, the derivative or variant comprises the substitution E542D, P of the mature polypeptide of SEQ ID NO: 31 or SEQ ID NO: 1.

In another embodiment, the derivative or variant comprises an alteration at a position corresponding to position 550. In another embodiment, the amino acid at a position corresponding to position 550 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn to reduce affinity, preferably with Glu to increase affinity.

In another embodiment, the derivative or variant comprises an alteration at a position corresponding to position 573. In another embodiment, the amino acid at a position corresponding to position 573 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr, Trp, Pro, His. Phe, Val, Ile, Thr, Asn, Ser, Gly, Met, Cys, Ala, Glu, Gin, Arg, Leu, Asp. In another embodiment, the derivative or variant comprises the substitution K573Y, W, P, H, F, V, I, T, N, S, G, M, C, A, E, Q, R, L, D of the mature polypeptide of SEQ ID NO: 31 or SEQ ID NO: 1.

In another embodiment, the derivative or variant comprises an alteration at a position corresponding to position 574. In another embodiment, the amino acid at a position corresponding to position 574 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another embodiment, the derivative or variant comprises the substitution K574N of the mature polypeptide of SEQ ID NO: 31 or SEQ ID NO: 1.

In another embodiment, the derivative or variant comprises an alteration at a position corresponding to position 575. In another embodiment, the amino acid at a position corresponding to position 575 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another embodiment, the derivative or variant comprises the substitution L575F of the mature polypeptide of SEQ ID NO: 31 or SEQ ID NO: 1.

In another embodiment, the derivative or variant comprises an alteration at a position corresponding to position 577. In another embodiment, the amino acid at a position corresponding to position 577 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr or Glu. In another embodiment, the derivative or variant comprises the substitution A577TE of the mature polypeptide of SEQ ID NO: 31 or SEQ ID NO: 1.

In another embodiment, the derivative or variant comprises an alteration at a position corresponding to position 578. In another embodiment, the amino acid at a position corresponding to position 578 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg or Ser. In another embodiment, the derivative or variant comprises the substitution A578R, S of the mature polypeptide of SEQ ID NO: 31 or SEQ ID NO: 1.

In another embodiment, the derivative or variant comprises an alteration at a position corresponding to position 579. In another embodiment, the amino acid at a position corresponding to position 579 is substituted with Ala, Arg, Asn, Asp, Cys, Gln, Glu, Gly, His, Ile, Leu, Lys, Met, Phe, Pro, Ser, Thr, Trp, Tyr, or Val, preferably with Cys or Thr. In another embodiment, the derivative or variant comprises the substitution S579C, T of the mature polypeptide of SEQ ID NO: 31 or SEQ ID NO: 1.

In another embodiment, the derivative or variant comprises an alteration at a position corresponding to position 580. In another embodiment, the amino acid at a position corresponding to position 580 is substituted with Ala, Arg, Asn, Asp, Cys, Gln, Glu, Gly, His, Ile, Leu, Lys, Met, Phe, Pro, Ser, Thr, Trp, Tyr, or Val, preferably with Lys. In another embodiment, the derivative or variant comprises the substitution Q580K of the mature polypeptide of SEQ ID NO: 31 or SEQ ID NO: 1.

In another embodiment, the derivative or variant comprises an alteration at a position corresponding to position 581. In another embodiment, the amino acid at a position corresponding to position 581 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another embodiment, the derivative or variant comprises the substitution A581D of the mature polypeptide of SEQ ID NO: 31 or SEQ ID NO: 1.

In another embodiment, the derivative or variant comprises an alteration at a position corresponding to position 582. In another embodiment, the amino acid at a position corresponding to position 582 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another embodiment, the derivative or variant comprises the substitution A582T of the mature polypeptide of SEQ ID NO: 31 or SEQ ID NO: 1.

In another embodiment, the derivative or variant comprises an alteration at a position corresponding to position 584. In another embodiment, the amino acid at a position corresponding to position 584 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another embodiment, the derivative or variant comprises the substitution G584A of the mature polypeptide of SEQ ID NO: 31 or SEQ ID NO: 1.

In another embodiment, the derivative or variant comprises an alteration at positions corresponding to positions 494 and 496 in SEQ ID NO: 31 or SEQ ID NO: 1, such as those described above.

In another embodiment, the derivative or variant comprises alterations at positions corresponding to positions 492 and 493 in SEQ ID NO: 31 or SEQ ID NO: 1, such as those described above.

In another embodiment, the derivative or variant comprises alterations at positions corresponding to positions 494 and 417 in SEQ ID NO: 31 or SEQ ID NO: 1, such as those described above.

In another embodiment, the derivative or variant comprises alterations at positions corresponding to positions 492 and 503 in SEQ ID NO: 31 or SEQ ID NO: 1, such as those described above.

In another embodiment, the derivative or variant comprises alterations at positions corresponding to positions 492 and 573 in SEQ ID NO: 31 or SEQ ID NO: 1, such as those described above.

In another embodiment, the derivative or variant comprises alterations at positions corresponding to positions 492, 503, and 573 in SEQ ID NO: 31 or SEQ ID NO: 1, such as those described above.

In one embodiment the derivative or variant albumin or fragments thereof, or fusion polypeptides comprising the derivative or variant albumin or fragments thereof according to the invention contains one substitution at a position corresponding to a position in HSA selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1 provided that the derivative or variant albumin is not the derivative or variant consisting of SEQ ID NO: 31 or SEQ ID NO: 1 with the substitution D494N, E501K, K541E, D550G, A, K573E or K574N. The derivative or variant albumin, fragment thereof or fusion polypeptides comprising derivative or variant albumin or a fragment thereof according to the invention may comprise additional substitutions, insertions or deletions at one or more (several) positions corresponding to other positions in HSA.

In another embodiment the derivative or variant albumin or fragments thereof, or fusion polypeptides comprising derivative or variant albumin or fragments thereof according to the invention contains two, three, four, five, six, seven, eight, nine, ten, eleven, twelve, thirteen, fourteen fifteen, sixteen, seventeen, eighteen, nineteen twenty or even more substitutions at positions corresponding to positions in HSA selected from the group consisting of 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of SEQ ID NO: 31 or SEQ ID NO: 1. The derivative or variant albumin or fragments thereof, or fusion polypeptides comprising or consisting of a derivative or variant albumin or fragments thereof according to the invention may comprise additional substitutions, insertions or deletions at positions corresponding to other positions in HSA.

In a further embodiment the derivatives or variants of albumin or fragments thereof, or fusion polypeptides comprising or consisting of a derivative or variant albumin or a fragment thereof according to the invention have a plasma half-life that is longer than the plasma half-life of the parent albumin fragment thereof or fusion polypeptide comprising or consisting of the parent albumin or a fragment thereof. Examples according to this embodiment include derivatives or variants of albumin or fragments thereof, or fusion polypeptides comprising or consisting of a derivative or variant albumin or a fragment thereof comprising a substitution in the position corresponding to 492, 503, 542, 550, 573, 574, 580, 581, 582 or 584 in SEQ ID NO: 31 or SEQ ID NO: 1. Preferred substitutions according to this embodiment of the invention include the substitution of the amino acid residue in the position corresponding to 492 in SEQ ID NO: 31 or SEQ ID NO: 1 with a G residue, substitution of the amino acid residue in the position corresponding to 503 in SEQ ID NO: 31 or SEQ ID NO: 1 with a H or a K residue, substitution of the amino acid residue in the position corresponding to 550 in SEQ ID NO: 31 or SEQ ID NO: 1 with an E residue, the substitution of the amino acid residue in a position corresponding to 573 in SEQ ID NO: 31 or SEQ ID NO: 1 with an Y, W, P, H, F, V, I, T, N, S, G, M, C, A, E, Q, R, L or a D, the substitution of the amino acid residue in a position corresponding to 574 in SEQ ID NO: 31 or SEQ ID NO: 1 with an N residue, or the substitution of the amino acid residue in the position corresponding to 580 in SEQ ID NO: 31 or SEQ ID NO: 1 with an K residue. Other preferred derivatives or variants have a substitution in the position corresponding to 492 in SEQ ID NO: 31 or SEQ ID NO: 1 with a G residue and a substitution in the position corresponding to 573 in SEQ ID NO: 31 or SEQ ID NO: 1 with an A or a P residue. Other preferred derivative or variant has a number of substitutions corresponding to position 492 in SEQ ID NO: 31 or SEQ ID NO: 1 with an H residue in position 503 in SEQ ID NO: 31 or SEQ ID NO: 1.

Other preferred derivatives or variants have a substitution in the position corresponding to 492 in SEQ ID NO: 31 or SEQ ID NO: 1 with a G residue and a substitution in the position corresponding to position 503 in SEQ ID NO: 31 or SEQ ID NO: 1 corresponding to a H or a K and a substitution in position 573 in SEQ ID NO: 31 or SEQ ID NO: 1 with an A or a P residue.

In a further embodiment the derivatives or variants of albumin or fragments thereof, or fusion polypeptides comprising or consisting of a derivative or variant albumin or fragments thereof according to the invention have a plasma half-life that is shorter than the plasma half-life of the parent albumin fragment thereof or fusion polypeptide comprising the parent albumin or a fragment thereof. Examples according to this embodiment include derivatives or variants of albumin or fragments thereof, or fusion polypeptides comprising derivative or variant albumin or a fragment thereof comprising a substitution in the position corresponding to 417, 440, 494, 495, 496, 499, 500, 501, 536, 537, 538, 541, 494+496 or 492+493 in SEQ ID NO: 31 or SEQ ID NO: 1. Preferred substitutions include the substitutions corresponding to Q417A, H440Q, D494E+Q417H, D494N, Q, A, E495Q, A, T496A, D494N+T496A or, P499A, K500A, E501A, E501Q, K536A, P537A, K538A, K541G, K541A K541D or D550N in SEQ ID NO: 31 or SEQ ID NO: 1.

In another embodiment of the invention the derivatives or variants of albumin or fragments thereof, or fusion polypeptides comprising derivative or variant albumin or a fragment thereof according to the invention have lost their ability to bind FcRn. In this connection derivatives or variants of albumin or fragments thereof, or fusion polypeptides comprising derivative or variant albumin or fragments thereof is considered to have lost the ability to bind FcRn if the measured resonance units for the derivative or variant in the SPR assay described below is less than 10% of the measured resonance units for the corresponding parent albumin or fragment thereof. Examples according to this embodiment include derivatives or variants of albumin or fragments thereof, or fusion polypeptides comprising derivative or variant albumin or fragments thereof comprising a substitution at a position corresponding to 464, 500, 510 or 535 in SEQ ID NO: 31 or SEQ ID NO: 1. Preferred substitutions include the substitutions corresponding to H464Q, K500A, P, C, S, A, D. G H510Q or H535Q in SEQ ID NO: 31 or SEQ ID NO: 1.

In addition to the one or more (several) substitutions at one or more (several) positions corresponding to positions 417, 464, 490, 492, 493, 494, 495, 496, 499, 500, 501, 503, 504, 505, 506, 510, 535, 536, 537, 538, 540, 541, 542, 550, 573, 574, 580 581, 582 and 584 in SEQ ID NO: 31 or SEQ ID NO: 1 the derivative or variant albumin or fragments thereof, or fusion polypeptides comprising derivative or variant albumin or fragments thereof according to the invention may contain additional substitutions, deletions or insertions in other positions of the molecules. Such additional substitutions, deletions or insertions may be useful in order to alter other properties of the molecules such as but not limited to altered glycosylation; introduction of reactive groups of the surface such a thiol groups, removing/generating a carbamoylation site; etc.

Residues that might be altered in order to provide reactive residues on the surface and which advantageously could be applied to the invention has been disclosed in the unpublished patent application WO 2010/092135 (Included by reference). Particular preferred residues include the positions corresponding to positions in SEQ ID NO: 31 or SEQ ID NO: 1.

As examples of alterations that can be made in SEQ ID NO: 31 or SEQ ID NO: 1 or in corresponding positions in other albumins in order to provide a reactive thiol group on the surface includes alterations corresponding to following alterations in SEQ ID NO: 31 or SEQ ID NO: 1: L585C, D1C, A2C, D562C, A364C, A504C, E505C, T79C, E86C, D129C, D549C, A581C, D121C, E82C, S270C, A578C, L595LC, D1DC, A2AC, D562DC, A364AC, A504AC, E505EC, T79TC, E86EC, D129DC, D549DC, A581AC, A581AC, D121DC, E82EC, S270SC, A579AC, C360*, C316*, C75*, C168*, C558*, C361*, C91*, C124*, C169* and C567*. Alternatively a cysteine residue may be added to the N or C terminal of albumin.

In a second aspect, the invention relates to isolated polynucleotides that encode any of the polypeptides of the invention, for example: (i) nucleic acids encoding the albumin derivative or variant, fragment thereof or fusion polypeptide comprising said albumin derivative or variant or fragment thereof, (ii) plasmids comprising said nucleic acids and (iii) host cells comprising said plasmid. The invention also relates to nucleic acid constructs comprising a polynucleotide encoding a derivative or variant of the invention operably linked to one or more (several) control sequences that direct the expression of the coding sequence in a suitable host cell under conditions compatible with the control sequences. In the second aspect of the invention, preferably, the parent is encoded by a polynucleotide that hybridizes under very low stringency conditions, low stringency conditions, medium stringency conditions, medium-high stringency conditions, high stringency conditions, or very high stringency conditions with (i) the mature polypeptide-coding sequence of SEQ ID NO: 2 (SEQ ID NO: 3: NCBI Reference Sequence: NM_000477.5, SEQ ID NO: 3 is genomic DNA), (ii) the cDNA sequence encoding the mature polypeptide (cDNA is SEQ ID NO: 2), or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 2 or a subsequence thereof, as well as the amino acid sequence of SEQ ID NO: 2 or a fragment thereof, may be used to design nucleic acid probes to identify and clone DNA encoding a parent from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the invention.

A genomic DNA or cDNA library prepared from such other organisms may be screened for DNA that hybridizes with the probes described above and encodes a parent. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 2 or a subsequence thereof, the carrier material is used in a Southern blot.

For purposes of the invention, hybridization indicates that the polynucleotide hybridizes to a labeled nucleotide probe corresponding to the polynucleotide shown in SEQ ID NO: 2, its complementary strand, or a subsequence thereof, under low to very high stringency conditions. Molecules to which the probe hybridizes can be detected using, for example, X-ray film or any other detection means known in the art.

In one embodiment, the nucleic acid probe is the mature polypeptide coding sequence of SEQ ID NO: 2. In another embodiment, the nucleic acid probe is nucleotides 1 to 1758 of SEQ ID NO: 2. In another embodiment, the nucleic acid probe is a polynucleotide that encodes the polypeptide of SEQ ID NO: 1 or a fragment thereof. In another embodiment, the nucleic acid probe is SEQ ID NO: 2.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 45° C. (very low stringency), 50° C. (low stringency), 55° C. (medium stringency), 60° C. (medium-high stringency), 65° C. (high stringency), or 70° C. (very high stringency).

For short probes that are about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48: 1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The parent may be encoded by a polynucleotide with a sequence identity to the mature polypeptide coding sequence of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, which encodes a polypeptide which is able to function as an albumin. In an embodiment, the parent is encoded by a polynucleotide comprising or consisting of SEQ ID NO: 2.

According to a third aspect of the invention, the albumin derivative or variant, fragment thereof or fusion polypeptide comprising said albumin derivative or variant or fragment thereof according to the invention may be conjugated to a second molecule using techniques well known within the art. Said second molecule may comprise or consist of a diagnostic moiety, and in this embodiment the conjugate may be useful as a diagnostic tool such as in imaging; or the second molecule may be a therapeutic compound and in this embodiment the conjugate may be used for therapeutic purposes where the conjugate will have the therapeutic properties of the therapeutic compound as well as an altered plasma half-life, derived from its association with the albumin derivative, fragment, variant thereof. Conjugates of albumin and a therapeutic molecule are known in the art and it has been verified that such conjugates have long plasma half-lives, compared with the non-conjugated free therapeutic molecule, as such. The conjugates may conveniently be linked via a free thiol group present on the surface of the albumin derivate, fragment or derivative or variant thereof. The presence of this thiol group could be either naturally occurring (for example, the free thiol group may be equivalent to amino acid residue 34 of mature HSA) or engineered into the polypeptide, using techniques well known within the art for genetic engineering and conjugation chemistry. Alternatively the conjugates may be linked via other free thiol groups provided on the surface of the HSA domain III derivative, fragment, or variant thereof e.g. such as disclosed in the co-pending patent application (EP 2009 152 625.1, incorporated herein by reference).

The half-life of an albumin conjugation according to the invention may be longer or shorter than the half-life of the conjugation partner molecule alone. The half-life of an albumin conjugation according to the invention may be longer or shorter than the half-life of the analogous/equivalent albumin conjugation comprising native HSA (instead of an albumin variant or derivative according to the invention) and the conjugation molecule.

In one particularly preferred embodiment the derivative or variant albumin or fragment thereof is conjugated to a beneficial therapeutic compound and the conjugate is used for treatment of a condition in a patient in need thereof, which condition is responsive to the particular selected therapeutic compound. Techniques for conjugating such a therapeutically compound to the derivative or variant albumin or fragment thereof are known in the art. WO 2009/019314 discloses examples of techniques suitable for conjugating a therapeutically compound to a polypeptide which techniques can also be applied to the invention. Further WO 2009/019314 discloses examples of compounds and moieties that may be conjugated to substituted transferrin and these examples may also be applied to the invention. The teaching of WO 2009/019314 is included herein by reference.

HSA contains in its natural form one free thiol group that conveniently may be used for conjugation. As a particular embodiment within this embodiment the derivative or variant albumin or fragment thereof may comprise further modifications provided to generate additional free thiol groups on the surface. This has the benefit that the payload of the derivative or variant albumin or fragment thereof is increased so that more than one molecule of the therapeutic compound can be conjugated to each molecule of derivative or variant albumin or fragment thereof, or two or more different therapeutic compounds may be conjugated to each molecule of derivative or variant albumin or fragment thereof, e.g., a compound having targeting properties such as an antibody specific for example a tumour; and a cytotoxic drug conjugated to the derivative or variant albumin or fragment thereof thereby creating a highly specific drug against a tumour. Teaching of particular residues that may be modified to provide for further free thiol groups on the surface can be found in co-pending patent application WO 2010/092135, which is incorporated by reference.

According to a fourth aspect of the invention, the albumin derivative, fragment, or variant thereof, according to the invention, may also be fused with a non-albumin polypeptide fusion partner. The fusion partner may in principle be any polypeptide, but generally it is preferred that the fusion partner is a polypeptide having therapeutic or diagnostic properties. Fusion polypeptides comprising albumin are known in the art. It has been found that such a fusion polypeptide comprising or consisting of albumin and a fusion partner polypeptide have a longer plasma half-life compared to the unfused fusion partner polypeptide alone. According to the invention it is possible to alter the plasma half-life of the fusion polypeptides according to the invention compared to the corresponding fusion polypeptides of the prior art. Further teaching regarding albumin fusions to fusion partner polypeptides and examples of suitable fusion partner polypeptides can be found in WO 01/79271 A and WO 03/59934 A. The half-life of an albumin fusion according to the invention may be longer or shorter than the half-life of the fusion partner polypeptide alone. The half-life of an albumin fusion according to the invention may be longer or shorter than the half-life of the analogous/equivalent albumin fusion comprising or consisting of native HSA (instead of an albumin variant or derivative according to the invention) and the fusion partner.

For all aspects of the invention fusion partner polypeptides and/or conjugates may comprise one or more (several) of: 4-1BB ligand, 5-helix, A human C-C chemokine, A human L105 chemokine, A human L105 chemokine designated huL105_3., A monokine induced by gamma-interferon (MIG), A partial CXCR4B protein, A platelet basic protein (PBP), α1-antitrypsin, ACRP-30 Homologue; Complement Component C1q C, Adenoid-expressed chemokine (ADEC), aFGF; FGF-1, AGF, AGF Protein, albumin, an etoposide, angiostatin, Anthrax vaccine, Antibodies specific for collapsin, antistasin, Anti-TGF beta family antibodies, antithrombin III, APM-1; ACRP-30; Famoxin, apo-lipoprotein species, Arylsulfatase B, b57 Protein, BCMA, Beta-thromboglobulin protein (beta-TG), bFGF; FGF2, Blood coagulation factors, BMP Processing Enzyme Furin, BMP-10, BMP-12, BMP-15, BMP-17, BMP-18, BMP-2B, BMP-4, BMP-5, BMP-6, BMP-9, Bone Morphogenic Protein-2, calcitonin, Calpain-10a, Calpain-10b, Calpain-10c, Cancer Vaccine, Carboxypeptidase, C-C chemokine, MCP2, CCR5 variant, CCR7, CCR7, CD11a Mab, CD137; 4-1BB Receptor Protein, CD20 Mab, CD27, CD27L, CD30, CD30 ligand, CD33 immunotoxin, CD40, CD40L, CD52 Mab, Cerebus Protein, Chemokine Eotaxin., Chemokine hIL-8, Chemokine hMCP1, Chemokine hMCP1a, Chemokine hMCP1b, Chemokine hMCP2, Chemokine hMCP3, Chemokine hSDF1b, Chemokine MCP-4, chemokine TECK and TECK variant, Chemokine-like protein IL-8M1 Full-Length and Mature, Chemokine-like protein IL-8M10 Full-Length and Mature, Chemokine-like protein IL-8M3, Chemokine-like protein IL-8M8 Full-Length and Mature, Chemokine-like protein IL-8M9 Full-Length and Mature, Chemokine-like protein PF4-414 Full-Length and Mature, Chemokine-like protein PF4-426 Full-Length and Mature, Chemokine-like protein PF4-M2 Full-Length and Mature, Cholera vaccine, Chondromodulin-like protein, c-kit ligand; SCF; Mast cell growth factor; MGF; Fibrosarcoma-derived stem cell factor, CNTF and fragment thereof (such as CNTFAx15'(Axokine™)), coagulation factors in both pre and active forms, collagens, Complement C5 Mab, Connective tissue activating protein-III, CTAA16.88 Mab, CTAP-III, CTLA4-Ig, CTLA-8, CXC3, CXC3, CXCR3; CXC chemokine receptor 3, cyanovirin-N, Darbepoetin, designated exodus, designated huL105_7., DIL-40, Dnase, EDAR, EGF Receptor Mab, ENA-78, Endostatin, Eotaxin, Epithelial neutrophil activating protein-78, EPO receptor; EPOR, erythropoietin (EPO) and EPO mimics, Eutropin, Exodus protein, Factor IX, Factor VII, Factor VIII, Factor X and Factor XIII, FAS Ligand Inhibitory Protein (DcR3), FasL, FasL, FasL, FGF, FGF-12; Fibroblast growth factor homologous factor-1, FGF-15, FGF-16, FGF-18, FGF-3; INT-2, FGF-4; gelonin, HST-1; HBGF-4, FGF-5, FGF-6; Heparin binding secreted transforming factor-2, FGF-8, FGF-9; Glia activating factor, fibrinogen, flt-1, flt-3 ligand, Follicle stimulating hormone Alpha subunit, Follicle stimulating hormone Beta subunit, Follitropin, Fractalkine, fragment. myofibrillar protein Troponin I, FSH, Galactosidase, Galectin-4, G-CSF, GDF-1, Gene therapy, Glioma-derived growth factor, glucagon, glucagon-like peptides, Glucocerebrosidase, glucose oxidase, Glucosidase, Glycodelin-A; Progesterone-associated endometrial protein, GM-CSF, gonadotropin, Granulocyte chemotactic protein-2 (GCP-2), Granulocyte-macrophage colony stimulating factor, growth hormone, Growth related oncogene-alpha (GRO-alpha), Growth related oncogene-beta (GRO-beta), Growth related oncogene-gamma (GRO-gamma), hAPO-4; TROY, hCG, Hepatitis B surface Antigen, Hepatitis B Vaccine, HER2 Receptor Mab, hirudin, HIV gp120, HIV gp41, HIV Inhibitor Peptide, HIV Inhibitor Peptide, HIV Inhibitor Peptide, HIV protease inhibiting peptides, HIV-1 protease inhibitors, HPV vaccine, Human 6CKine protein, Human Act-2 protein, Human adipogenesis inhibitory factor, human B cell stimulating factor-2 receptor, Human beta-chemokine H1305 (MCP-2), Human C-C chemokine DGWCC, Human CC chemokine ELC protein, Human CC type chemokine interleukin C, Human CCC3 protein, Human CCF18 chemokine, Human CC-type chemokine protein designated SLC (secondary lymphoid chemokine), Human chemokine beta-8 short forms, Human chemokine C10, Human chemokine CC-2, Human chemokine CC-3, Human chemokine CCR-2, Human chemokine Ckbeta-7, Human chemokine ENA-78, Human chemokine eotaxin, Human chemokine GRO alpha, Human chemokine GROalpha, Human chemokine GRObeta, Human chemokine HCC-1, Human chemokine HCC-1, Human chemokine 1-309, Human chemokine IP-10, Human chemokine L105_3, Human chemokine L105_7, Human chemokine MIG, Human chemokine MIG-beta protein, Human chemokine MIP-1alpha, Human chemokine MIP1beta, Human chemokine MIP-3alpha, Human chemokine MIP-3beta, Human chemokine PF4, Human chemokine protein 331D5, Human chemokine protein 61164, Human chemokine receptor CXCR3, Human chemokine SDF1alpha, Human chemokine SDF1beta, Human chemokine ZSIG-35, Human Chr19Kine protein, Human CKbeta-9, Human CKbeta-9, Human CX3C 111 amino acid chemokine, Human DNAX interleukin-40, Human DVic-1 C-C chemokine, Human EDIRF I protein sequence, Human EDIRF II protein sequence, Human eosinocyte CC type chemokine eotaxin, Human eosinophil-expressed chemokine (EEC), Human fast twitch skeletal muscle troponin C, Human fast twitch skeletal muscle troponin I, Human fast twitch skeletal muscle Troponin subunit C, Human fast twitch skeletal muscle Troponin subunit I Protein, Human fast twitch skeletal muscle Troponin subunit T, Human fast twitch skeletal muscle troponin T, Human foetal spleen expressed chemokine, FSEC, Human GM-CSF receptor, Human gro-alpha chemokine, Human gro-beta chemokine, Human gro-gamma chemokine, Human IL-16 protein, Human IL-1RD10 protein sequence, Human IL-1RD9, Human IL-5 receptor alpha chain, Human IL-6 receptor, Human IL-8 receptor protein hIL8RA, Human IL-8 receptor protein hIL8RB, Human IL-9 receptor protein, Human IL-9 receptor protein variant #3, Human IL-9 receptor protein variant fragment, Human IL-9 receptor protein variant fragment#3, Human interleukin 1 delta, Human Interleukin 10, Human Interleukin 10, Human interleukin 18, Human interleukin 18 derivatives, Human interleukin-1 beta precursor, Human interleukin-1 beta precursor, Human interleukin-1 receptor accessory protein, Human interleukin-1 receptor antagonist beta, Human interleukin-1 type-3 receptor, Human Interleukin-10 (precursor), Human Interleukin-10 (precursor), Human interleukin-11 receptor, Human interleukin-12 40 kD subunit, Human interleukin-12 beta-1 receptor, Human interleukin-12 beta-2 receptor, Human Interleukin-12 p35 protein, Human Interleukin-12 p40 protein, Human interleukin-12 receptor, Human interleukin-13 alpha receptor, Human interleukin-13 beta receptor, Human interleukin-15, Human interleukin-15 receptor from clone P1, Human interleukin-17 receptor, Human interleukin-18 protein (IL-18), Human interleukin-3, human interleukin-3 receptor, Human interleukin-3 variant, Human interleukin-4 receptor, Human interleukin-5, Human interleukin-6, Human interleukin-7, Human interleukin-7, Human interleukin-8 (IL-8), Human intracellular IL-1 receptor antagonist, Human IP-10 and HIV-1 gp120 hypervariable region fusion protein, Human IP-10 and human Muc-1 core epitope (VNT) fusion protein, human liver and activation regulated chemokine (LARC), Human Lkn-1 Full-Length and Mature protein, Human mammary associated chemokine (MACK) protein Full-Length and Mature, Human mature chemokine Ckbeta-7, Human mature gro-alpha, Human mature gro-gamma polypeptide used to treat sepsis, Human MCP-3 and human Muc-1 core epitope (VNT) fusion protein, Human MI10 protein, Human MI1A protein, Human monocyte chemoattractant factor hMCP-1, Human monocyte chemoattractant factor hMCP-3, Human monocyte chemotactic proprotein (MCPP) sequence, Human neurotactin chemokine like domain, Human non-ELR CXC chemokine H174, Human non-ELR CXC chemokine IP10, Human non-ELR CXC chemokine Mig, Human PAI-1 mutants, Human protein with IL-16 activity, Human protein with IL-16 activity, Human secondary lymphoid chemokine (SLC), Human SISD protein, Human STCP-1, Human stromal cell-derived chemokine, SDF-1, Human T cell mixed lymphocyte reaction expressed chemokine (TMEC), Human thymus and activation regulated cytokine (TARC), Human thymus expressed, Human TNF-alpha, Human TNF-alpha, Human TNF-beta (LT-alpha), Human type CC chemokine eotaxin 3 protein sequence, Human type II interleukin-1 receptor, Human wild-type interleukin-4 (hIL-4) protein, Human ZCHEMO-8 protein, Humanized Anti-VEGF Antibodies, and fragments thereof, Humanized Anti-VEGF Antibodies, and fragments thereof, Hyaluronidase, ICE 10 kD subunit, ICE 20 kD subunit, ICE 22 kD subunit, Iduronate-2-sulfatase, Iduronidase, IL-1 alpha, IL-1 beta, IL-1 inhibitor (IL-1i), IL-1 mature, IL-10 receptor, IL-11, IL-11, IL-12 p40 subunit, IL-13, IL-14, IL-15, IL-15 receptor, IL-17, IL-17 receptor, Il-17 receptor, Il-17 receptor, IL-19, IL-1i fragments, IL1-receptor antagonist, IL-21 (TIF), IL-3 containing fusion protein, IL-3 mutant proteins, IL-3 variants, IL-3 variants, IL-4, IL-4 mutein, IL-4 mutein Y124G, IL-4 mutein Y124X, IL-4 muteins, Il-5 receptor, IL-6, II-6 receptor, IL-7 receptor clone, IL-8 receptor, IL-9 mature protein variant (Met117 version), immunoglobulins or immunoglobulin-based molecules or fragment of either (e.g. a Small Modular ImmunoPharmaceutical™ ("SMIP") or dAb, Fab' fragments, F(ab')2, scAb, scFv or scFv fragment), including but not limited to plasminogen, Influenza Vaccine, Inhibin alpha, Inhibin beta, insulin, insulin-like growth factor, Integrin Mab, inter-alpha trypsin inhibitor, inter-alpha trypsin inhibitor, Interferon gamma-inducible protein (IP-10), interferons (such as interferon alpha species and sub-species, interferon beta species and sub-species, interferon gamma species and sub-species), interferons (such as interferon alpha species and sub-species, interferon beta species and sub-species, interferon gamma species and sub-species), Interleukin 6, Interleukin 8 (IL-8) receptor, Interleukin 8 receptor B, Interleukin-1alpha, Interleukin-2 receptor associated protein p43, interleukin-3, interleukin-4 muteins, Interleukin-8 (IL-8) protein, interleukin-9, Interleukin-9 (IL-9) mature protein (Thr117 version), interleukins (such as IL0, IL11 and IL2), interleukins (such as IL0, IL11 and IL2), Japanese encephalitis vaccine, Kalikrein Inhibitor, Keratinocyte growth factor, Kunitz domain protein (such as aprotinin, amyloid precursor protein and those described in WO 03/066824, with or without albumin fusions), Kunitz domain protein (such as aprotinin, amyloid precursor protein and those described in WO 03/066824, with or without albumin fusions), LACI, lactoferrin, Latent TGF-beta binding protein II, leptin, Liver expressed chemokine-1 (LVEC-1), Liver expressed chemokine-2 (LVEC-2), LT-alpha, LT-beta, Luteinization Hormone, Lyme Vaccine, Lymphotactin, Macrophage derived chemokine analogue MDC (n+1), Macrophage derived chemokine analogue MDC-eyfy, Macrophage derived chemokine analogue MDC-yl, Macrophage derived chemokine, MDC, Macrophage-derived chemokine (MDC), Maspin; Protease Inhibitor 5, MCP-1 receptor, MCP-1a, MCP-1b, MCP-3, MCP-4 receptor, M-CSF, Melanoma inhibiting protein, Membrane-bound proteins, Met117 human interleukin 9, MIP-3 alpha, MIP-3 beta, MIP-Gamma, MIRAP, Modified Rantes, monoclonal antibody, MP52, Mutant Interleukin 6 S176R, myofibrillar contractile protein Troponin I, Natriuretic Peptide, Nerve Growth Factor-beta, Nerve Growth Factor-beta2, Neuropilin-1, Neuropilin-2, Neurotactin, Neurotrophin-3, Neurotrophin-4, Neurotrophin-4a, Neurotrophin-4b, Neurotrophin-4c, Neurotrophin-4d, Neutrophil activating peptide-2 (NAP-2), NOGO-66 Receptor, NOGO-A, NOGO-B, NOGO-C, Novel beta-chemokine designated PTEC, N-terminal modified chemokine GroHEK/hSDF-1alpha, N-terminal modified chemokine GroHEK/hSDF-1beta, N-terminal modified chemokine met-hSDF-1 alpha, N-terminal modified chemokine met-hSDF-1 beta, OPGL, Osteogenic Protein-1; OP-1; BMP-7, Osteogenic Protein-2, OX40; ACT-4, OX40L, Oxytocin (Neurophysin I), parathyroid hormone, Patched, Patched-2, PDGF-D, Pertussis toxoid, Pituitary expressed chemokine (PGEC), Placental Growth Factor, Placental Growth Factor-2, Plasminogen Activator Inhibitor-1; PAI-1, Plasminogen Activator Inhibitor-2; PAI-2, Plasminogen Activator Inhibitor-2; PAI-2, Platelet derived growth factor, Platelet derived growth factor Bv-sis, Platelet derived growth factor precursor A, Platelet derived growth factor precursor B, Platelet Mab, platelet-derived endothelial cell growth factor (PD-ECGF), Platelet-Derived Growth Factor A chain, Platelet-Derived Growth Factor B chain, polypeptide used to treat sepsis, Preproapolipoprotein "milano" variant, Preproapolipoprotein "paris" variant, pre-thrombin, Primate CC chemokine "ILINCK", Primate CXC chemokine "IBICK", proinsulin, Prolactin, Prolactin2, prosaptide, Protease inhibitor peptides, Protein C, Protein S, pro-thrombin, prourokinase, RANTES, RANTES 8-68, RANTES 9-68, RANTES peptide, RANTES receptor, Recombinant interleukin-16, Resistin, restrictocin, Retroviral protease inhibitors, ricin, Rotavirus Vaccine, RSV Mab, saporin, sarcin, Secreted and Transmembrane polypeptides, Secreted and Transmembrane polypeptides, serum cholinesterase, serum protein (such as a blood clotting factor), Soluble BMP Receptor Kinase Protein-3, Soluble VEGF Receptor, Stem Cell Inhibitory Factor, Straphylococcus Vaccine, Stromal Derived Factor-1 alpha, Stromal Derived Factor-1 beta, Substance P (tachykinin), T1249 peptide, T20 peptide, T4 Endonuclease, TACI, Tarc, TGF-beta 1, TGF-beta 2, Thr117 human interleukin 9, thrombin, thrombopoietin, Thrombopoietin derivative1, Thrombopoietin derivative2, Thrombopoietin derivative3, Thrombopoietin derivative4, Thrombopoietin derivative5, Thrombopoietin derivative6, Thrombopoietin derivative7, Thymus expressed chemokine (TECK), Thyroid stimulating Hormone, tick anticoagulant peptide, Tim-1 protein, TNF-alpha precursor, TNF-R, TNF-RII; TNF p75 Receptor; Death Receptor, tPA, transferrin, transforming growth factor beta, Troponin peptides, Truncated monocyte chemotactic protein 2 (6-76), Truncated monocyte chemotactic protein 2 (6-76), Truncated RANTES protein (3-68), tumour necrosis factor, Urate Oxidase, urokinase, Vasopressin (Neurophysin II), VEGF R-3; flt-4, VEGF Receptor; KDR; flk-1, VEGF-110, VEGF-121, VEGF-138, VEGF-145, VEGF-162, VEGF-165, VEGF-182, VEGF-189, VEGF-206, VEGF-D, VEGF-E; VEGF-X; von Willebrand's factor, Wild type monocyte chemotactic protein 2, Wild type monocyte chemotactic protein 2, ZTGF-beta 9.

Furthermore, conjugates may comprise one or more (several) of chemotherapy drugs such as: 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, A, Abraxane, Accutane®, Actinomycin-D, Adriamycin®, Adrucil®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin diftitox, DepoCyt™, Dexamethasone, Dexamethasone acetate, Dexamethasone Sodium Phosphate, Dexasone, Dexrazoxane, DHAD, DIC, Diodex, Docetaxel, Doxil®, Doxorubicin, Doxorubicin liposomal, Droxia™, DTIC, DTIC-Dome®, Duralone®, Efudex®, Eligard™, Ellence™, Eloxatin™, Elspar®, Emcyt®, Epirubicin, Epoetin alfa, Erbitux™, Erlotinib, Erwinia L-asparaginase, Estramustine, Ethyol, Etopophos®, Etoposide, Etoposide Phosphate, Eulexin®, Evista®, Exemestane, Fareston®, Faslodex®, Ferrara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar®, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Tositumomab, Trastuzumab, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®; radiopharmaceuticals such as: Carbon-11, Carbon-14, Chromium-51, Cobalt-57, Cobalt-58, Erbium-169, Fluorine-18, Gallium-67, Gold-198, Indium-111, Indium-113m, Iodine-123, Iodine-125, Iodine-131, Iron-59, Krypton-81m, Nitrogen-13, Oxygen-15, Phosphorous-32, Rhenium-186, Rubidium-82, Samarium-153, Selenium-75, Strontium-89, Technetium-99m, Thallium-201, Tritium, Xenon-127, Xenon-133, Yttrium-90; imaging agents such as Gadolinium, magnetite, manganese, technetium, 1125, 1131, P32, TI201, Iopamidol, PET-FDG.

Such polypeptides and chemical compounds may be referred to as diagnostic moieties, therapeutic moieties or beneficial moieties.

One or more (several) therapeutic polypeptides may be fused to the N-terminus, the C-terminus of albumin, inserted into a loop in the albumin structure or any combination thereof. It may or it may not comprise linker sequences separating the various components of the fusion polypeptide.

Teachings relating to fusions of albumin or a fragment thereof are known in the art and the skilled person will appreciate that such teachings can also be applied to the invention. WO 2001/79271 A and WO 2003/59934 A also contain examples of therapeutic polypeptides that may be fused to albumin or fragments thereof, and these examples apply also to the invention.

The albumin derivative, fragment, or variant thereof part of a fused or conjugated polypeptide according to the invention has generally a sequence identity to the sequence of the corresponding parts of its parent albumin of at least 60%, preferably at least 70%, preferably at least 80%, preferably at least 81%, 82%, 83%, 84%, 85%, 86%, 87%, 88%, 89%, 90%, 91%, 92%, 93%, or 94%, more preferred at least 95%, more preferred at least 96%, more preferred at least 97%, more preferred at least 98% and most preferred at least 99%.

In a preferred embodiment the albumin derivative, fragment, or variant thereof part of a fused or conjugated polypeptide according to the invention has generally a sequence identity to the sequence of the corresponding parts of HSA shown in SEQ ID NO: 31 or SEQ ID NO: 1 of at least 60%, preferably at least 70%, preferably at least 80%, preferably at least 85%, preferably at least 90%, more preferred at least 95%, more preferred at least 96%, more preferred at least 97%, more preferred at least 98% and most preferred at least 99%.

The relatedness between two amino acid sequences or between two nucleotide sequences is described by the parameter "sequence identity".

For purposes of the invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–Total Number of Gaps in Alignment).

In describing the various derivatives or variants of the invention, the nomenclature described below is adapted for ease of reference. In all cases, the accepted IUPAC single letter or triple letter amino acid abbreviation is employed.

For purposes of the invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows: (Identical Deoxyribonucleotides× 100)/(Length of Alignment–Total Number of Gaps in Alignment).

For purposes of the invention, the mature polypeptide disclosed in SEQ ID NO: 31 or SEQ ID NO: 1 is used to determine the corresponding amino acid residue in another albumin. The amino acid sequence of another albumin is aligned with the mature polypeptide disclosed in SEQ ID NO: 31 or SEQ ID NO: 1, and based on the alignment, the amino acid position number corresponding to any amino acid residue in the mature polypeptide disclosed in SEQ ID NO: 31 or SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later.

Identification of the corresponding amino acid residue in another albumin can be confirmed by an alignment of multiple polypeptide sequences using "ClustalW" (Larkin et al., 2007, *Bioinformatics* 23: 2947-2948).

When the other polypeptide (or protein) has diverged from the mature polypeptide of SEQ ID NO: 31 or SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as inputs to a neural network that predicts the structural fold for a query sequence. Similarly, the method of Gough et al., 2000, *J. Mol. Biol.* 313: 903-919, can be used to align a sequence of unknown structure within the superfamily models present in the SCOP database. These alignments can in turn be used to generate homology models for the polypeptide, and such models can be assessed for accuracy using a variety of tools developed for that purpose. For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementations of these algorithms can additionally be utilized to query structure databases with a structure of interest in order to discover possible structural homologs (e.g., Holm and Park, 2000, *Bioinformatics* 16: 566-567). Another alignment program is MUSCLE (Multiple sequence comparison by log-expectation, Robert C. Edgar, Version 3.6, http://www.drive5.com/muscle; Edgar (2004) Nucleic Acids Research 32(5), 1792-97 and Edgar (2004) BMC Bioinformatics, 5(1):113) which may be used with the default settings as described in the User Guide (Version 3.6, September 2005). Versions of MUSCLE later than 3.6 may also be used for any aspect of the invention.

In describing the albumin derivatives or variants of the invention, the nomenclature described below is adapted for ease of reference. The accepted IUPAC single letter abbreviation or three letter amino acid abbreviation is employed.

Substitutions.

For an amino acid substitution, the following nomenclature is used: Original amino acid, position, substituted amino acid. Accordingly, the substitution of threonine with alanine at position 226 is designated as "Thr226Ala" or "T226A". Multiple mutations are separated by addition marks ("+"), e.g., "Gly205Arg+Ser411Phe" or "G205R+S411F", representing mutations at positions 205 and 411 substituting glycine (G) with arginine (R), and serine (S) with phenylalanine (F), respectively. The Figures also use ("/"), e.g., "E492T/N503D" this should be viewed as interchangeable with ("+").

Deletions.

For an amino acid deletion, the following nomenclature is used: Original amino acid, position*. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, new inserted amino acid. Accordingly the insertion of lysine after glycine at position 195 is designated "Gly195GlyLys" or "G195GK". An insertion of multiple amino acids is designated [Original amino acid, position, original amino acid, new inserted amino acid #1, new inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example the sequences would thus be:

| Parent: | Variant: |
|---------|----------|
| 195     | 195 195a 195b |
| G       | G - K - A |

Multiple Alterations.

Variants or derivatives comprising multiple alterations are separated by addition marks ("+"), e.g., "Arg170Tyr+Gly195Glu" or "R170Y+G195E" representing a substitution of tyrosine and glutamic acid for arginine and glycine at positions 170 and 195, respectively.

Different Substitutions.

Where different substitutions can be introduced at a position, the different substitutions are separated by a comma, e.g., "Arg170Tyr, Glu" represents a substitution of arginine with tyrosine or glutamic acid at position 170. Thus, "Tyr167Gly, Ala+Arg170Gly, Ala" designates the following variants or derivatives:
"Tyr167Gly+Arg170Gly", "Tyr167Gly+Arg170Ala", "Tyr167Ala+Arg170Gly", and "Tyr167Ala+Arg170Ala". The single letter code may also be used, e.g. "Y167G+R170G", "Y167G+R170A", "R167A+R170G", and "R167A+R170A".

The expression "amino acid position corresponding to" a position in a reference sequence and similar expression is intended to identify the amino acid residue that in the primary or spatial structure corresponds to the particular position in the reference sequence. The skilled person will appreciate that this can be done by aligning a given sequence with the reference sequence and identifying the amino acid residue that aligns with the particular position in the reference sequence. For example in order to find the amino acid residue in a given albumin sequence that corresponds to position 492 in HSA, the given albumin sequence is aligned with HSA and the amino acid that aligns with position 492 in HSA (SEQ ID NO: 31 or SEQ ID NO: 1) is identified as the amino acid in the given albumin sequence that corresponds to position 492 in HSA.

The expression Xnnn means an amino acid residue X located in a position corresponding to position nnn in HSA and the expression XnnnY means a substitution of any amino acid X located in a position corresponding to position nnn in HSA with the amino acid residue Y.

Throughout this specification amino acid positions are defined in relation to full-length mature human serum albumin (i.e. without leader sequence). However, the equivalent positions can be identified in fragments of human serum albumin, in animal albumins and in fragments, fusions and other derivative or variants thereof by comparing amino acid sequences using pairwise (e.g. ClustalW) or multiple (e.g. MUSCLE) alignments. For example, FIG. 4 shows that positions equivalent to 500, 550 and 573 in full length human serum albumin are easily identified in fragments of human serum albumin and in albumins of other species. Positions 500, 550 and 573 are indicated by arrows. Further details are provided in Table 1 below:

TABLE 1

Albumins from different animals showing positions equivalent to 500, 550 and 573 of HSA.

| Organism (accession number of protein) | Albumin | | Total length of mature protein | Position equivalent to human serum albumin (native amino acid): | | |
|---|---|---|---|---|---|---|
| | Full length or fragment | Fragment details | | 500 (K) | 550 (D) | 573 (K) |
| Homo sapiens (AAA98797) | Full length | — | 585 | 500 (K) | 550 (D) | 573 (K) |
| Homo sapiens | Fragment | DI, DIII | 399 | 314 (K) | 364 (D) | 387 (K) |
| Homo sapiens | Fragment | DI, DIII | 403 | 318 (K) | 368 (D) | 391 (K) |
| Macaca mulatta (NP_001182578) | Full length | — | 584 | 500 (K) | 550 (N) | 573 (P) |
| Rattus norvegicus (AAH85359) | Full length | — | 584 | 500 (K) | 550 (D) | 573 (P) |
| Mus musculus (AAH49971) | Full length | — | 584 | 500 (K) | 550 (D) | 573 (P) |

FIG. 4 was generated by MUSCLE using the default parameters including output in ClustalW 1.81 format. The raw output data was shaded using BoxShade 3.21 (http://www.ch.embnet.orq/software/BOX form.html) using Output Format: RTF_new; Font Size: 10; Consensus Line: no consensus line; Fraction of sequences (that must agree for shading): 0.5; Input sequence format: ALN. Therefore, throughout this specification amino acid positions defined in human serum albumin also apply to equivalent positions in fragments, derivatives or variants and fusions of human serum albumin, animals from other species and fragments and fusions thereof. Such equivalent positions may have (i) a different residue number in its native protein and/or (ii) a different native amino acid in its native protein.

Plasma half-life is ideally determined using in vivo determinations in suitable individuals. However, since it is time consuming and expensive and there inevitably are ethical concerns connected with doing experiments in animals or man it is desirable to use an in vitro assay for determining whether plasma half-life is extended or reduced. It is thought that the binding of albumin to its receptor FcRn is important for plasma half-life and the correlation between receptor binding and plasma half-life is that a higher affinity of albumin to its receptor FcRn leads to longer plasma half-life. Thus, for the invention a higher affinity of the albumin derivative, fragment, or variant thereof to FcRn is considered indicative of an increased (longer) plasma half-life and a lower affinity of the albumin derivative, fragment, or variant thereof to the FcRn receptor is considered indicative of a reduced (shorter) plasma half-life.

In this application the binding of the albumin derivative, fragment, or variant thereof to the receptor FcRn is described using the term affinity (KD) and the expressions "stronger" or "weaker". Thus, it should be understood that a molecule having a higher affinity to FcRn than HSA is considered to bind stronger to FcRn than HSA and a molecule having a lower affinity to FcRn than HSA is considered to bind weaker to FcRn than HSA.

The terms "longer plasma half-life" or "shorter plasma half-life" and similar expressions are understood to be in relationship to the corresponding parent albumin molecule which maybe a full-length albumin, an albumin fragment or variant or derivative or an albumin fusion protein. Thus, a longer plasma half-life with respect to a variant albumin of the invention means that the variant has longer plasma half-life than the corresponding albumin having the same sequences except for the alteration(s) in positions corresponding to 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 in SEQ ID NO: 31 or SEQ ID NO: 1. Therefore, for example, a full-length human serum albumin having a mutation at position 535 must be compared with a full-length human serum albumin not having a mutation at position 535. Likewise, a mouse albumin fragment comprising domains 2 and 3 of mouse albumin and having a mutation at position 582 must be compared to a mouse albumin fragment comprising domains 2 and 3 of mouse albumin but not having a mutation at position 582.

A 'long' or 'short' plasma half-life, for example in blood, may be relative to (i) serum albumin (or a fragment thereof) and/or (ii) serum albumin (or a fragment thereof) fused to a polypeptide of interest. For example, long plasma half-life may be at least 5% longer than that of serum albumin or a serum albumin fused to a polypeptide of interest, preferably at least 10%, 20%, 30%, 40%, 50%, 60%, 70%, 80%, 90%, 100%, 150%, 200%, 250%, 300%, 350%, 400%, 450%, 500% longer. Long plasma half-life includes from at least 5 to 100 days, for example at least 5, 6, 7, 8, 9, 10, 14, 15, 20, 21, 28, 30, 35, 40, 42, 50, 60, 70, 80, 90, 100 days. Short plasma half-life may be at least 5% shorter than that of serum albumin or a serum albumin fused to a polypeptide of interest, more preferably at least 10%, 20%, 30%, 40%, 50%, 60%, 70%, 80%, 90%, 95%, 96%, 97%, 98%, or 99% shorter. Short plasma half-life includes at most 5, 4, 3, 2, 1, 0.5, or 0.25 days. Preferably, the half-life of an unfused albumin derivative or variant is compared to an unfused parent or native albumin. Likewise, preferably, the half-life of a fused albumin derivative or variant ("albumin fusion") is compared to a fused parent or native albumin.

The binding of an albumin derivative, fragment or variant thereof to FcRn may also be described using kinetic factors, in particular "on-rate" (ka) and "off-rate" (kd), which describes the reaction rate whereby the albumin derivative, fragment or variant thereof of the invention associated or dissociated with FcRn respectively. The inventors have further realized that the kinetics whereby albumin derivative, fragment or variant thereof interacts with FcRn may have an impact on the plasma half-life, and have realized that an albumin derivative, fragment or variant thereof having a slow off-rate has a higher plasma half-life than a comparable molecule having a faster off-rate.

The correlation between binding of the albumin derivative, fragment, or variant thereof to the FcRn receptor and plasma half-life has been realized by the inventors based on the prior art within the field of this invention.

One way to determine whether the affinity of the albumin derivative, fragment, or variant thereof is higher or lower than wild-type albumins is using the Surface Plasmon Resonance assay (SPR) as described below. The skilled person will understand that other method might be useful to determine whether the affinity of the albumin derivative, fragment, or variant thereof to FcRn is higher or lower than the affinity of the corresponding wild-type albumin to FcRn, e.g. determination and comparison of the binding constants KD. Thus, according to the invention the albumin derivative, fragment, or variant thereof having a KD that is lower than the KD for natural HSA is considered to have a higher plasma half-life than HSA and albumin derivatives, fragments of variants thereof having a KD that is higher than the KD for natural HSA is considered to have a lower plasma half-life than HSA.

Preparation of Derivatives and Variants

The albumin derivative, fragment, or variant thereof of the invention can be prepared using techniques well known to the skilled person. One convenient way is by cloning a nucleic acid encoding the parent albumin, fragment thereof or fusion polypeptide comprising the HSA domain III derivative, fragment, or variant thereof. A polynucleotide may be manipulated in a variety of ways to provide for expression of a derivative or variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, which is recognized by a host cell for expression of the polynucleotide. The promoter sequence contains transcriptional control sequences that mediate the expression of the derivative or variant. The promoter may be any nucleic acid sequence that shows transcriptional activity in the host cell including mutant, truncated, and hybrid promoters, and may be obtained from genes encoding extracellular or intracellular polypeptides either homologous or heterologous to the host cell.

In a yeast host, useful promoters are obtained from the genes for *Saccharomyces cerevisiae* enolase (ENO1), *Saccharomyces cerevisiae* protease A (PRA1), *Saccharomyces cerevisiae* protease B (PRB1), *Saccharomyces cerevisiae* translation elongation factor (TEF1), *Saccharomyces cerevisiae* translation elongation factor (TEF2), *Saccharomyces cerevisiae* galactokinase (GAL1), *Saccharomyces cerevisiae* alcohol dehydrogenase/glyceraldehyde-3-phosphate dehydrogenase (ADH1, ADH2/TDH1), *Saccharomyces cerevisiae* triose phosphate isomerase (TPI1), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the derivative or variant. Any terminator that is functional in the host cell may be used.

Preferred terminators for yeast host cells are obtained from the genes for *Saccharomyces cerevisiae* enolase, *Saccharomyces cerevisiae* cytochrome C (CYC1), *Saccharomyces cerevisiae* alcohol dehydrogenase (ADH1) and *Saccharomyces cerevisiae* glyceraldehyde-3-phosphate dehydrogenase (TDH1). Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5'-terminus of the polynucleotide encoding the derivative or variant. Any leader sequence that is functional in the host cell may be used.

The albumin derivative, fragment, or variant thereof of the invention may also be connected to a signal sequence (also known as a 'signal peptide' or as a 'leader sequence') in order to have the polypeptide secreted into the growth medium during culturing of the transformed host organism. It is generally advantageous to have the derivative or variant polypeptide secreted into the growth medium in order to ease recovery and purification. Suitable leaders for yeast host cells are obtained from the genes for *Saccharomyces cerevisiae* enolase (ENO1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/TDH1).

The control sequence may also be a polyadenylation sequence, a sequence operably linked to the 3'-terminus of the derivative- or variant-encoding sequence and, when transcribed, is recognized by the host cell as a signal to add polyadenosine residues to transcribed mRNA. Any polyadenylation sequence that is functional in the host cell may be used.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a derivative or variant and directs the derivative or variant into the cell's secretory pathway. The 5'-end of the coding sequence of the polynucleotide may inherently contain a signal peptide coding region naturally linked in translation reading frame with the segment of the coding region that encodes the derivative or variant. Alternatively, the 5'-end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the derivative or variant. However, any signal peptide coding region that directs the expressed derivative or variant into the secretory pathway of a host cell may be used.

Useful signal peptides for yeast host cells are obtained from the genes for *Saccharomyces cerevisiae* alpha-factor (MATALPHA) and *Saccharomyces cerevisiae* invertase (SUC2). Other useful signal peptide coding sequences are described by Romanos et al., 1992, supra.

Where both signal peptide and pro-peptide regions are present at the N-terminus of a derivative or variant, the propeptide region is positioned next to the N-terminus of the derivative or variant and the signal peptide region is positioned next to the N-terminus of the propeptide region.

Techniques for preparing derivative or variant polypeptides have also been disclosed in WO 2009019314 and PCT/EP2010/066572 (incorporated herein by reference) and these techniques may also be applied to the invention.

Albumins have been successfully expressed as recombinant proteins in a range of hosts including fungi (including but not limited to Aspergillus (WO06066595), *Kluyveromyces* (Fleer 1991, *Bio/technology* 9, 968-975), *Pichia* (Kobayashi 1998 Therapeutic Apheresis 2, 257-262) and *Saccharomyces* (Sleep 1990, Bio/technology 8, 42-46)), bacteria (Pandjaitab 2000, J. Allergy Clin. Immunol 105, 279-285)), animals (Barash 1993, Transgenic Research 2, 266-276) and plants (including but not limited to potato and tobacco (Sijmons 1990, Bio/technology 8, 217 and Farran 2002, Transgenic Research 11, 337-346). The HSA domain III derivative, fragment, or variant thereof of the invention is preferably produced recombinantly in a suitable host cell. In principle any host cell capable of producing a polypeptide in suitable amounts may be used and it is within the skills of the average practitioner to select a suitable host cell according to the invention. A preferred host organism is yeast, preferably selected among *Saccharomycacae*, more preferred *Saccharomyces cerevisiae*.

The albumin derivative, fragment, or variant thereof of the invention may be recovered and purified from the growth medium using a combination of known separation techniques such as filtrations, centrifugations, chromatography, affinity separation techniques etc. It is within the skills of the average practitioner to purify the albumin derivative, fragment, or variant thereof of the invention using a particular combination of such known separation steps. As an example of purification techniques that may be applied to the derivatives or variants of the invention can be mentioned the teaching of WO0044772.

The albumin derivative, fragment, or variant thereof of the invention may be used for delivering a therapeutically beneficial compound to an animal or a human individual in need thereof. Such therapeutically beneficial compounds include but are not limited to labels and readily detectable compounds for use in diagnostics, such as various imaging techniques; pharmaceutical active compounds such as drugs, or specifically binding moieties such as antibodies. The albumin derivative, fragment, or variant thereof of the invention may even be connected to two or more different therapeutically beneficial compounds e.g. an antibody and a drug, which gives the combined molecule the ability to bind specifically to a desired target and thereby provide a high concentration of the connected drug at that particular target.

In one particular preferred embodiment the albumin derivative, fragment, or variant thereof is conjugated to a beneficial therapeutic compound and the conjugate is used for treatment of a condition in a patient in need therefore, which condition is responsive to the particular selected therapeutic compound. Techniques for conjugating such a therapeutically compound to the albumin derivative, fragment, or variant thereof are known in the art. WO2009019314 discloses examples of techniques suitable for conjugating a therapeutically compound to a polypeptide which techniques can also be applied to the invention. Further WO2009019314 discloses examples of compounds and moieties that may be conjugated to substituted transferrin and these examples may also be applied to the invention. The teaching of WO2009019314 and PCT/EP2010/066572 are incorporated herein by reference.

HSA contains in its natural form one free thiol group in Domain I that conveniently may be used for conjugation provided that the albumin derivative or variant, fragment thereof or fusion polypeptide comprising the albumin derivative or variant, fragment thereof comprises Domain I.

As a particular embodiment within this, the albumin derivative, fragment, or variant thereof may comprise further modifications provided to generate additional free thiol groups on the surface. This has the benefit that the pay load of the albumin derivative, fragment, or variant thereof is increased so that more than one molecule of the therapeutic compound can be conjugated to each albumin derivative, fragment, or variant thereof molecule, or two or more different therapeutic compounds may be conjugated to each molecule of the albumin derivative, fragment, or variant thereof, e.g. It may be a compound having targeting properties such as an antibody specific for e.g. a tumour; and a cytotoxic drug conjugated to the albumin derivative, fragment, or variant thereof thereby creating a highly specific drug against a tumour. Teaching of particular residues that may be modified to provide for further free thiol groups on the surface can be found in the co-pending patent application (EP 2009 152 625.1, incorporated herein by reference), which is incorporated herein by reference.

In another preferred the fusion polypeptide comprising the albumin derivative, fragment, or variant thereof comprises one or more (several) therapeutic polypeptides. In this the HSA domain III derivative, fragment, or variant thereof and the one or more (several) therapeutic polypeptides is produced as one single polypeptide.

The one or more (several) therapeutic polypeptides may be fused to the N-terminus, the C-terminus of the albumin derivative, fragment, or variant thereof, inserted into a loop in the albumin derivative, fragment, or variant thereof structure or any combination thereof. It may or it may not comprise linker sequences separating the various components of the fusion polypeptide.

Teachings relating to fusions of albumin or a fragment thereof are known in the art and the skilled person will appreciate that such teachings can also be applied to the invention. WO 01/79271 A and WO 03/59934 A also contains examples of therapeutic polypeptides that may be fused to the HSA domain III derivative, fragment, or variant thereof, and these examples applies also for the invention.

The albumin derivative, fragment, or variant thereof or fusion polypeptides comprising the albumin derivative, fragment, or variant thereof according to the invention have the benefit that their plasma half-life is altered compared to the parent albumin, fragments thereof or fusion polypeptides comprising the parent albumin or fragment thereof. This has the advantage that the plasma half-life of conjugates comprising the albumin derivative, fragment, or variant thereof or fusion polypeptide comprising the albumin derivative, fragment, or variant thereof according to the invention can be selected in accordance with the particular therapeutic purpose.

For example for a conjugate or fusion polypeptide used for imaging purposes in animals or human beings, where the imaging moiety has an very short half-life and a conjugate or a fusion polypeptide comprising the albumin derivative, fragment, or variant thereof has a plasma half-life that is far longer than needed for the imaging purposes it would be advantageous to use an albumin derivative, fragment, or variant thereof of the invention having a shorter plasma half-life than the parent albumin or fragment thereof, to provide conjugates of fusion polypeptides having a plasma half-life that is sufficiently long for the imaging purpose but sufficiently short to be cleared form the body of the particular patient on which it is applied.

In another example for a conjugate or fusion polypeptide comprising a therapeutic compound effective to treat or alleviate a particular condition in a patient in need for such a treatment it would be advantageous to use the albumin derivative, fragment, or variant thereof having longer plasma half-life than the parent albumin or fragment thereof, to provide conjugates or fusion polypeptides having longer plasma half-life which would have the benefit that the administration of the conjugate or fusion polypeptide of the invention would be needed less frequent compared to the situation where the parent albumin or fragment thereof were used.

A fifth aspect of the invention provides 'associates' of the derivatives or variants of albumin or fragments thereof. In this connection the term "associate" means a compound comprising or consisting of a derivative or variant of albumin or a fragment thereof and another compound bound or associated to the derivative or variant albumin or fragment thereof by non-covalent binding. As an example of such an associate can be mentioned an associate consisting of derivative or variant albumin and a lipid associated to albumin by a hydrophobic interaction. Such associates are known in the art and they may be prepared using well known techniques. As an example of a preferred associate according to the invention can be mentioned an associate comprising a derivative or variant albumin and paclitaxel or paclitaxel protein bound. The half-life of an albumin associate according to the invention may be longer or shorter than the half-life of the 'other compound' alone. The half-life of an albumin associate according to the invention may be longer or shorter than the half-life of the analogous/equivalent albumin associate comprising or consisting of native HSA (instead of an albumin variant or derivative according to the invention) and the 'other compound'. Methods for the preparation of associates are well-known to the skilled person, for example, formulation (by association) of HSA with Lipo-compounds is described in Hussain, R. and Siligardi, G. (2006) International Journal of Peptide Research and Therapeutics, Vol. 12, No. 3, pp. 311-315

In a sixth aspect the invention relates to compositions comprising or consisting of the albumin derivative, fragment, or variant thereof or fusion polypeptide comprising the albumin derivative, fragment, or variant thereof according to the invention conjugated, fused or associated with a therapeutic, pharmaceutical or other beneficial polypeptide. The compositions are preferably pharmaceutical compositions. The composition may be prepared using techniques known in the area such as disclosed in recognized handbooks within the pharmaceutical field.

In a particular embodiment the compositions comprise or consist of the albumin derivative, fragment, or variant thereof according to the invention and a compound comprising a pharmaceutically beneficial moiety and an albumin binding domain (ABD). According to the invention ABD means a site, moiety or domain capable of bind to circulating albumin in vivo and thereby confer transport in the circulation of the ABD and any compound or moiety bound to said ABD. ABDs are known in the art and it has been shown that ABDs bind very tight to albumin so a compound comprising an ABD bound to albumin will to a certain extent behave as a single molecule. The inventors have realized by using the albumin derivative, fragment, or variant thereof according to the invention together with a compound comprising a pharmaceutically beneficial moiety and an ABD makes it possible to alter the plasma half-life of the compound comprising a pharmaceutically beneficial moiety and an ABD compared to the situation where said compound were injected as such in a patient having need thereof or administered in a formulation comprising natural albumin or a fragment thereof.

Therefore, the invention is directed to the use of a derivative or variant of albumin or a fragment thereof or fusion polypeptides comprising a derivative or variant albumin or fragment thereof, or a conjugate comprising a derivative or variant of albumin or a fragment thereof, or an associate comprising a derivative or variant of albumin or a fragment thereof for the manufacture of a pharmaceutical composition, where in the derivative or variant of albumin or a fragment thereof or fusion polypeptides comprising derivative or variant albumin or fragments thereof, or a conjugate comprising a derivative or variant of albumin or a fragment thereof, or an associate comprising a derivative or variant of albumin or a fragment thereof has an altered plasma half-life compared with HSA or the corresponding fragment thereof or fusion polypeptide comprising HSA or fragment thereof or conjugate comprising HSA.

In this connection the corresponding fragment of HSA means a fragment of HSA that aligns with and has same number of amino acids as the fragment of the derivative or variant albumin with which it is compared. Similarly the corresponding fusion polypeptide comprising HSA or conjugate comprising HSA means molecules having same size and amino acid sequence as the fusion polypeptide of conjugate comprising derivative or variant albumin, with which it is compared.

Preferably the derivative or variant of albumin or a fragment thereof or fusion polypeptides comprising or consisting of a derivative or variant albumin or fragments thereof, or a conjugate comprising a derivative or variant of albumin or a fragment thereof has a plasma half-life that is higher than the plasma half-life of HSA or the corresponding fragment thereof or fusion polypeptide comprising HSA or fragment thereof.

Alternatively, this may be expressed as the derivative or variant of albumin or a fragment thereof or fusion polypeptides comprising derivative or variant albumin or fragments thereof, fragment thereof, or a conjugate comprising a derivative or variant of albumin or a fragment thereof has a KD to FcRn that is lower that the corresponding KD for HSA or the corresponding fragment thereof or fusion polypeptide comprising HSA or fragment thereof. Preferably, is KD for the derivative or variant of albumin or a fragment thereof or fusion polypeptides comprising derivative or variant albumin or fragments thereof, fragment thereof, or a conjugate comprising a derivative or variant of albumin or a fragment thereof less than 0.9×KD for HSA, more preferred less than 0.5×KD for HSA, more preferred less than 0.1×KD for HSA, even more preferred less than 0.05×KD for HSA, even more preferred less than 0.02×KD for HSA and most preferred less than 0.01×KD for HSA.

The derivative or variant of albumin or a fragment thereof or fusion polypeptides comprising derivative or variant albumin or fragments thereof, fragment thereof, or a conjugate comprising a derivative or variant of albumin or a fragment thereof is preferably the derivative or variant of albumin or a fragment thereof or fusion polypeptides comprising derivative or variant albumin or fragments thereof, fragment thereof, or a conjugate comprising a derivative or variant of albumin or a fragment thereof according to the invention.

A seventh aspect of the invention relates to methods of production of the derivatives or variants or associates. The derivatives or variants of the invention can be prepared using techniques well known to the skilled person. One convenient way is by cloning nucleic acid encoding the parent albumin or a fragment thereof or fusion polypeptide comprising albumin or a fragment thereof, modifying said nucleic acid to introduce the desired substitution(s) at one or more (several) positions corresponding to positions 417, 464, 490, 492, 493, 494, 495, 496, 499, 500, 501, 503, 504, 505, 506, 510, 535, 536, 537, 538, 540, 541, 542, 550, 573, 574 and 580 in SEQ ID NO: 31 or SEQ ID NO: 1, where the derivative or variant is not the derivative or variant consisting of SEQ ID NO: 31 or SEQ ID NO:1 with the substitution D494N, E501K, K541E, D550G, A, K573E or K574N, preparing a suitable genetic construct where the modified nucleic acid is placed in operative connection with suitable regulatory genetic elements, such as promoter, terminator, activation sites, ribosome binding sites etc., introducing the genetic construct into a suitable host organism, culturing the transformed host organism under conditions leading to expression of the derivative or variant and recovering the derivative or variant. Optionally the derivative or variant or associate is formulated, for example with a pharmaceutically acceptable excipient. Optionally the derivative or variant or associate is presented in unit dosage form. All these techniques are known in the art and it is within the skills of the average practitioner to design a suitable method for preparing a particular derivative or variant according to the invention.

The derivative or variant polypeptide of the invention may also be connected to a signal sequence in order to have the derivative or variant polypeptide secreted into the growth medium during culturing of the transformed host organism. It is generally advantageous to have the derivative or variant polypeptide secreted into the growth medium in order to ease recovery and purification.

Techniques for preparing derivative or variant polypeptides have also been disclosed in WO 2009019314 and PCT/EP2010/066572 (incorporated herein by reference) and these techniques may also be applied to the invention.

Albumins have been successfully expressed as recombinant proteins in a range of hosts including fungi (including but not limited to Aspergillus (WO06066595), *Kluyveromyces* (Fleer 1991, *Bio/technology* 9, 968-975), *Pichia* (Kobayashi 1998 *Therapeutic Apheresis* 2, 257-262) and *Saccharomyces* (Sleep 1990, *Bio/technology* 8, 42-46)), bacteria (Pandjaitab 2000, *J. Allergy Clin. Immunol.* 105, 279-285)), animals (Barash 1993, *Transgenic Research* 2, 266-276) and plants (including but not limited to potato and tobacco (Sijmons 1990, *Bio/technology* 8, 217 and Farran 2002, *Transgenic Research* 11, 337-346). The derivative or variant polypeptide of the invention is preferably produced recombinantly in a suitable host cell. In principle any host cell capable of producing a polypeptide in suitable amounts may be used and it is within the skills of the average practitioner to select a suitable host cell according to the invention. A preferred host organism is yeast, preferably selected among *Saccharomycacae*, more preferred *Saccharomyces cerevisiae*.

The derivative or variant polypeptides of the invention may be recovered and purified from the growth medium using a combination of known separation techniques such as filtration, centrifugation, chromatography, and affinity separation techniques etc. It is within the skills of the average practitioner to purify the derivative or variants of the invention using a particular combination of such known separation steps. As an example of purification techniques that may be applied to the derivative or variants of the invention can be mentioned the teaching of WO0044772.

The derivative or variant polypeptides of the invention may be used for delivering a therapeutically beneficial compound to an animal or a human individual in need thereof. Such therapeutically beneficial compounds include, but are not limited to, labels and readily detectable compounds for use in diagnostics, such as various imaging techniques; pharmaceutical active compounds such as drugs, or specifically binding moieties such as antibodies. The derivatives or variants of the invention may even be connected to two or more different therapeutically beneficial compounds, e.g., an antibody and a drug, which gives the combined molecule the ability to bind specifically to a desired target and thereby provide a high concentration of the connected drug at that particular target.

The derivative or variant albumin, fragments thereof or fusion polypeptides comprising derivative or variant albumin or fragments thereof according to the invention have the benefit that their plasma half-life is altered compared to the parent albumin or fragments thereof or fusion polypeptides comprising parent albumin or fragments thereof or the unfused, unconjugated or unassociated therapeutic, diagnostic or other beneficial moiety. This has the advantage that the plasma half-life of conjugates comprising derivative or variant albumin or a fragment thereof or fusion polypeptide comprising derivative or variant albumin or a fragment thereof, or an associate comprising derivative or variant albumin or a fragment thereof according to the invention can be selected in accordance with the particular therapeutic purpose.

An eighth aspect of the invention relates to imaging. For example for a conjugate, associate or fusion polypeptide used for imaging purposes in animals or human beings, where the imaging moiety has an very short half-life and a conjugate or a fusion polypeptide comprising HSA has a plasma half-life that is far longer than needed for the imaging purposes it would be advantageous to use a derivative or variant albumin or fragment thereof of the invention having a shorter plasma half-life than the parent albumin or fragment thereof, to provide conjugates of fusion polypeptides having a plasma half-life that is sufficiently long for the imaging purpose but sufficiently short to be cleared form the body of the particular patient on which it is applied. Examples of imaging agents comprising albumin includes those of WO 2004/071536.

A ninth aspect of the invention relates to a method of treatment and/or use in a method of treatment. The method may comprise use of a therapeutic compound effective to treat or alleviate a particular condition in a patient in need for such a treatment it would be advantageous to use the derivative or variant albumin or fragment thereof having a longer plasma half-life than the parent albumin or fragment thereof, to provide associates or conjugates or fusion polypeptides having longer plasma half-lives, compared to the therapeutic compound alone or the therapeutic compound fused, conjugated or associated with native HSA, which would have the benefit that the administration of the associate or conjugate or fusion polypeptide of the invention would be needed less frequently or reduced dose with less side affects compared to the situation where the parent albumin or associates thereof or fragment thereof was used. The invention also includes methods in which the albumin variant, derivative, fusion, conjugate or associate has a shorter half-life compared to the therapeutic compound alone or the therapeutic compound fused, conjugated or associated with native HSA.

In a tenth aspect, the invention relates to compositions comprising the derivative or variant albumin, associates thereof or fragment thereof, derivative or variant albumin fragment or associates thereof or fusion polypeptide comprising variant albumin or fragment thereof according to the invention. The compositions are preferably pharmaceutical compositions. The composition may be prepared using techniques known in the area such as disclosed in recognized handbooks within the pharmaceutical field.

In a particular embodiment the compositions comprise or consist of a derivative or variant albumin or a fragment thereof according to the invention and a compound comprising a pharmaceutically beneficial moiety and an albumin binding domain (ABD). According to the invention ABD means a site, moiety or domain capable of binding to circulating albumin in vivo and thereby conferring transport in the circulation of the ABD and any compound or moiety bound to said ABD. ABDs are known in the art and have been shown to bind very tight to albumin so a compound comprising an ABD bound to albumin will to a certain extent behave as a single molecule. The inventors have realized by using the derivative or variant albumin or fragment thereof according to the invention together with a compound comprising a pharmaceutically beneficial moiety and an ABD makes it possible to alter the plasma half-life of the compound comprising a pharmaceutically beneficial moiety and an ABD compared to the situation where said compound were injected as such in a patient having need thereof or administered in a formulation comprising natural albumin or a fragment thereof.

The derivative or variant albumin or fragments thereof, conjugates comprising derivative or variant albumin or a fragment thereof or fusion polypeptide comprising derivative or variant albumin or a fragment thereof, or an associate comprising derivative or variant albumin or a fragment thereof according to the invention may also be incorporated into nano- or microparticles using techniques well known within the art. A preferred method for preparing nano- or microparticles that may be applied to the derivative or variant albumins or fragments thereof according to the invention is disclosed in WO 2004/071536, which is incorporated herein by reference.

The following definitions also apply to the invention disclosed herein:

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "coding sequence" means a polynucleotide, which directly specifies the amino acid sequence of its translated polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the invention.

The term "control sequences" means all components necessary for the expression of a polynucleotide encoding a derivative or variant of the invention. Each control sequence may be native or foreign to the polynucleotide encoding the derivative or variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences within the coding region of the polynucleotide encoding a derivative or variant.

The term "operably linked" means a configuration in which a control sequence is placed at an appropriate position relative to the coding sequence of a polynucleotide such that the control sequence directs the expression of the coding sequence.

The term "expression" includes any step involved in the production of the derivative or variant including, but not limited to, transcription, post-transcriptional modification, translation, post-translational modification, and secretion.

The term "expression vector" means a linear or circular DNA molecule that comprises a polynucleotide encoding a derivative or variant and is operably linked to additional nucleotides that provide for its expression.

The term "host cell" means any cell type that is susceptible to transformation, transfection, transduction, and the like with a nucleic acid construct or expression vector comprising a polynucleotide of the invention. The term "host cell" encompasses any progeny of a parent cell that is not identical to the parent cell due to mutations that occur during replication.

The term "mutant" means a polynucleotide encoding a derivative or variant.

The term "wild-type albumin" means an albumin expressed by a naturally occurring organism, such as a eukaryote, e.g. a mammal such as a human.

The term "parent" or "parent albumin" means an albumin to which an alteration is made to produce the albumin derivatives or variants of the invention. The parent may be a naturally occurring (wild-type) polypeptide or a derivatives or variant thereof.

The invention is further described with reference to the following examples that should not be construed as limiting the scope of the invention.

EXAMPLES

Material and Methods:

(a) ELISA:

Wells were coated with HSA wt or mutants diluted in PBS with concentrations ranging from 100-0.045 µg/ml, incubated over night at 4° C. and then blocked with 4% skimmed milk (Acumedia) for 1 h at room temperature. The wells were then washed four times with phosphate buffered saline (PBS)/0.005% Tween 20 (PBS/T) pH 6.0 before GST-fused shFcRn (0.5 µg/ml (FEBS J. 2008 August; 275(16):4097-110.)) pre-incubated with an HRP-conjugated polyclonal anti-GST from goat (1:5000; GE Healthcare), diluted in 4% skimmed milk PBS/0.005% Tween 20 (PBS/T) pH 6.0 was added to each well and incubated for 1.5 h at room temperature followed by four times washing with PBS/T pH 6.0. 100 µl of the substrate TMB (Calbiochem) was added to each well and incubated for 45 minutes before 100 µl of 0.25 M HCl was added. The absorbance was measured at 450 nm using a Sunrise TECAN spectrophotometer (TECAN, Maennedorf, Switzerland).

The same ELISA was repeated with PBS/T pH 7.4.

(b) Surface Plasmon Resonance (SPR):

SPR experiments were carried out using a Biacore 3000 instrument (GE Healthcare). Flow cells of CM5 sensor chips were coupled with shFcRn-GST (~1400-5000 RU) using amine coupling chemistry as described in the protocol provided by the manufacturer. The coupling was performed by injecting 10 µg/ml of the protein in 10 mM sodium acetate pH 5.0 (GE Healthcare). Phosphate buffer (67 mM phosphate buffer, 0.15 M NaCl, 0.005% Tween 20) at pH 6.0) was used as running buffer and dilution buffer. Regeneration of the surfaces were done using injections of HBS-EP buffer (0.01 M HEPES, 0.15 M NaCl, 3 mM EDTA, 0.005% surfactant P20) at pH 7.4 (Biacore AB). For binding to immobilized shFcRn-GST, 1.0-0.5 µM of each HSA derivative or variant was injected over the surface at constant flow rate (40 µl/ml) at 25° C. In all experiments, data was zero adjusted and the reference cell subtracted. Data evaluation was performed using BIAevaluation 4.1 software (BIAcore AB).

The same SPR assay was repeated with HBS-EP buffer pH 7.4.

SPR experiments were carried out using a Biacore 3000 instrument (GE Healthcare). Flow cells of CM5 sensor chips were coupled with HSA (~2600 RU) using amine coupling chemistry as described in the protocol provided by the manufacturer. The coupling was performed by injecting 10 µg/ml of the protein in 10 mM sodium acetate pH 5.0 (GE Healthcare). Phosphate buffer (67 mM phosphate buffer, 0.15 M NaCl, 0.005% Tween 20) at pH 6.0) was used as running buffer and dilution buffer. Regeneration of the surfaces were done using injections of HBS-EP buffer (0.01 M HEPES, 0.15 M NaCl, 3 mM EDTA, 0.005% surfactant P20) at pH 7.4 (Biacore AB). Competitive binding was measured by injecting shFcRn (50 nM) alone or together with different amounts of HSA or RSA domain constructs over immobilized HSA. In all experiments, data were zero adjusted and the reference cell subtracted. Data evaluation was performed using BIAevaluation 4.1 software (BIAcore AB).

HSA:

Recombinant Human Serum Albumin commercially available under the registered tradename RECOMBUMIN was used for the examples.

Serum Albumin from Other Species:

The albumins were produced recombinantly using sequences provided from publicly available databases (data not shown).

FcRn:

PCR and subcloning. cDNA segments encoding truncated soluble hFcRn (shFcRn) HC and hβ2m were PCR amplified from a U937 cell line (ATCC) cDNA library followed by subcloning of the fragments into the pCDNA3-GST vector, all as previously described (Berntzen et al. (2005) J Immunol Methods 298:93-104). A mouse liver cDNA library (Zyagen) was used to PCR amplify a cDNA encoding a truncated version of the mFcRn HC (encoding the endogenous native leader sequence, α1, α2 and α3 domains; 293 amino acids) using the primers mFcRnForw and mFcRnRev:

```
mFcRnForw
5-ATT ATG AAT TCA TGG GGA TGC CAC TGC CCT GG-3 mFcRnRev
5-ATA TAC TCG AGT AGG TCC ACA GTG AGA GGC TG-3
```

Primers were designed to allow in frame ligation of the fragment upstream of a cDNA encoding a GST-tag from *Schistosoma japonicum* into the pcDNA3-GST-hβ2m-oriP vector, which also contains a cDNA encoding hβ2m and the Epstein Barr virus origin of replication (oriP). The final vector was sequenced and denoted pcDNA3-mFcRn$^{wt}$-GST-hβ2m-oriP.

Expression and Purification of Soluble Human FcRn Variants (shFcRn-GST)—

For transient transfections, the hFcRn and mFcRn encoding plasmids were transfected into HEK 293E cells (ATCC) using Lipofectamine 2000 (Invitrogen) following the manufacturer's instructions. HEK 293E cells were cultured in Dulbecco modified eagle medium (BioWhittaker) using standard conditions. Pooled media were filtrated and applied on a GSTrap FF column 5 ml column (GE Healthcare) connected to a semiautomatic workstation and recorder, and purifications were performed essentially as recommended in the manufacturer's manual. Eluted fractions were pooled, concentrated and analyzed under non-reducing or reducing condition using β-mercaptoethanol (Sigma-Aldrich). Samples of 2 µg of each receptor were applied on a 12% SDS-PAGE (Bio-Rad). Protein concentrations were determined using a NanoDrop N-1000 spectrophotometer (NanoDrop Technologies).

Methods for the generation of shFcRn expression plasmids, expression and purification of each heterodimer can also be found in Berntzen et al. (2005) J. Immunol. Methods 298:93-104) and Andersen et al. (2010) J. Biol. Chem., 285:4826-4836.

Alternatively His-tagged shFcRn FcRn heterodimer was produced by GeneArt AG (Germany). Sequences for the two sub units of the heterodimer can be found in SEQ ID NO: 32 (truncated heavy chain of the major histocompatibility complex class I-like Fc receptor (FCGRT)) and SEQ ID NO: 33 (beta-2-microglobulin). Together, SEQ ID NO: 32 and 33 form FcRn. The soluble receptor was expressed in HEK293 cells and purified from culture supernatant using Ni-HiTrap chromatography columns. The His tag is genetically fused to the C-terminus of beta-2-microglobulin.

(c) Construction of Plasmids and Strains

Standard molecular biology techniques were employed throughout such as those described in Sambrook, J. and D. W. Russell, 2001. Molecular Cloning: a laboratory manual, 3rd ed. Cold Spring Harbor Laboratory Press, Cold Spring Harbor, N.Y.

Figure 6:
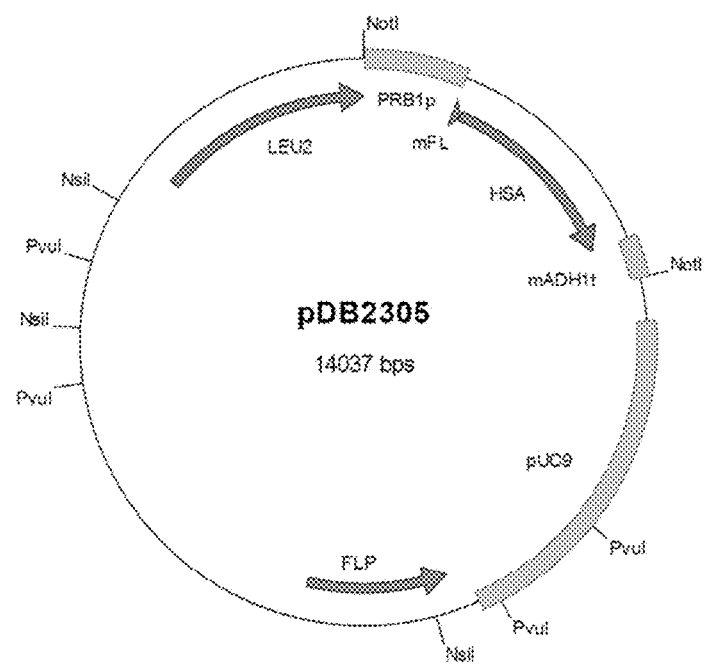
FIG. 6, Schematic diagram of plasmid pDB2305

Plasmids containing expression cassettes are listed in Table 2. All expression cassettes comprise the *S. cerevisiae* PRB1 promoter and a modified *S. cerevisiae* ADH1 terminator (mADHt), and encode a leader sequence [either: fusion leader (FL. The same as that in plasmid pDB2244, WO 0044772A), modified fusion leader (mFL. The same as that described in plasmid pDB2305, EP1788084, incorporated herein by reference), the *S. cerevisiae* invertase leader sequence (Suc2p: MLLQAFLFLLAGFAAKISA) or a modified *S. cerevisiae* invertase leader sequence (MLLQAFFIVSIGFAAKISA)], and an albumin-derived protein (e.g. full-length, domains, mutants and fusions etc). FIG. 6 shows an example of a plasmid map (pDB2305) to illustrate the components of a typical expression cassette. Unless otherwise stated, final expression plasmids were generated in vivo (i.e. via homologous recombination in *S. cerevisiae*; a technique referred to as gap repair or in vivo cloning—see Orr-Weaver & Szostak. 1983. *Proc. Natl. Acad. Sci. USA*. 80:4417-4421). Typically, for gap-repair experiments, 100 ng of Acc65I/BamHI pDB3936 (disclosed in WO 2010/092135) was mixed with equimolar concentrations of DNA fragments containing the expression cassette required to generate the desired final expression plasmid. These were used directly to co-transform *S. cerevisiae* strains using a Yeast Transformation kit (Sigma) described below.

Expression plasmids were also generated using PCR (polymerase chain reactions) fragments and Acc65I/BamHI pDB3936 (100 ng) at equimolar concentrations using in vivo cloning. Table 3 lists the constructs generated using PCR fragments and Acc65I/BamHI pDB3936. All PCR reactions were performed using Phusion polymerase (New England Biolabs) following the manufacturer's instructions. A typical PCR reaction mixture is: 20 µl Buffer HF (5×), 2 µl dNTP mix (10 mM), 2 µl primer (10 µM), 2 µl primer (10 µM), 1 µl Phusion polymerase 2 U/µl), 1 µl plasmid DNA (~5 ng) or total DNA (~100 ng), 72 µl distilled H$_2$O.

TABLE 2

Summary of plasmid constructs

| Construct | Plasmid | SEQ ID |
|---|---|---|
| HSA DI + DIII wt | pDB4372 | 22 |
| HSA DI + DIII K500A | pDB4373 | — |
| HSA DI + DIII D550N | pDB4480 | — |
| HSA DI + DIII K573P | pDB4374 | — |
| HSA DI + DIII K573Y | pDB4375 | — |
| HSA DI + DIII wt + GSL + IL1Ra | pDB4382 | — |
| HSA DI + DIII K500A + GSL + IL1Ra | pDB4383 | — |
| HSA DI + DIII D550N + GSL + IL1Ra | pDB4481 | — |
| HSA DI + DIII K573P + GSL + IL1Ra | pDB4385 | — |
| HSA DI + DIII K573Y + GSL + IL1Ra | pDB4384 | — |
| HSA DII + DIII wt | pDB2217/pDB4386 | 21 |
| HSA DII + DIII D550N | pDB4482 | — |
| HSA DII + DIII K573P | pDB4387 | — |
| HSA DII + DIII K573Y | pDB4388 | — |
| HSA DII + DIII wt + GSL + IL1Ra | pDB4483 | — |
| HSA DII + DIII D550N + GSL + IL1Ra | pDB4484 | — |
| HSA DII + DIII K573P + GSL + IL1Ra | pDB4485 | — |
| HSA DII + DIII K573Y + GSL + IL1Ra | pDB4486 | — |
| HSA DIII K573F | pDB4460 | — |
| HSA DIII wt | pDB4461 | 23 |
| HSA DIII E492G | pDB4462 | — |
| HSA DIII K500A | pDB4463 | — |
| HSA DIII D550N | pDB4464 | — |
| HSA DIII K573A | pDB4465 | — |
| HSA DIII K573D | pDB4466 | — |
| HSA DIII K573H | pDB4467 | — |
| HSA DIII K573P | pDB4468 | — |
| HSA DIII K573W | pDB4469 | — |
| HSA DIII K573Y | pDB4470 | — |
| HSA DIII K574N | pDB4471 | — |
| HSA DIII Q580K | pDB4472 | — |
| HSA DIII E492G/N503K | pDB4473 | — |
| HSA DIII::GSL:: Il1Ra | pDB4474 | — |
| HSA DIII K573P::GSL:: Il1Ra | pDB4475 | — |
| HSA DIII D550N::GSL:: Il1Ra | pDB4476 | — |
| HSA DIII::GSL:: scFv::flag | pDB4477 | — |
| HSA DIII D550N::GSL:: scFv::flag | pDB4478 | — |
| HSA DIIIK573P::GSL:: scFv::flag | pDB4479 | — |
| HSA DIII wt + HSA DIII wt | pDB4522 | 24 |
| HSA DIII E492G + HSA DIII E492G | pDB4112 | — |
| HSA DIII D550N + HSA DIII D550N | pDB4523 | — |
| HSA DIII K573P + HSA DIII K573P | pDB4524 | — |
| HSA DIII wt + HSA DIII K573P | pDB4525 | — |
| HSA DIII K573P + HSA DIII wt | pDB4526 | — |
| HSA DIII wt + HSA DIII wt + GS + IL1Ra | pDB4527 | — |
| HSA DIII wt + HSA DIII wt + scFv + FLAG | pDB4528 | — |
| HSA DIII D550N + HSA DIII D550N + GS + IL1Ra | pDB4529 | — |
| HSA DIII D550N + HSA DIII D550N + scFv + FLAG | pDB4530 | — |
| HSA DIII K573P + HSA DIII K573P + GS + IL1Ra | pDB4531 | — |
| HSA DIII K573P + HSA DIII K573P + scFv + FLAG | pDB4526 | — |
| HSA DIII + DI | pDB4487 | — |
| HSA DIII + DII | pDB4488 | — |
| HSA DIII + DIII + DIII | pDB4534 | — |
| MSA | pDB3442 | 9 |
| RSA | pDB3257 | 14 |
| SSA | pDB3994 | 16 |

TABLE 3

Constructs generated in vivo using PCR and Acc65I/BamHI pDB3936 (100 ng) at equimolar concentrations

| Construct | Reference Number | SEQ ID NO: |
|---|---|---|
| IL1Ra + GSL + HSA DI + DIII wt | 9506 | — |
| IL1Ra + GSL + HSA DI + DIII K573P | 9507 | — |
| IL1Ra + GSL + HSA DII + DIII wt | 9508 | — |
| IL1Ra + GSL + HSA DII + DIII K573P | 9509 | — |
| IL1Ra + GSL + HSA DIII | 9504 | — |
| IL1Ra + GSL + HSA DIII K573P | 9505 | — |
| HSA DI + DII + MSA DIII | 9226 | 29 |
| HSA DI + DII + RSA DIII | 9009 | 25 |
| HSA DI + DII + SSA DIII | 9114 | 28 |
| MSA DI + DII + HSA DIII | 9225 | 30 |
| RSA DI + DII + HSA DIII | 9010 | 26 |
| SSA DI + DII + HSA DIII | 9113 | 27 |
| MSA DI + DIII | 9008 | — |
| RSA DI + DIII | 9007 | — |

(i) Construction of Plasmids for the Expression of Human/Animal Chimeras and Animal Albumin DI+DIII Constructs Plasmids are summarised in Table 2 and Table 3 unless otherwise stated. Plasmids for the expression of full-length rabbit (SEQ ID NO: 14) and mouse albumin (SEQ ID NO: 9) were prepared as follows. BfrI/SphI synthetic DNA fragments (2.087 kb) containing the 3' region of the PRB1 promoter, DNA encoding a modified fusion leader sequence, rabbit or mouse albumin and the 5' region of the mADHt were generated by gene assembly (GeneArt AG, Germany). An artificial SphI site was added directly upstream of the naturally present BfrI site to aid subsequent cloning. Synthetic SphI DNA fragments were cloned into pCR-script (Agilent Technologies), producing pDB3248 and pDB3429. pDB2541 (a sub-cloning plasmid containing the PRB1 promoter, DNA-encoding modified fusion leader and HSA, and the mADHt) was digested with BfrI/SphI to remove the gene encoding HSA and portions of the PRB1 and mADHt terminator flanking it. This DNA was replaced with the analogous BfrI/SphI fragments from pDB3248 and pDB3429 to produce pDB3256 and pDB3435, respectively. pDB3256 and pDB3435 were digested with NotI and the 2.989 kb products were individually ligated into NotI-digested pSAC35 (disclosed in EP-A-286 424 and described by Sleep, D., et al. (1991) Bio/Technology 9, 183-187, incorporated herein by reference) to produce pDB3257 and pDB3442, respectively.

pDB3257 and pDB3442 were used to directly transform *S. cerevisiae* Strain A (described in WO 2010/092135).

A plasmid for the expression of sheep albumin was prepared as follows. A 2.207 kb PstI/SphI synthetic DNA fragment (containing 3' region of the PRB1 promoter, DNA-encoding the fusion leader sequence and sheep albumin (SEQ ID NO: 16), and a portion of the mADHt) was generated by gene assembly (GeneArt AG, Germany). The synthetic PstI/SphI fragment was cloned into PstI/SphI-digested pDB3927 (described in WO 2010/092135) to produce pDB3994.

The final expression plasmid was generated by in vivo cloning/gap-repair, that is, pDB3994 was digested with BstEII/BsrBI, purified using a Qiagen PCR-Purification kit following the manufacturer's instructions, and 100 ng of the digest was combined with 100 ng Acc65I/BamHI-digested pDB3936 (disclosed in WO 2010/092135) and used to transform S. cerevisiae BXP10 cir⁰ (described in WO2001/079480).

Expression plasmids for the various albumin chimeras were generated using PCR and in vivo cloning. Table 4 lists the oligonucleotide pairs and template DNA used to generate each construct, Table 5 provides the sequences of the oligonucleotides. That is, PCR was used to amplify two PCR fragments. Fragment 1 contained the LEU2 ORF and 3' UTR, PRB1 promoter, the DNA encoding a leader sequence (either modified fusion or fusion leader sequence), DNA-encoding DI+DII of albumin (e.g. from human, mouse rabbit or sheep) and 27-30 bp of DNA encoding the 5' sequence of DIII of albumin (e.g. from human, mouse rabbit or sheep). Fragment 2 contained the DNA-encoding DIII of albumin (e.g. from human, mouse rabbit or sheep), the mADHt terminator and 217 bp flanking sequence homologous with nucleotide sequence in pDB3936 (disclosed in WO 2010/092135).

Figure 7:
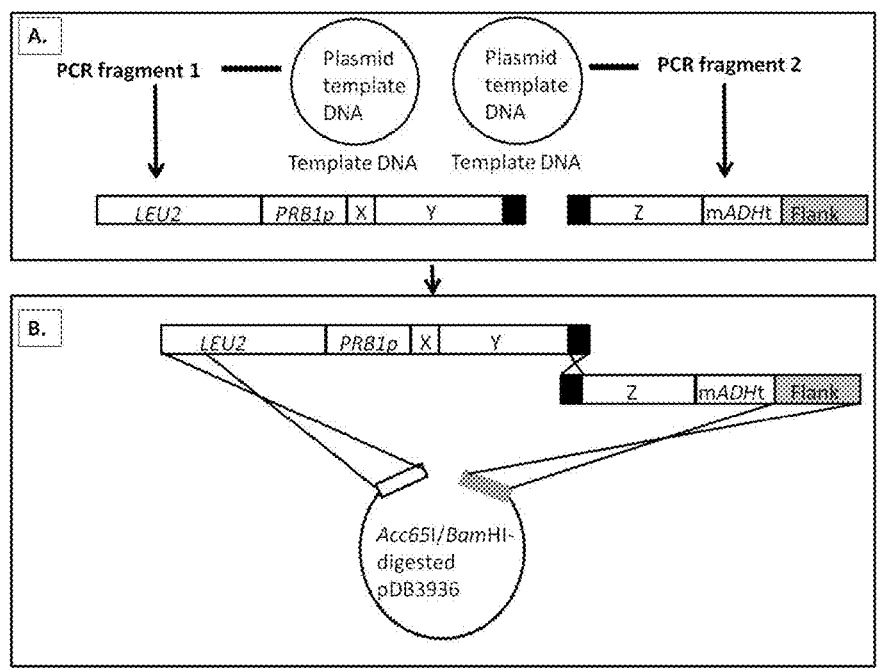
FIG. 7, Schematic diagram summarising the generation of expression plasmids in vivo. A. PCR was used to generate two PCR fragments. Fragments 1 and 2 share 247 base pair (bp) and 217 bp homology with Acc65I/BamHI-digested pDB3936 at their 5' and 3'ends, respectively. Fragments 1 and 2 share 27-30 bp homology with each other at their 3' and 5' ends, respectively. B Purified-PCR fragments were used, along with Acc65I/BamHI-digested pDB3936 to co-transform *S. cerevisiae* BXP10 cir$^0$. X=Leader sequence. Y=albumin DI+DII. Z=albumin DIII. Crosses represent in vivo recombination.
Figure 8A:
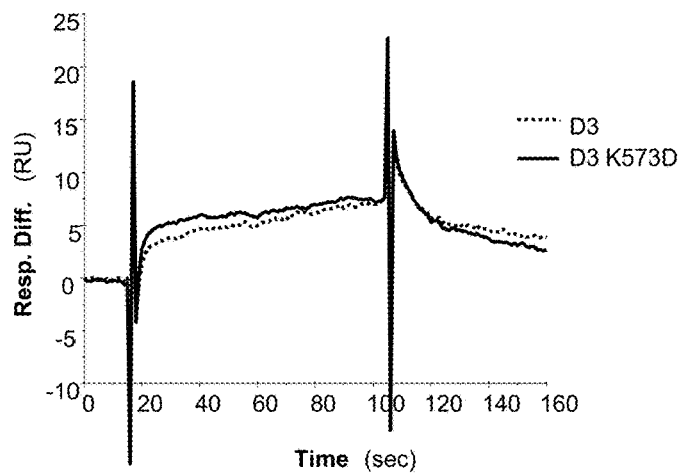
FIG. 8a: DIII wt and DIII K573D.
Figure 8B:
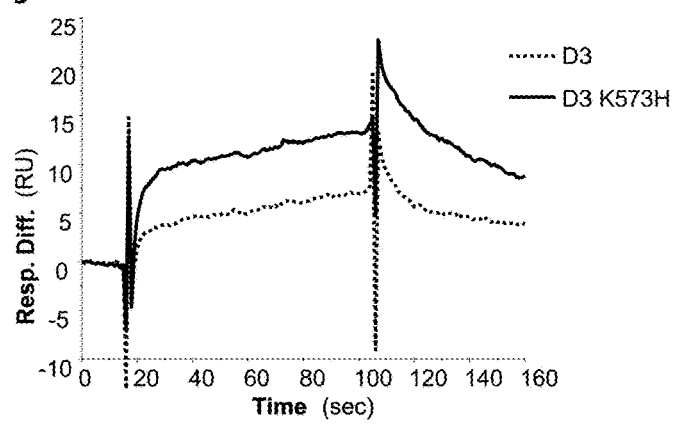
FIG. 8b: DIII wt and DIII K573H.
Figure 8C:
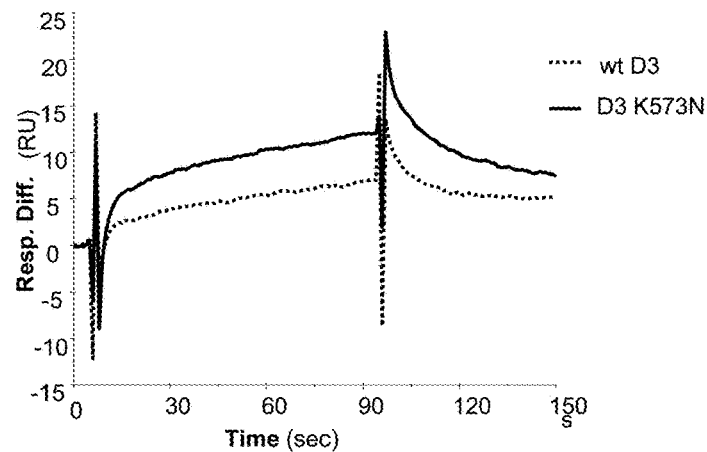
FIG. 8c: DIII wt and DIII K573N.
Figure 8D:
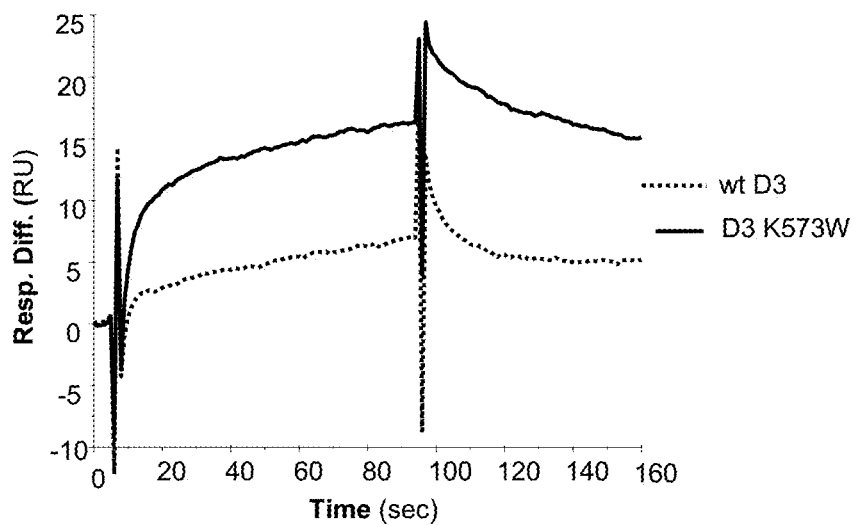
FIG. 8d: DIII wt and DIII K573W.
Figure 8E:
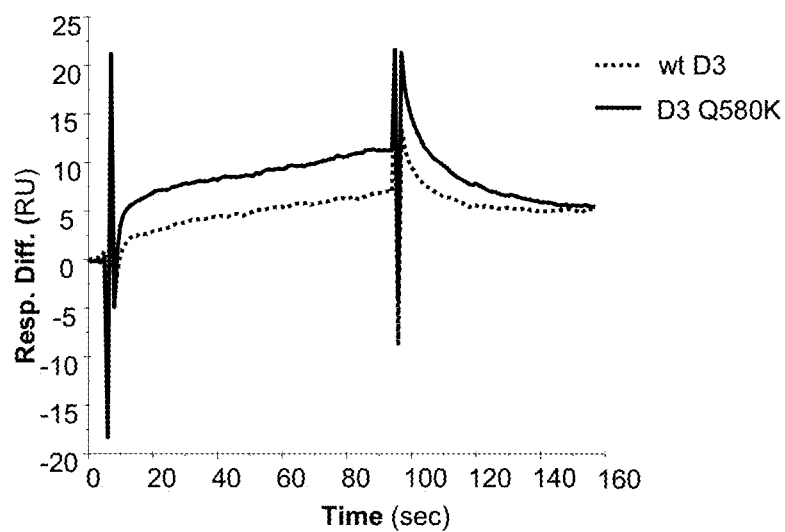
FIG. 8e: DIII and DIII Q580K.

PCR-products were purified using a Qiagen PCR Purification kit (following the manufacturer's instructions). FIG. 7 summarises the generation of expression plasmids by in vivo cloning. That is, purified PCR-products were used, along with Acc65I/BamHI-digested pDB3936, to co-transform S. cerevisiae BXP10 cir⁰.

The expression plasmids for mouse albumin and rabbit albumin DI+DIII were prepared using PCR and in vivo cloning using identical methods as those described above for generating the human/animal chimera expression constructs (e.g. HSA DI+DII+mouse DIII, and vice versa). Oligonucleotide pairs (Table 5) and template DNA used to generate PCR fragments are listed in Table 4.

TABLE 4

Oligonucleotide pairs and template DNA used to generate PCR fragments.

| Construct | SEQ ID NO: | Oligonucleotide pairs used PCR fragment 1 | PCR fragment 2 |
|---|---|---|---|
| HSA DI + DII + MSA DIII | 29 | xAP032/xAP161 (pDB2305)* | xAP160/xAP033 (pDB3442) |
| HSA DI + DII + RSA DIII | 25 | xAP032/xAP091 (pDB2305) | xAP086/xAP033 (pDB3257) |
| HSA DI + DII + SSA DIII | 28 | xAP032/xAP121 (pDB2305) | xAP122/xAP033 (pDB3994) |
| MSA DI + DII + HSA DIII | 30 | xAP032/xAP162 (pDB3442) | xAP093/xAP033 (pDB2305) |
| RSA DI + DII + HSA DIII | 26 | xAP032/xAP092 (pDB3257) | xAP093/xAP033 (pDB2305) |
| SSA DI + DII + HSA DIII | 27 | xAP032/xAP120 (pDB3994) | xAP093/xAP033 (pDB2305) |
| MSA DI + DIII | — | xAP032/xAP087 (pDB3442) | xAP088/xAP033 (pDB3442) |
| RSA DI + DIII | — | xAP032/xAP085 (pDB3257) | xAP086/xAP033 (pDB3257) |

*pDB2305 is shown in FIG. 6 and is also described in (disclosed in EP1788084, incorporated herein by reference)
Template DNA is shown in brackets e.g. (pDB2305)

TABLE 5

Oligonucleotide sequences of oligonucleotides mentioned in Table 4

| Oligonucleotide | Sequence (5'-3') |
|---|---|
| xAP032 | ATGTCTGCCCCTAAGAAGATCGTC |
| xAP033 | AACTTGCATCTAAACTCGACCTCTAC |
| xAP058 | GTTTGATTAAATTCTGAGGCTCTTCCACGGCAGACGAAGCCTTCCCTTCATC |
| xAP059 | GTGGAAGAGCCTCAGAATTTAATCAAAC |
| xAP075 | GACCTGACCATTTGATGGAG |
| xAP085 | GTTTAACCAAATTCTTTGGTTCATCAACAGCAGCAGAAATTAAAGATTTACCTTCC |
| xAP086 | GTTGATGAACCAAAGAATTTGGTTAAAC |
| xAP087 | GTTTTAACCAAATTCTTTGGTTCTTCTACAACTGAAGAAACCAATGCTTTTTCC |
| xAP088 | GTAGAAGAACCAAAGAATTTGGTTAAAAC |
| xAP091 | GTTTAACCAAATTCTTTGGTTCATCAACCAATGGCTTGAATTCATCGAAAACCTTAG |
| xAP092 | CTTGATCAAGTTTTGTGGTTCTTCGACCAATGGTTGAAATTCATCCAAAACTTAGC |
| xAP093 | GTCGAAGAACCACAAAACTTGATCAAG |
| xAP120 | CTTGATCAAGTTTTGTGGTTCTTCGACCAAGTGCTTCAATTTGTCGAAAACAGTAG |
| xAP121 | GTTGACGAACCACAAAACTTGATCAAGAAG |
| xAP122 | CTTCTTGATCAAGTTTTGTGGTTCGTCAACCAATGGCTTGAATTCATCGAAA |

TABLE 5-continued

Oligonucleotide sequences of oligonucleotides mentioned in Table 4

| Oligonucleotide | Sequence (5'-3') |
|---|---|
| | ACCTTAG |
| xAP138 | CCTAAGGCAGCTTGACTTG |
| xAP160 | GTAGAAGAACCAAAGAATTTGGTTAAAAC |
| xAP161 | GTTTTAACCAAATTCTTTGGTTCTTCTACCAATGGCTTGAATTCATCGAAAACCTTAG |
| xAP162 | GCTTGATCAAGTTTTGTGGTTCTTCGACCAATGGTTGAAATTCTGCCAAAACTGTAC |
| xAP253 | AAGCTTATTATAAGCCTAAGGCAGCTTGACTTGCAGCAACAAGTTTAAAACCCTCCTCG |
| xAP260 | GGATTTGCAGCAAAGATCTCCGCTGTGGAAGAGCCTCAGAATTTAATCAAACAAAATTGTGAGCTTTTTG |
| xAP290 | GTCAAGCTGCCTTAGGCTTAGATGCACACAAGAGTGAGGTTGCTCATC |
| xAP291 | AATTAAGCTTATTAGGCAGACGAAGCCTTCCCTTCATCCCGAAGTTCATC |
| xAP293 | AATTAAGCTTATTAAAGAGGTTTAAATTCATCGAACACTTTGGCATAGCATTCATG |
| xAP323 | AATCTAAGCCTAAGGCAGCTTGGGAAGCAGCGAC |
| xAP324 | CCAAGCTGCCTTAGGCTTAGTGGAAGAGCCTCAGAATTTAATCAAAC |
| xAP325 | AGAATTAAGCTTATTATAAGCCTAAAGCAGCTTGACTTGCAGCAAC |
| xAP330 | GAGAGCGCTATTTTTCTAACAAAGCATC |
| xAP332 | GTGGAAGAGCCTCAGAATTTAATCAAAC |
| xAP333 | CACACAGGAAACAGCTATGACCATG |
| xAP334 | GTTTGATTAAATTCTGAGGCTCTTCCACACCACCGGAACCACCAGAACCACCGGAACCACCGGATCCAC |
| xAP337 | CGATGAGCAACCTCACTCTTGTGTGCATCACCACCGGAACCACCAGAACCACCGGAACCACCGGATCCACC |
| xAP338 | TGATGCACACAAGAGTGAGGTTGCTCATC |
| xAP339 | GACGAAGCCTTCCCTTCATCCCGAAGTTCATCACCACCGGAACCACCAGAACCACCGGAACCACCGGATCCACC |
| xAP340 | GATGAACTTCGGGATGAAGGGAAGGCTTCG |
| B01 | GCATGCGGCCGCCCGAAGACCCTACACAGGGCTTAAGGGC |
| B02 | CCACGCGTCGTACGGGATTGCTGCTTATGAGGATA |
| B03 | ACGCGTGAATTCAAAAAGGGAACCCGTATATTTCAGC |
| B04 | TATCGATAGTCTTCCTAATATACACATTTTAGCAGATGC |
| B05 | GCATGCATACGCGTCACGCATGTGCCTCAGCGGCCGGCCGGCGCCGGGCCCCGGACCGCCTGCAGGCTCGAGTTAATTAAGTTTAAACGAATTCGCATGCAT |
| B06 | ATGCATGCGAATTCGTTTAAACTTAATTAACTCGAGCCTGCAGGCGGTCCGGGGCCCGGCGCCGGCCGGCCGCTGAGGCACATGCGTGACGCGTATGCATGC |
| B07 | CTAGAGTTAATTAAGTTTCAATTCAATTCATC |
| B08 | GCCTGAGTTTAAACGTTTTCTTTCCAATTTTT |

(ii) Preparation of Plasmids Encoding HSA DI+DIII Mutants and HSA DI+DIII Mutants Fusions An initial HSA DI+DIII expression plasmid/yeast strain was generated by PCR and in vivo cloning using methods described herein for the mouse and rabbit DI+DIII expression constructs. Oligonucleotides xAP032/xAP058 (Table 5) and xAP059/xAP033 (Table 5) were used to generated PCR fragments 1 and 2, respectively, (using pDB2244 (described in WO 00/44772) as template DNA). The resulting strain was named 8822.

Total DNA (i.e. genomic and plasmid DNA) were extracted from yeast 8822 as follows. A 10 μL sterile loop was used to scrape yeast cells from an agar plate and the cells were re-suspended in 200 4 extraction buffer [50 mM Tris-HCl (pH7.5), 10 mM EDTA (pH8.0), 100 mM NaCl, 2% w/v SDS] in a 1.5 mL microfuge tube, before being heated at 80° C. for 2 mins. The DNA extraction mixture was centrifuged at 13,000 rpm in a bench-top microfuge for 1 min before the supernatant was removed. Total DNA was precipitated with 3 volumes of ethanol and 0.1 volume of 3M sodium acetate (pH5.4) at −80° C. for 10 mins. Precipitated DNA was centrifuged at 13,000 rpm in a bench top microfuge for 20 mins, the supernatant was removed, and the DNA pellet was washed with 70% v/v ethanol. The pellet was air-dried briefly before the DNA was re-suspended in 100 4 TE buffer.

To generate HSA DI+DIII mutant expression cassettes, oligonucleotide xAP075 and xAP138 (Table 5) were used to PCR-amplify a 2.1 kb DNA fragment from the DNA prepared from yeast strain 8822. The PCR fragment contained the 3' region of the LEU2 marker, the PRB1 promoter, DNA-encoding the fusion leader and HSA DI and DIII. The PCR fragment was digested with NgoMIV/AvrII and the 1.395 kb product was ligated into NgoMIV/AvrII-digested pDB3927 (described in WO 2010/092135), pDB4086, pDB4110 and pDB4184 (all described in PCT/EP10/066,572, incorporated herein by reference) to produce pDB4372 to pDB4375 and pDB4480, respectively. pDB4372 to pDB4375 and pDB4480 were digested with NsiI/PvuI, DNA was purified using a Qiagen PCR-Purification kit following the manufacturer's instructions. Final expression plasmids were generated by in vivo cloning by co-transforming S. cerevisiae BXP10 cir$^0$ with each NsiI/PvuI-digested DNA and Acc65I/BamHI-digested pDB3936.

Plasmids containing the expression cassettes for the production of IL-1ra (SEQ ID NO: 34) genetically fused to the C-terminus of HSA DI+DIII and mutants thereof, were prepared as follows. pDB2588 (described in PCT/EP10/066, 572, incorporated herein by reference) was digested with Bsu36I/SphI and the 705 bp DNA fragment encoding the '3 region of the HSA DIII, a GS linker, and human IL1-RA (N84Q) and the 5' region of a modified S. cerevisiae mADHt, was purified using a Qiagen PCR-purification kit following the manufacturer's instructions. Purified fragments were ligated into Bsu36I/SphI-digested pDB4372, pDB4373, pDB4374, pDB4375 and pDB4480 to generate pDB4382, pDB4383, pDB4385, pDB4384 and pDB4481, respectively. Final expression plasmids were generated by in vivo cloning which involved digesting pDB4382 to pDB4385 and pDB4481 with NsiI/PvuI, purifying the DNA using a Qiagen PCR-Purification kit following the manufacturer's instructions, before being used, along with Acc65I/BamHI-digested pDB3936 to directly transform S. cerevisiae BXP10 cir$^0$.

Plasmids containing the expression cassettes for the production of IL-1ra (N84Q) genetically fused to the N-terminus of HSA DI+DIII and HSA DI+DIII K573P were prepared using PCR and in vivo cloning using methods described above. Oligonucleotides used to generate the two PCR fragments are listed in Table 5. PCR fragment 1 was generated using oligonucleotides xAP330/xAP337 and plasmid pDB2590 as the template DNA. Plasmid pDB2590 is identical to pDB2305 (described in WO2006/013859) but contains DNA sequence-encoding the fusion leader, IL-1ra (N84Q), a GS linker followed by HSA. PCR fragment 1 contained 774 bp of nucleotide sequence upstream of the LEU2 ORF, PRB1 promoter, and DNA-encoding the fusion leader sequence, IL1-RA (N84Q), a GS-linker, and the first 29 bp of HSA DI. PCR fragment 2 (generated using oligonucleotides xAP338/xAP333 using either pDB4372 or pDB4374) contained DNA-encoding HSA DI+DIII (wt or K573P), mADHt and 2.031 kb flanking sequence, homologous with nucleotide sequence in pDB3936. PCR-fragments were purified using a Qiagen PCR Purification kit following the manufacturer's instructions. Final expression plasmids were generated in vivo which involved co-transformation of S. cerevisiae BXP10 cir$^0$ with PCR fragments 1 and 2, along with Acc65I/BamHI-digested pDB3936.

(iii) Preparation of Plasmids Encoding HSA DII+DIII Mutants and Fusions Thereof.

Expression plasmids for HSA DII+DIII and mutants thereof were generated as follows. pDB2202, containing a HSA DII+DIII expression cassette (i.e. PRB1 promoter, DNA-encoding the fusion leader and HSA DII+DIII, and the mADHt), was digested with NgoMIV/AvrII and a 1.407 kb fragment was purified using a Qiagen Gel Extraction kit (following the manufacturer's instructions). The NgoMIV/AvrII fragment was ligated into NgoMIV/AvrII-digested pDB3927 (described in WO 2010/092135), pDB4010, pDB4110 and pDB4184 (described in PCT/EP10/066,572, incorporated herein by reference) to generate pDB4386, pDB4482, pDB4387, pDB4388, respectively. pDB4386-pDB4388 and pDB4482 were digested with NsiI/PvuI, DNA was purified using a Qiagen PCR-Purification kit following the manufacturer's instructions. Final expression plasmids were generated in vivo which involved co-transformation of S. cerevisiae BXP10 cir$^0$ with each NsiI/PvuI-digested plasmid DNA, along with Acc65I/BamHI-digested pDB3936.

Plasmids containing the expression cassettes for the production of IL-1ra genetically fused to the C-terminus of HSA DII+DIII and mutants thereof were prepared following the methods described for generating the IL-1ra genetically fused to the C-terminus of HSA DI+DIII mutants constructs. Plasmids generated were named pDB4483, pDB4485, pDB4486 and pDB4484. pDB4483 to pDB4486 NsiI/PvuI, DNA was purified using a Qiagen PCR-Purification kit following the manufacturer's instructions. Final expression plasmids were generated in vivo as described for the HSA DI+DIII mutant fusion constructs.

Plasmids containing the expression cassettes for the production of IL-1ra genetically fused to the N-terminus of HSA DII+DIII and HSA DII+DIII K573P were prepared using PCR and in vivo cloning, as described for the generation of IL-1ra genetically fused to the N-terminus of HSA DI+DIII and HSA DI+DIII K573P. PCR fragment 1 was generated using oligonucleotides xAP330/xAP339 (Table 5) (pDB2590 was used as template DNA) and shared 32 bp of nucleotide sequence homology with that encoding HSA DII (i.e. in pDB4386 and pDB4387). PCR fragment 2 was generated using oligonucleotides xAP340/xAP333 (Table 5 (using pDB4386 or pDB4387 as template DNA)) and shared 2.031 kb homologous flanking sequence with nucleotide sequence in pDB3936. PCR fragments were purified using a Qiagen PCR-purification kit following the manufacturer's instructions. Final expression plasmids were generated in vivo as described for the HSA DI+DIII mutant fusion constructs.

(iv) Preparation of Plasmid Encoding HSA DIII and Mutants and Fusions Thereof

PCR was used to generate a 649 bp fragment encoding the HSA DIII, introduce a change at the codon corresponding to position 573 of the mature albumin protein sequence so that a phenylalanine would be incorporated instead of a lysine and to tailor the fragment to allow it to be cloned into the expression plasmid pDB4284 (described in PCT/EP10/066, 572, incorporated herein by reference). Specifically, this was achieved using oligonucleotides xAP260 and xAP253 (Table 5) and the plasmid pDB3927 (described in WO 2010/092135) as template DNA. The PCR fragment was purified using a Qiagen PCR Purification kit (according to the manufactures instructions), digested with BglII/Bsu36I, before the digested DNA was purified using a Qiagen PCR Purification kit. The purified BglII/Bsu36I fragment was ligated into Bg/II/Bsu36I-digested pDB4284 to create pDB4460.

A series of expression plasmids encoding HSA DIII mutants was made by the replacement of the 666 bp AvrII/SphI fragment from pDB4460 with analogous sequences from plasmids pDB3927 (described in WO 2010/092135), pDB3883, pDB4086, pDB4010, pDB4006, pDB4175, pDB4189, pDB4110, pDB4182, pDB4184, pDB4200, pDB4202 and pDB4094 (described in PCT/EP10/066,572, incorporated herein by reference) that contain mutations within the nucleotide sequence encoding HSA DIII to create plasmids pDB4461 to pDB4473.

Plasmids containing the expression cassettes for the production of IL-1ra or scFv (FITC8) (SEQ ID NO: 35) genetically fused to the C-terminus of HSA DIII and DIII variants were prepared as follows. For the IL-1ra fusions, a 1.164 kb AvrII/SphI fragment from plasmids pDB2588, pDB4288 and pDB4286 (described in PCT/EP10/066,572, incorporated herein by reference) [containing the 3' end of the DNA-encoding HSA DIII or mutants thereof, and DNA-encoding a GS linker and IL-1ra (N84Q), and the 5' region of the mADHt) was obtained and subsequently ligated into AvrII/SphI-digested pDB4460. This resulted in the plasmids pDB4474-pDB4476, respectively.

Plasmids containing expression cassettes for the production of the scFv fusions were made by the isolation of the 1.005 kb Bsu36I/SphI fragment from plasmid pDB3008 (described in, Evans et al., 2010. Protein Expression and Purification. 73, 113-124) (containing DNA-encoding the C-terminal region of HSA DIII, a GS linker and the scFv and the 5' region of the mADHt) and the subsequent cloning of this into Bsu36I/SphI-digested pDB4461, pDB4464 and pDB4468. This resulted in the plasmids pDB4477-pDB4479.

Plasmids pDB4460-pDB4479 were digested with NsiI/PvuI and purified using the Qiagen PCR Purification kit. Purified DNAs were mixed with Acc65I/BamH-digested pDB3936 and used to directly transform *S. cerevisiae* Strain B cir$^0$.

*S. cerevisiae* strain B cir$^0$ is a derivative of *S. cerevisiae* strain A cir$^0$ (described in WO 2010/092135) and its construction is described below. Following chemical mutagenesis, a *S. cerevisiae* ura3 mutant (i.e. auxotrophic for uracil) was isolated and named *S. cerevisiae* strain A-ura3. *S. cerevisiae* strain A-ura3 was transformed with pDB3837. pDB3837 was generated as follows: 5' and 3' regions of the HO open reading frame were amplified by PCR from *S. cerevisiae* BY4741 (described in Brachmann, et al., (1998) Yeast 14, 115) genomic DNA using the primers B01/BO2 and BO3/B04, respectively (Table 5). PCR-products were purified and restriction digested with the enzymes NotI/MluI (5' region fragment) and MluI/ClaI (3' region fragment). The digested fragments were purified and ligated in a three way ligation with NotI/ClaI digested pBST+[described in Sleep, D. (2001). Yeast 18: 403-421]. A polylinker (generated from hybridised oligonucleotides B05 and BO6, Table 5) was cloned at the MluI site between the 5' and 3' regions to create pDB3343. The *S. cerevisiae* URA3 gene was PCR-amplified from the plasmid YCplac50 [Described in Rose et al. (1987). *Gene* 60: 237-243] using primers B07 and B08 (Table 5). The URA3 product was digested with PacI and PmeI and ligated into PacI/PmeI-digested pDB3343 create pDB3514. A 2.94 kb KpnI fragment containing the *S. cerevisiae* PDI1 gene was obtained from pDB2389 (Finnis et al. (2010). *Microbial Cell Factories* 9: 87), blunted using T4 Polymerase, before being ligated into SfoI-digested pDB3514. The resulting plasmid, pDB3837, contained two tandem copies of the PDI1 fragment. pDB3837 was used to directly transform *S. cerevisiae* strain A-ura3 cir$^0$ to generate strain B cir$^0$. *S. cerevisiae* strain B contains the native copy of the PDI1 gene, 2 copies of the PDI1 gene at the HO locus and an additional copy of the PDI1 gene at an unknown location in the genome of this strain.

(v) Preparation of Plasmid Encoding HSA DIII and Mutants and Fusions Thereof.

Plasmids containing expression cassettes for HSA DIII+DIII, and mutants thereof, were generated as follows. PCR, using oligonucleotides xAP323/xAP324 (Table 5), was used to amplify a 636 bp DNA fragments from pDB4282, pDB4283 and pDB4284 (described in PCT/EP10/066,572, incorporated herein by reference). PCR fragments were purified using a Qiagen PCR Purification kit following the manufacturer's instructions, digested with BglII/HindIII, purified using a Qiagen PCR-purification kit following the manufacturer's instructions, before being ligated into BglII/HindIII-digested pDB4284 (described in PCT/EP10/066,572, incorporated herein by reference). Resulting plasmids were named pDB4489-pDB4491.

A second round series of PCRs were performed to amplify DNA-encoding a second HSA DIII and variants thereof. Oligonucleotides xAP324/xAP325 (Table 5) were using to PCR-amplify DNA fragments encoding HSA DIII and variants thereof from pDB3927 (described in WO 2010/092135, incorporated herein by reference), pDB4010 and pDB4110 (described in PCT/EP10/066,572, incorporated herein by reference). PCR fragments were purified using a Qiagen PCR-purification kit following the manufacturer's instructions, digested with Bsu36I, purified using a Qiagen PCR-purification kit following the manufacturer's instructions, before being ligated into Bsu36I-digested pDB4489-pDB4491. Resulting plasmids were named pDB4522-pDB4526. pDB4522-pDB4526 were digested with NsiI/PvuI, DNA was purified using a Qiagen PCR-Purification kit following the manufacturer's instructions, before being used, along with Acc65I/BamHI-digested pDB3936 to directly transform *S. cerevisiae* strain B cir$^0$.

(vi) Preparation of Plasmids Encoding HSA DIII E492G+DIII E492G (i.e. a Tandem Domain III)

A plasmid containing a HSA DIII E492G+DIII E492G expression cassette was prepared as follows. A 1.488 kb synthetic DNA fragment containing the 3' region of the PRB1 promoter, DNA-encoding the FIVSI modified invertase leader and HSA DIII E492G+DIII E492G and 5' region of the mADHt, was generated by gene assembly (DNA2.0, USA). The synthetic PstI/PacI fragment was ligated into PstI/PacI-digested pDB4181 (described in PCT/EP10/066,572, incorporated herein by reference) to generate pDB4112. pDB4112 was digested with BstEII/BsrBI, purified using a Qiagen PCR Purification kit following the manufacturer's instructions, before 100 ng was mixed with 100 ng Acc65I/BamHI-digested pDB3936 (disclosed in WO 2010/092135, incorporated herein by reference) and used to directly transform *S. cerevisiae* strain B cir$^0$.

Plasmids containing the expression cassettes for the production of IL-1ra or scFv (FITC8) genetically fused to the C-terminus of HSA DIII+DIII and mutants thereof were prepared as follows. pDB4522, pDB4523 and pDB4524 were digested with AvrII/SphI and 7.564 kb from each reaction were purified a Qiagen Gel Extraction kit following the manufacturer's instructions. pDB4474 to pDB4479 were digested with AvrII/SphI and 1.164 kb and 1.464 kb fragments (containing DNA-encoding IL-1Ra and scFv, respectively) were purified using a Qiagen Gel Extraction kit following the manufacturer's instructions. Purified AvrII/SphI fragments from pDB4474 to pDB4479 were ligated into AvrII/SphI-digested pDB4522 to pDB4524 to produce pDB4527-pDB4531 and pDB4533. pDB4527-pDB4531 and pDB4533 were digested with NsiI/PvuI, DNA was purified using a Qiagen PCR-Purification kit following the manufacturer's instructions, before being used, along with Acc65I/BamHI-digested pDB3936 to directly transform S. cerevisiae strain B cir$^0$.

(vii) Preparation of Plasmids Encoding DIII+DI and DIII+DII

Plasmids containing expression cassettes for HSA DIII+DI and DIII+DII were generated as follows. Oligonucleotide pairs xAP290/xAP291 and xAP292/xAP293 (Table 5) were used to PCR-amplify the DNA-encoding HSA DI (PCR fragment=616 bp) and HSA DII (PCR-produce=628 bp), respectively, using pDB3927 (described in WO 2010/092135) as template DNA. Both PCR fragments were digested with Bsu36I/HindIII, purified using a Qiagen PCR-purification kit (following the manufacturer's instructions), then ligated into Bsu36I/HindIII-digested pDB4478 to produce pDB4487 and pDB4488. pDB4487 and pDB4488 were digested with NsiI/PvuI, DNA was purified using a Qiagen PCR-Purification kit following the manufacturer's instructions, before being used, along with Acc65I/BamHI-digested pDB3936 to directly transform S. cerevisiae strain B cir$^0$.

(viii) Preparation of Plasmids Encoding DIII+DIII+DIII

The expression construct for HSA DIII+DIII+DIII (i.e. triple domain III) was prepared as follows: A 615 bp Bsu36I DNA fragment, containing DNA-encoding HSA DIII, was obtained from pDB4527 and ligated into Bsu36I-digested pDB4522 to create pDB4534. pDB4534 was digested with NsiI/PvuI, DNA was purified using a Qiagen PCR-Purification kit following the manufacturer's instructions, before being used, along with Acc65I/BamHI-digested pDB3936 to directly transform S. cerevisiae strain B cir$^0$.

(d) Transformation of S. cerevisiae

S. cerevisiae strains were streaked on to YEPD plates (1% (w/v) yeast extract, 2% (w/v) Bactopeptone, 2% (w/v) glucose), 1.5% agar) and allowed to grow for 4 days at 30° C. prior to transformation. One μg of whole plasmid (i.e. circular plasmid) or, for gap repair, BstEII/BsrBI- or NsiI/PvuI-digested HSA variant or HSA variant fusion containing plasmid and Acc65I/BamHI digested pDB3936 (100 ng) was used (at equimolar concentrations) to transform S. cerevisiae using a Sigma Yeast Transformation kit using a modified lithium acetate method (Sigma yeast transformation kit, YEAST-1, protocol 2; Ito et al. (1983) J. Bacteriol., 153, 16; Elble, (1992) Biotechniques, 13, 18). The protocol was amended slightly by incubating the transformation at room temperature for up to 4 h prior to heat shock. Following heat shock, the cells were briefly centrifuged before being re-suspended in 200 μl μM sorbitol then spread over BMMD agar plates, the composition of BMMD is described by Sleep et al., (2001), Yeast, 18, 403. Plates were incubated at 30° C. for 4 days before individual colonies were patched on to fresh BMMD plates.

Stocks were prepared for each yeast strain as follows: BMMD broth was inoculated with a heavy loop of each yeast patch and grown for 24 h at 30° C. with orbital shaking at 200 rpm. Cells were harvested by centrifugation at 1900×g for 5 min in a Sorval RT600 centrifuge, 15 mL supernatant was removed and replaced by trehalose 40% (w/v). The cells were re-suspended and transferred to cyrovials (1 mL) for storage at −80° C.

(e) Shake Flask Growth of S. cerevisiae

BMMD (recipe 0.17% (w/v) yeast nitrogen base without amino acid and ammonium sulphate (Difco), 37.8 mM ammonium sulphate, 29 mM citric acid, 142 mM disodium hydrogen orthophosphate dehydrate pH6.5, 2% (w/v) glucose) media (10 mL) was inoculated with each yeast strain and grown for 24 h at 30° C. with orbital shaking at 200 rpm. An aliquot of each starter culture (4 mL) was used to inoculate 2×200 mL BMMD media and grown for 96 h at 30° C. with orbital shaking at 200 rpm. Cells were harvested by filtration through 0.2 μm vacuum filter membranes (Stericup, Millipore) including a GF-D pre-filter (Whatman) and the supernatant retained for purification.

(f) Primary Concentration

Retained culture supernatant was concentrated using Tangential Flow Filtration using a Pall Filtron LV system fitted with a Omega 10 KD (0.093 sq·m2) filter (LV Centramate™ cassette, Pall Filtron) with a transmembrane pressure of 20 psi and a recirculation rate of 180 mL·min$^{-1}$.

(g) Purification of Albumin Derivatives and Fusions Thereof from Shake Flask

Albumin derivatives, variants and fusions thereof were purified from shake flask (either culture supernatant or concentrated culture supernatant) using a single chromatographic step using an albumin affinity matrix (AlbuPure™—ProMetic BioSciences, Inc.). Chromatography was performed at a constant linear velocity of 240 cm/h throughout. Culture supernatant was applied to a 6 cm bed height, 2.0 mL packed bed pre-equilibrated with 50 mM sodium acetate pH5.3. Following load the column was washed with 10 column volume (CV) of equilibration buffer, then 50 mM ammonium acetate pH8.0 (10CV). Product was eluted with either 50 mM ammonium acetate 10 mM octanoate pH8.0, 50 mM Ammonium Acetate 30 mM Sodium Octanoate pH8.0, 50 mM Ammonium Acetate 100 mM Sodium Octanoate pH8.0 or 200 mM Potassium thiocyanate. The column was cleaned with 0.5M NaOH (3cv) and 20 mM NaOH (3.5cv). Eluate fraction from each albumin variant were concentrated and diafiltered against 10 volumes of Tris buffered saline (25 mM Tris, 150 mM NaCl, 2 mM KCl, pH7.4) using Vivaspin20 10,000 MWCO PES with optional diafiltration cups (Sartorius). Purified albumin variants were quantified by GP-HPLC as described below (section (j)).

(h) 2 L and 10 L Fermentations

10 L Fermentation

Transformants were cultivated as fed-batch fermentations, carried out in a 10 L Sartorius Biostat C fermenter, at 30° C. The pH was monitored and adjusted by the addition of ammonia or sulphuric acid, as appropriate. The ammonia also provided the nitrogen source for the cultures. The level of dissolved oxygen was monitored and linked to the stirrer speed, to maintain the level at >20% of saturation. Inocula were grown in shake flasks in buffered minimal media. For the batch-phase, the culture was inoculated into fermenter media (approximately 50% of the fermenter volume) containing 2% (w/v) sucrose. The feed stage was automatically triggered by a sharp rise in the level of dissolved oxygen. Sucrose was kept at growth-limiting concentrations by controlling the rate of feed to a set nominal growth rate. The feed consisted of fermentation media containing 50% (w/v) sucrose, all essentially as described by Collins. (Collins, S.

H., (1990) Production of secreted proteins in yeast, in: T.J.R. Harris (Ed.) Protein production by biotechnology, Elsevier, London, pp. 61-77).

2 L Fermentation

Transformants were cultivated as fed-batch fermentations Fed-batch fermentations were carried out in a 2 L Pierre Guerin Tryton fermenter, at 30° C. The pH was monitored and adjusted by the addition of ammonia or sulphuric acid, as appropriate. The ammonia also provided the nitrogen source for the cultures. The level of dissolved oxygen was monitored and linked to the stirrer speed, to maintain the level at >20% of saturation. Inocula were grown in shake flasks in buffered minimal media. For the batch-phase, the culture was inoculated into fermenter media (approximately 50% of the fermenter volume) containing 2% (w/v) sucrose. The feed stage was automatically triggered by a sharp decrease in the level of oxygen consumption. Sucrose was kept at growth-limiting concentrations by controlling the rate of feed to a set nominal growth rate. The feed consisted of fermentation media containing 50% (w/v) sucrose, all essentially as described by Collins. (Collins, S. H., (1990) Production of secreted proteins in yeast, in: T.J.R. Harris (Ed.) Protein production by biotechnology, Elsevier, London, pp. 61-77).

(i) Purification of Albumin Derivatives and Fusions Thereof from Fermentation

Albumin derivatives and fusions therein were purified from high cell density fed batch fermentation supernatants after separation by centrifugation, using a Sorvall RC 3C centrifuge (DuPont). Culture supernatant was chromatographed through an 11 cm bed height column 22 mL packed bed packed with a custom synthesised albumin affinity matrix (AlbuPure™—ProMetic BioSciences, Inc.) as described above. Product was eluted using elution buffers describe above at a flow rate of 120 cm/h. The eluate fraction(s) was analysed by GP-HPLC (below) and reducing SDS PAGE for purity. Eluate fraction from each albumin variant were evaluated by GP-HPLC (as described below) and reducing SDS-PAGE and if required further separated by preparative gel filtration performed using a 90 cm bed height column 488 mL packed bed, packed with Sephacryl S200 (GE Healthcare) and run in Tris buffered saline (25 mM Tris, 150 mM NaCl, 2 mM KCl, pH7.4 at 4 mL·min 1. Eluate fractions from either AlbuPure™ or AlbuPure™ and Sephacryl S200 chromatography were concentrated using either Vivaspin20 10,000 MWCO PES with optional diafiltration cups (Sartorius) or tangential flow filtration using a Pall Filtron LV system fitted with a Omega 10 KD (0.093 sq·m2) filter (LV Centramate™ cassette, Pall Filtron) with a transmembrane pressure of 20 psi and a recirculation rate of 180 mL·min 1. For those eluates derived only from AlbuPure™ chromatography, after concentration, diafiltration was then performed against 10 volumes of Tris buffered saline (25 mM Tris, 150 mM NaCl, 2 mM KCl, pH7.4) Purified albumin variants were quantified by GP-HPLC as described below.

All proteins to be assayed for receptor (shFcRn) binding properties and or other analysis were quantified by GP-HPLC as described below corrected for their relative extinction coefficients.

(j) Quantitative Analysis of Albumin Derivatives, Variants, Fusions and Conjugates Thereof by GP-HPLC Purified albumin derivatives, variants, fusions and conjugates thereof were analysed by GP-HPLC and quantification as follows. Injections of 25 µL were made onto a 7.8 mm id×300 mm length TSK G3000SWXL column (Tosoh Bioscience), with a 6.0 mm id×40 mm length TSK SW guard column (Tosoh Bioscience). Samples were chromatographed in 25 mM sodium phosphate, 100 mM sodium sulphate, 0.05% (w/v) sodium azide, pH 7.0 at 1 mL/min, Samples were quantified by UV detection at 280 nm, by peak area, relative to a recombinant human albumin standard of known concentration (10 mg/mL) and corrected for their relative extinction coefficients.

(k) Conjugation of Horse Radish Peroxidase (HRP) to Albumin and Derivatives and Variants Thereof.

Albumin and derivatives and variants thereof were purified as described above (sections (g) and (i)), concentrated and subjected to buffer exchange in Tris Buffer Saline (TBS), pH 7.2-7.3.

HRP was conjugated to the molecules by incubating with 2 mg/mL EZ-Link® Maleimide Activated Horseradish Peroxidase (HRP, Thermo Scientific) to react with the free sulphydryl in Domain I. The HRP was dissolved in Phosphate Buffer Saline (PBS), pH 6.5 and incubation provided approximately 2-fold molar excess of HRP relative to the albumin or variant or derivative thereof. This mixture was incubated at 4° C., for at least 24 hours. The reaction mixtures were then analysed using GP-HPLC to confirm that conjugation had taken place. GP-HPLC analysis is described above (section (j)).

To separate unconjugated species (DI+DIII, DI+DIII+DIII or domain variants and unreacted HRP) from the corresponding conjugated species, the samples were first concentrated (Vivaspin20, 10,000 MWCO PES, Sartorius), and then individually applied to a Tricorn Superdex™ 200, 10/300 GL column (GE Healthcare), and run at a flow rate of 45 cm/hr in TBS. The elution peak was fractionated and analysed by GP-HPLC. Fractions containing the conjugated species were pooled, concentrated and subsequently analysed by GP-HPLC and non-reducing SDS PAGE to demonstrate conjugated species.

(l) Conjugation of Fluorescein-5-Maleimide (F5M) to Albumin and Derivatives and Variants Thereof.

Fluorescein-5-Maleimide, Thermo Scientific (F5M) was dissolved in dimethylformamide, to give a final concentration of 12.5 mg/mL. This was then further diluted into 18 mls of PBS, pH adjusted to approximately pH 6.5. HSA DI+DIII variants were added to give an approximate 20 fold final molar excess of F5M, in the final mixture. These samples were then incubated and allowed to conjugate overnight at 4° C., in the dark, to allow the maleimide groups on the F5M to react with predominantly the free sulfhydryl, present in the albumin species.

Following overnight incubation aliquots of the reaction mixtures were extensively diafiltered against TBS to remove unconjugated F5M, (Vivaspin20, 10,000 MWCO PES, Sartorius). Conjugation was confirmed by ultraviolet visualization of conjugated Fluorescein::DI+DIII, and variants therein, using standard SDS-PAGE Example 1. Construction of Albumin Derivatives or Variants In order to demonstrate the binding of albumin derivatives or variants or fragments, the following constructs were made starting from HSA. The positions cited under the headline "mutation/construct" refer to positions in SEQ ID NO: 31.

TABLE 6

Albumin derivatives and variants

| Sample Details | SEQ ID NO: | Concentration (mg/mL) | Mutation/construct (amino acid residues relative to mature HSA) |
|---|---|---|---|
| a) Domains I + II | 20 | 82.0 | 1-387 |
| b) Domains II + III | 21 | 33.0 | 183-585 |
| c) Domains I + III | 22 | 62.4 | 1-194 + 381-585 |
| d) Domain III | 23 | 89.7 | 381-585 |
| e) 2 × Domain III | 24 | 35.5 | 381-585** |

**The nucleotide sequence encoding the N-terminal Domain III was codon optimised, the nucleotide sequence encoding the C-terminal Domain III was non optimised. This was done to prevent recombination of the nucleotide sequences encoding the identical Domain III amino acid sequences and therefore ensures that a double-Domain III molecule was generated instead of a single Domain III which could arise if the nucleic sequences had recombined.

Example 2. Binding of Albumin Variants to Soluble FcRn (shFcRn)

Three established FcRn binding assays were used, ELISA, SPR and a Dynabead binding assay. There are major differences between the assays:

In the ELISA system HSA is coated directly in wells and soluble hFcRn (shFcRn)-GST is added in solution whereas in the SPR assay shFcRn-GST is immobilized to a CM5 chip and HSA injected in solution. The pH can be varied in both systems.

The FcRn Dynabead binding assay is based on site-specific biotinylated shFcRn captured on streptavidin coupled beads. GST-tagged HSA is added in solution and binding is detected using a chicken HRP-conjugated anti-GST Ab.

In addition, competitive binding was measured by injecting shFcRn (50 nM) alone or together with different concentrations of HSA (55-500 nM), HSA DI-DII (500+1500 nM), HSA DII-DIII (500+1500 nM), HSA DI-DIII (500+1500 nM), HSA DIII (500+1500 nM) and HSA DIII-DIII (500+1500 nM) over immobilized HSA (2600 RU). Injections were performed at 25° C. and at a flow rate of 50 µl/min. The variants of Example 2 were analysed for FcRn binding using ELISA (results shown in FIG. 1), and using SPR (results shown in FIG. 2 and Table 7) and competitive SPR based assay (the results are shown in FIG. 3). The SPR and competitive SPR based assays were carried out using shFcRn-GST.

The kinetics of the shFcRn interaction with HSA domains were calculated and shown below (Table 7).

TABLE 7

Kinetics of the shFcRn-GST interaction with HSA domains

| Albumin variant[a] | SEQ ID NO: | ka ($10^3$/Ms) | kd ($10^{-3}$/s) | $KD^b$ (µM) | KD Req[c] (µM) |
|---|---|---|---|---|---|
| HSA wt | 31 | 3.2 ± 0.2 | 15.5 ± 2.5 | 4.8 | 5.4 |
| HSA DII-DIII | 21 | 0.7 | 7.1 | 9.8 | ND |
| HSA DI-DIII | 22 | 2.6 ± 0.3 | 18.3 ± 0.2 | 7.0 ± 0.2 | ND |
| HSA DIII wt | 23 | ND | ND | ND | 17.6 ± 2.3 |

[a]titrated amounts of albumin or DIII derivatives or variants were injected over immobilized shFcRn (~1500 RU) at pH6.0.
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of triplicates.
[d]Not determined (ND).

The SPR results show that: DI+III, DII+III, DIII, double DIII and full-length albumin binds shFcRn in a pH-dependent manner (FIG. 2) In contrast, ELISA data showed that DIII wt, when immobilized, does not interact with shFcRn. The DIII-shFcRn association/dissociation rates are fast, and thus, kinetic values could not be determined directly, however calculation of the steady state affinity constant shows DIII binds less shFcRn than does full-length HSA and there is a 3-fold reduction in binding affinity. This data suggests that other parts of HSA are important for optimal binding to shFcRn of domain III, which is further supported when analyzing DI-DIII and DII-DIII. DII-DIII binds shFcRn, although the binding affinity is reduced compare with that measured for full-length albumin. DI-DIII also binds shFcRn with a higher affinity than DII-DIII, both have an affinity higher than for domain III alone again supporting the observation that other parts of HSA are important for optimal binding to shFcRn receptor. Competitive SPR assay shows that the double domain III construct competes for wt albumin in the assay more effectively than DI+III, DII+III and DIII but not as effectively as wt albumin, i.e. HSA.

Example 3. Binding of Domain Swap Derivatives to shFcRn

The following domain swap derivatives were generated following the methods section (above):

HSA 1/2-RSA 3: HSA (human serum albumin) domain I and II and RSA (rabbit serum albumin) domain III RSA 1/2-HSA3: RSA domain I and II and HSA domain III SSA 1/2-HSA3: SSA (sheep serum albumin) domain I and II and HSA domain III HSA 1/2-SSA3: HSA domain I and II and SSA domain III HSA 1/2-MSA3: HSA domain I and II and MSA (mouse serum albumin) domain III MSA 1/2-HSA3: MSA domain I and II and HSA domain III.

In the examples, the domains used are shown in Table 8:

TABLE 8

Domains of human, rabbit, sheep and mouse serum albumins

| Abbreviation | Albumin Source | Amino acid residues Domain I | Domain II | Domain III |
|---|---|---|---|---|
| HSA | Human (SEQ ID NO: 31) | 1-194 | 195-380 | 381-585 |
| RSA | Rabbit (SEQ ID NO: 14) | 1-194 | 195-380 | 381-584 |
| SSA | Sheep (SEQ ID NO: 16) | 1-194 | 195-380 | 381-583 |
| MSA | Mouse (SEQ ID NO: 9) | 1-194 | 195-380 | 381-584 |

These are further shown in the alignment of FIG. 5.

The derivatives or variants of Example 3 were analysed for shFcRn binding (shFcRn-GST) using SPR and the results shown below (Table 9).

TABLE 9

Albumin derivatives and characteristics

| Albumin derivative or variant[a] | Source of Domain | | | SEQ ID NO: | ka (10³/Ms) | kd (10⁻³/s) | KD[b] (μM) | KD Req[c] (μM) |
|---|---|---|---|---|---|---|---|---|
| | I | II | III | | | | | |
| HSA | Human | Human | Human | 31 | 3.2 ± 0.2 | 15.5 ± 2.5 | 4.8 | 5.4 |
| MSA | Mouse | Mouse | Mouse | 9 | 2.3 ± 0.0 | 4.2 ± 0.0 | 1.8 | ND |
| RSA | Rabbit | Rabbit | Rabbit | 14 | 1.9 ± 0.3 | 1.7 ± 0.1 | 0.9 | ND |
| HSA½ - RSA3 | Human | Human | Rabbit | 25 | 2.2 ± 0.1 | 1.8 ± 0.0 | 0.8 | ND |
| RSA½ - HSA3 | Rabbit | Rabbit | Human | 26 | 1.2 ± 0.1 | 14.5 ± 0.5 | 12.1 | ND |
| SSA | Sheep | Sheep | Sheep | 16 | ND | ND | ND | ND |
| SSA½ - HSA3 | Sheep | Sheep | Human | 27 | 3.5 ± 0.0 | 8.2 ± 0.2 | 2.3 | ND |
| HSA½ - SSA3 | Human | Human | Sheep | 28 | ND | ND | ND | ND |
| HSA½ - MSA3 | Human | Human | Mouse | 29 | 6.2 ± 0.0 | 9.7 ± 0.0 | 0.2 | ND |
| MSA½ - HSA3 | Mouse | Mouse | Human | 30 | ND | ND | ND | ND |

[a]Dilutions of HSA derivatives or variants were injected over immobilized shFcRn (~1500 RU) at pH6.0.
[b]The kinetic rate constants were obtained using a simple first-order (1:1) bimolecular interaction model.
[c]The steady state affinity constant was obtained using an equilibrium (Req) binding model supplied by the BIAevaluation 4.1 software. The kinetic values represent the average of triplicates.
[d]Not determined (ND) (i.e. KD not obtained).

SSA (SEQ ID NO: 16) and the derivative comprising SSA domain III (SEQ ID NO: 28), and the MSA1/2-HSA3 (SEQ ID NO: 30) did not bind FcRn in this experiment.

HSA DI+DII+RSA DIII and HSA DI+DII+MSA DIII had increased affinity for shFcRn compared to HSA, MSA and RSA. The data also shows that various species albumin DI+DII can modulate the affinity (i.e. increase or decrease) of albumin DIII from a different species.

Example 4. Binding of the HSA Derivative DI+DIII and Fusions Thereof to shFcRn

The HSA derivative DI+DIII and fusions thereof (Table 10) were prepared according to the methods section (above).

SPR assays were performed using a Biacore X and Biacore 3000 instrument (G E Healthcare). CM5 chips were coupled with shFcRn-HIS (GeneArt) via amine coupling chemistry as per manufacturer's instructions (1600-2500RU). The coupling was performed by diluting shFcRn in 10 mM sodium acetate pH4.5 (G E Healthcare). Phosphate buffer (67 mM phosphate buffer, 0.15M NaCl, 0.005% Tween 20 at pH5.5±0.25) was used as running buffer and dilution buffer. Regeneration was performed using HBS-EP buffer pH7.4. For binding to immobilised shFcRn, HSA derivatives or variants were injected for 90 s over the active cell surface at a constant flow rate (30 μl/min) at 25° C. For binding assays at pH7.4, HBS-EP (GE Healthcare) was used as dilution and running buffer. In all experiments, data were zero adjusted and the reference cell subtracted. For data interpretation and kinetic value determination, Biaevaluation software was used for kinetic binding modelling.

The kinetic values of shFcRn binding the molecules is provided in Table 10.

TABLE 10

Kinetic values of shFcRn binding HSA Domain I + III (unfused and fused)

| Molecule | KD (μM) |
|---|---|
| wt DI + DIII | 3.0 |
| DI + DIII K500A | ND |
| DI + DIII K573P | 0.86 |
| DI + DIII K573Y | 0.45 |
| DI + DIII D550N | 8.4 |
| wt DI + DIII::GSL::IL-1ra | 5.5 |

TABLE 10-continued

Kinetic values of shFcRn binding HSA Domain I + III (unfused and fused)

| Molecule | KD (μM) |
|---|---|
| DI + DIII K500A ::GSL::IL-1ra | ND |
| DI + DIII K573P ::GSL::IL-1ra | 0.42 |
| DI + DIII K573Y ::GSL::IL-1ra | 0.26 |
| DI + DIII D550N ::GSL::IL-1ra | 11 |

ND: not determined due to weak binding wt DI+DIII and derivatives thereof bind to shFcRn in a pH-dependent manner (data not shown), i.e. binding was detected at pH5.5 but not at pH7.4. The results show that the hierarchy of binding of the DI+DIII derivatives and fusions, thereof to shFcRn was K573Y>K573P>wt>D550N (highest to lowest affinity). Weak binding was detected between DI+DIII K500A (fused and unfused to IL1 Ra) and shFcRn at either pH5.5 or pH 7.4.

Example 5. Binding of HSA Derivative DII+DIII and Fusions Thereof to shFcRn

HSA DII+DIII and fusions thereof (Table 11) were prepared according to the methods section (above). SPR analysis and interpetation were carried out according to Example 4.

TABLE 11

Kinetic values of shFcRn-HIS binding HSA DII + DIII (unfused and fused)

| Molecule | KD (μM) |
|---|---|
| wt DII + DIII | 6.8 |
| DII + DIII K573P | 0.48 |
| DII + DIII K573Y | 0.47 |
| DII + DIII D550N | 7.3 |
| wt DII + DIII::GSL::IL-1ra | 5.1 |
| DII + DIII K573Y::GSL::IL-1ra | 0.5 |
| DII + DIII D550N::GSL::IL-1ra | 6.0 |
| DII + DIII K573P::GSL::IL-1ra | 0.98 |

All of the HSA DII+DIII derivatives and fusions thereof interact with shFcRn in a pH-dependent manner (data not shown), i.e. binding was detected at pH5.5 but not at pH7.4.

The hierarchy of binding of HSA DI+DIII derivatives, fused and unfused, is identical to that described for HSA DI+DIII derivatives and fusions thereof (Example 4), i.e. K573Y>K573P>wt>D550N (highest to lowest affinity for shFcRn).

Example 6. Binding of the HSA Derivative DIII and Derivatives Thereof to shFcRn Unfused DIII derivatives (Table 12a) were prepared according to the methods section (above). SPR analysis and interpetation was carried out according to Example 4.

TABLE 12a

Kinetic values of shFcRn-HIS binding HSA DIII

| Molecule | KD (μM) |
|---|---|
| wt DIII | 12 |
| DIII K573F | 0.42 |
| DIII K500A | 21.4 |
| DIII D550N | 5.9 |
| DIII K573A | 1.1 |
| DIII K573P | 0.22 |
| DIII K573Y | 0.09 |
| DIII E492G/N503K | 14.1 |
| DIII E492G | 4.9 |

All of the HSA DIII derivatives interact with shFcRn in a pH-dependent manner (data not shown), i.e. binding was detected at pH5.5 but not at pH7.4. The binding hierarchy to shFcRn is DIII K573Y, DIII K573P, DIII K573F, DIII K573A, DIII E492G, DIII D550N, wt DIII, DIII E492/N503K, DIII K500A (highest to lowest affinity for shFcRn).

DIII derivatives that could not have kinetic values determined, were analysed for binding response (RUs) compared to wt DIII. No binding was detected at pH7.4, only pH5.5. The results are shown in Table 12b. A higher RU value indicates tighter binding. Therefore, compared to wt HSA, all of the mutants tested in Table 12b show weaker binding to shFcRn. wt HSA DIII and derivatives thereof bind to shFcRn in a pH-dependent manner. Representative sensorgrams for HSA DIII K573D, DIII K573H, DIII K573N, DIII K573W and DIII Q580K are shown in FIG. 8.

TABLE 12b

Binding response values of shFcRn interacting with HSA DIII

| Molecule | Binding response (RUs) |
|---|---|
| wt HSA | 34.2 |
| wt DIII | 7.0 |
| DIII K573D | 7.2 |
| DIII K573H | 13.3 |
| DIII K573W | 16.5 |
| DIII K573N | 12.2 |
| DIII Q580K | 11.5 |

Presented binding responses (RU values) represent relative absolute values recorded at the point the injection has stopped and maximum complexes have formed during the injection period. A higher RU value equates to higher affinity.

Example 7. Binding of HSA Derivatives Genetically Fused to IL-1Ra or scFv, to shFcRn Molecules (Table 13) were prepared according to the methods section (above). SPR analysis and interpetation were carried out according to Example 4.

TABLE 13

Kinetic values of shFcRn-HIS binding HSA DIII derivatives genetically fused to IL-1ra or an scFv

| Molecule | KD (μM) |
|---|---|
| wt DIII::GSL::IL-1ra | 10.9 |
| DIII K573P::GSL::IL-1ra | 3.0 |
| DIII D550N::GSL::IL-1ra | 1.8 |
| wt DIII::GSL::scFv | 6.9 |
| DIII K573P::GSL::scFv | 1.4 |
| DIII D550N::GSL::scFv | 5.9 |

Results show that the hierarchy of binding of HSA DIII derivatives genetically fused to IL-1ra to shFcRn is D550N>K573P>wt. In contrast, the hierarchy of binding of HSA DIII derivatives genetically fused to an scFv to shFcRn is K573P>D550N>wt.

Figure 9:
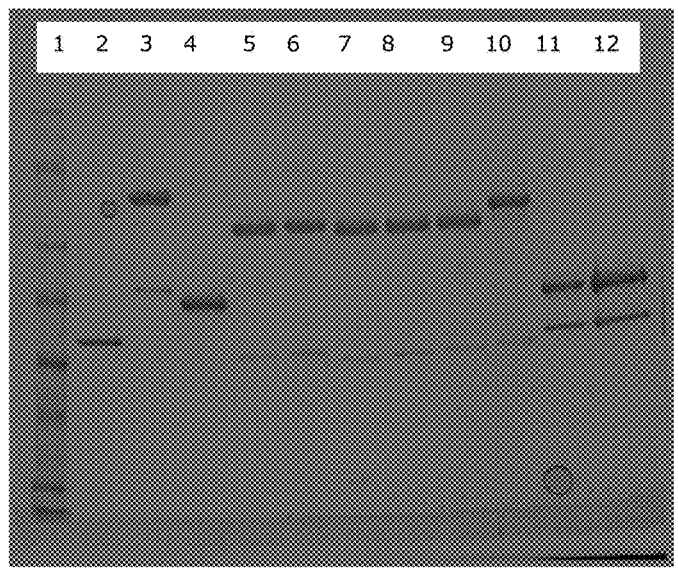
FIG. 9, Non-reducing SDS-PAGE analysis of albumin and derivatives and variants thereof, some conjugated to HRP: (1) Marker (SeeBlue™), (2) HRP Standard (1 µg), (3) DI+DIII+DIII:HRP (1 µg), (4) Albumin Standard (1 µg), (5) DI+DIII-HRP (1 µg), (6) DI+DIII K500A-HRP (1 µg), (7) DI+DIII K573P-HRP (1 µg), (8) DI+DIII K573Y-HRP (1 µg), (9) DI+DIII D550N-HRP (1 µg), (10) DIII+DI-HRP (1 µg). (11) mixture of HRP and Albumin Standards (1 µg each), (12) mixture of HRP+ and Albumin Standard (2 µg each).

Example 8. Conjugation of Horseradish Peroxidase to Albumin and to Albumin Derivatives HRP was conjugated to albumin derivatives to form albumin variants (Table 14) according to the methods (above). Molecules were analysed by GP-HPLC (results not shown) and non-reducing SDS-PAGE (FIG. 9) to confirm that the molecules were of the expected molecular weight and therefore that conjugation had taken place to produce the desired molecules. SPR analysis and interpetation were carried out according to Example 4.

TABLE 14

Binding analysis of shFcRn-HIS interacting with HSA DI + DIII and derivatives thereof conjugated to HRP

| Molecule | Response (RUs) |
|---|---|
| wt HSA (un-conjugated) | 178 |
| wt DI + DIII-HRP | 58 |
| DI + DIII K573P -HRP | 213 |
| DI + DIII K500A -HRP | ND |

Figure 10:
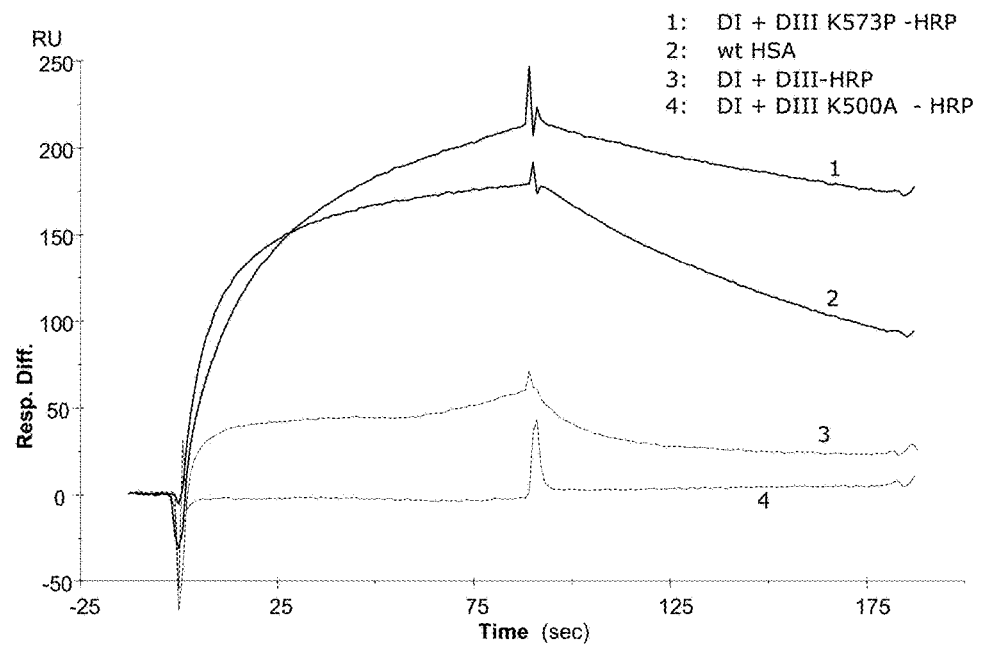
FIG. 10, Representative sensorgrams showing binding of 10 µM HSA DI+III (and variants thereof) conjugated to HRP to immobilized shFcRn-HIS (~1500 RU) at pH 5.5. (1) DI+DIII K573P-HRP, (2) wt HSA, (3) DI+DIII wt-HRP and (4) DI+DIII K500A-HRP.

ND—Not determined due to weak binding.
Presented binding responses (RU values) represent relative absolute values recorded at the point the injection has stopped and maximum complexes have formed during the injection period. A higher RU value equates to higher affinity FIG. 10 confirms an increased binding response for the HSA DI+DIII K573P-HRP variant and shFcRn interaction compared to the binding response for wt HSA DI+DIII and wild-type HSA. Furthermore, FIG. 10 shows that the binding interaction of DI+DIII K500A-HRP and shFcRn is reduced compared to wt HSA DI+DIII and wild-type HSA DI+DIII wt and variants thereof bind to shFcRn in a pH-dependent manner, i.e. binding was detected at pH 5.5 but not at pH7.4. Conjugated DI+DIII variants show the same affinity modulation seen in unconjugated DI+DIII (Example 4).

Example 9. Binding Analysis of shFcRn Interacting with IL-1ra Genetically Fused to the N-Terminus of HSA DII+DIII IL-1ra genetically fused to HSA DII+DIII and HSA DII+DIII K573P (Table 15) were prepared according to the methods section (above). SPR analysis and interpetation were carried out according to Example 4.

TABLE 15

Binding analysis of shFcRn-HIS interacting with
IL-1ra N-terminally fused to HSA DII + DIII

| Molecule | Response (RUs) |
|---|---|
| wt HSA | 162 |
| IL-1ra::GSL::DII DIII | 145 |
| IL-1ra::GSL::K573P DII DIII | 246 |

Figure 11:
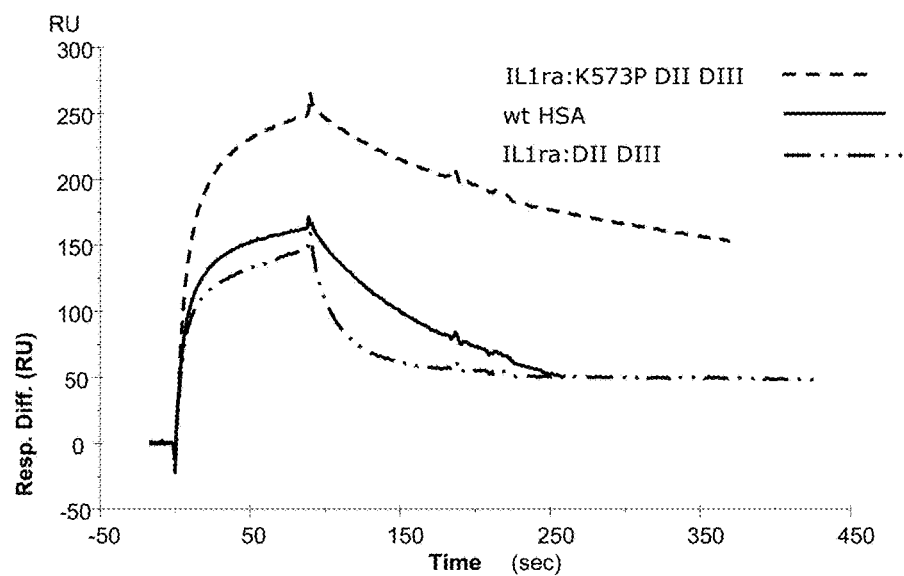
FIG. 11, Representative sensorgrams showing binding of 10 µM IL-1ra fused to the N-terminus of HSA DII+III and DII+III K573P to immobilized shFcRn-HIS (~2100 RU) at pH 5.5.
Figure 12:
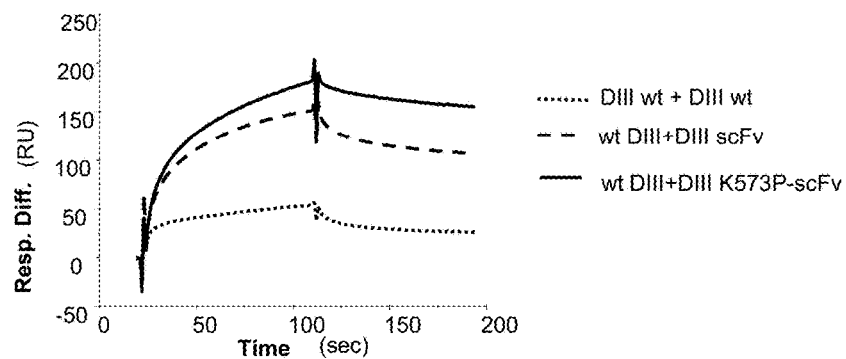
FIG. 12, Representative sensorgrams showing binding of 10 µM HSA tandem repeats of DIII, DIII fused and DIII K573P fused to scFv (~1500 RU) at pH 5.5.
Figure 13:
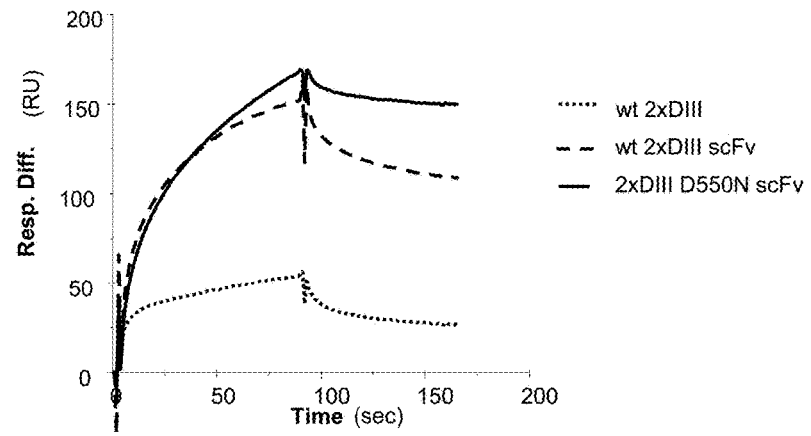
FIG. 13, Representative sensorgrams showing binding of 10 µM of HSA tandem repeats of DIII, DIII fused and DIII D550N fused to scFv (~1500 RU) at pH 5.5
Figure 14:
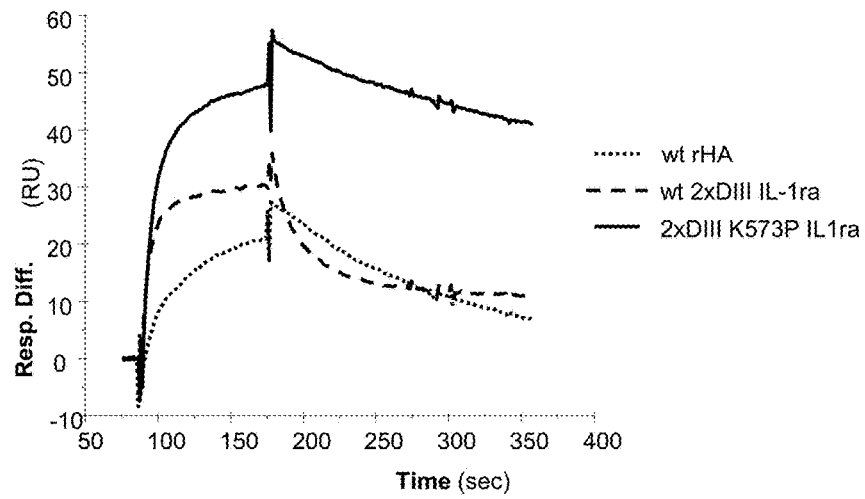
FIG. 14, Representative sensorgrams showing binding of 10 µM HSA tandem repeats of DIII, DIII fused and DIII K573P fused to IL-1ra (~1500 RU) at pH 5.5.
Figure 15:
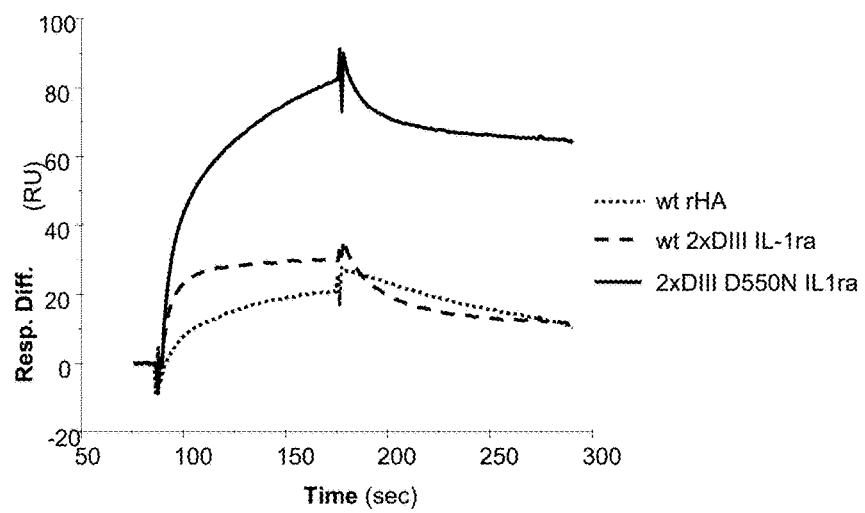
FIG. 15, Representative sensorgrams showing binding of 10 µM of HSA tandem repeats of DIII, DIII fused and DIII D550N fused to IL-1ra (~1500 RU) at pH 5.5
Figure 16:
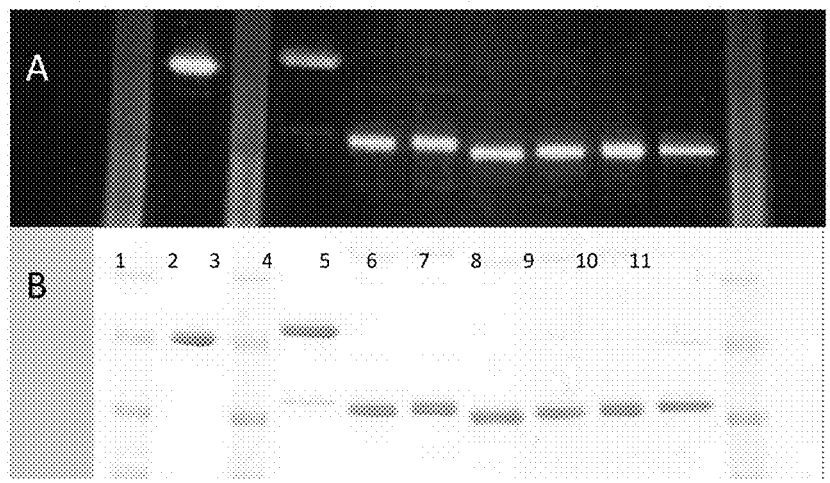
FIG. 16, Visualization of DI+DIII Variant Proteins fused to Fluorescein, with UV Light (A) and a Commercial Protein Stain (B). Non-reducing SDS-PAGE analysis of albumin and derivatives and variants thereof, some conjugated to F5M: (1) Marker (SeeBlue™) (10 µL), (2) HSA-F5M control (1 µg), (3) Marker (See Blue™) (10 µL), (4) DI+DIII+ DIII-F5M (1 µg), (5) DI+DIII wt-F5M (1 µg), (6) DI+DIII K500A-F5M (1 µg), (7) DI+DIII K573P-F5M (1 µg), (8) DI+DIII K573Y-F5M (1 µg), (9) DI+DIII D550N-F5M (1 µg), (10) DIII+DI-F5M (1 µg). (11) Marker (SeeBlue™) (10 µL).
Figure 17:
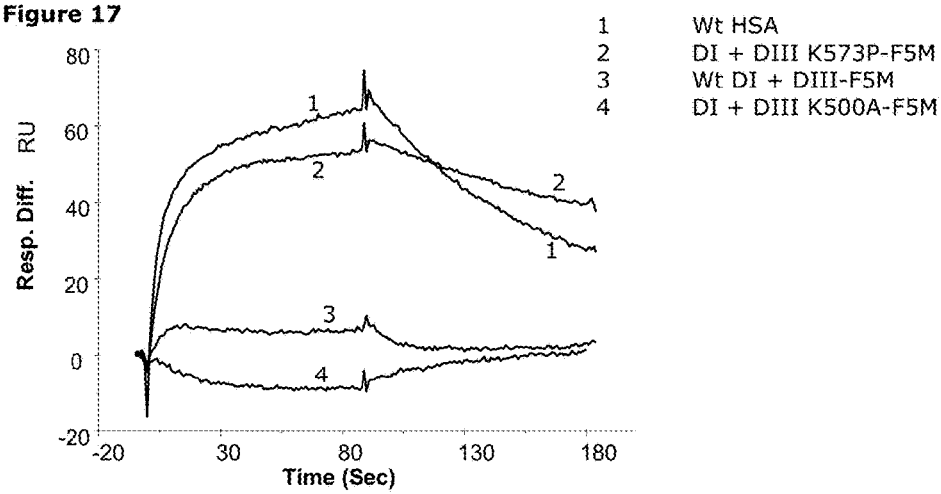
FIG. 17, Representative sensorgrams showing binding of 10 µM wt HSA, HSA DI+DIII K573P-F5M, HSA DI+DIII K500A-F5M to immobilized shFcRn-HIS (~1500RU) at pH5.5.
Figure 18:
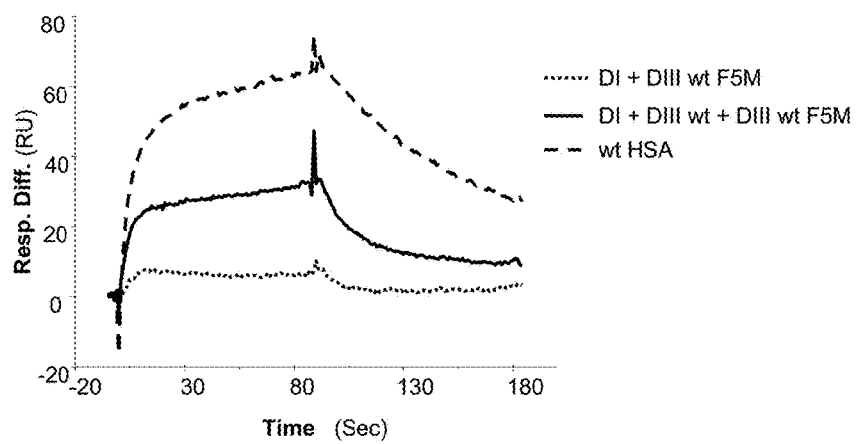
FIG. 18, Representative sensorgrams showing binding of 10 µM wt HSA, HSA DI+DIII+DIII-F5M, HSA DI+DIII-F5M to immobilized shFcRn-HIS (~1500RU) at pH5.5.

Presented binding responses (RU values) represent relative absolute values recorded at the point the injection has stopped and maximum complexes have formed during the injection period. A higher RU value equates to higher affinity IL-1ra N-terminally fused to HSA DII+DIII and IL-1ra N-terminally fused to K573P DII DIII bind to shFcRn in a pH-dependent manner, i.e. binding was detected at pH 5.5 but not at pH7.4. FIG. 11 shows that an N-terminal fusion to DII+DIII lengthens the dissociation time without interfering with the binding of the molecules to shFcRn. Results show an increased binding response between shFcRn and the K573P variant compared to the wild type HSA DII+DIII and HSA.

Example 10. Binding Analysis of shFcRn Interaction with Molecules which are Fusions of Tandem Repeats of DIII and Derivatives Thereof HSA derivatives, and fusions thereof (Table 16) were prepared according to the methods section (above). SPR analysis and interpetation were carried out according to Example 4.

TABLE 16

Binding analysis of shFcRn-HIS interacting
with fusions of tandem repeats of DIII

| Molecule | Binding response (RUs) |
|---|---|
| DIII wt + DIII wt::GSL::IL-1ra | 30.1 |
| DIII D550N + DIII D550N ::GSL::IL-1ra | 82.3 |
| DIII K573P + DIII K573P ::GSL::IL-1ra | 48.0 |
| DIII wt + DIII wt::GSL::scFv | 151.4 |
| DIII D550N + DIII D550N ::GSL::scFv | 167.5 |
| DIII K573P + DIII K573P ::GSL::scFv | 181.6 |

Presented binding responses (RU values) represent relative absolute values recorded at the point the injection has stopped and maximum complexes have formed during the injection period. A higher RU value equates to higher affinity Tandem DIII fusions bind to shFcRn in a pH-dependent manner (i.e. binding at pH 5.5 but not at pH 7.4). Binding responses (Table 16) show for the tandem DIII fusions the following order:
(i) IL-1ra fusions: DIII D550N+DIII D550N-IL-1ra, DIII K573P+DIII K573P-IL-1ra, wt DIII-IL-1ra (highest to lowest affinity);
(ii) scFv fusions: DIII K573P+DIII K573P-scFv, D550N+DIII D550N-scFv wt DIII-scFy (highest to lowest affinity).

Example 11. Conjugation of Fluorescein-5-Maleimide (F5M) to DI+DIII Wt and Derivatives Thereof Conjugated HSA derivatives and variants thereof (Table 17) were prepared according to the methods section (above). Molecules were analysed by GP-HPLC (results not shown) and non-reducing SDS-PAGE (FIG. 16). Conjugation was confirmed by UV visualisation of conjugated DI+DIII wt and variants. SPR analysis and interpetation were carried out according to Example 4.

TABLE 17

| Binding analysis of shFcRn-HIS interacting with HSA DI + DIII and variants thereof conjugated to F5M. | |
|---|---|
| Molecule | Response (RUs) |
| wt HSA | 63.8 |
| DI + DIII wt -F5M | 6.5 |
| DI + DIII- K573P F5M | 53.5 |
| DI + DIII- K500A F5M | ND |

ND—Not determined due to weak binding.

Presented binding responses (RU values) represent relative absolute values recorded at the point the injection has stopped and maximum complexes have formed during the injection period. A higher RU value equates to higher affinity FIG. 17 confirms an increased binding response for the HSA DI+DIII K573P-F5M variant and shFcRn interaction compared to the binding response for HSA DI+DIII-F5M but not wild-type HSA. Furthermore, FIG. 17 shows that the binding interaction of DI+DIII K500A-F5M and shFcRn is significantly reduced compared to HSA DI+DIII K573P-F5M and wild-type HSA DI+DIII wt and variants thereof bind to shFcRn in a pH-dependent manner, i.e. binding was detected at pH 5.5 but not at pH7.4. Conjugated DI+DIII variants show the same affinity modulation seen in unconjugated DI+DIII variants and full length HSA (Example 4).

Example 12. Conjugation of Fluorescein-5-Maleimide (F5M) to DI+DIII+DIII Wt

Conjugated of the HSA derivative (Table 18) was prepared according to the methods section (above). The molecule was analysed by GP-HPLC (results not shown) and non-reducing SDS-PAGE (FIG. 16). Conjugation was confirmed by UV visualisation of conjugated DI+DIII wt+DIII wt. SPR analysis and interpetation was carried out according to Example 4.

TABLE 18

| Binding analysis of shFcRn-HIS interacting with HSA DI + DIII wt + DIII wt conjugated to F5M. | |
|---|---|
| Molecule | Response (RUs) |
| wt HSA | 62.8 |
| DI + DIII wt-F5M | 6.5 |
| DI + DIII wt + DIII wt-F5M | 31.8 |

Presented binding responses (RU values) represent relative absolute values recorded at the point the injection has stopped and maximum complexes have formed during the injection period. A higher RU value equates to higher affinity FIG. 18 confirms an increased binding response for the HSA DI+DIII wt+DIII wt–F5M variant and shFcRn interaction compared to the binding response for HSA DI+DIII–F5M but not wt HSA.

Conjugated DI+DIII wt and DI+DIII wt+DIII wt bind to shFcRn in a pH-dependent manner, i.e. binding was detected at pH 5.5 but not at pH7.4.

Example 13. Binding Analysis of shFcRn Interaction with the HSA Derivatives DIII+DI and DI+DIII HSA derivatives (Table 19) were prepared according to the methods section (above). SPR analysis and interpetation were carried out according to Example 4.

TABLE 19

Binding analysis of shFcRn-HIS interacting with HSA DIII + DI and DI + DIII

| Molecule | KD (µM) |
|---|---|
| DIII wt + DI | 8.4 |
| DI + DIII wt | 3.0 |

Table 19 shows that the HSA derivative DIII+DI has reduced affinity for shFcRn compared to HSA DI+DIII.

Example 14. Binding Analysis of shFcRn-GST Interaction with Albumin Derivatives DI+DIII Compared to Wild-Type Albumin Species wt albumins and DI+DIII derivatives thereof (Table 20) were prepared according to the methods section (above). SPR analysis and interpetation were carried out according to Example 4.

TABLE 20

Binding analysis of shFcRn-GST interacting with species albumins and DI + DIII derivatives thereof

| Molecule[a] | Ka ($10^3$/Ms) | kd ($10^{-3}$/s) | KD[b] (µM) |
|---|---|---|---|
| HSA wt | 3.2 ± 0.2 | 15.5 ± 2.5 | 4.8 |
| MSA wt | 3.8 ± 0.0 | 3.1 ± 0.1 | 0.8 ± 0.2 |
| RSA wt | 1.9 ± 0.3 | 1.7 ± 0.1 | 0.9 |
| HSA DI-DIII | 2.6 ± 0.3 | 18.3 ± 0.2 | 7.0 ± 0.2 |
| RSA DI-DIII | 4.8 ± 0.0 | 3.1 ± 0.1 | 0.6 ± 0.0 |
| MSA DI-DIII | 5.6 ± 0.1 | 2.5 ± 0.0 | 0.4 ± 0.0 |

[a]titrated amounts of albumins or DI + DIII derivatives thereof were injected over immobilized shFcRn (~1500 RU).
[b]The kinetic rate constants were obtained using a simple first-order (1:1) bimolecular interaction model.

The results show that: MSA DI-DIII and RSA DI-DIII both have higher binding affinities to shFcRn than wt MSA, wt HSA and HSA DI-DIII. All DI-DIII variants bound to immobilized shFcRn in a pH-dependent manner (i.e. binding at pH6.0 but not at pH7.4). HSA DI-DIII bound shFcRn with a slightly reduced affinity compared with HSA wt, while the RSA and MSA DI-DIII albumin derivatives showed superior binding affinities compared with HSA wt.

The invention claimed is:

1. An albumin derivative or variant, fragment thereof or fusion polypeptide comprising said albumin derivative or variant or fragment thereof wherein the albumin derivative or variant or fragment thereof has a molecular weight from 40 to 91 kDA, and comprises:
   (i) a first albumin domain III or a derivative or variant thereof having at least 90% sequence identity to human serum albumin (HSA) domain III; and
   (ii) a second albumin domain III or a derivative or variant thereof having at least 90% identity to human serum albumin (HSA) domain III.

2. The albumin derivative or variant, fragment thereof or fusion polypeptide of claim 1, wherein the first and/or second albumin domain III or derivative or variant thereof is derived, independently, from human serum albumin, chimpanzee serum albumin, or macaque serum albumin.

3. The albumin derivative or variant, fragment thereof or fusion polypeptide of claim 1, wherein the first and/or second albumin domain III or derivative or variant thereof has at least 95% sequence identity to Domain III of SEQ ID NO: 31 or SEQ ID NO: 1.

4. The albumin derivative or variant, fragment thereof or fusion polypeptide of claim wherein the Domain III or derivative or variant thereof has at least 95% sequence identity to amino acids 381 to 585 of SEQ ID NO: 31 or SEQ ID NO: 1.

5. The albumin derivative or variant, fragment thereof or fusion polypeptide according to claim 1 in which the albumin derivative or variant, fragment thereof or fusion polypeptide comprises two copies of human serum albumin domain III.

6. The albumin derivative or variant, fragment thereof or fusion polypeptide according to claim 1, wherein at least one domain III comprises one or more substitutions in positions corresponding to the positions in SEQ ID NO: 31 or SEQ ID NO:1 (HSA) selected from: 573, 500, 550, 417, 440, 464, 490, 492, 493, 494, 495, 496, 499, 501, 503, 504, 505, 506, 510, 535, 536, 537, 538, 540, 541, 542, 574, 575, 577, 578, 579, 580, 581, 582 or 584.

7. The albumin derivative or variant, fragment thereof or fusion polypeptide according to claim 6, wherein the one or more substitutions in positions corresponding to the positions in SEQ ID NO: 31 or SEQ ID NO:1 (HSA) is selected from: K573P, K573Y, K573W, K573H, K573F, K573V, K573I, K573T, K573N, K573S, K573G, K573M, K573C, K573A, K573E, K573Q, K573R, K573L, K573D, K500E, K500G, K500D, K500A, K500S, K500C, K500P, K500H, K500F, K500N, K500W, K500T, K500M, K500Y, K500V, K500Q, K500L, K500I, K500R Q417A, H440A, H464Q, E492G, D494N, D494Q, D494A, E495Q, E495A, T496A, D494E+Q417H, D494N+T496A, E492G+V493P, P499A, E501A, E501Q, N503H, N503K, H510Q, H535Q, K536A, P537A, K538A, K541G, K541D, D550E, D550N, E492G+K573P, E492G+K573A, or E492G+N503H+K573P/N503H/K573P.

8. The albumin derivative or variant, fragment thereof or fusion polypeptide according to claim 1, comprising one or more additional mutations that creates one or more thiol groups on the surface of the molecule.

9. The albumin derivative or variant, fragment thereof or fusion polypeptide according to claim 8, having a substitution selected from the group of substitutions corresponding to: L585C, D1C, A2C, D562C, A364C, A504C, E505C, T79C, E86C, D129C, D549C, A581C, D121C, E82C, S270C, A578C, L595LC, D1DC, A2AC, D562DC, A364AC, A504AC, E505EC, T79TC, E86EC, D129DC, D549DC, A581AC, A581AC, D121DC, E82EC, S270SC, or A579AC, or a deletion at a position selected from the group corresponding to: C360, C316, C75, C168, C558, C361, C91, C124, C169 and or C567 in SEQ ID NO: 31 or SEQ ID NO: 1.

10. A conjugate comprising an albumin derivative or variant or fragment thereof according to claim 1, and a therapeutic or diagnostic moiety bound to the albumin part.

11. A pharmaceutical composition comprising: an albumin derivative, fragment thereof or fusion polypeptide or associate of claim 1.

12. An albumin variant according to claim 1, which albumin variant has (i) a longer plasma half-life than native HSA or (ii) a shorter plasma half-life than native HSA.

13. A fusion of an albumin variant according to claim 1, which fusion has (i) a longer plasma half-life than an albumin fusion, conjugate, associate or composition comprising native HSA or (ii) a shorter than a fusion, conjugate, associate or composition comprising native HSA.

14. A fusion of an albumin variant according to claim 1 wherein the fusion comprises one or more moiety selected from the group consisting of:
   4-1BB ligand, 5-helix, A human C-C chemokine, A human L105 chemokine, A human L105 chemokine designated huL105_3, A monokine induced by gamma-interferon, A partial CXCR4B protein, A platelet basic protein, α1-antitrypsin, ACRP-30 Homologue, Complement Component C1q C, Adenoid-expressed chemokine, aFGF, FGF-1, AGF, AGF Protein, albumin, an etoposide, angiostatin, Anthrax vaccine, Antibodies specific for collapsin, antistasin, Anti-TGF beta family antibodies, antithrombin III, APM-1, ACRP-30, Famoxin, apo-lipoprotein species, Arylsulfatase B, b57 Protein, BCMA, Beta-thromboglobulin protein, bFGF, FGF2, Blood coagulation factors, BMP Processing Enzyme Furin, BMP-10, BMP-12, BMP-15, BMP-17, BMP-18, BMP-2B, BMP-4, BMP-5, BMP-6, BMP-9, Bone Morphogenic Protein-2, calcitonin, Calpain-10a, Calpain-10b, Calpain-10c, Cancer Vaccine, Carboxypeptidase, C-C chemokine, MCP2, CCR5 variant, CCR7, CCR7, CD11a Mab, CD137; 4-1BB Receptor Protein, CD20 Mab, CD27, CD27L, CD30, CD30 ligand, CD33 immunotoxin, CD40, CD40L, CD52 Mab, Cerebus Protein, Chemokine Eotaxin, Chemokine hIL-8, Chemokine hMCP1, Chemokine hMCP1a, Chemokine hMCP1b, Chemokine hMCP2, Chemokine hMCP3, Chemokine hSDF1b, Chemokine MCP-4, chemokine TECK and TECK variant, Chemokine-like protein IL-8M1 Full-Length and Mature, Chemokine-like protein IL-8M10 Full-Length and Mature, Chemokine-like protein IL-8M3, Chemokine-like protein IL-8M8 Full-Length and Mature, Chemokine-like protein IL-8M9 Full-Length and Mature, Chemokine-like protein PF4-414 Full-Length and Mature, Chemokine-like protein PF4-426 Full-Length and Mature, Chemokine-like protein PF4-M2 Full-Length and Mature, Cholera vaccine, Chondromodulin-like protein, c-kit ligand, SCF, Mast cell growth factor, MGF, Fibrosarcoma-derived stem cell factor, CNTF and fragment thereof, coagulation factors in both pre and active forms, collagens, Complement C5 Mab, Connective tissue activating protein-III, CTAA16.88 Mab, CTAP-III, CTLA4-Ig, CTLA-8, CXC3, CXC3, CXCR3, CXC chemokine receptor 3, cyanovirin-N, Darbepoetin, designated exodus, designated huL105_7, DIL-40, Dnase, EDAR, EGF Receptor Mab, ENA-78, Endostatin, Eotaxin, Epithelial neutrophil activating protein-78, EPO receptor, EPOR, erythropoietin, EPO mimics, Eutropin, Exodus protein, Factor IX, Factor VII, Factor VIII, Factor X, Factor XIII, FAS Ligand Inhibitory Protein, FasL, FasL, FasL, FGF, FGF-12, Fibroblast growth factor homologous factor-1, FGF-15, FGF-16, FGF-18, FGF-3, INT-2, FGF-4, gelonin, HST-1, HBGF-4, FGF-5, FGF-6, Heparin binding secreted transforming factor-2, FGF-8, FGF-9, Glia activating factor, fibrinogen, flt-1, flt-3 ligand, Follicle stimulating hormone Alpha subunit, Follicle stimulating hormone Beta subunit, Follitropin, Fractalkine, myofibrillar protein Troponin I, FSH, Galactosidase, Galectin-4, G-CSF, GDF-1, Gene therapy, Glioma-derived growth factor, glucagon, glucagon-like peptides, Glucocerebrosidase, glucose oxidase, Glucosidase, Glycodelin-A, Progesterone-associated endometrial protein, GM-CSF, gonadotropin, Granulocyte chemotactic protein-2, Granulocyte-macrophage colony stimulating factor, growth hormone, Growth related oncogene-alpha, Growth related oncogene-beta, Growth related oncogene-gamma, hAPO-4, TROY, hCG, Hepatitus B surface Antigen, Hepatitus B Vaccine, HER2 Receptor Mab, hirudin, HIV gp120, HIV gp41, HIV Inhibitor Peptide, HIV Inhibitor Peptide, HIV Inhibitor Peptide, HIV protease inhibiting peptides, HIV-1 protease inhibitors, HPV vaccine, Human 6CKine protein, Human Act-2 protein, Human adipogenesis inhibitory factor, human B cell stimulating factor-2 receptor, Human beta-chemokine H1305, Human C-C chemokine DGWCC, Human CC chemokine ELC protein, Human CC type chemokine interleukin C, Human CCC3 protein, Human CCF18 chemokine, Human CC-type chemokine protein designated SLC, Human chemokine beta-8 short forms, Human chemokine C10, Human chemokine CC-2, Human chemokine CC-3, Human chemokine CCR-2, Human chemokine Ckbeta-7, Human chemokine ENA-78, Human chemokine eotaxin, Human chemokine GRO alpha, Human chemokine GROalpha, Human chemokine GRObeta, Human chemokine HCC-1, Human chemokine HCC-1, Human chemokine 1-309, Human chemokine IP-10, Human chemokine L105_3, Human chemokine L105_7, Human chemokine MIG, Human chemokine MIG-beta protein, Human chemokine MIP-1 alpha, Human chemokine MIP1beta, Human chemokine MIP-3alpha, Human chemokine MIP-3beta, Human chemokine PF4, Human chemokine protein 331D5, Human chemokine protein 61164, Human chemokine receptor CXCR3, Human chemokine SDF1alpha, Human chemokine SDF1beta, Human chemokine ZSIG-35, Human Chr19Kine protein, Human CKbeta-9, Human CKbeta-9, Human CX3C 111 amino acid chemokine, Human DNAX interleukin-40, Human DVic-1 C-C chemokine, Human EDIRF I protein sequence, Human EDIRF II protein sequence, Human eosinocyte CC type chemokine eotaxin, Human eosinophil-expressed chemokine, Human fast twitch skeletal muscle troponin C, Human fast twitch skeletal muscle troponin I, Human fast twitch skeletal muscle Troponin subunit C, Human fast twitch skeletal muscle Troponin subunit I Protein, Human fast twitch skeletal muscle Troponin subunit T, Human fast twitch skeletal muscle troponin T, Human foetal spleen expressed chemokine, FSEC, Human GM-CSF receptor, Human gro-alpha chemokine, Human gro-beta chemokine, Human gro-gamma chemokine, Human IL-16 protein, Human IL-1RD10 protein sequence, Human IL-1RD9, Human IL-5 receptor alpha chain, Human IL-6 receptor, Human IL-8 receptor protein hIL8RA, Human IL-8 receptor protein hIL8RB, Human IL-9 receptor protein, Human IL-9 receptor protein variant #3, Human IL-9 receptor protein variant fragment, Human IL-9 receptor protein variant fragment#3, Human interleukin 1 delta, Human Interleukin 10, Human Interleukin 10, Human interleukin 18, Human interleukin 18 derivatives, Human interleukin-1 beta precursor, Human interleukin-1 beta precursor, Human interleukin-1 receptor accessory protein, Human interleukin-1 receptor antagonist beta, Human interleukin-1 type-3 receptor, Human Interleukin-10 precursor, Human Interleukin-10 precursor, Human interleukin-11 receptor, Human interleukin-12 40 kD subunit, Human interleukin-12 beta-1 receptor, Human interleukin-12 beta-2 receptor, Human Interleukin-12 p35 protein, Human Interleukin-12 p40 protein, Human interleukin-12 receptor, Human interleukin-13 alpha receptor, Human interleukin-13 beta receptor, Human interleukin-15, Human interleukin-15 receptor from clone P1, Human interleukin-17 receptor, Human interleukin-18 protein, Human interleukin-3, human interleukin-3 receptor, Human interleukin-3 variant, Human interleukin-4 receptor, Human interleukin-5, Human interleukin-6, Human interleukin-7, Human interleukin-7, Human interleukin-8, Human intracellular IL-1 receptor antagonist, Human IP-10 fusion protein, HIV-1 gp120 hypervariable region fusion protein, Human IP-10-human Muc-1 core epitope fusion protein, human liver—activation regulated chemokine, Human Lkn-1 Full-Length and Mature protein, Human mammary associated chemokine protein Full-Length and Mature, Human mature chemokine Ckbeta-7, Human mature gro-alpha, Human mature gro-gamma polypeptide used to treat sepsis, Human MCP-3 and human Muc-1 core epitope fusion protein, Human MI10 protein, Human MI1A protein, Human monocyte chemoattractant factor hMCP-1, Human monocyte chemoattractant factor hMCP-3, Human monocyte chemotactic proprotein sequence, Human neurotactin chemokine like domain, Human non-ELR CXC chemokine H174, Human non-ELR CXC chemokine IP10, Human non-ELR CXC chemokine Mig, Human PAI-1 mutants, Human protein with IL-16 activity, Human protein with IL-16 activity, Human secondary lymphoid chemokine, Human SISD protein, Human STCP-1, Human stromal cell-derived chemokine, SDF-1, Human T cell mixed lymphocyte reaction expressed chemokine, Human thymus and activation regulated cytokine, Human thymus expressed, Human TNF-alpha, Human TNF-alpha, Human TNF-beta, Human type CC chemokine eotaxin 3 protein sequence, Human type II interleukin-1 receptor, Human wild-type interleukin-4 protein, Human ZCHEMO-8 protein, Humanized Anti-VEGF Antibodies, Humanized Anti-VEGF Antibodies, Hyaluronidase, ICE 10 kD subunit, ICE 20 kD subunit, ICE 22 kD subunit, Iduronate-2-sulfatase, Iduronidase, IL-1 alpha, IL-1 beta, IL-1 inhibitor, IL-1 mature, IL-10 receptor, IL-11, IL-11, IL-12 p40 subunit, IL-13, IL-14, IL-15, IL-15 receptor, IL-17, IL-17 receptor, Il-17 receptor, 11-17 receptor, IL-19, IL-1i fragments, IL1-receptor antagonist, IL-21, IL-3 containing fusion protein, IL-3 mutant proteins, IL-3 variants, IL-3 variants, IL-4, IL-4 mutein, IL-4 mutein Y124G, IL-4 mutein Y124X, IL-4 muteins, 11-5 receptor, IL-6, 11-6 receptor, IL-7 receptor clone, IL-8 receptor, IL-9 mature protein variant, immunoglobulins or immunoglobulin-based molecules or fragment of either, dAb, Fab' fragments, F(ab')2, scAb, scFv, scFv fragment, plasminogen, Influenza Vaccine, Inhibin alpha, Inhibin beta, insulin, insulin-like growth factor, Integrin Mab, inter-alpha trypsin inhibitor, inter-alpha trypsin inhibitor, Interferon gamma-inducible protein, interferons, interferons, Interleukin 6, Interleukin 8 receptor, Interleukin 8 receptor B, Interleukin-1alpha, Interleukin-2 receptor associated protein p43, interleukin-3, interleukin-4 muteins, Interleukin-8 protein, interleukin-9, Interleukin-9 mature protein, interleukins, interleukins, Japanese encephalitis vaccine, Kalikrein Inhibitor, Keratinocyte growth factor, Kunitz domain protein, Kunitz domain protein, LACI, lactoferrin, Latent TGF-beta binding protein II, leptin, Liver expressed chemokine-1, Liver expressed chemokine-2, LT-alpha, LT-beta, Luteinization Hormone, Lyme Vaccine, Lymphotactin, Macrophage derived chemokine analogue MDC (n+1), Macrophage derived chemokine analogue MDC-eyfy, Macrophage derived chemokine analogue MDC-yl, Macrophage derived chemokine, MDC, Macrophage-derived chemokine, Maspin, Protease Inhibitor 5, MCP-1 receptor, MCP-1a, MCP-1b, MCP-3, MCP-4 receptor, M-CSF, Melanoma inhibiting protein, Membrane-bound proteins, Met117 human interleukin 9, MIP-3 alpha, MIP-3 beta, MIP-Gamma, MIRAP, Modified Rantes, monoclonal antibody, MP52, Mutant Interleukin 6 S176R, myofibrillar contractile protein Troponin I, Natriuretic Peptide, Nerve Growth Factor-beta, Nerve Growth Factor-beta2, Neuropilin-1, Neuropilin-2, Neurotactin, Neurotrophin-3, Neurotrophin-4, Neurotrophin-4a, Neurotrophin-4b, Neurotrophin-4c, Neurotrophin-4d, Neutrophil activating peptide-2, NOGO-66 Receptor, NOGO-A, NOGO-B, NOGO-C, Novel beta-chemokine designated PTEC, N-terminal modified chemokine GroHEK/hSDF-1alpha, N-terminal modified chemokine GroHEK/hSDF-1beta, N-terminal modified chemokine met-hSDF-1 alpha, N-terminal modified chemokine met-hSDF-1 beta, OPGL, Osteogenic Protein-1, OP-1, BMP-7, Osteogenic Protein-2, OX40, ACT-4, OX40L, Oxytocin, parathyroid hormone, Patched, Patched-2, PDGF-D, Pertussis toxoid, Pituitary expressed chemokine, Placental Growth Factor, Placental Growth Factor-2, Plasminogen Activator Inhibitor-1, PAI-1, Plasminogen Activator Inhibitor-2, PAI-2, Plasminogen Activator Inhibitor-2, PAI-2, Platelet derived growth factor, Platelet derived growth factor Bv-sis, Platelet derived growth factor precursor A, Platelet derived growth factor precursor B, Platelet Mab, platelet-derived endothelial cell growth factor, Platelet-Derived Growth Factor A chain, Platelet-Derived Growth Factor B chain, polypeptide used to treat sepsis, Preproapolipoprotein "milano" variant, Preproapolipoprotein "paris" variant, pre-thrombin, Primate CC chemokine "ILINCK", Primate CXC chemokine "IBICK", proinsulin, Prolactin, Prolactin2, prosaptide, Protease inhibitor peptides, Protein C, Protein S, pro-thrombin, prourokinase, RANTES, RANTES 8-68, RANTES 9-68, RANTES peptide, RANTES receptor, Recombinant interleukin-16, Resistin, restrictocin, Retroviral protease inhibitors, ricin, Rotavirus Vaccine, RSV Mab, saporin, sarcin, Secreted, polypeptides, Transmembrane polypeptides, Secreted and Transmembrane polypeptides, serum cholinesterase, serum protein, Soluble BMP Receptor Kinase Protein-3, Soluble VEGF Receptor, Stem Cell Inhibitory Factor, Straphylococcus Vaccine, Stromal Derived Factor-1 alpha, Stromal Derived Factor-1 beta, Substance P, T1249 peptide, T20 peptide, T4 Endonuclease, TACI, Tarc, TGF-beta 1, TGF-beta 2, Thr117 human interleukin 9, thrombin, thrombopoietin, Thrombopoietin derivative1, Thrombopoietin derivative2, Thrombopoietin derivative3, Thrombopoietin derivative4, Thrombopoietin derivative5, Thrombopoietin derivative6, Thrombopoietin derivative7, Thymus expressed chemokine, Thyroid stimulating Hormone, tick anticoagulant peptide, Tim-1 protein, TNF-alpha precursor, TNF-R, TNF-RII, TNF p75 Receptor, Death Receptor, tPA, transferrin, transforming growth factor beta, Troponin peptides, Truncated monocyte chemotactic protein 2, Truncated monocyte chemotactic protein 2, Truncated RANTES protein, tumour necrosis factor, Urate Oxidase, urokinase, Vasopressin, VEGF R-3, flt-4, VEGF Receptor, KDR, flk-1, VEGF-110, VEGF-121, VEGF-138, VEGF-145, VEGF-162, VEGF-165, VEGF-182, VEGF-189, VEGF-206, VEGF-D, VEGF-E, VEGF-X, von Willebrand's factor, Wild type monocyte chemotactic protein 2, Wild type monocyte chemotactic protein 2, and ZTGF-beta 9.

15. A fusion of an albumin variant according to claim 1 wherein the fusion comprises one or more moiety of chemotherapeutic drug or imaging agent.

16. The albumin derivative or variant, fragment thereof or fusion polypeptide according to claim 1 in which the albumin derivative or variant, fragment thereof or fusion polypeptide comprises two copies of human serum albumin domain III, the first copy having at least 95% sequence identity to amino acid residues 1 to 205 of SEQ ID NO: 24, and the second copy having at least 95% sequence identity to amino acid residues 1 to 205 of SEQ ID NO: 24.

17. The albumin derivative or variant, fragment thereof or fusion polypeptide according to claim 1 in which the albumin derivative or variant, fragment thereof or fusion polypeptide consists of two copies of human serum albumin domain III.

18. An albumin derivative or variant, fragment thereof or fusion polypeptide comprising said albumin derivative or variant or fragment thereof, wherein the albumin derivative or variant or fragment thereof comprises:
(i) a first albumin domain III or a derivative or variant thereof having at least 90% sequence identity to human serum albumin (HSA) domain III; and
(ii) a second albumin domain III or a derivative or variant thereof having at least 90% identity to human serum albumin (HSA) domain III; and
wherein the albumin derivative or variant or fragment thereof contains not more than one copy of domain I or a derivative or variant thereof having at least 90% sequence identity to human serum albumin (HSA) domain I.

* * * * *